US011013782B2

(12) United States Patent
Francois et al.

(10) Patent No.: US 11,013,782 B2
(45) Date of Patent: May 25, 2021

(54) METHODS OF TREATING CHRONIC DISORDERS WITH COMPLEMENT INHIBITORS

(71) Applicant: Apellis Pharmaceuticals, Inc., Crestwood, KY (US)

(72) Inventors: Cedric Francois, Prospect, KY (US); Pascal Deschatelets, Lexington, MA (US)

(73) Assignee: Apellis Pharmaceuticals, Inc., Waltham, MA (US)

( * ) Notice: Subject to any disclaimer, the term of this patent is extended or adjusted under 35 U.S.C. 154(b) by 0 days.

(21) Appl. No.: 16/714,252

(22) Filed: Dec. 13, 2019

(65) Prior Publication Data
US 2020/0338155 A1  Oct. 29, 2020

Related U.S. Application Data

(62) Division of application No. 16/023,383, filed on Jun. 29, 2018, now abandoned, which is a division of application No. 14/128,477, filed as application No. PCT/US2012/043845 on Jun. 22, 2012, now Pat. No. 10,039,802.

(60) Provisional application No. 61/499,895, filed on Jun. 22, 2011.

(51) Int. Cl.
*A61K 38/10* (2006.01)
*A61K 39/395* (2006.01)
*A61K 38/12* (2006.01)
*A61B 5/145* (2006.01)
*G01N 33/68* (2006.01)
*A61B 5/00* (2006.01)

(52) U.S. Cl.
CPC .......... *A61K 38/12* (2013.01); *A61B 5/14546* (2013.01); *A61B 5/414* (2013.01); *A61K 38/10* (2013.01); *A61K 39/3955* (2013.01); *G01N 33/6869* (2013.01); *G01N 33/6884* (2013.01); *G01N 2800/12* (2013.01); *G01N 2800/122* (2013.01); *G01N 2800/14* (2013.01); *G01N 2800/24* (2013.01)

(58) Field of Classification Search
CPC ............................ A61K 38/10; A61K 39/3955
See application file for complete search history.

(56) References Cited

U.S. PATENT DOCUMENTS

| | | | |
|---|---|---|---|
| 8,501,705 | B2 | 8/2013 | Christadoss et al. |
| 10,039,802 | B2 | 8/2018 | Francois et al. |
| 2008/0200645 | A1 | 8/2008 | Kotwal et al. |
| 2009/0209459 | A1 | 8/2009 | Hamer et al. |
| 2010/0015145 | A1 | 1/2010 | Sheriff et al. |
| 2010/0119530 | A1 | 5/2010 | Song |
| 2010/0135998 | A1 | 6/2010 | Bowman et al. |
| 2010/0166862 | A1 | 7/2010 | Francois et al. |
| 2011/0243893 | A1 | 10/2011 | Axtell et al. |
| 2011/0245107 | A1 | 10/2011 | Kuchroo et al. |
| 2012/0178694 | A1* | 7/2012 | Lambris ................. A61K 47/64 514/15.2 |
| 2013/0244924 | A1 | 9/2013 | Krishna et al. |
| 2014/0127209 | A1 | 5/2014 | Grabstein et al. |
| 2014/0371133 | A1 | 12/2014 | Francois et al. |
| 2016/0184391 | A1 | 6/2016 | Wang et al. |
| 2019/0192617 | A1 | 6/2019 | Francois et al. |

FOREIGN PATENT DOCUMENTS

| | | |
|---|---|---|
| JP | 2010-540654 A | 12/2010 |
| JP | 2018-093590 A | 6/2018 |
| WO | WO-2008/010902 A2 | 1/2008 |
| WO | WO-2008/097525 A2 | 8/2008 |
| WO | WO-2009/046198 A2 | 4/2009 |
| WO | WO-2010/054403 A1 | 5/2010 |
| WO | WO-2011/163394 A2 | 12/2011 |
| WO | WO-2012/178083 A1 | 12/2012 |

OTHER PUBLICATIONS

Gauvreau, G. et al., The effect of C5 inhibition by eculizumab on allergen-induced asthmatic responses in patients, Abstracts/ Molecular Immunology, 46:2837-2838 (2009).
Hashimoto, M. et al., Complement drives Th17 cell differenctiation and triggers autoimmune arthritis, J. Exp. Med., 207(6):1135-1143 (2010.
International Search Report and Written Opinion for PCT/US2012/043845, dated Nov. 9, 2012.
Laumonnier, Y. et al., The Role of Complement in the Diagnosis and Management of Allergic Rhinitis and Allergic Asthma, Current Allergy and Asthma Reports, 11(2):122-130 (2011).
Morikis, D. et al., Solution structure of Compstatin, a potent complement inhibitor, Protein Science, 7:619-627 (1998).
Taube, C. et al., Inhibition of complement activation decreases airway inflammation and hyperresponsiveness, American Journal of Respiratory and Critical Care Medicine, 168(11):1333-1341 (2003).

(Continued)

*Primary Examiner* — Jeffrey E. Russel
(74) *Attorney, Agent, or Firm* — Choate, Hall & Stewart LLP; Rolando Medina; Melissa M. Adams

(57) ABSTRACT

In some aspects, the invention provides methods of treating a subject in need of treatment for a chronic complement-mediated disorder. In some aspects, the invention provides methods of treating a subject in need of treatment for a Th17-associated disorder. In some aspects, the invention provides methods of treating a subject in need of treatment for a chronic respiratory system disorder. In some aspects, the invention provides methods of administering a complement inhibitor to a subject. In some embodiments, a method of treating a subject comprises administering multiple doses of a complement inhibitor to the subject according to a dosing schedule that leverages the prolonged effect of complement inhibition in chronic respiratory disorders. In some embodiments, a subject has chronic obstructive pulmonary disease. In some embodiments, a subject has asthma.

24 Claims, 11 Drawing Sheets

Specification includes a Sequence Listing.

(56) References Cited

OTHER PUBLICATIONS

Vojdani, A. et al., The role of Th17 in neuroimmune disorders: target for CAM therapy. Part I, Evidence-Based Complementary and Alternative Medicine, vol. 2011, Artile ID 927294, 8 pages (2011).
Yoshimura, T. et al., Involvement of Th17 cells and the effect of anti-IL-6 therapy in autoimmune uveitis, Theumatology, Abstract only, 48(4):347-354 (2009).

* cited by examiner

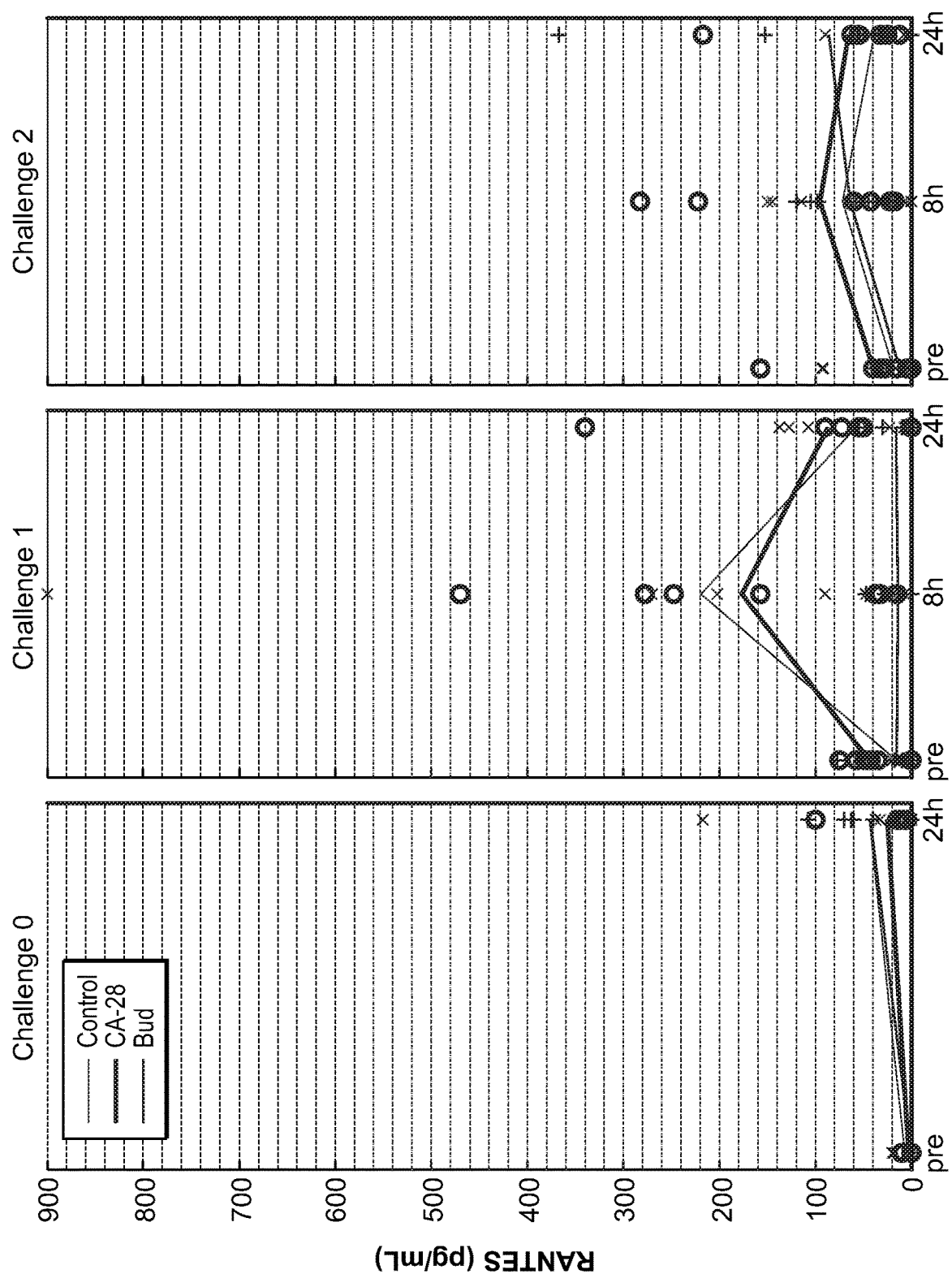

METHODS OF TREATING CHRONIC DISORDERS WITH COMPLEMENT INHIBITORS

CROSS-REFERENCE TO RELATED APPLICATIONS

The present application is a divisional of U.S. application Ser. No. 16/023,383, filed Jun. 29, 2018, which is a divisional of U.S. application Ser. No. 14/128,447, filed on Jul. 29, 2014, which is the National Stage of International Application No. PCT/US12/43845, filed Jun. 22, 2012, which claims priority to U.S. provisional patent application No. 61/499,895, filed Jun. 22, 2011, the entire contents of all of which are hereby incorporated by reference in their entirety.

SEQUENCE LISTING

The instant application contains a Sequence Listing, which has been submitted electronically as a .txt file named "2008575-0068_SL.txt." The .txt file was created on Dec. 17, 2013, and is 37,872 bytes in size. The entire contents of the Sequence Listing are herein incorporated by reference.

BACKGROUND OF THE INVENTION

Chronic disorders of the respiratory system are significant causes of morbidity and mortality whose incidence is increasing worldwide. According to World Health Organization estimates, about 80 million people have moderate to severe chronic obstructive lung disease (COPD), and more than 3 million people died of COPD in 2005 (~5% of all deaths globally). COPD was the fifth leading cause of death in 2002, and estimates suggest that it will be the third leading cause of death worldwide in 2030 unless major risk factors, particularly tobacco use, can be successfully curbed. Asthma is also a significant global health problem, affecting an estimated 300 million individuals worldwide. Both asthma and COPD can have debilitating effects on patients' daily functioning and quality of life, particularly when severe. These diseases also represent significant burdens in terms of health care costs and lost productivity.

Pharmacological therapies such as bronchodilators and corticosteroids are widely used in the treatment of asthma and COPD. However, a significant proportion of patients experience persistent symptoms despite such interventions. Furthermore, these agents can be associated with significant side effects. There is a need for additional pharmacological therapies for treating disorders affecting the respiratory system.

SUMMARY OF THE INVENTION

The invention provides, among other things, methods of treating a chronic complement-mediated disorder, the methods comprising administering a complement inhibitor to a subject in need of treatment for the disorder. In some aspects, the invention provides methods of treating a chronic disorder of the respiratory system, the methods comprising administering a complement inhibitor to a subject in need of treatment for the disorder. In some embodiments, the disorder is asthma. In some embodiments, the disorder is COPD. Certain aspects of the invention are based at least in part on the recognition that complement inhibitors exhibit a prolonged duration of effect in the treatment of chronic complement-mediated disorders, e.g., chronic complement-mediated disorders of the respiratory system, such as asthma or COPD. For example, in some embodiments, the duration of action of a complement inhibitor for significantly reducing one or more manifestation(s) of a chronic complement-mediated disorder, e.g., a chronic respiratory disorder, is greater than the duration of action of the complement inhibitor for substantially inhibiting plasma complement activation capacity when administered intravenously.

In some aspects, the invention provides a method of treating a subject in need of treatment for a chronic respiratory disorder or other chronic complement-mediated disorder, the method comprising administering multiple doses of a complement inhibitor to the subject according to a dosing schedule in which successive doses are administered on average (i) at least 2 weeks after the plasma concentration of the complement inhibitor decreases to no more than 20% of the maximum plasma concentration that was reached after the previous dose; (ii) at least 2 weeks after plasma complement activation capacity has returned to at least 50% of baseline after the previous dose; (iii) at intervals equal to at least 2 times the terminal plasma half-life of the complement inhibitor; or (iv) at intervals at least 3 weeks apart. In some embodiments successive doses of the complement inhibitor are administered on average (i) between 2 weeks and 6 weeks after the plasma concentration of the complement inhibitor decreases to no more than 20% of the maximum plasma concentration that was reached after the previous dose; (ii) between 2 weeks and 6 weeks after plasma complement activation capacity has returned to at least 50% of baseline after the previous dose; (iii) at intervals equal to between 2 and 5 times the terminal plasma half-life of the complement inhibitor; or (iv) at intervals between 3 weeks and 6 weeks apart. In some embodiments successive doses of the complement inhibitor are administered on average at least 4 weeks apart. In some embodiments successive doses of the complement inhibitor are administered on average at least 2 weeks after plasma complement activation capacity has returned to within the normal range after the previous dose. In some embodiments successive doses of the complement inhibitor are administered on average at least 2 weeks after the plasma concentration of the complement inhibitor decreases to no more than 10% of the maximum plasma concentration that was reached after the previous dose. In some embodiments successive doses of the complement inhibitor are administered on average at least 2 weeks after the plasma concentration of the complement inhibitor decreases to no more than 5% of the maximum plasma concentration that was reached after the previous dose. In some embodiments wherein the dosing schedule is determined based at least in part on values of the complement inhibitor plasma concentration, complement inhibitor plasma half-life, and/or plasma complement activation capacity, as measured in a population of subjects. In some embodiments the dosing schedule is determined based at least in part on values of the complement inhibitor plasma concentration, complement inhibitor plasma half-life, and/or plasma complement activation capacity, of the subject being treated.

In some embodiments of any method comprising dosing, at least 5 doses are administered.

In some embodiments a subject is in need of treatment for asthma, chronic obstructive pulmonary disease (COPD), or both. In some embodiments a subject is in need of treatment for severe asthma.

In some embodiments a complement inhibitor is administered by the respiratory route. In some embodiments a complement inhibitor is administered using a nebulizer, metered dose inhaler, or dry powder inhaler. In some embodiments a complement inhibitor is administered using a vibrating mesh nebulizer.

In some embodiments a complement inhibitor is administered by the intravenous route.

In some embodiments a complement inhibitor acts on C3 or upstream of C3 in the complement cascade. In some embodiments the complement inhibitor inhibits cleavage of C3, C5, or factor B.

In some embodiments a complement inhibitor comprises an antibody, aptamer, peptide, polypeptide, or small molecule.

In some embodiments a complement inhibitor comprises an antibody, aptamer, peptide, polypeptide, or small molecule that binds to C3, C5, factor B, or factor D.

In some embodiments a complement inhibitor comprises a compstatin analog.

In some embodiments a complement inhibitor comprises a compstatin analog whose sequence comprises SEQ ID NO: 14, 21, 28, 29, 32, 33, 34, or 36.

In some embodiments a complement inhibitor comprises a compstatin analog whose sequence comprises any of SEQ ID NOs: 3-41.

In some embodiments a complement-mediated disorder is a Th17-associated disorder.

In some embodiments any method of treatment comprises detecting a Th17 biomarker in the subject or in a sample obtained from the subject. In some embodiments the Th17 biomarker is detected in a sample comprising a body fluid, wherein the body fluid is optionally selected from blood, BAL fluid, sputum, nasal secretion, or urine or a combination thereof. In some embodiments the biomarker comprises at least one cytokine that is produced by or promotes formation, survival, or activity of Th17 cells. In some embodiments an increased level of the Th17 biomarker as compared to a reference indicates that the subject is in need of a dose of the complement inhibitor. In some embodiments the reference is within the normal range for persons not suffering from the disorder or is a baseline value for the subject when the disorder is well controlled. In some embodiments the Th17 biomarker is detected prior to administration of a dose of the complement inhibitor and serves as an indicator that the subject is in need of a dose of the complement inhibitor. In some embodiments the biomarker is detected prior to administration of a dose of the complement inhibitor and serves as an indicator that the subject is in need of a dose of the complement inhibitor, and the method comprises administering the complement inhibitor within a predetermined time period following detection of the biomarker. In some embodiments a predetermined time period is 1, 2, 3, 4, 5, 6, or 7 days or 2, 3, or 4 weeks.

In some aspects, a method of treating a subject in need of treatment for a chronic complement-mediated disorder comprises: (a) administering at least one dose of a complement inhibitor to the subject; and (b) monitoring the subject for a Th17 biomarker in the subject or in a sample obtained from the subject. In some embodiments the method, further comprises: (c) administering at least one additional dose of the complement inhibitor to the subject. In some embodiments step (b) comprises detecting a Th17 biomarker in the subject or in a sample obtained from the subject. In some embodiments step (b) comprises detecting an increased level of the biomarker as compared to a reference, wherein the increased level indicates that the subject is in need of a dose of the complement inhibitor. In some embodiments step (b) comprises detecting an increased level of the biomarker as compared to a reference, wherein the increased level indicates that the subject is in need of a dose of the complement inhibitor, and the method further comprises (c) administering at least one additional dose of the complement inhibitor to the subject. In some embodiments step (b) comprises detecting an increased level of the biomarker as compared to a reference, wherein the increased level indicates that the subject is in need of a dose of the complement inhibitor, and the method further comprises (c) administering at least one additional dose of the complement inhibitor to the subject within a predetermined time of detecting the biomarker. In some embodiments a predetermined time period is 1, 2, 3, 4, 5, 6, or 7 days or 2, 3, or 4 weeks. In some embodiments a method further comprises administering an anti-Th17 agent to the subject.

In some embodiments an anti-Th17 agent comprises an agent that inhibits formation or activity of Th17 cells. In some embodiments an anti-Th17 agent comprises an agent that inhibits the production or activity of a cytokine produced by Th17 cells or that promotes formation or activity of Th17 cells. In some embodiments an anti-Th17 agent comprises an agent that inhibits the production or activity of IL-1β, IL-6, IL-21, IL-22, IL-17, or IL-23. In some embodiments an anti-Th17 agent comprises an antibody, small molecule, aptamer, polypeptide, or RNAi agent. In some embodiments an anti-Th17 agent comprises an antibody, small molecule, aptamer, or polypeptide that binds to IL-1β, IL-6, IL-21, IL-22, IL-17, or IL-23 or binds to receptor for any of the foregoing.

In some aspects, a pharmaceutical composition comprising a complement inhibitor and an anti-Th17 agent is provided. In some embodiments wherein the complement inhibitor inhibits C3 activity or C3 activation. In some embodiments the complement inhibitor comprises a compstatin analog. In some embodiments wherein the anti-Th17 agent comprises an antibody, small molecule, aptamer, or polypeptide that binds to IL-1β, IL-6, IL-21, IL-22, IL-17, or IL-23 or binds to receptor for any of the foregoing.

In some aspects, a method of treating a complement-mediated disorder comprises administering a composition comprising a complement inhibitor and an anti-Th17 agent to a subject in need thereof.

In some aspects, a method of treating a Th17-associated disorder comprises administering a complement inhibitor and an anti-Th17 agent to a subject in need thereof.

In some aspects, a method of method of disrupting a DC-Th17-B-Ab-C-DC cycle is provided, the method comprising administering comprising a complement inhibitor and an anti-Th17 agent to a subject in need thereof.

In some aspects, a method of treating a Th17-associated disorder comprises administering a complement inhibitor and an anti-Th17 agent to a subject in need thereof.

In some aspects, a method of treating a Th17-associated disorder comprises administering a composition comprising a complement inhibitor and an anti-Th17 agent to a subject in need thereof.

In some aspects, a method of method of disrupting a DC-Th17-B-Ab-C-DC cycle is provided, the method comprising administering comprising a complement inhibitor and an anti-Th17 agent to a subject in need thereof.

In some embodiments, any of the methods comprises monitoring the subject for evidence of a DC-Th17-B-Ab-C-DC cycle.

In some embodiments, any of the methods comprises monitoring the subject for evidence of a DC-Th17-B-Ab-C cycle and administering a complement inhibitor, anti-Th17 agent, or composition comprising a complement inhibitor, anti-Th17 agent to the subject based at least in part on a result of said monitoring.

In some embodiments, any of the methods comprises monitoring the subject for a Th17 biomarker.

In some embodiments, any of the methods comprises monitoring the subject for a Th17 biomarker and administering a complement inhibitor, anti-Th17 agent, or composition comprising a complement inhibitor, anti-Th17 agent to the subject based at least in part on a result of the monitoring.

In some aspects, a method of treating a subject having or at risk of a complement-mediated disorder, comprises monitoring the subject for evidence of a DC-Th17-B-Ab-C-DC cycle and administering a complement inhibitor to the subject based at least in part on a result of said monitoring. In some embodiments the method further comprises administering an anti-Th17 agent to the subject.

In some aspects, a method of treating a subject having or at risk of a complement-mediated disorder, comprises monitoring the subject for evidence of a DC-Th17-B-Ab-C-DC cycle and administering a complement inhibitor and an anti-Th17 agent to the subject based at least in part on a result of said monitoring.

In some aspects, a method of treating a subject having or at risk of a Th17-associated disorder, the method comprising monitoring the subject for evidence of a DC-Th17-B-Ab-C-DC cycle and administering a complement inhibitor to the subject based at least in part on a result of said monitoring. In some embodiments the method further comprises administering an anti-Th17 agent to the subject.

In some aspects, a method of treating a subject having or at risk of a Th17-associated disorder is provided, the method comprising monitoring the subject for evidence of a DC-Th17-B-Ab-C-DC cycle and administering a complement inhibitor and an anti-Th17 agent to the subject based at least in part on a result of said monitoring. In some embodiments the complement inhibitor inhibits C3 activity or C3 activation. In some embodiments the complement inhibitor comprises a compstatin analog.

In some embodiments of a composition or method relating at least in part to an anti-Th17 agent, the anti-Th17 agent comprises an antibody, small molecule, aptamer, or polypeptide that binds to IL-1β, IL-6, IL-21, IL-22, IL-17, or IL-23 or binds to receptor for any of the foregoing.

In some embodiments of any method comprising monitoring a subject for evidence of a DC-Th17-B-Ab-C-DC cycle, such monitoring comprises assessing a Th17-associated biomarker in the subject or in a sample obtained from the subject.

In some embodiments of any method comprising monitoring a subject, the monitoring occurs approximately every 1-2 weeks, 2-4 weeks, or approximately every 1, 2, 3, 4, 5, 6, 7, 8, 9, 10, 11, or 12 months.

In some embodiments of any method comprising administering a complement inhibitor, anti-Th17 agent, or both, administration occurs within no more than 1, 2, 3, 4, 5, 6, or 7 days or 2, 3, or 4 weeks of having detected evidence of a DC-Th17-B-Ab-C-DC cycle or increased level of a Th17-associated biomarker.

In some aspects, a method of treating a subject in need of treatment for AMD is provided, the method comprising administering an anti-IL-23 agent to the subject. In some embodiments the agent is administered locally to the eye, e.g., by intravitreal injection. In some embodiments of the subject has dry AMD.

All articles, books, patent applications, patents, other publications, websites, and databases mentioned in this application are incorporated herein by reference. In the event of a conflict between the specification and any of the incorporated references the specification (including any amendments thereto) shall control. Unless otherwise indicated, art-accepted meanings of terms and abbreviations are used herein.

BRIEF DESCRIPTION OF THE DRAWING

FIGS. 1-11 are plots that show concentrations in broncheoalveolar lavage (BAL) fluid of the indicated cytokines, measured in samples obtained from individual cynomolgus monkeys at the indicated time points prior to or following *Ascaris suum* challenges 0, 1, and 2. Control animals (triangles); budesonide-treated animals (+); CA-28-treated animals (circles). Plots of mean cytokine concentration at each time point are superimposed and shown as continuous lines to more clearly depict changes over the 24 hour time period.

DETAILED DESCRIPTION OF CERTAIN EMBODIMENTS OF THE INVENTION

I. Definitions

Figure 1:
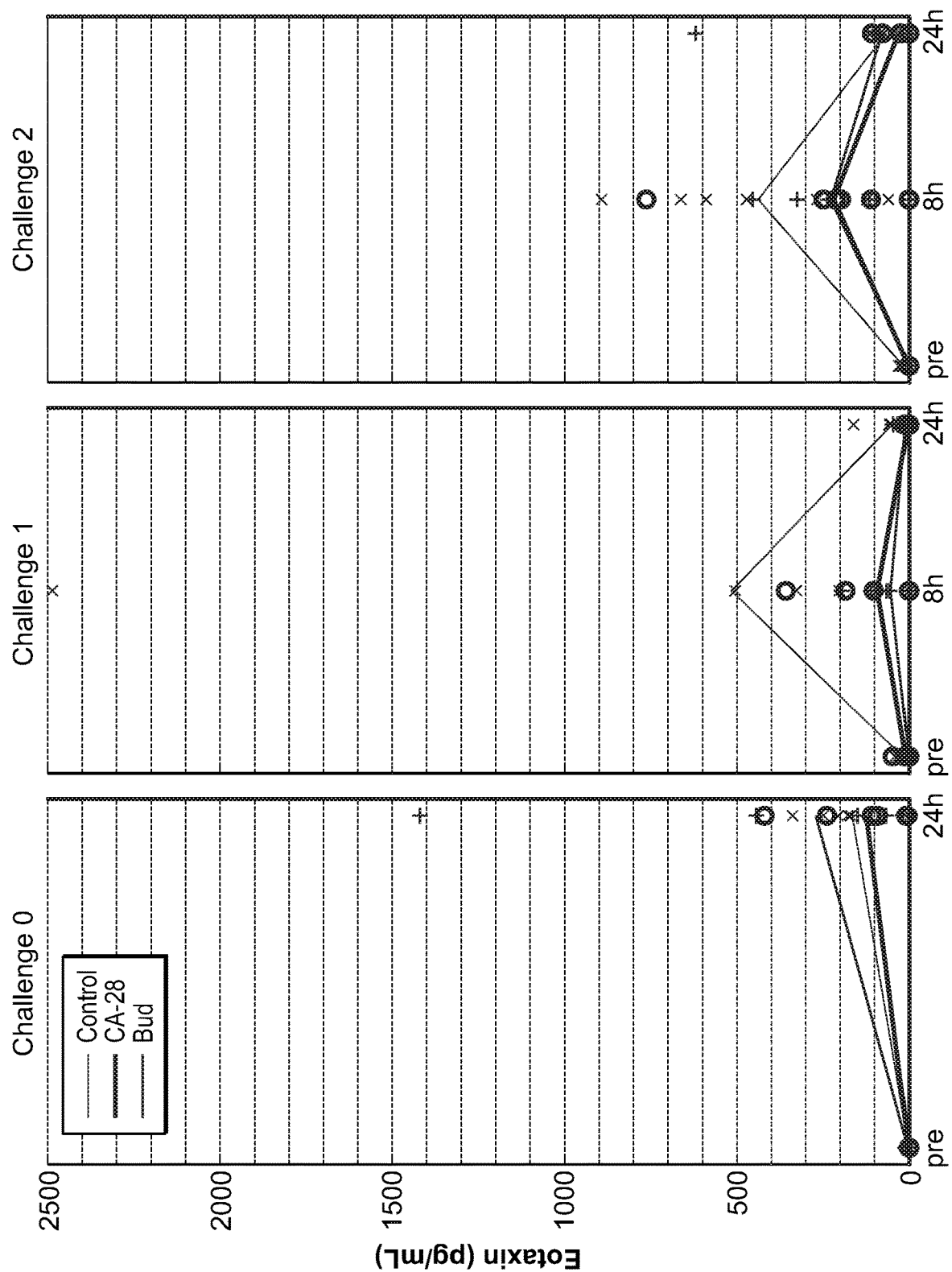
Figure 2:
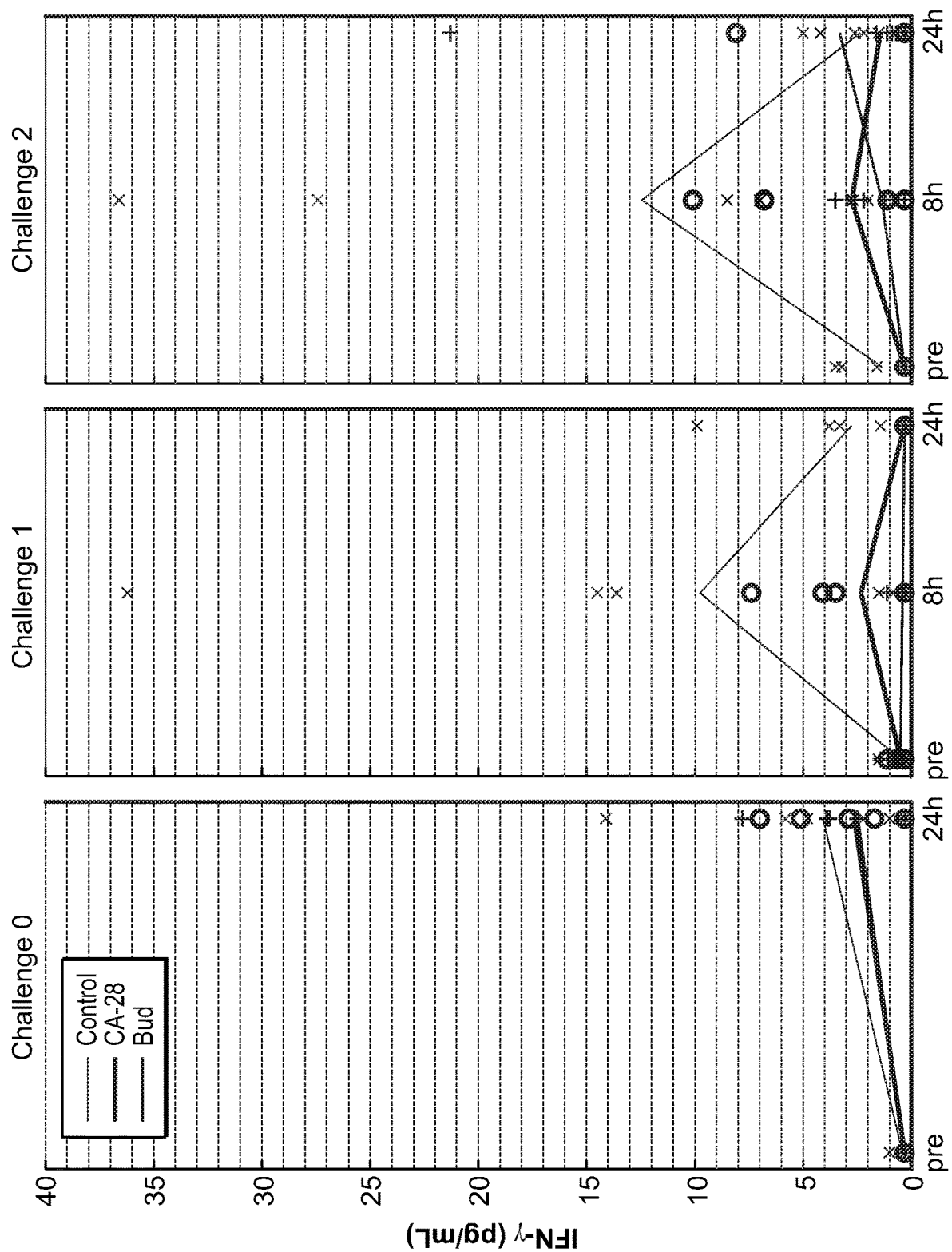

As used herein, the term "antibody" encompasses antibodies and antibody fragments comprising an antigen binding site. Antibodies useful in certain embodiments of the invention could originate from or be derived from various species, e.g., human, non-human primate, rodent (e.g., mouse, rat, rabbit), goat, chicken, and/or could be of various antibody classes, e.g., the human classes: IgG (e.g., IgG1, IgG2, IgG3, IgG4), IgM, IgA, IgD, and IgE. An antibody fragment (Fab) can be, for example, a Fab', F(ab')$_2$, scFv (single-chain variable) or other fragment that retains or contains an antigen binding site. See, e.g., Allen, T., Nature Reviews Cancer, Vol. 2, 750-765, 2002, and references therein. Antibodies known in the art as diabodies, minibodies, or nanobodies can be used in various embodiments. Bispecific or multispecific antibodies may be used in various embodiments. The heavy and light chain of IgG immunoglobulins (e.g., rodent or human IgGs) contain four framework regions (FR1 through FR4) separated respectively by three complementarity determining regions (CDR1 through CDR3). The CDRs, particularly the CDR3 regions, especially the heavy chain CDR3, are largely responsible for antibody specificity. An antibody may be a chimeric antibody in which, for example, a variable domain of rodent origin or non-human primate origin is fused to a constant domain of human origin, or a "humanized" antibody in which some or all of the complementarity-determining region (CDR) amino acids that constitute an antigen binding site (sometimes along with one or more framework amino acids or regions) are "grafted" from a rodent antibody (e.g., murine antibody) or phage display antibody to a human antibody, thus retaining the specificity of the rodent or phage display antibody. Thus, humanized antibodies may be recombinant proteins in which only the antibody complementarity-determining regions are of non-human origin. It will be appreciated that the alterations to antibody sequence that are involved in the humanization process are generally carried out through techniques at the nucleic acid level, e.g., standard recombinant nucleic acid techniques. In some embodiments only the specificity determining residues (SDRs), the CDR residues that are most crucial in the antibody-ligand interaction, are grafted. The SDRs may be identified, e.g., through use of a database of the three-dimensional structures of the antigen-antibody complexes of known structures or by mutational analysis of the antibody-combining site. In some embodiments an approach is used that involves retention of more CDR residues, namely grafting of so-called "abbreviated" CDRs, the stretches of CDR residues that include all the SDRs. See, e.g., Kashmiri, S V, Methods. 36(1):25-34 (2005), for further discussion of SDR grafting. See, e.g., Almagro J C, Fransson J. Humanization of antibodies. Front Biosci. 13:1619-33 (2008) for review of various methods of obtaining humanized antibodies. It will be understood that "originate from or derived from" refers to the original source of the genetic information specifying an antibody sequence or a portion thereof, which may be different from the species in which an antibody is initially synthesized. For example, "human" domains may be generated in rodents whose genome incorporates human immunoglobulin genes. See, e.g., Vaughan, et al, (1998), Nature Biotechnology, 16: 535-539, e.g., to generate a fully human antibody. An antibody may be polyclonal or monoclonal, though for purposes of the present invention monoclonal antibodies are generally preferred as therapeutic agents. Methods for generating antibodies that specifically bind to virtually any molecule of interest are known in the art. For example, monoclonal or polyclonal antibodies can be purified from natural sources, e.g., from blood or ascites fluid of an animal that produces the antibody (e.g., following immunization with the molecule or an antigenic fragment thereof) or can be produced recombinantly, in cell culture and, e.g., purified from culture medium. Affinity purification may be used, e.g., protein A/G affinity purification and/or affinity purification using the antigen as an affinity reagent. Suitable antibodies can be identified using phage display and related techniques. See, e.g., Kaser, M. and Howard, G., "Making and Using Antibodies: A Practical Handbook" and Sidhu, S., "Phage Display in Biotechnology and Drug Discovery", CRC Press, Taylor and Francis Group, 2005, for further information. Methods for generating antibody fragments are well known. For example, F(ab')$_2$ fragments can be generated, for example, through the use of an Immunopure F(ab')$_2$ Preparation Kit (Pierce) in which the antibodies are digested using immobilized pepsin and purified over an immobilized Protein A column. The digestion conditions (such as temperature and duration) may be optimized by one of ordinary skill in the art to obtain a good yield of F(ab')$_2$. The yield of F(ab')$_2$ resulting from the digestion can be monitored by standard protein gel electrophoresis. F(ab') can be obtained by papain digestion of antibodies, or by reducing the S—S bond in the F(ab')$_2$. As used herein, a "single-chain Fv" or "scFv" antibody fragment comprises the $V_H$ and $V_L$ domains of an antibody, wherein these domains are present in a single polypeptide chain. Typically, a scFv antibody further comprises a polypeptide linker between the $V_H$ and $V_L$ domains, although other linkers could be used to connect the domains in certain embodiments.

The terms "approximately" or "about" in reference to a number generally include numbers that fall within ±10%, in some embodiments ±5%, in some embodiments ±1%, in some embodiments ±0.5% of the number unless otherwise stated or otherwise evident from the context (except where such number would impermissibly exceed 100% of a possible value).

"Complement activation capacity" refers to the level of complement activation that would result from exposure to a stimulus that causes maximum complement activation. Typically, complement activation capacity is assessed using a sample obtained from a subject (e.g., a blood, plasma, serum, or other fluid sample, which may be diluted appropriately), which sample may be exposed in vitro to a complement activating stimulus. A heat-inactivated sample can be used as a control. It will be understood that the stimulus need not be sufficient to cause maximum complement activation in order to provide a measurement of complement activation capacity. For example, the extent to which complement activation occurs within a defined time period can provide an indication of complement activation capacity. Complement activation may be measured using, e.g., a suitable assay such as a functional assay based on hemolysis (e.g., lysis of sheep or chicken red blood cells); deposition or capture of complement activation products (e.g., C3a, C3b, iC3b, C5a, MAC), etc. Pathway-specific complement activation capacity may be assessed using, e.g., appropriate stimuli and assay conditions (e.g., presence or absence of calcium ions in the assay composition) to activate one or more than one of the pathways. For example, antibody (e.g., IgM or immune complexe) can be used to activate the classical pathway; lipopolysaccharide (LPS) can be used to activate the alternative pathway, mannan can be used to activate the mannose-binding lectin portion of the lectin pathway, etc. In some embodiments, the total classical complement activity in a sample is measured using a CH50 test using antibody-sensitized sheep or chicken erythrocytes as the activator of the classical complement pathway and various dilutions of the test sample to determine the amount required to give 50% lysis. The percent hemolysis can be determined spectrophotometrically. The higher the dilution of the sample that can still achieve 50% lysis (i.e., the more diluted the sample), the greater complement activation capacity. In some embodiments, an ELISA-based assay is used. In some embodiments, complement activation is assessed based on iC3b levels, e.g., substantially as described in PCT/US2010/035871 (WO2010135717) (see Examples). In some embodiments, complement activation is assessed based on C3b levels, substantially as described in PCT/US2008/001483 (WO/2008/097525) Examples 1 and 2, respectively. In some embodiments, complement activation via the classical pathway is assessed using the MicroVue CH50 Eq EIA Kit (classical pathway), MicroVue Bb Plus EIA Kit (alternative pathway), MicroVue iC3b EIA Kit, or MicroVue C3a Plus EIA Kit (all from Quidel Corp.). In some embodiments, the amount of a complement activation product is normalized to the amount of intact C3 present in the sample prior to exposure to a complement activation stimulus.

A "complement component" or "complement protein" is a protein that is involved in activation of the complement system or participates in one or more complement-mediated activities. Components of the classical complement pathway include, e.g., C1q, C1r, C1s, C2, C3, C4, C5, C6, C7, C8, C9, and the C5b-9 complex, also referred to as the membrane attack complex (MAC) and active fragments or enzymatic cleavage products of any of the foregoing (e.g., C3a, C3b, C4a, C4b, C5a, etc.). Components of the alternative pathway include, e.g., factors B, D, and properdin. Components of the lectin pathway include, e.g., MBL2, MASP-1, and MASP-2. Complement components also include cell-bound receptors for soluble complement components, wherein such receptor mediates one or more biological activities of such soluble complement component following binding of the soluble complement component. Such receptors include, e.g., C5a receptor (C5aR), C3a receptor (C3aR), Complement Receptor 1 (CR1), Complement Receptor 2 (CR2), Complement Receptor 3 (CR3, also known as CD45), etc. It will be appreciated that the term "complement component" is not intended to include those molecules and molecular structures that serve as "triggers" for complement activation, e.g., antigen-antibody complexes, foreign structures found on microbial or artificial surfaces, etc.

A "complement regulatory protein" is a protein involved in regulating complement activity. A complement regulatory protein may down-regulate complement activity by, e.g., inhibiting complement activation or by inactivating or accelerating decay of one or more activated complement proteins. Examples of complement regulatory proteins include C1 inhibitor, C4 binding protein, clusterin, vitronectin, CFH, factor I, and the cell-bound proteins CD46, CD55, CD59, CR1, CR2, and CR3.

"Linked", as used herein with respect to two or more moieties, means that the moeities are physically associated or connected with one another to form a molecular structure that is sufficiently stable so that the moieties remain associated under the conditions in which the linkage is formed and, preferably, under the conditions in which the new molecular structure is used, e.g., physiological conditions. In certain preferred embodiments of the invention the linkage is a covalent linkage. In other embodiments the linkage is noncovalent. Moieties may be linked either directly or indirectly. When two moieties are directly linked, they are either covalently bonded to one another or are in sufficiently close proximity such that intermolecular forces between the two moieties maintain their association. When two moieties are indirectly linked, they are each linked either covalently or noncovalently to a third moiety, which maintains the association between the two moieties. In general, when two moieties are referred to as being linked by a "linking moiety" or "linking portion", the linkage between the two linked moieties is indirect, and typically each of the linked moieties is covalently bonded to the linking moiety. Two moieties may be linked using a "linker". A linker can be any suitable moiety that reacts with the entities to be linked within a reasonable period of time, under conditions consistent with stability of the entities (portions of which may be protected as appropriate, depending upon the conditions), and in sufficient amount, to produce a reasonable yield. Typically the linker will contain at least two functional groups, one of which reacts with a first entity and the other of which reacts with a second entity. It will be appreciated that after the linker has reacted with the entities to be linked, the term "linker" may refer to the part of the resulting structure that originated from the linker, or at least the portion that does not include the reacted functional groups. A linking moiety may comprise a portion that does not participate in a bond with the entities being linked, and whose main purpose may be to spatially separate the entities from each other. Such portion may be referred to as a "spacer".

"Polypeptide", as used herein, refers to a polymer of amino acids, optionally including one or more amino acid analogs. A protein is a molecule composed of one or more polypeptides. A peptide is a relatively short polypeptide, typically between about 2 and 60 amino acids in length, e.g., between 8 and 40 amino acids in length. The terms "protein", "polypeptide", and "peptide" may be used interchangeably. Polypeptides used herein may contain amino acids such as those that are naturally found in proteins, amino acids that are not naturally found in proteins, and/or amino acid analogs that are not amino acids. As used herein, an "analog" of an amino acid may be a different amino acid that structurally resembles the amino acid or a compound other than an amino acid that structurally resembles the amino acid. A large number of art-recognized analogs of the 20 amino acids commonly found in proteins (the "standard" amino acids) are known. One or more of the amino acids in a polypeptide may be modified, for example, by the addition of a chemical entity such as a carbohydrate group, a phosphate group, a farnesyl group, an isofarnesyl group, a fatty acid group, a linker for conjugation, functionalization, or other modification, etc. Certain non-limiting suitable analogs and modifications are described in WO2004026328 and/or below. The polypeptide may be acetylated, e.g., at the N-terminus and/or amidated, e.g., at the C-terminus.

In general, polypeptides may be obtained or produced using any suitable method known in the art. For example, polypeptides may be isolated from natural sources, produced in vitro or in vivo using recombinant DNA technology in suitable expression systems (e.g., by recombinant host cells or transgenic non-human animals or plants), synthesized through chemical means such as solid phase peptide synthesis and/or using methods involving chemical ligation of synthesized peptides (see, e.g., Kent, S., J Pept Sci., 9(9): 574-93, 2003 and U.S. Pub. No. 20040115774), or a combination of these. One of ordinary skill in the art would readily select appropriate method(s). A polypeptide may comprise a tag, e.g., an epitope tag, which tag may facilitate purification and/or detection of the polypeptide. Exemplary tags include, e.g., 6Xhis (SEQ ID NO: 70), HA, Myc, SNUT, FLAG, TAP, etc. In some embodiments, a tag is cleavable, e.g., the tag comprises a recognition site for cleavage by a protease, or is separated from a portion complement inhibiting portion of the polypeptide by a linking portion that comprises a recognition site for cleavage by a protease. For example, a TEV protease cleavage site can be used.

"Poxvirus" refers to a family of complex, double-stranded DNA viruses constituting the family Poxyiridae. The family includes the orthopoxviruses, a genus of the family Poxyiridae, subfamily Chordopoxyirinae, comprising many species infecting mammals, including human beings. Poxviruses are described in Fields, B N, et al., Fields Virology, $3^{rd}$ ed., Lippincott Williams & Wilkins, 2001. Orthopoxviruses include, but are not limited to, vaccinia virus, variola virus major, variola virus minor, cowpox virus, monkeypox virus, camelpox virus, swinepox virus, and ectromelia virus.

"Poxvirus complement control protein" refers to members of a family of homologous proteins encoded by a number of different poxviruses that bind to one or more complement pathway proteins and inhibit either the classical pathway of complement activation, the alternative pathway of complement activation, the lectin pathway, or any combination of these. Poxvirus complement control proteins are members of the complement control protein (CCP), also called regulators of complement activation (RCA) superfamily (Reid, K B M and Day, A J, Immunol Today, 10:177-80, 1989).

"Recombinant host cells", "host cells", and other such terms, denote prokaryotic or eukaryotic cells or cell lines that contain an exogenous nucleic acid (typically DNA) such as an expression vector comprising a nucleic acid that encodes a polypeptide of interest. It will be understood that such terms include the descendants of the original cell(s) into which the vector or other nucleic acid has been introduced. Appropriate host cells include any of those routinely used in the art for expressing polynucleotides (e.g., for purposes of producing polypeptide(s) encoded by such polynucleotides) including, for example, prokaryotes, such as *E. coli*; and eukaryotes, including for example, fungi, such as yeast (e.g., *Pichia pastoris*); insect cells (e.g., Sf9), plant cells, and animal cells, e.g., mammalian cells such as CHO, R1.1, B-W, L-M, African Green Monkey Kidney cells (e.g. COS-1, COS-7, BSC-1, BSC-40 and BMT-10) and cultured human cells. The exogenous nucleic acid may be stably maintained as an episome such as a plasmid or may at least in part be integrated into the host cell's genome, optionally after being copied or reverse transcribed. Terms such as "host cells", etc., are also used to refer to cells or cell lines that can be used as recipients for an exogenous nucleic acid, prior to introduction of the nucleic acid. A "recombinant polynucleotide" is a polynucleotide that contains nucleic acid sequences that are not found joined directly to one another in nature. For example, the nucleic acid sequences may occur in different genes or different species or one or more of the sequence(s) may be a variant of a naturally occurring sequence or may at least in part be an artificial sequence that is not homologous to a naturally occurring sequence. A "recombinant polypeptide" is a polypeptide that is produced by transcription and translation of an exogenous nucleic acid by a recombinant host cell or by a cell-free in vitro expression system and/or that contains amino acid sequences that are not found joined directly to one another in nature. In the latter case, the recombinant polypeptide may be referred to as a "chimeric polypeptide". The amino acid sequences in a chimeric polypeptide may, for example, occur in different genes or in different species or one or more of the sequence(s) may be a variant of a naturally occurring sequence or may at least in part be an artificial sequence that is not homologous to a naturally occurring sequence. It will be understood that a chimeric polypeptide may comprise two or more polypeptide. For example, first and second polypeptides A and B of a chimeric polypeptide may be directly linked (A-B or B-A) or may be separated by a third polypeptide portion C (A-C-B or B-C-A). In some embodiments, portion C represents a polypeptide linker which may, for example, comprise multiple glycine and/or serine residues. In some embodiments, two or more polypeptides may be linked by non-polypeptide linker(s).

"Reactive functional groups" as used herein refers to groups including, but not limited to, olefins, acetylenes, alcohols, phenols, ethers, oxides, halides, aldehydes, ketones, carboxylic acids, esters, amides, cyanates, isocyanates, thiocyanates, isothiocyanates, amines, hydrazines, hydrazones, hydrazides, diazo, diazonium, nitro, nitriles, mercaptans, sulfides, disulfides, sulfoxides, sulfones, sulfonic acids, sulfinic acids, acetals, ketals, anhydrides, sulfates, sulfenic acids isonitriles, amidines, imides, imidates, nitrones, hydroxylamines, oximes, hydroxamic acids thiohydroxamic acids, allenes, ortho esters, sulfites, enamines, ynamines, ureas, pseudoureas, semicarbazides, carbodiimides, carbamates, imines, azides, azo compounds, azoxy compounds, and nitroso compounds, N-hydroxysuccinimide esters, maleimides, sulfhydryls, and the like. Methods to prepare each of these functional groups are well known in the art and their application to or modification for a particular purpose is within the ability of one of skill in the art (see, for example, Sandler and Karo, eds. ORGANIC FUNCTIONAL GROUP PREPARATIONS, Academic Press, San Diego, 1989, and Hermanson, G., *Bioconjugate Techniques*, $2^{nd}$ ed., Academic Press, San Diego, 2008).

"Specific binding" generally refers to a physical association between a target polypeptide (or, more generally, a target molecule) and a binding molecule such as an antibody or ligand. The association is typically dependent upon the presence of a particular structural feature of the target such as an antigenic determinant, epitope, binding pocket or cleft, recognized by the binding molecule. For example, if an antibody is specific for epitope A, the presence of a polypeptide containing epitope A or the presence of free unlabeled A in a reaction containing both free labeled A and the binding molecule that binds thereto, will reduce the amount of labeled A that binds to the binding molecule. It is to be understood that specificity need not be absolute but generally refers to the context in which the binding occurs. For example, it is well known in the art that numerous antibodies cross-react with other epitopes in addition to those present in the target molecule. Such cross-reactivity may be acceptable depending upon the application for which the antibody is to be used. One of ordinary skill in the art will be able to select antibodies or ligands having a sufficient degree of specificity to perform appropriately in any given application (e.g., for detection of a target molecule, for therapeutic purposes, etc). It is also to be understood that specificity may be evaluated in the context of additional factors such as the affinity of the binding molecule for the target versus the affinity of the binding molecule for other targets, e.g., competitors. If a binding molecule exhibits a high affinity for a target molecule that it is desired to detect and low affinity for nontarget molecules, the antibody will likely be an acceptable reagent. Once the specificity of a binding molecule is established in one or more contexts, it may be employed in other, preferably similar, contexts without necessarily re-evaluating its specificity. In some embodiments, the affinity (as measured by the equilibrium dissociation constant, Kd) of two molecules, e.g., two molecules that exhibit specific binding, is $10^{-3}$ M or less, e.g., $10^{-4}$ M or less, e.g., $10^{-5}$ M or less, e.g., $10^{-6}$ M or less, $10^{-7}$ M or less, $10^{-8}$ M or less, or $10^{-9}$ M or less under the conditions tested, e.g., under physiological conditions (e.g., conditions such as salt concentration, pH, and/or temperature, etc., that reasonably approximate corresponding conditions in vivo), or other conditions of the assay. Binding affinity can be measured using any of a variety of methods known in the art. For example, assays based on isothermal titration calorimetry or surface plasmon resonance (e.g., Biacore® assays) can be used in certain embodiments.

A "subject" treated according to the instant invention is typically a human, a non-human primate, or another mammal (e.g., a mouse or rat). It will be appreciated that, at least in embodiments wherein a complement inhibitor is administered, the subject should express at least one complement component that can be inhibited by the particular complement inhibitor used. For example, a complement inhibitor specific for primate complement would typically be administered to a human or non-human primate or an animal model that has been genetically engineered to express human complement component(s). In some embodiments the subject is male. In some embodiments the subject is female. In some embodiments, a human subject is at least 12 years of age. In some embodiments a subject is an adult, e.g., a human at least 18 years of age, e.g., between 18 and 100 years of age. In some embodiments a subject is at least 40, 45, 50, 55, 60, 65, 70, 75, or 80 years of age. In some embodiments the subject is a child, e.g., a human between 0 and 4 years of age, or between 5 and 11 years of age.

"Treating", as used herein in regard to treating a subject, refers to providing treatment, i.e, providing any type of medical or surgical management of a subject. The treatment can be provided in order to reverse, alleviate, inhibit the progression of, prevent or reduce the likelihood of a disease, or in order to reverse, alleviate, inhibit or prevent the progression of, prevent or reduce the likelihood of one or more symptoms or manifestations of a disease. "Prevent" refers to causing a disease or symptom or manifestation of a disease not to occur for at least a period of time in at least some individuals, e.g., individuals at risk of developing the disease, symptom, or manifestation. Treating can include administering a compound or composition to the subject following the development of one or more symptoms or manifestations indicative of a disease, e.g., in order to reverse, alleviate, reduce the severity of, and/or inhibit or prevent the progression of the disease and/or to reverse, alleviate, reduce the severity of, and/or inhibit or one or more symptoms or manifestations of the disease. A compound or composition can be administered to a subject who has developed a disease, or is at increased risk of developing the disease relative to a member of the general population, optionally a member who is matched with the subject in terms of age, sex, and/or other demographic variable(s).

A "variant" of a particular polypeptide or polynucleotide has one or more alterations (e.g., additions, substitutions, and/or deletions, which may be referred to collectively as "mutations") with respect to the polypeptide or nucleic acid, which may be referred to as the "original polypeptide" or "original polynucleotide", respectively. Thus a variant can be shorter or longer than the polypeptide or polynucleotide of which it is a variant. The terms "variant" encompasses "fragments". A "fragment" is a continuous portion of a polypeptide that is shorter than the original polypeptide. In certain embodiments of the invention a variant polypeptide has significant sequence identity to the original polypeptide over a continuous portion of the variant that comprises at least 50%, preferably at least 60%, at least 70%, at least 80%, at least 90%, at least 95%, or more, of the length of the variant or the length of the polypeptide, (whichever is shorter). In certain embodiments of the invention a variant polypeptide has substantial sequence identity to the original polypeptide over a continuous portion of the variant that comprises at least 50%, preferably at least 60%, at least 70%, at least 80%, at least 90%, at least 95%, or more, of the length of the variant or the length of the polypeptide, (whichever is shorter). In a non-limiting embodiment a variant has at least 80% identity to the original sequence over a continuous portion of the variant that comprises between 90% and 100% of the variant, e.g., over 100% of the length of the variant or the length of the polypeptide, (whichever is shorter). In another non-limiting embodiment a variant has at least 80% identity to the original sequence over a continuous portion of the variant that comprises between 90% and 100% of the variant, e.g., over 100% of the length of the variant or the length of the polypeptide, (whichever is shorter). In specific embodiments the sequence of a variant polypeptide has N amino acid differences with respect to an original sequence, wherein N is any integer between 1 and 10. In other specific embodiments the sequence of a variant polypeptide has N amino acid differences with respect to an original sequence, wherein N is any integer between 1 and 20. An amino acid "difference" refers to a substitution, insertion, or deletion of an amino acid.

In certain embodiments of the invention a fragment or variant possesses sufficient structural similarity to the original polypeptide so that when its 3-dimensional structure (either actual or predicted structure) is superimposed on the structure of the original polypeptide, the volume of overlap is at least 70%, preferably at least 80%, more preferably at least 90% of the total volume of the structure of the original polypeptide. A partial or complete 3-dimensional structure of the fragment or variant may be determined by crystallizing the protein, which can be done using standard methods. Alternately, an NMR solution structure can be generated, also using standard methods. A modeling program such as MODELER (Sali, A. and Blundell, T L, *J. Mol. Biol.*, 234, 779-815, 1993), or any other modeling program, can be used to generate a predicted structure. If a structure or predicted structure of a related polypeptide is available, the model can be based on that structure. The PROSPECT-PSPP suite of programs can be used (Guo, J T, et al., *Nucleic Acids Res.* 32(Web Server issue):W522-5, Jul. 1, 2004).

In many embodiments one, more than one, or all biological functions or activities of a variant or fragment is substantially similar to that of the corresponding biological function or activity of the original molecule. In certain embodiments the activity of a variant or fragment may be at least 20%, at least 50%, at least 60%, at least 70%, at least 80%, or at least 90% of the activity of the original molecule, up to approximately 100%, approximately 125%, or approximately 150% of the activity of the original molecule. In certain embodiments an activity of a variant or fragment is such that the amount or concentration of the variant needed to produce an effect is within 0.5 to 5-fold of the amount or concentration of the original molecule needed to produce that effect. The invention contemplates use of variants of any of the complement inhibiting polypeptides disclosed herein, wherein the variant inhibits complement sufficiently to be useful in a method described herein. In some embodiments, a variant lacks or has a substantially reduction in a property that may be undesired such as immunogenicity.

As used herein, "alkyl" refers to a saturated straight, branched, or cyclic hydrocarbon having from about 1 to about 22 carbon atoms (and all combinations and subcombinations of ranges and specific numbers of carbon atoms therein), with from about 1 to about 12, or about 1 to about 7 carbon atoms being preferred in certain embodiments of the invention. Alkyl groups include, but are not limited to, methyl, ethyl, n-propyl, isopropyl, n-butyl, isobutyl, t-butyl, n-pentyl, cyclopentyl, isopentyl, neopentyl, n-hexyl, isohexyl, cyclohexyl, cyclooctyl, adamantyl, 3-methylpentyl, 2,2-dimethylbutyl, and 2,3-dimethylbutyl.

As used herein, "halo" refers to F, Cl, Br or I.

As used herein, "alkanoyl" refers to an optionally substituted straight or branched aliphatic acyclic residue having about 1 to 10 carbon atoms (and all combinations and subcombinations of ranges and specific number of carbon atoms) therein, e.g., from about 1 to 7 carbon atoms which, as will be appreciated, is attached to a terminal C=O group with a single bond (and may also be referred to as an "acyl group"). Alkanoyl groups include, but are not limited to, formyl, acetyl, propionyl, butyryl, isobutyryl, pentanoyl, isopentanoyl, 2-methyl-butyryl, 2,2-dimethoxypropionyl, hexanoyl, heptanoyl, octanoyl, and the like, and for purposes of the present invention a formyl group is considered an alkanoyl group. "Lower alkanoyl" refers to an optionally substituted straight or branched aliphatic acyclic residue having about 1 to about 5 carbon atoms (and all combinations and subcombinations of ranges and specific number of carbon atoms). Such groups include, but are not limited to, formyl, acetyl, propionyl, butyryl, isobutyryl, pentanoyl, isopentanoyl, etc.

As used herein, "aryl" refers to an optionally substituted, mono- or bicyclic aromatic ring system having from about 5 to about 14 carbon atoms (and all combinations and subcombinations of ranges and specific numbers of carbon atoms therein), with from about 6 to about 10 carbons being preferred. Non-limiting examples include, for example, phenyl and naphthyl.

As used herein, "aralkyl" refers to alkyl radicals bearing an aryl substituent and having from about 6 to about 22 carbon atoms (and all combinations and subcombinations of ranges and specific numbers of carbon atoms therein), with from about 6 to about 12 carbon atoms being preferred in certain embodiments. Aralkyl groups can be optionally substituted. Non-limiting examples include, for example, benzyl, naphthylmethyl, diphenylmethyl, triphenylmethyl, phenylethyl, and diphenylethyl.

As used herein, the terms "alkoxy" and "alkoxyl" refer to an optionally substituted alkyl-O— group wherein alkyl is as previously defined. Exemplary alkoxy and alkoxyl groups include methoxy, ethoxy, n-propoxy, i-propoxy, n-butoxy, and heptoxy.

As used herein, "carboxy" refers to a —C(=O)OH group.

As used herein, "alkoxycarbonyl" refers to a —C(=O)O-alkyl group, where alkyl is as previously defined.

As used herein, "aroyl" refers to a —C(=O)-aryl group, wherein aryl is as previously defined. Exemplary aroyl groups include benzoyl and naphthoyl.

The term "cyclic ring system" refers to an aromatic or non-aromatic, partially unsaturated or fully saturated, 3- to 10-membered ring system, which includes single rings of 3 to 8 atoms in size and bi- and tri-cyclic ring systems which may include aromatic 5- or 6-membered aryl or aromatic heterocyclic groups fused to a non-aromatic ring. These heterocyclic rings include those having from 1 to 3 heteroatoms independently selected from the group consisting of oxygen, sulfur, and nitrogen. In certain embodiments, the term heterocyclic refers to a non-aromatic 5-, 6-, or 7-membered ring or a polycyclic group wherein at least one ring atom is a heteroatom selected from the group consisting of O, S, and N, including, but not limited to, a bi- or tri-cyclic group, comprising fused six-membered rings having between one and three heteroatoms independently selected from the group consisting of the oxygen, sulfur, and nitrogen. In some embodiments, "cyclic ring system" refers to a cycloalkyl group which, as used herein, refers to groups having 3 to 10, e.g., 4 to 7 carbon atoms. Cycloalkyls include, but are not limited to cyclopropyl, cyclobutyl, cyclopentyl, cyclohexyl, cycloheptyl and the like, which, is optionally substituted. In some embodiments, "cyclic ring system" refers to a cycloalkenyl or cycloalkynyl moiety, which is optionally substituted.

Typically, substituted chemical moieties include one or more substituents that replace hydrogen. Exemplary substituents include, for example, halo, alkyl, cycloalkyl, aralkyl, aryl, sulfhydryl, hydroxyl (—OH), alkoxyl, cyano (—CN), carboxyl (—COOH), —C(=O)O-alkyl, aminocarbonyl (—C(=O)NH$_2$), —N-substituted aminocarbonyl (—C(=O)NHR"), CF$_3$, CF$_2$CF$_3$, and the like. In relation to the aforementioned substituents, each moiety R" can be, independently, any of H, alkyl, cycloalkyl, aryl, or aralkyl, for example.

As used herein, "L-amino acid" refers to any of the naturally occurring levorotatory alpha-amino acids normally present in proteins or the alkyl esters of those alpha-amino acids. The term "D-amino acid" refers to dextrorotatory alpha-amino acids. Unless specified otherwise, all amino acids referred to herein are L-amino acids.

As used herein, an "aromatic amino acid" is an amino acid that comprises at least one aromatic ring, e.g., it comprises an aryl group.

As used herein, an "aromatic amino acid analog" is an amino acid analog that comprises at least one aromatic ring, e.g., it comprises an aryl group.

II. Methods of Treating Disorders Using Complement Inhibitors

The present invention provides, among other things, methods of treating chronic complement-mediated disorders using complement inhibitors. For example, the invention provides methods of treating chronic respiratory system disorders using complement inhibitors. In some aspects, the inventive methods are based at least in part on the recognition that complement inhibitors have a prolonged duration of action in treating a variety of disorders, e.g., chronic respiratory disorders, as compared, for example, with their plasma half-life and/or their duration of action for inhibiting plasma complement activation capacity. In some aspects, the invention provides methods of treating a chronic complement-mediated disorder by administering multiple doses of a complement inhibitor, wherein the complement inhibitor is administered according to a dosing schedule that utilizes the prolonged effect of complement inhibition.

As used herein, a "chronic disorder" is a disorder that persists for at least 3 months and/or is accepted in the art as being a chronic disorder. In many embodiments, a chronic disorder persists for at least 6 months, e.g., at least 1 year, or more, e.g., indefinitely. One of ordinary skill in the art will appreciate that at least some manifestations of various chronic disorders may be intermittent and/or may wax and wane in severity over time. A chronic disorder may be progressive, e.g., having a tendency to become more severe or affect larger areas over time. A number of chronic complement-mediated disorders are discussed herein. Various embodiments of the invention pertaining to chronic, complement-mediated respiratory disorders, in particular asthma and COPD, are discussed in most detail herein, but it should be understood that the various aspects of the invention encompass embodiments pertaining to any chronic complement-mediated disorder including, but not limited to, the specific disorders disclosed herein. Accordingly, where an embodiment herein refers to a chronic respiratory disorder, the invention provides analogous embodiments pertaining to other complement-mediated disorders, e.g., chronic disorders in which complement activation (e.g., excessive or inappropriate complement activation) is involved, e.g., as a contributing and/or at least partially causative factor. For convenience, disorders are sometimes grouped by reference to an organ or system that is often particularly affected in subjects suffering from the disorder. It will be appreciated that a number of disorders can affect multiple organs or systems, and the classification herein is in no way limiting. Furthermore, a number of manifestations (e.g., symptoms) may occur in subjects suffering from any of a number of different disorders. In some aspects, the invention provides methods of treating a subject in need of treatment for such manifestation(s), e.g., methods for alleviating such manifestation(s), the methods comprising administering a complement inhibitor to the subject according to an inventive dosing schedule (e.g., a dosing schedule that employs an inventive dosing interval). In some embodiments, a subject suffers from multiple complement-mediated disorders. Non-limiting information regarding disorders of interest herein may be found, e.g., in standard textbooks of internal medicine such as Cecil Textbook of Medicine (e.g., 23rd edition), Harrison's Principles of Internal Medicine (e.g., 17th edition), and/or standard textbooks focusing on particular areas of medicine, particular body systems or organs, and/or particular disorders.

In some embodiments, a chronic complement-mediated disorder is a Th2-associated disorder. As used herein, a Th2-associated disorder is a disorder characterized by an excessive number and/or excessive or inappropriate activity of CD4+ helper T cells of the Th2 subtype ("Th2 cells") in the body or a portion thereof, e.g., in at least one tissue, organ, or structure. For example, there may be a predominance of Th2 cells relative to CD4+ helper T cells of the Th1 subtype ("Th1 cells") e.g., in at least one tissue, organ, or structure affected by a disorder. As known in the art, Th2 cells typically secrete characteristic cytokines such as interleukin-4 (IL-4), interleukin-5 (IL-5), and interleukin-13 (IL-13), while Th1 cells typically secrete interferon-γ (IFN-γ) and tumor necrosis factor β (TNF β). In some embodiments, a Th2-associated disorder is characterized by excessive production and/or amount of IL-4, IL-5, and/or IL-13, e.g., relative to IFN-γ and/or TNF β e.g., in at least some at least one tissue, organ, or structure.

In some embodiments, a chronic complement-mediated disorder is a Th17-associated disorder. As used herein, a Th17-associated disorder is a disorder characterized by an excessive number and/or excessive or inappropriate activity of CD4+ helper T cells of the Th17 subtype ("Th17 cells") in the body or a portion thereof, e.g., in at least one tissue, organ, or structure. For example, there may be a predominance of Th17 cells relative to Th1 and/or Th2 cells, e.g., in at least one tissue, organ, or structure affected by a disorder. In some embodiments a predominance of Th17 cells is a relative predominance, e.g., the ratio of Th17 cells to Th1 cells and/or the ratio of Th17 cells to Th2 cells, is increased relative to normal values. In some embodiments the ratio of Th17 cells to T regulatory cells ($CD4^+CD25^+$ regulatory T cells, also termed "Treg cells"), is increased relative to normal values. Formation of Th17 cells and/or activation of Th 17 cells is promoted by various cytokines, e.g., interleukin 6 (IL-6), interleukin 21 (IL-21), interleukin 23 (IL-23), and/or interleukin 1β (IL-1β). Formation of Th17 cells encompasses differentiation of precursor T cells, e.g., naïve CD4+ T cells, towards a Th17 phenotype and their maturation into functional Th17 cells. In some embodiments, formation of Th17 cells encompasses any aspect of development, proliferation (expansion), survival, and/or maturation of Th17 cells. In some embodiments, a Th17-associated disorder is characterized by excessive production and/or amount of IL-6, IL-21, IL-23, and/or IL-1β. Th17 cells typically secrete characteristic cytokines such as interleukin-17A (IL-17A), interleukin-17F (IL-17F), interleukin-21 (IL-21), and interleukin-22 (IL-22). In some embodiments, a Th17-associated disorder is characterized by excessive production and/or amount of a Th17 effector cytokine, e.g., IL-17A, IL-17F, IL-21, and/or IL-22. In some embodiments excessive production or amount of a cytokine is detectable in the blood. In some embodiments excessive production or amount of a cytokine is detectable locally, e.g., in at least one tissue, organ or structure. In some embodiments a Th17-associated disorder is associated with a decreased number of Tregs and/or decreased amount of a Treg-associated cytokine. In some embodiments a Th17 disorder is any chronic inflammatory disease, which term encompasses a range of ailments characterized by self-perpetuating immune insults to a variety of tissues and that seem to be dissociated from the initial insult that caused the ailment (which may be unknown). In some embodiments a Th17-associated disorder is any autoimmune disease. Many if not most "chronic inflammatory diseases" may in fact be autoimmune diseases. Examples of Th17-associated disorders include inflammatory skin diseases such as psoriasis and atopic dermatitis; systemic scleroderma and sclerosis; inflammatory bowel disease (IBD) (such as Crohn's disease and ulcerative colitis); Behcet's Disease; dermatomyositis; polymyositis; multiple sclerosis (MS); dermatitis; meningitis; encephalitis; uveitis; osteoarthritis; lupus nephritis; rheumatoid arthritis (RA), Sjorgen's syndrome, multiple sclerosis, vasculitis; central nervous system (CNS) inflammatory disorders, chronic hepatitis; chronic pancreatitis, glomerulonephritis; sarcoidosis; thyroiditis, pathologic immune responses to tissue/organ transplantation (e.g., transplant rejection); COPD, asthma, bronchiolitis, hypersensitivity pneumonitis, idiopathic pulmonary fibrosis (IPF), periodontitis, and gingivitis. In some embodiments a Th17 disease is a classically known auto-immmune disease such as Type I diabetes or psoriasis. In some embodiments a Th17-associated disorder is age-related macular degeneration.

In some aspects, the present disclosure provides the insight that complement activation and Th17 cells participate in a cycle that involves dendritic cells and antibodies and that contributes to maintenance of a pathologic immunologic microenvironment underlying a range of disorders. Without wishing to be bound by any theory, the pathologic immunologic microenvironment, once established, is self-sustaining and contributes to cell and tissue injury. Dendritic cells (DCs) are a type of white blood cell that occur in most tissues of the body, particularly those exposed to the external environment, such as skin and mucosal surfaces, and in the blood (where they may be found in an immature state). Immature DCs sample the surrounding environment for pathogens through, e.g., pattern recognition receptors such as toll-like receptors (TLRs). In response to various stimuli (e.g., pathogen-associated substances or other danger signals, inflammatory cytokines, and/or antigen-activated T cells), DCs mature and migrate to lymphoid tissues, where they act as antigen-presenting cells and activate other immune system cells, such as T cells and B cells, by presenting them with antigen fragments together with non-antigen specific costimulatory molecules. DC stimulation promotes Th cell proliferation, activation, and differentiation into effector Th cells. Effector Th cells "help" cytotoxic T cells, B cells, and macrophages by, e.g., secreting cytokines that have various stimulatory effects. Th help can, for example, enhance proliferation and activation of cytotoxic T cells, stimulate B cell proliferation and maturation and antibody production. Of particular importance in accordance with certain aspects of the present disclosure, mature DCs are capable of causing CD4+ helper T cells to differentiate into Th17 cells, which in turn stimulate maturation and activation of B cells, resulting in production of antibodies.

The antibody response is generally polyclonal, with most antibodies being of low affinity. However, certain of these antibodies may be cross-reactive with self proteins, such as self proteins that have been enzymatically or non-enzymatically chemically modified in the body post-translationally in any of a variety of ways. Such self proteins may, for example, be exposed at the surface of cells, present in the interstitial space, and/or circulating in the blood. Modifications of self proteins may include, e.g., acylation and/or glycation (non-enzymatic formation of a covalent bond between a protein or lipid and a sugar). For example, proteins can be oxidized in numerous ways, which can be classified into at least three categories. A first mechanism involves oxidative cleavages in either the protein backbone or amino acid side chains, e.g., side chains of Pro, Arg, Lys, Thr, Glu or Asp residues, which may occur by direct oxidation with reactive oxygen species (ROS). Certain ROS are produced during normal cellular metabolism, and various mechanisms exist to defend against the potentially damaging effects of such compounds. Examples of ROS include, e.g., superoxide anion, hydrogen peroxide, and peroxynitrite. Excessive levels of reactive oxygen species (ROS) can result from the environment and/or defects in cellular processes or antioxidant mechanisms, resulting in high levels of oxidative stress. A second mechanism of protein oxidation is by addition of lipid oxidation products such as 4-hydroxy-2-noneal, 2-propenal or malondialdehyde to proteins. In a third mechanism, carbonyl groups are generated in proteins by oxidation of advanced glycation end (AGE) products. AGEs can form as a result of a chain of chemical reactions after an initial glycation reaction. Examples of AGE-modified sites are carboxymethyllysine (CML) and carboxyethyllysine (CEL). ROS can degrade polyunsaturated lipids, forming malondialdehyde, a reactive aldehyde that forms covalent protein adducts referred to as advanced lipoxidation end-products (ALEs). Carboxyethylpyrrole (CEP) protein modifications are generated from oxidation of docosahexaenoate-containing lipids.

Modified self proteins (e.g., malondialdehyde-modified proteins, CEP-modified proteins) may contain epitopes recognized as non-self by the immune system, e.g., by antibodies. Binding of antibodies to self proteins leads to complement activation, e.g., via the classical pathway. Once initiated, classical pathway-mediated complement activation is amplified by the alternative pathway. In accordance with certain aspects of the present disclosure, activated complement polarizes DCs to sustain the Th17 phenotype. For example, DCs may be polarized towards secretion of cytokines such as IL-23 that promote Th17 formation and/or activation. Complement cleavage products such as the anaphylotoxins (e.g., C3a, C4a, and/or C5a) and/or products of C3 cleavage and degradation such as iC3b or C3d may bind to DC cell surface receptors and contribute towards polarizing DCs to sustain the Th17 phenotype. An example of how complement can polarize DCs is the activation of dendritic cells by aluminum oxide. Aluminum oxide is widely used as an adjuvant to vaccines. Aluminum oxide activates complement and this stimulates DCs into promoting and sustaining Th2 and Th17 phenotypes. Complement can polarize other types of antigen-presenting cells as well. Monocytes and macrophages can act as antigen-presenting cells and can similarly be polarized by complement activation. In some aspects, the cycle may be summarized as follows: (1) Mature dendritic cells in an environment of high complement activation stimulate Th17 cell phenotypic differentiation; (2) Th17 T cells stimulate polyclonal B-cell expansion, leading to the production of polyclonal, self-reactive antibodies against, e.g., modified self proteins, such as carbonyl-modified self-proteins; (3) Carbonyl-modified self-proteins can be generated as a result of oxidative stress. This can arise, for example, from pollutants, cigarette smoke, or allergens; (4) Self-reactive antibodies against carbonyl-modified self-proteins help promote or sustain an environment of high complement activation; (5) High complement activation drives antigen-presenting cells into sustaining a Th17 micro-environment.

The effector pathways that lead this cycle to inflict tissue damage can be varied, but, without wishing to be bound by any theory, it is believed that a principal pathway is via macrophages. In some aspects, IL-17 secreted by Th17 cells, itself or in combination with one or more other cytokines such as interferon gamma (IFN-γ) contributes to macrophage activation and/or polarization towards an M1 phenotype. M1-polarized macrophages are immune effector cells that are characterized by expression of high levels of proinflammatory cytokines, high production of reactive nitrogen and oxygen intermediates, and may exhibit strong cytotoxic activity against targets such as microbes and tumor cells. Macrophages, e.g., M1-polarized macrophages, and the products they produce can lead to tissue damage and are important mediators of immunopathology. Modification of self proteins and other cellular components by reactive nitrogen and oxygen species can render them dysfunctional, thereby interfering with normal cellular processes. Dysfunctional modified proteins can accumulate to toxic levels, which can lead to cell death. Macrophages are also capable of direct killing of altered self cells, e.g., self cells that have oxidatively modified proteins or lipids exposed at their cell surface. Reactive nitrogen and oxygen species produced by macrophages can amplify oxidative stress, resulting in further modification of self proteins by mechanisms such as those described above, which produces new targets for self-reactive antibodies and macrophages. The antibodies further activate complement, which maintains DC polarization towards a Th17-promoting phenotype. Thus, a vicious cycle is perpetuated in which Th17 cells activate B cells, resulting in polyclonal antibody production and consequent complement activation, which in turn promotes DC polarization towards a Th17-promoting phenotype that drives continued stimulation of B cells and antibody production. For purposes hereof, this cycle, also summarized above, may be referred to as the "dendritic cell-Th 17 cell-B cell-antibody-complement-dendritic cell" cycle, abbreviated as DC-Th17-B-Ab-C-DC cycle. Polarization of macrophages to an M1 phenotype and production of ROS that can directly damage cellular components may occur as "outputs" of this feedback loop. The pathologic consequences that result from DC-Th17-B-Ab-C-DC cycle and its outputs may vary in different tissues or organs. For example, in the respiratory system, they may at least in part underlie chronic respiratory diseases such as asthma and COPD. In the eye, they may at least in part underlie chronic disorders such as age-related macular degeneration. In the skin, they may at least in part underlie psoriasis. In the pancreas, they may at least in part underlie Type I diabetes.

In some embodiments, a chronic complement-mediated disorder is an IgE-associated disorder. As used herein, an "IgE-associated disorder" is a disorder characterized by excessive and/or inappropriate production and/or amount of IgE, excessive or inappropriate activity of IgE producing cells (e.g., IgE producing B cells or plasma cells), and/or excessive and/or inappropriate activity of IgE responsive cells such as eosinophils or mast cells. In some embodiments, an IgE-associated disorder is characterized by elevated levels of total IgE and/or in some embodiments, allergen-specific IgE, in the plasma of a subject and/or locally.

In some embodiments, a chronic complement-mediated disorder is characterized by complement-mediated hemolysis, e.g., complement-mediated hemolysis attributable to deficiency or mutation of one or more endogenous complement regulatory proteins. In some embodiments, a chronic complement-mediated disorder is not characterized by hemolysis attributable, e.g., to deficiency or mutation of one or more endogenous complement regulatory proteins.

In some embodiments, a chronic complement-mediated disorder is characterized by the presence of autoantibodies and/or immune complexes in the body, which may activate complement via, e.g., the classical pathway. Autoantibodies may, for example, bind to self antigens, e.g., on cells or tissues in the body. In some embodiments, autoantibodies bind to antigens in blood vessels, skin, nerves, muscle, connective tissue, heart, kidney, thyroid, etc. In some embodiments, a chronic complement-mediated disorder is not characterized by autoantibodies and/or immune complexes.

In some embodiments, the invention provides methods for treating a chronic complement-mediated disorder by administering multiple doses of a complement inhibitor, wherein the complement inhibitor is administered according to a dosing schedule that utilizes the prolonged effect of complement inhibition. "Dosing schedule" refers to the timing of administration of a compound (or composition containing a compound). In some embodiments, an inventive method utilizes an increased dosing interval as compared, for example, with a dosing interval that aims to maintain a significant level of complement inhibitor and/or a significant level of complement inhibition in the body substantially throughout a treatment period. In some embodiments, an inventive method utilizes an increased dosing interval as compared, for example, with a dosing interval that aims to expose tissue(s) or organ(s) affected by a complement-mediated disorder to a significant level of complement inhibitor and/or maintain a significant level of complement inhibition in such tissue(s) or organ(s) (and/or in body fluids contacting or within such tissue(s) or organ(s)) substantially throughout a treatment period. As used herein, "dosing interval" refers to the time interval between administration of successive doses of a compound (or composition comprising a compound).

In some embodiments, a chronic complement-mediated disorder is a respiratory disorder. In some embodiments, a chronic respiratory disorder is asthma or chronic obstructive pulmonary disease (COPD). In some embodiments, a chronic respiratory disorder is pulmonary fibrosis (e.g., idiopathic pulmonary fibrosis), radiation-induced lung injury, allergic bronchopulmonary aspergillosis, hypersensitivity pneumonitis (also known as allergic alveolitis), eosinophilic pneumonia, interstitial pneumonia, sarcoid, Wegener's granulomatosis, or bronchiolitis obliterans.

In some embodiments, a chronic complement-mediated disorder is allergic rhinitis, rhinosinusitis, or nasal polyposis. In some embodiments, the invention provides a method of treating a subject in need of treatment for allergic rhinitis, rhinosinusitis, or nasal polyposis, the method comprising administering a complement inhibitor according to a dosing schedule described herein to a subject in need of treatment for the disorder.

In some embodiments, a chronic complement-mediated disorder is a disorder that affects the musculoskeletal system. Examples of such disorders include inflammatory joint conditions (e.g., arthritis such as rheumatoid arthritis or psoriatic arthritis, juvenile chronic arthritis, spondyloarthropathies Reiter's syndrome, gout). In some embodiments, a musculoskeletal system disorder results in symptoms such as pain, stiffness and/or limitation of motion of the affected body part(s). Inflammatory myopathies include dermatomyositis, polymyositis, and various others are disorders of chronic muscle inflammation of unknown etiology that result in muscle weakness. In some embodiments, a a chronic complement-mediated disorder is myasthenia gravis. In some embodiments, the invention provides a method of treating any of the foregoing disorders affecting the musculoskeletal system, the method comprising administering a complement inhibitor according to a dosing schedule described herein to a subject in need of treatment for the disorder.

In some embodiments, a chronic complement-mediated disorder is a disorder that affects the integumentary system. Examples of such disorders include, e.g., atopic dermatitis, psoriasis, pemphigus, systemic lupus erythematosus, dermatomyositis, scleroderma, sclerodermatomyositis, Sjögren syndrome, and chronic urticaria. In some aspects, the invention provides a method of treating any of the foregoing disorders affecting the integumentary system, the method comprising administering a complement inhibitor according to a dosing schedule described herein to a subject in need of treatment for the disorder.

In some embodiments, a chronic complement-mediated disorder affects the nervous system, e.g., the central nervous system (CNS) and/or peripheral nervous system (PNS). Examples of such disorders include, e.g., multiple sclerosis, other chronic demyelinating diseases, amyotrophic lateral sclerosis, chronic pain, stroke, allergic neuritis, Huntington's disease, Alzheimer's disease, and Parkinson's disease. In some embodiments, the invention provides a method of treating any of the foregoing disorders affecting the nervous system, the method comprising administering a complement inhibitor according to a dosing schedule described herein to a subject in need of treatment for the disorder.

In some embodiments, a chronic complement-mediated disorder affects the circulatory system. For example, in some embodiments the disorder is a vasculitis or other disorder associated with vessel inflammation, e.g., blood vessel and/or lymph vessel inflammation. In some embodiments, a vasculitis is polyarteritis nodosa, Wegener's granulomatosis, giant cell arteritis, Churg-Strauss syndrome, microscopic polyangiitis, Henoch-Schonlein purpura, Takayasu's arteritis, Kawasaki disease, or Behcet's disease. In some embodiments, a subject, e.g., a subject in need of treatment for vasculitis, is positive for antineutrophil cytoplasmic antibody (ANCA).

In some embodiments, a chronic complement-mediated disorder affects the gastrointestinal system. For example, the disorder may be inflammatory bowel disease, e.g., Crohn's disease or ulcerative colitis. In some embodiments, the invention provides a method of treating a chronic complement-mediated disorder that affects the gastrointestinal system, the method comprising administering a complement inhibitor according to a dosing schedule described herein to a subject in need of treatment for the disorder.

In some embodiments, a chronic complement-mediated disorder is a thyroiditis (e.g., Hashimoto's thyroiditis, Graves' disease, post-partum thyroiditis), myocarditis, hepatitis (e.g., hepatitis C), pancreatitis, glomerulonephritis (e.g., membranoproliferative glomerulonephritis or membranous glomerulonephritis), or panniculitis.

In some embodiments, the invention provides methods of treating a subject suffering from chronic pain, the methods comprising administering a complement inhibitor to a subject according to a dosing schedule of the present invention. In some embodiments, a subject suffers from neuropathic pain. Neuropathic pain has been defined as pain initiated or caused by a primary lesion or dysfunction in the nervous system, in particular, pain arising as a direct consequence of a lesion or disease affecting the somatosensory system. For example, neuropathic pain may arise from lesions that involve the somatosensory pathways with damage to small fibres in peripheral nerves and/or to the spino-thalamocortical system in the CNS. In some embodiments, neuropathic pain arises from autoimmune disease (e.g., multiple sclerosis), metabolic disease (e.g., diabetes), infection (e.g., viral disease such as shingles or HIV), vascular disease (e.g., stroke), trauma (e.g., injury, surgery), or cancer. For example, neuropathic pain can be pain that persists after healing of an injury or after cessation of a stimulus of peripheral nerve endings or pain that arises due to damage to nerves. Exemplary conditions of or associated with neuropathic pain include painful diabetic neuropathy, post-herpetic neuralgia (e.g., pain persisting or recurring at the site of acute herpes zoster 3 or more months after the acute episode), trigeminal neuralgia, cancer related neuropathic pain, chemotherapy-associated neuropathic pain, HIV-related neuropathic pain (e.g., from HIV neuropathy), central/post-stroke neuropathic pain, neuropathy associated with back pain, e.g., low back pain (e.g., from radiculopathy such as spinal root compression, e.g., lumbar root compression, which compression may arise due to disc herniation), spinal stenosis, peripheral nerve injury pain, phantom limb pain, polyneuropathy, spinal cord injury related pain, myelopathy, and multiple sclerosis. In certain embodiments of the invention a complement inhibitor is administered according to an inventive dosing schedule to treat neuropathic pain in a subject with one or more of the afore-mentioned conditions.

In some embodiments, a chronic complement-mediated disorder is a chronic eye disorder. In some embodiments, the chronic eye disorder is characterized by macular degeneration, choroidal neovascularization (CNV), retinal neovascularization (RNV), ocular inflammation, or any combination of the foregoing. Macular degeneration, CNV, RNV, and/or ocular inflammation may be a defining and/or diagnostic feature of the disorder. Exemplary disorders that are characterized by one or more of these features include, but are not limited to, macular degeneration related conditions, diabetic retinopathy, retinopathy of prematurity, proliferative vitreoretinopathy, uveitis, keratitis, conjunctivitis, and scleritis. Macular degeneration related conditions include, e.g., age-related macular degeneration (AMD). In some embodiments, a subject is in need of treatment for wet AMD. In some embodiments, a subject is in need of treatment for dry AMD. In some embodiments, a subject is in need of treatment for geographic atrophy (GA). In some embodiments, a subject is in need of treatment for ocular inflammation. Ocular inflammation can affect a large number of eye structures such as the conjunctiva (conjunctivitis), cornea (keratitis), episclera, sclera (scleritis), uveal tract, retina, vasculature, and/or optic nerve. Evidence of ocular inflammation can include the presence of inflammation-associated cells such as white blood cells (e.g., neutrophils, macrophages) in the eye, the presence of endogenous inflammatory mediator(s), one or more symptoms such as eye pain, redness, light sensitivity, blurred vision and floaters, etc. Uveitis is a general term that refers to inflammation in the uvea of the eye, e.g., in any of the structures of the uvea, including the iris, ciliary body or choroid. Specific types of uveitis include iritis, iridocyclitis, cyclitis, pars planitis and choroiditis. In some embodiments, a subject is in need of treatment for geographic atrophy (GA). In some embodiments, the chronic eye disorder is an eye disorder characterized by optic nerve damage (e.g., optic nerve degeneration), such as glaucoma.

In some embodiments, a chronic complement-mediated disorder is chronic rejection of a transplanted organ, tissue, cells or populations of cells (collectively "grafts"). Examples of grafts include, e.g., solid organs such as kidney, liver, lung, pancreas, heart; tissues such as cartilage, tendons, cornea, skin, heart valves, and blood vessels; pancreatic islets or islet cells. Transplant rejection is one of the major risks associated with transplants between genetically different individuals of the same species (allografts) or between individuals of different species (xenografts) and can lead to graft failure and a need to remove the graft from the recipient. As used herein, "chronic rejection" refers to rejection occurring at least 6 months post-transplant, e.g., between 6 months and 1, 2, 3, 4, 5 years, or more post-transplant, often after months to years of good graft function. For purposes hereof, chronic rejection can include chronic graft vasculopathy, a term used to refer to fibrosis of the internal blood vessels of the transplanted tissue. In some embodiments, the invention provides a method of treating a subject in need of treatment to inhibit chronic rejection of a graft, the method comprising administering a complement inhibitor to the subject according to a dosing schedule described herein. In some embodiments, the invention provides a method of treating a subject who has undergone a transplant or is scheduled to undergo a transplant within the subsequent 12 weeks. In some embodiments, treatment is initiated no later than 1, 2, 3, 6, or 12 months following the transplant.

In some aspects, the invention provides a method of treating a subject in need of treatment for a chronic complement-mediated disorder, e.g., a chronic respiratory disorder, the method comprising administering multiple doses of a complement inhibitor to the subject according to a dosing schedule in which successive doses are administered on average (i) at least 2 weeks after the plasma concentration of the complement inhibitor decreases to no more than 20% of the maximum plasma concentration that was reached after the previous dose; (ii) at least 2 weeks after plasma complement activation capacity has returned to at least 50% of baseline or to within the normal range after the previous dose; (iii) at intervals equal to at least 2 times the terminal plasma half-life of the complement inhibitor; or (iv) at intervals at least 3 weeks apart. In some embodiments, an inventive method comprises administration of a complement inhibitor with an average dosing interval of at least 3 weeks, e.g., between 3 and 15 weeks, e.g., between 3 and 12 weeks, e.g., between 3 and 10 weeks, e.g, between 4 and 8 weeks, e.g., about every 4, 5, 6, 7, or 8 weeks. In some embodiments, at least 2 of the foregoing conditions are met. In some embodiments, at least 3 of the foregoing conditions are met. In some embodiments, all of the foregoing conditions are met.

In certain embodiments of the invention, a complement inhibitor is administered according to a dosing schedule that is selected based at least in part on local complement activation capacity and/or local concentration of the complement inhibitor. For purposes of the present invention, "local complement activation capacity" refers to complement activation capacity in a tissue or organ affected by a complement-mediated disorder, which may be determined, for example, using a relevant sample obtained from such tissue or organ. For purposes of the present invention, "local concentration", e.g., local concentration of a complement inhibitor or a Th17 biomarker such as a Th17-associated cytokine, refers to concentration in a tissue or organ (e.g., a tissue or organ affected by a complement-mediated disorder) which may be determined, for example, using a relevant sample obtained from such tissue or organ. In some embodiments, a sample comprises a body fluid obtained from a tissue or organ (or portion thereof) affected by a complement-mediated disorder. In some embodiments, a fluid is BAL fluid, sputum (e.g., induced sputum), pleural fluid, synovial fluid, vitreous or aqueous humor, or cerebrospinal fluid. The invention provides variations of any of the methods described herein, in which local complement activation capacity is used instead of, or in addition to, plasma complement activation capacity. For example, in certain embodiments of the invention, a complement inhibitor is administered at least 2 weeks after local complement activation capacity has returned to at least 50% of baseline or to within the normal range following the previous dose. In some embodiments of the invention, a complement inhibitor is administered between 2 and 15 weeks after local complement activation capacity has returned to at least 50% of baseline or to within the normal range following the previous dose. In some embodiments, a complement inhibitor is administered according to a dosing schedule in which successive doses are administered on average (i) at least 2 weeks after the local concentration of the complement inhibitor decreases to no more than 20% of the maximum local concentration that was reached after the previous dose In some embodiments of any of the afore-mentioned methods, a complement inhibitor is administered locally.

In some embodiments, an inventive method comprises administration of a complement inhibitor with an average dosing interval of at least 3 weeks, e.g., between 3 and 15 weeks, e.g., between 3 and 12 weeks e.g., between 3 and 10 weeks, e.g, between 4 and 8 weeks, e.g., about every 4, 5, 6, 7, or 8 weeks. In some embodiments, an inventive method comprises administration of a complement inhibitor with an average dosing interval of between 4 and 6 weeks. In some embodiments, a dose sufficient to substantially inhibit plasma complement activation capacity is administered. In some embodiments, a dose sufficient to substantially inhibit local complement activation capacity in a tissue or organ affected by a complement-mediated disorder is administered. In some embodiments, complement activation capacity, e.g., plasma complement activation capacity or local complement activation capacity, is considered "substantially inhibited" if reduced to no more than twice background levels, e.g., to approximately background levels. Background levels (e.g., for any aspect or embodiment of the invention) may be levels determined using a variety of suitable approaches. For example, a control sample, e.g., a control plasma sample or other body fluid sample, in which complement has been inactivated, e.g., by heat inactivation, or that has been depleted of one or more complement components such as C3 can be used, and/or a control assay can be performed in which an essential assay component is omitted. In some embodiments, a dose sufficient to reduce and/or maintain plasma complement to within the normal range administered. In some embodiments, a dose sufficient to reduce and/or maintain local complement activation in a tissue or organ affected by a complement-mediated disorder to within the normal range is administered.

In some embodiments of an inventive method, element (i) comprises administering multiple doses of a complement inhibitor to the subject according to a dosing schedule in which successive doses are administered on average at least 2 weeks after the plasma concentration of the complement inhibitor decreases to no more than 10%, or in some embodiments no more than 5%, or in some embodiments no more than 1%, of the maximum plasma concentration that was reached after the previous dose. In some embodiments of an inventive method, element (i) comprises administering multiple doses of a complement inhibitor to the subject according to a dosing schedule in which successive doses are administered on average at least 3, 4, 5, 6, 7, 8, 9, 10, 11, 12, 13, 14, or 15 weeks after the plasma concentration of the complement inhibitor decreases to no more than 20% of the maximum plasma concentration that was reached after the previous dose or, in some embodiments at least 3, 4, 5, 6, 7, 8, 9, 10, 11, 12, 13, 14, or 15 weeks after the plasma concentration of the complement inhibitor decreases to no more than 10%, or in some embodiments no more than 5%, or in some embodiments no more than 1%, of the maximum plasma concentration that was reached after the previous dose.

In some embodiments, an inventive method comprises administering a complement inhibitor at intervals such that the subject's plasma complement activation capacity is at least 50% of baseline or within the normal range for on average at least 2 weeks between doses. In some embodiments, an inventive method comprises administering a complement inhibitor at intervals such that the subject's plasma complement activation capacity is at least 50% of baseline for on average at least 2 weeks between doses. "Baseline" in this context refers to the subject's typical complement activation capacity when not affected by administration of an agent or exposure to a stimulus that significantly affects the complement system; and not having experienced an exacerbation of asthma or COPD (or, in some aspects of the invention, another complement-mediated disorder, as applicable) within the preceding 6 weeks. In some embodiments, an inventive dosing regimen comprises administering a complement inhibitor at intervals such that the subject's plasma complement activation capacity is within the normal range for on average at least 2 weeks between doses. "Normal range" in this context typically refers to a range of within ±2 standard deviations from a mean value (e.g., an arithmetic mean value) in a population of subjects. One of ordinary skill in the art will appreciate that the specific values for a "normal range" may at least in part depend on the particular assay used to assess complement activation capacity and/or factors such as the specific reagents used. In some embodiments, a normal range may be determined using published data. In some embodiments, a normal range may be appropriately defined by a laboratory, testing center, ordinary skilled artisan, etc.

In some embodiments, the complement inhibitor is administered with a dosing interval such that the subject's complement activation capacity is at least 50% of baseline or within the normal range for on average at least 3 weeks, e.g., between 3 and 15 weeks, e.g., e.g., between 3 and 12 weeks, e.g., between 3 and 10 weeks, e.g, between 4 and 8 weeks, e.g., about 4, 5, 6, 7, or 8 weeks between doses. For purposes of the present invention, it will be assumed that plasma and serum complement activation capacity are not significantly different and can be used interchangeably absent evidence to the contrary. If a difference is determined to exist, the invention provides embodiments in which plasma complement activation capacity is used, embodiments in which the serum complement activation capacity is used, and embodiments in which an average value is used.

In some embodiments, an inventive method comprises administering a complement at intervals at least equal on average to twice (2×) the plasma half-life of the complement inhibitor when administered intravenously. In some embodiments, an inventive dosing regimen comprises administering a complement inhibitor at intervals at least equal on average to 3×, 4×, 5×, 6×, 7×, 8×, 9×, or 10× the plasma half-life of the complement inhibitor when administered intravenously. In some embodiments an inventive method comprises administering a complement inhibitor by a selected administration route, at intervals at least equal on average to twice (2×) the plasma half-life of the complement inhibitor when administered by the same route. In some embodiments, an inventive method comprises administering a complement inhibitor at intervals at least equal on average to 3×, 4×, 5×, 6×, 7×, 8×, 9×, or 10× the plasma half-life of the complement inhibitor when administered by the same route. In some embodiments, an administration route is the respiratory route. In some embodiments, a complement inhibitor has a mean plasma half-life of between 1 and 5 days. In some embodiments, a complement inhibitor has a mean plasma half-life of between 5 and 10 days. In some embodiments, a complement inhibitor has a mean plasma half-life of between 10 and 20 days. In some embodiments, a complement inhibitor has a mean plasma half-life of between 20 and 30 days.

It will be appreciated that a variety of approaches to determining pharmacokinetic (PK) parameters such as half-life can be used. An appropriate method can be selected by one of ordinary skill in the art. In general, half-life can be determined by a method comprising: administering one or more doses of the compound to subjects, obtaining blood samples from the subject at various times after administration, measuring the concentration of the compound in said samples, and calculating a half-life based at least in part on said measurements. For example, in some embodiments, samples may be obtained at times 0 (pre-dose), 5 min, 15 min, 30 min, 1 hr, 4 hr, 8 hr, 24 hr (1 day), 48 hr (2 days), 96 hr (4 days), 192 hr (8 days), 14 days, 21 days, 28 days post-dose. It will be appreciated that these time points are exemplary. Different time points and/or more or fewer time points could be used in various embodiments. One of ordinary skill in the art would select appropriate time points. The blood samples are typically processed to obtain plasma or serum prior to making the measurements. For purposes of the present invention, it will be assumed that plasma and serum concentrations (and pharmacokinetic parameters such as half-life) are not significantly different and can be used interchangeably absent evidence to the contrary. If a difference is determined to exist, the invention provides embodiments in which plasma concentrations (and/or plasma half-life) is used, embodiments in which the serum concentrations (and/or serum half-life therein) is used, and embodiments in which an average value is used.

One of ordinary skill in the art would select an appropriate method for measuring the compound. For example, in some embodiments an immunoassay is used. In some embodiments, a chromatography-based method is used (e.g., liquid chromatography (LC), liquid chromatography-mass spectrometry (LC-MS) or liquid chromatography-tandem mass spectrometry (LC-MS-MS). In some embodiments, a bioassay is used. In many embodiments, the half-life is a terminal (elimination) half-life. In some embodiments, a terminal half-life is calculated following administration of a single dose. In some embodiments, a terminal half-life is calculated following administration of multiple doses and allowing the concentration to reach steady state. In some embodiments, a half-life determined for the initial (distribution) phase is used. For example, if the majority of the compound is removed from circulation during the distribution phase, an initial half-life may be used in some embodiments.

In some embodiments, half-life is determined by conducting a PK analysis using non-compartmental analysis on multiple dose PK data from a group of subjects. In some embodiments, half-life is determined by conducting a PK analysis using a standard 1-compartment model on multiple dose PK data from a group of subjects. In some embodiments, a half-life determined in subjects suffering from a chronic respiratory disorder (e.g., asthma or COPD) is used. In some embodiments, a half-life determined in subjects who are healthy and not known to be suffering from a disorder is used. In some embodiments, a half-life determined in subjects suffering from a complement-mediated disorder other than a chronic respiratory disorder is used. In some embodiments, a half-life determined in adults (persons at least 18 years of age) is used.

In some embodiments, half-life is determined using a dose suitable for treating a chronic complement-mediated disorder, e.g., a chronic respiratory disorder, e.g., asthma or COPD. In some embodiments, a dose is sufficient to reduce plasma complement activation capacity to no more than 50% of the lower limit of the normal range. In some embodiments, a dose is sufficient to reduce plasma complement activation capacity to no more than twice background levels, e.g., to approximately background levels. In some embodiments, half-life is determined using a composition comprising the complement inhibitor, wherein the composition is the same or substantially similar to a composition to be used to treat a chronic complement-mediated disorder.

In certain embodiments, a complement inhibitor is modified by conjugation with a polypeptide or non-polypeptide component of use to stabilize the compound, reduce its immunogenicity, increase its lifetime in the body, increase or decrease its solubility, and/or increase its resistance to degradation. For example, a polymer such as polyethylene glycol (PEG), albumin, or albumin-binding peptide, may be used. In such embodiments, "half-life" typically refers to the half-life of the complement inhibitor as so modified.

A variety of software tools are available to facilitate calculation of PK parameters. For example, Phoenix NMLE or Phoenix WinNonlin software (PharSight Corp, St. Louis, Mo.) or Kinetica (Thermo Scientific) can be used. It will be appreciated that a reasonable estimate of half-life based on a model can be used. In some embodiments, a half-life determined in a Phase I, II, or III clinical trial of a particular compound and/or submitted in an application to a regulatory agency such as the FDA (e.g., an IND or NDA) is used as a half-life in determining an inventive dosing interval.

In some embodiments, a method comprises administering at least 5, 10, 15, 20, or 25 doses are to a subject according to an inventive dosing schedule (i.e., using a dosing interval according to the invention). In some embodiments, treatment is continued over a period at least 3, 6, 9, 12 months, or more, e.g., 1-2 years, 2-5 years, 5-10 years, or more, e.g., indefinitely.

It will be appreciated that minor deviations, such as occasional use of a shorter or longer dosing interval as compared with a dosing interval or range specified herein (e.g., up to about 5%, 10%, or 20% of doses, e.g., within a time span such as 6 months, 1 year, etc.) would fall within the scope of the invention. In some embodiments, a dosing interval for a subject may vary over time and/or may be selected at least in part based on a measurement of complement activation capacity and/or assessment of disease activity (or a biomarker thereof) between doses.

In some embodiments of any of the inventive methods, a complement inhibitor is administered intravenously. In some embodiments of any of the inventive methods, a complement inhibitor is administered by the respiratory route. In some embodiments of any of the inventive methods, a complement inhibitor is administered subcutaneously. In some embodiments of any of the inventive methods, a complement inhibitor is administered intramuscularly. In some embodiments of any of the inventive methods, a complement inhibitor is administered orally.

In some embodiments, a complement inhibitor is administered in a formulation that provides sustained release (also referred to as "extended release" or "controlled release") of the complement inhibitor. In some embodiments in which a sustained release formulation is used, the time interval between doses is calculated based at least in part on the length of time that the sustained release formulation releases complement inhibitor. For example, if a sustained release formulation releases a complement inhibitor for N weeks after administration before becoming depleted, the invention provides a method of treating a subject comprising administering multiple doses of said sustained release formulation according to a dosing schedule in which successive doses are administered with an average dosing interval of at least N+3 weeks, e.g., between N+3 and N+15 weeks, e.g., between N+3 and N+12 weeks, e.g., between N+3 and N+10 weeks, e.g, between N+4 and N+8 weeks, e.g., about every N+4, N+5, N+6, N+7, or N+8 weeks. In some embodiments, a sustained release formulation is considered to be depleted if it no longer releases sufficient complement inhibitor to maintain the subject's plasma complement activation capacity and/or local complement activation capacity (e.g., in a tissue or organ affected by a complement-mediated disorder) below the normal range or reduced by at least 50% of baseline. In some embodiments, a sustained release formulation is considered to be depleted if it no longer releases sufficient complement inhibitor to maintain the subject's plasma complement activation and/or local complement activation (e.g., in a tissue or organ affected by a complement-mediated disorder) below the normal range or reduced by at least 50% of baseline. In some embodiments, a sustained release formulation is considered to be depleted if at least 80%, 85%, 90%, 95%, 96%, 97%, 98%, 99%, or more of the complement inhibitor contained in the formulation when administered has been released or the formulation has essentially ceased releasing complement inhibitor.

All combinations of the various complement inhibitors, complement inhibitor characteristics (e.g., compound class, molecular weight, half-life, molecular target, etc.), and dosing parameters (e.g., dosing interval, route of administration, etc.), and disorders, e.g., respiratory disorders disclosed herein are contemplated in various embodiments of the invention. For example, in some embodiments, an inventive method comprises intravenous administration of a complement inhibitor with an average dosing interval of at least 3 weeks, e.g., between 3 and 15 weeks, e.g., between 3 and 12 weeks, e.g., between 3 and 10 weeks, e.g, between 4 and 8 weeks, e.g., about every 4, 5, 6, 7, or 8 weeks. In some embodiments, an inventive method comprises pulmonary administration of a complement inhibitor with an average dosing interval of at least 3 weeks, e.g., e.g., between 3 and 15 weeks, e.g., between 3 and 12 weeks, e.g., between 3 and 10 weeks, e.g, about every 4, 5, 6, 7, or 8 weeks.

Further provided are methods of selecting a dosing interval for administering a complement inhibitor. In some embodiments, a method of selecting a dosing interval for administering a complement inhibitor comprises (a) obtaining a half-life of the complement inhibitor; and (b) selecting a dosing interval at least 2-10 weeks longer than the half-life. In some embodiments, a method of selecting a dosing interval for administering a complement inhibitor comprises (a) obtaining a half-life of the complement inhibitor; and (b) selecting a dosing interval at least 3 times as long as the half-life. In some embodiments, a method of selecting a dosing interval for a complement inhibitor comprises: (a) determining the length of time that the complement inhibitor reduces plasma complement activation capacity by at least 50% of baseline and/or the length of time that the complement inhibitor reduces plasma complement activation capacity to below the normal range; and (b) selecting any of the inventive dosing intervals set forth above based on said measured length of time. In some embodiments, a method of selecting a dosing interval can further comprise testing a complement inhibitor administered according to an inventive dosing schedule to an animal that serves as a model for a chronic complement-mediated disorder, e.g., a chronic complement-mediated respiratory disorder.

In some embodiments, an inventive treatment method comprises an induction phase and a maintenance phase. In many embodiments, the induction phase (if used) occurs when a subject initiates therapy. The induction phase can consist of a period of time during which a complement inhibitor is administered at a higher dose and/or at more frequent intervals and/or using a different route of administration than during the maintenance phase. During the maintenance phase, the complement inhibitor may be administered using any of the inventive dosing schedules and/or dosing intervals described above. For example, the complement inhibitor may be administered weekly during an induction phase and on average every 4-15 weeks, e.g., every 4-8 weeks, during a maintenance phase. In some embodiments a complement inhibitor is administered once or more times daily during an induction phase. In some embodiments a complement inhibitor is administered at least 1, 2, 3, 4, 5, 6, or 7 times weekly during an induction phase. In some embodiments an induction phase lasts for up to 1, 2, 3, 4, 5, 6, 7, or 8 weeks. In some embodiments a dose or dosing interval is adjusted during an induction phase. For example, in some embodiments the dosing interval may be increased over time and/or the dose may be decreased or increased over time during the induction phase.

As noted above, in some embodiments the chronic respiratory disease is asthma. Information regarding risk factors, epidemiology, pathogenesis, diagnosis, current management of asthma, etc., may be found, e.g., in "Expert Panel Report 3: Guidelines for the Diagnosis and Management of Asthma". National Heart Lung and Blood Institute. 2007. ("NHLBI Guidelines"), Global Initiative for Asthma, Global Strategy for Asthma Management and Prevention 2010 "GINA Report") and/or standard textbooks of internal medicine such as Cecil Textbook of Medicine (20th edition), Harrison's Principles of Internal Medicine (17th edition), and/or standard textbooks focusing on pulmonary medicine. Asthma is a chronic inflammatory disorder of the airways in which many cells and cellular elements play a role, such as, mast cells, eosinophils, T lymphocytes, macrophages, neutrophils, and epithelial cells Asthmatic individuals experience recurrent episodes associated with symptoms such as wheezing, breathlessness (also termed dyspnea or shortness of breath), chest tightness, and coughing. These episodes are usually associated with widespread but variable airflow obstruction that is often reversible, either spontaneously or with treatment. The inflammation also causes an associated increase in the existing bronchial hyperresponsiveness to a variety of stimuli. Airway hyperresponsiveness (an exaggerated bronchoconstrictor response to stimuli) is a typical feature of asthma. In general, airflow limitation results from bronchoconstriction and airway edema. Reversibility of airflow limitation may be incomplete in some patients with asthma. For example, airway remodeling can lead to fixed airway narrowing. Structural changes can include thickening of the sub-basement membrane, subepithelial fibrosis, airway smooth muscle hypertrophy and hyperplasia, blood vessel proliferation and dilation, and mucous gland hyperplasia, and hypersecretion.

Individuals with asthma may experience exacerbations, which are identified as events characterized by a change from the individual's previous status. Severe asthma exacerbations can be defined as events that require urgent action on the part of the individual and his/her physician to prevent a serious outcome, such as hospitalization or death from asthma. For example, a severe asthma exacerbation may require use of systemic corticosteroids (e.g., oral corticosteroids) in a subject whose asthma is usually well controlled without OCS or may require an increase in a stable maintenance dose. Moderate asthma exacerbations can be defined as events that are troublesome to the subject, and that prompt a need for a change in treatment, but that are not severe. These events are clinically identified by being outside the subject's usual range of day-to-day asthma variation.

Current medications for asthma are typically categorized into two general classes: long-term control medications ("controller medications") such as inhaled corticosteroids (ICS), oral corticost eroids (OCS), long-acting bronchodilators (LABAs), leukotriene modifiers (e.g., leukotriene receptor antagonists or leukotriene synthesis inhibitors, anti-IgE antibodies (omalizumab (Xolair®)), cromolyn and nedocromil, which are used to achieve and maintain control of persistent asthma and quick-relief medications such as short-acting bronchodilators (SABAs), which are used to treat acute symptoms and exacerbations. For purposes of the present invention, these treatments may be referred to as "conventional therapy". Treatment of exacerbations may also include increasing the dose and/or intensity of controller medication therapy. For example, a course of OCS can be used to regain asthma control. Current guidelines mandate daily administration of controller medication or, in many cases, administration of multiple doses of controller medication each day for subjects with persistent asthma (with the exception of Xolair, which is administered every 2 or 4 weeks).

Figure 3:
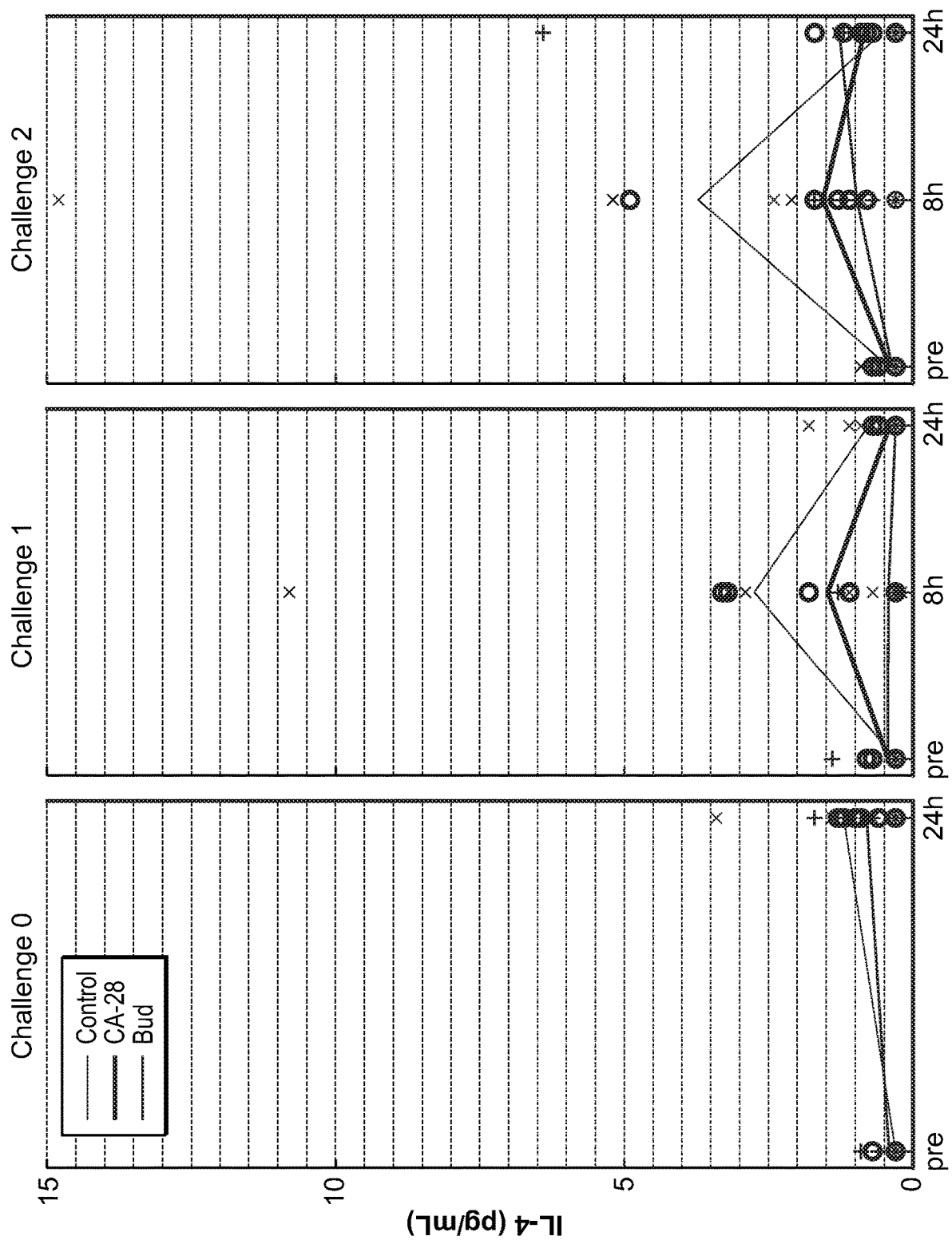

A subject is generally considered to have persistent asthma if the subject suffers from symptoms on average more than twice a week and/or typically uses a quick relief medication (e.g., SABA) more than twice a week for symptom control. "Asthma severity" can be classified based on the intensity of treatment required to control the subject's asthma once relevant comorbidities have been treated and inhaler technique and adherence have been optimized (see, e.g., GINA Report; Taylor, D R, Eur Respir J 2008; 32:545-554). The description of treatment intensity can be based on the medications and doses recommended in the stepwise treatment algorithm found in guidelines such as NHLBI Guidelines 2007, GINA Report, and their predecessors and/or in standard medical textbooks. For example, asthma can be classified as intermittent, mild, moderate, or severe as indicated in Table 1, where "treatment" refers to treatment sufficient to achieve subject's best level of asthma control. (It will be understood that the categories of mild, moderate, and severe asthma in general imply persistent rather than intermittent asthma). One of ordinary skill in the art will appreciate that Table 1 is exemplary, and that not all of these medications will be available in all healthcare systems, which may affect the assessment of asthma severity in some environments. It will also be appreciated that other emerging or new approaches may affect the classification of mild/moderate asthma. However, the same principle, of mild asthma being defined by the ability to achieve good control using very low-intensity treatment and severe asthma being defined by the requirement for high-intensity treatment, can still be applied. Asthma severity can also or alternately be classified based on intrinsic intensity of the disease in the absence of treatment (see, e.g., NHBLI Guidelines 2007). Assessment can be made on the basis of current spirometry and the patient's recall of symptoms over the previous 2-4 weeks. Parameters of current impairment and future risk may be assessed and included in a determination of the level of asthma severity. In some embodiments, asthma severity is defined as shown in Figure 3.4(a), 3.4(b), 3.4(c) of the NHBLI Guidelines, for individuals 0-4, 5-11, or ≥12 years of age, respectively.

TABLE 1

Treatment-based Asthma Classification

| Asthma Classification | Treatment |
|---|---|
| Intermittent | SABA as needed (typically no more than twice a week) |
| Mild | Low-dose ICS or other low-intensity treatment (e.g., LTRA, cromolyn, nedocromil, theophylline) |
| Moderate | Low to moderate dose ICS and LABA or other extra treatment |
| Severe | High-intensity treatment (high-dose ICS and LABA ± oral corticosteroids and/or other extra treatment) |

Figure 4:
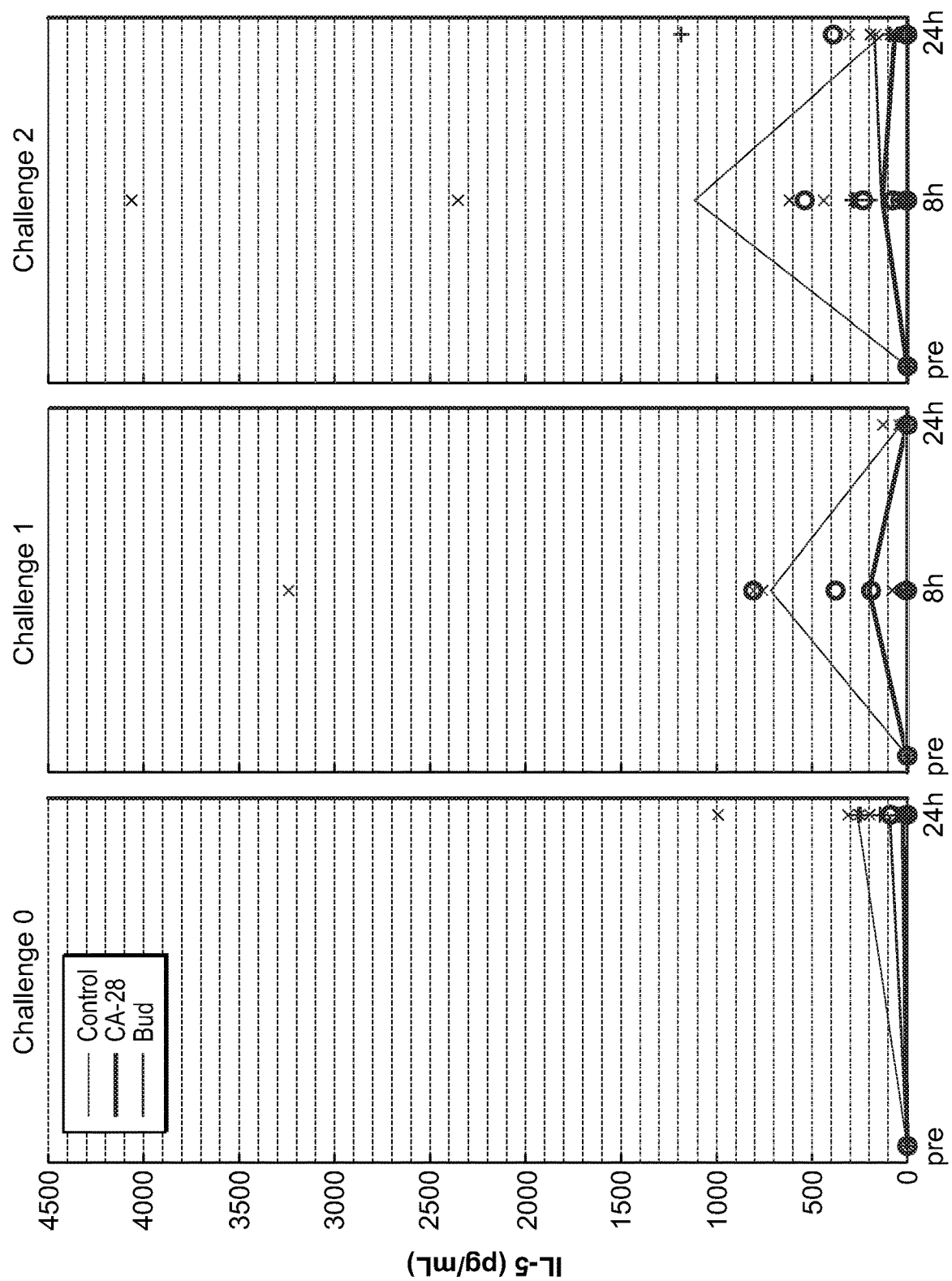
Figure 5:
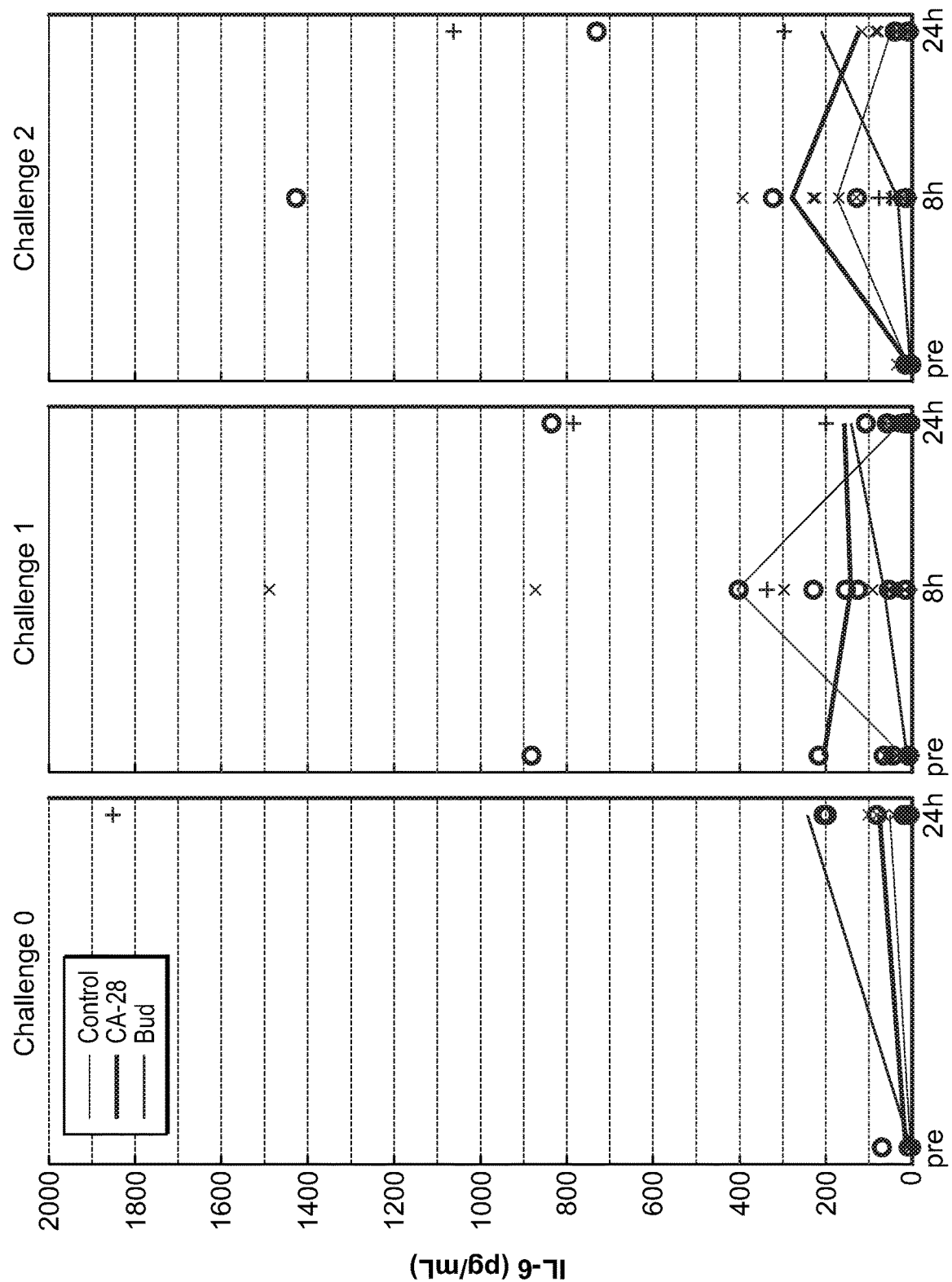

"Asthma control" refers to the extent to which the manifestations of asthma have been reduced or removed by treatment (whether pharmacological or non-pharmacological). Asthma control can be assessed based on factors such as symptom frequency, nighttime symptoms, objective measures of lung function such as spirometry parameters (e.g., % $FEV_1$ of predicted, $FEV_1$ variability, requirement for use of SABA for symptom control. Parameters of current impairment and future risk may be assessed and included in a determination of the level of asthma control. In some embodiments, asthma control is defined as shown in Figure 4.3(a), 4.3(b), or 4.3(c) of NHBLI Guidelines, for individuals 0-4, 5-11, or ≥12 years of age, respectively.

In general, one of ordinary skill in the art can select an appropriate means of determining asthma severity level and/or degree of control, and any classification scheme considered reasonable by those of ordinary skill in the art can be used.

In some embodiments of the invention, a subject suffering from persistent asthma is treated with a complement inhibitor using an inventive dosing regimen. In some embodiments, the subject suffers from mild or moderate asthma. In some embodiments, the subject suffers from severe asthma. In some embodiments, a subject has asthma that is not well controlled using conventional therapy. In some embodiments, a subject has asthma that, when treated using conventional therapy, requires use of ICS in order to be well controlled. In some embodiments, a subject has asthma that fails to be well controlled despite use of ICS. In some embodiments, a subject has asthma that, if treated using conventional therapy, would require use of OCS in order to be well controlled. In some embodiments, a subject has asthma that fails to be well controlled despite use of high intensity conventional therapy that includes OCS. In some embodiments of the invention, an inventive dosing regimen comprises administering a complement inhibitor as a controller medication, wherein the complement inhibitor is administered with reduced frequency and/or on a less regular basis, as compared with standard controller medications, while maintaining at least equivalent asthma control. In some embodiments, an inventive dosing regimen affords improved patient acceptability, compliance, and/or convenience, as compared with standard regimens of conventional controller medications, while maintaining at least equivalent asthma control. In some embodiments, a subject treated with a complement inhibitor, e.g., according to an inventive dosing regimen, can significantly decrease the dose (e.g., by at least 50%) or substantially avoid use of ICS, Xolair, and/or OCS as a controller medication.

In some embodiments, the subject suffers from allergic asthma, which is the case for most asthmatic individuals. In some embodiments, an asthmatic subject is considered to have allergic asthma if a non-allergic trigger for the asthma (e.g., cold, exercise) is not known and/or is not identified in a standard diagnostic evaluation. In some embodiments, an asthmatic subject is considered to have allergic asthma if the subject (i) reproducibly develops asthma symptoms (or worsening of asthma symptoms) following exposure to an allergen or allergen(s) to which the subject is sensitive; (ii) exhibits IgE specific for an allergen or allergen(s) to which the subject is sensitive; (iii) exhibits a positive skin-prick test to an allergen or allergen(s) to which the subject is sensitive; and/or (iv) exhibits other symptom(s) of characteristic(s) consistent with atopy such as allergic rhinitis, eczema, or elevated total serum IgE. It will be appreciated that a specific allergic trigger may not be identified but may be suspected or inferred if the subject experiences worsening symptoms in particular environments, for example.

Allergen challenge by inhalation is a technique that is widely used in evaluating allergic airway disease. Inhalation of allergen leads to cross-linking of allergen-specific IgE bound to IgE receptors on, e.g., mast cells and basophils. Activation of secretory pathways ensues, resulting in release of mediators of bronchoconstriction and vascular permeability. Individuals with allergic asthma may develop various manifestations following allergen challenge, e.g., early asthmatic response (EAR), late asthmatic response (LAR), airway hyperreactivity (AHR), and airway eosinophilia, each of which can be detected and quantified as known in the art. For example, airway eosiphophilia may be detected as an increase in eosinophils in sputum and/or BAL fluid. The EAR, sometimes referred to as the immediate asthmatic response (IAR), is a response to allergen challenge by inhalation that becomes detectable shortly after the inhalation, typically within 10 minutes (min) of the inhalation, e.g., as a decrease in $FEV_1$. The EAR typically reaches a maximum within 30 min and resolves within 2-3 hours (h) post-challenge. For example, a subject may be considered to exhibit a "positive" EAR if his/her $FEV_1$ decreases by at least 15%, e.g., at least 20%, within this time window relative to baseline $FEV_1$ (where "baseline" in this context refers to conditions before the challenge, e.g., conditions equivalent to the subject's usual condition when not experiencing an asthma exacerbation and not exposed to allergic stimuli to which the subject is sensitive). The late asthmatic response (LAR) typically starts between 3 h and 8 h post-challenge and is characterized by cellular inflammation of the airway, increased bronchiovascular permeability, and mucus secretion. It is typically detected as a decrease in $FEV_1$, which may be greater in magnitude than that associated with the EAR and potentially more clinically important. For example, a subject may be considered to exhibit a "positive" LAR if his/her $FEV_1$ decreases by at least 15%, e.g., at least 20%, relative to baseline $FEV_1$ within the relevant time period as compared with baseline $FEV_1$. A delayed airway response (DAR) may occur beginning between about 26 and 32 h, reaching a maximum between about 32 and 48 h and resolving within about 56 h after the challenge (Pelikan, Z. Ann Allergy Asthma Immunol. 2010, 104(5):394-404).

In some embodiments, the chronic respiratory disorder is chronic obstructive pulmonary disease (COPD). COPD encompasses a spectrum of conditions characterized by airflow limitation that is not fully reversible even with therapy and is usually progressive. Symptoms of COPD include dyspnea (breathlessness), decreased exercise tolerance, cough, sputum production, wheezing, and chest tightness. Persons with COPD can experience episodes of acute (e.g., developing over course of less than a week and often over the course of 24 hours or less) worsening of symptoms (termed COPD exacerbations) that can vary in frequency and duration and are associated with significant morbidity. They may be triggered by events such as respiratory infection, exposure to noxious particles, or may have an unknown etiology. Smoking is the most commonly encountered risk factor for COPD, and other inhalational exposures can also contribute to development and progression of the disease. The role of genetic factors in COPD is an area of active research. A small percentage of COPD patients have a hereditary deficiency of alpha-1 antitrypsin, a major circulating inhibitor of serine proteases, and this deficiency can lead to a rapidly progressive form of the disease.

Characteristic pathophysiologic features of COPD include narrowing of and structural changes in the small airways and destruction of lung parenchyma (in particular around alveoli), most commonly due to chronic inflammation. The chronic airflow limitation observed in COPD typically involves a mixture of these factors, and their relative importance in contributing to airflow limitation and symptoms varies from person to person. The term "emphysema" refers to enlargement of the air spaces (alveoli) distal to the terminal bronchioles, with destruction of their walls. It should be noted that the term "emphysema" is often used clinically to refer to the medical condition associated with such pathological changes. Some individuals with COPD have chronic bronchitis, which is defined in clinical terms as a cough with sputum production on most days for 3 months of a year, for 2 consecutive years. Further information regarding risk factors, epidemiology, pathogenesis, diagnosis, and current management of COPD may be found, e.g., in "Global Strategy for the Diagnosis, Management, and Prevention of Chronic Obstructive Pulmonary Disease" (updated 2009) available on the Global Initiative on Chronic Obstructive Pulmonary Disease, Inc. (GOLD) website), also referred to herein as the "GOLD Report", the American Thoracic Society/European Respiratory Society Guidelines (2004) available on the ATS website, referred to herein as "ATC/ERS COPD Guidelines" and standard textbooks of internal medicine such as Cecil Textbook of Medicine (20.sup.th edition), Harrison's Principles of Internal Medicine (17th edition), and/or standard textbooks focusing on pulmonary medicine.

In some embodiments methods disclosed herein inhibit (interfere with, disrupt) the DC-Th17-B-Ab-C-DC cycle discussed above. For example, administration of a complement inhibitor may break the cycle by which complement stimulates DC cells to promote the Th17 phenotype. As a result, the number and/or activity of Th17 cells diminishes, which in turn reduces the amount of Th17-mediated stimulation of B cells and polyclonal antibody production. In some embodiments, these effects result in "resetting" the immunological microenvironment to a more normal, less pathological state. As described in Example 1, evidence supporting the capacity of complement inhibition to have a prolonged inhibitory effect on Th17-associated cytokine production was obtained in an animal model of asthma.

In some embodiments, inhibiting the DC-Th17-B-Ab-C-DC cycle has a disease-modifying effect. Without wishing to be bound by any theory, rather than merely treating symptoms of a disorder, inhibiting the DC-Th17-B-Ab-C-DC cycle may interfere with fundamental pathologic mechanisms that may contribute to ongoing tissue damage even when symptoms are well controlled and/or that may contribute to exacerbations of the disease. In some embodiments, inhibiting the DC-Th17-B-Ab-C-DC cycle causes a chronic disorder to go into remission. In some embodiments, remission refers to a state of absence or substantial absence of disease activity in a subject with a chronic disorder, with the possibility of return of disease. In some embodiments remission may be sustained for a prolonged period of time (e.g., at least 6 months, e.g., 6-12 months, 12-24 months, or more) in the absence of continued therapy or with a reduced dose or increased dosing interval. In some aspects, inhibition of complement may change the immunological micro-environment of a tissue that is rich in Th17 cells and modify it into a micro-environment that is rich in regulatory T cells (Tregs). Doing so could allow the immune system to "reset" itself and go into a state of remission. In some embodiments, for example, remission may be sustained until occurrence of a triggering event. A triggering event may be, for example, an infection (which may result in production of polyclonal antibodies that react both with an infectious agent and a self protein), exposure to particular environmental conditions (e.g., high levels of air pollutants such as ozone or particulate matter or components of smoke such as cigarette smoke, allergens), etc. Genetic factors may play a role. For example, individuals having particular alleles of genes encoding complement components may have a higher baseline level of complement activity, a more reactive complement system and/or a lower baseline level of endogenous complement regulatory protein activity. In some embodiments an individual has a genotype associated with increased risk of AMD. For example, the subject may have a polymorphism in a gene encoding a complement protein or complement regulatory protein, e.g., CFH, C3, factor B, wherein the polymorphism is associated with an increased risk of AMD.

In some embodiments an immunologic microenvironment may become progressively more polarized towards a pathological state over time, e.g., in a subject who has not yet developed symptoms of a chronic disorder or in a subject who has developed the disorder and has been treated as described herein. Such a transition may occur stochastically (e.g., due at least in part to apparently random fluctuations in antibody levels and/or affinity) and/or as a result of accumulated "sub-threshold" trigger events that are not of sufficient intensity to trigger a symptomatic outbreak of a disorder.

In some aspects, methods disclosed herein comprise monitoring a subject for evidence of the DC-Th17-B-Ab-C-DC cycle. If such evidence is detected, the subject may be treated with a complement inhibitor and/or other agent that disrupts the DC-Th17-B-Ab-C-DC cycle. In some embodiments a subject is tested for Th17 cells (e.g., Th17 cell number or relative number) and/or for one or more biomarkers associated with Th17 cells and/or Th17 activity ("Th17 biomarker"). In some embodiments, a subject is treated with a complement inhibitor based at least in part on assessment of Th17 cells with a Th17 biomarker. "Th17 biomarker" encompasses any molecule or detectable indicator that correlates with Th17 cell presence (e.g., number or concentration of Th17 cells) and/or correlates with at least one Th17 cell activity. In some embodiments, a Th17 biomarker comprises a level of a Th17-associated cytokine. In some embodiments a Th17-associated cytokine is a cytokine that promotes formation and/or activation of Th17 cells, e.g., IL-6, IL-21, IL-23, and/or IL-1β. In some embodiments a Th17-associated cytokine is a cytokine produced by Th17 cells, e.g., IL-17 (e.g., IL-17A and/or IL-17F), IL-21, and/or IL-22. In some embodiments an increased amount or increased relative amount of a Th17-associated activity is indicative of increased Th17 cells and/or increased Th17-associated activity. In some embodiments a relative amount is an amount as compared with a different cytokine. In some embodiments the different cytokine is associated with Treg cells. In some embodiments the different cytokine is IL-10.

In some embodiments levels of 2, 3, 4, 5, or more Th17-associated cytokines are measured. A collective index or score indicative of the level of Th17-associated activity may be obtained and used as a Th17 biomarker. In some embodiments the presence or level of Th17 cells themselves is assessed for any purpose for which a Th17 biomarker may be assessed. In some embodiments the presence or level of Tregs is assessed. In some embodiments Tregs are identified based on expression of FOXP3.

In some embodiments, a Th17 biomarker level is measured in a sample obtained from a subject. In some embodiments a sample comprises a body fluid, e.g., blood, BAL fluid, sputum, nasal secretion, urine, etc. In some embodiments a sample comprises a tissue sample, which may be obtained from a tissue or organ affected by a complement-mediated disorder. In some embodiments two or more samples of different body fluids or a body fluid and a tissue sample are assessed. In some embodiments a level is compared with a reference value. In some embodiments a reference value may be a normal value (e.g., a value within a normal range, e.g., an upper limit of a normal range). In some embodiments a reference value may be a value established for the subject at a previous time, e.g., when the subject's disorder was well controlled or prior to development of the disorder. In some embodiments, if a measured value deviates significantly from a reference value or shows a trend towards increased deviation from a reference value, the subject may be treated with a complement inhibitor. In some embodiments the subject may be treated with a complement inhibitor and a second agent that disrupts the DC-Th17-B-Ab-C-DC cycle. A "normal range" may be a range that encompasses at least 95% of healthy individuals. In some embodiments a reference value may be a value associated with a disease, e.g., a value typically found in subjects suffering from a disease in an untreated state. In some embodiments a normal or disease-associated range may depend at least in part on demographic factors such as age, sex, etc., and can be adjusted accordingly. An appropriate reference value or range may be established empirically for different disorders and/or different Th17 biomarkers and/or, in some embodiments, for individual subjects.

In some embodiments, in vivo assessment of Th17 cells and/or a Th17 biomarker is envisioned. For example, in some embodiments a detectably labeled agent that binds to Th17 cells (e.g., to a cell surface marker or combination thereof that is reasonably specific for Th17 cells) or that bind to a Th17-associated cytokine is administered to a subject. A suitable imaging method is used to visualize the agent in vivo. In some embodiments, for example, an image is obtained of the lungs, skin, or other location that may be affected by a complement-mediated disorder. In some embodiments in vivo detection allows assessment of the immunological microenvironment in a tissue or organ of interest. In some embodiments a detectable label comprises a fluorescent, radioactive, ultrasound, or magnetically detectable moiety. In some embodiments an imaging method comprises magnetic resonance imaging, ultrasound imaging, optical imaging (e.g., fluorescence imaging or bioluminescence imaging), or nuclear imaging. In some embodiments a fluorescent moiety comprises a near-infrared or infrared fluorescent moiety (emitting in the near-infrared or infrared region of the spectrum). In some embodiments an imaging method comprises positron emission tomography (PET), and single photon emission computed tomography (SPECT) In some embodiments a detectable label is attached to an agent that binds directly to a target to be detected. In some embodiments a detectable label is associated with or incorporated into or comprises particles, which in some embodiments have at their surface an agent that binds directly to a target to be detected.

In some embodiments, information obtained from a Th17 biomarker assessment is used together with additional information, e.g., genotype information, environmental exposure information, and/or subject historical information, to determine whether or when to administer a complement-inhibitor and/or anti-Th17 agent and/or to select a dose or dosing regimen for a subject. In some embodiments any of the biomarker assessment and/or treatment decision methods may be performed at least in part by one or more computers. In some embodiments any of the biomarker assessment and/or treatment decision methods may be embodied or stored at least in part on a computer-readable medium having computer-executable instructions thereon. In some embodiments a computer-readable medium comprises any non-transitory and/or tangible computer-readable medium.

In some embodiments retreatment may occur on a fixed time schedule.

Wherever an aspect or embodiment herein is described in relation to complement-mediated disorders, analogous aspects and embodiments relating to Th17-associated disorders are provided. Wherever an aspect or embodiment herein is described in relation to complement-mediated disorders, analogous aspects and embodiments relating to Th17-associated disorders are provided. All combinations of the various complement inhibitors, complement inhibitor characteristics (e.g., compound class, molecular weight, half-life, molecular target, etc.), anti-Th17 agents, and dosing parameters (e.g., dosing interval, route of administration, etc.), and disorders disclosed herein are contemplated in various embodiments. All combinations of the various complement inhibitors, complement inhibitor characteristics (e.g., compound class, molecular weight, half-life, molecular target, etc.), anti-Th17 agents, anti-Th17 agent characteristics (e.g., compound class, molecular weight, half-life, molecular target, etc.), and dosing parameters (e.g., dosing interval, route of administration, etc.), and disorders disclosed herein are contemplated in various embodiments.

In some aspects, the invention provides methods of treating a chronic complement-mediated disorder or Th17-associated disorder comprising administering a complement inhibitor and an anti-Th17 agent to a subject in need thereof. In some embodiments the complement inhibitor and/or anti-Th17 agent are administered according to any suitable dosing regimen. In some embodiments the complement inhibitor and anti-Th17 agent are administered according to a dosing regimen described herein. In some embodiments the chronic disorder is any chronic complement-mediated disorder or any Th17-associated disorder. In some aspects, the invention provides methods of treating a chronic complement-mediated disorder comprising administering an anti-Th17 agent to a subject in need thereof. In some embodiments the anti-Th17 agent is administered according to any suitable dosing regimen. In some embodiments the anti-Th17 agent is administered according to a dosing regimen described herein. In some embodiments compositions, e.g., pharmaceutical compositions, comprising a complement inhibitor and an anti-Th17 agent are provided. Exemplary anti-Th17 agents are discussed in Section V.

III. Complement System

In order to facilitate understanding of the invention, and without intending to limit the invention in any way, this section provides an overview of complement and its pathways of activation. Further details are found, e.g., in *Kuby Immunology*, $6^{th}$ ed., 2006; Paul, W. E., *Fundamental Immunology*, Lippincott Williams & Wilkins; $6^{th}$ ed., 2008; and Walport M J., Complement. First of two parts. *N Engl J Med.*, 344(14):1058-66, 2001.

Complement is an arm of the innate immune system that plays an important role in defending the body against infectious agents. The complement system comprises more than 30 serum and cellular proteins that are involved in three major pathways, known as the classical, alternative, and lectin pathways. The classical pathway is usually triggered by binding of a complex of antigen and IgM or IgG antibody to C1 (though certain other activators can also initiate the pathway). Activated C1 cleaves C4 and C2 to produce C4a and C4b, in addition to C2a and C2b. C4b and C2a combine to form C3 convertase, which cleaves C3 to form C3a and C3b. Binding of C3b to C3 convertase produces C5 convertase, which cleaves C5 into C5a and C5b. C3a, C4a, and C5a are anaphylotoxins and mediate multiple reactions in the acute inflammatory response. C3a and C5a are also chemotactic factors that attract immune system cells such as neutrophils.

The alternative pathway is initiated by and amplified at, e.g., microbial surfaces and various complex polysaccharides. In this pathway, hydrolysis of C3 to C3(H2O), which occurs spontaneously at a low level, leads to binding of factor B, which is cleaved by factor D, generating a fluid phase C3 convertase that activates complement by cleaving C3 into C3a and C3b. C3b binds to targets such as cell surfaces and forms a complex with factor B, which is later cleaved by factor D, resulting in a C3 convertase. Surface-bound C3 convertases cleave and activate additional C3 molecules, resulting in rapid C3b deposition in close proximity to the site of activation and leading to formation of additional C3 convertase, which in turn generates additional C3b. This process results in a cycle of C3 cleavage and C3 convertase formation that signicantly amplifies the response. Cleavage of C3 and binding of another molecule of C3b to the C3 convertase gives rise to a C5 convertase. C3 and C5 convertases of this pathway are regulated by host cell molecules CR1, DAF, MCP, CD59, and fH. The mode of action of these proteins involves either decay accelerating activity (i.e., ability to dissociate convertases), ability to serve as cofactors in the degradation of C3b or C4b by factor I, or both. Normally the presence of complement regulatory proteins on host cell surfaces prevents significant complement activation from occurring thereon.

The C5 convertases produced in both pathways cleave C5 to produce C5a and C5b. C5b then binds to C6, C7, and C8 to form C5b-8, which catalyzes polymerization of C9 to form the C5b-9 membrane attack complex (MAC). The MAC inserts itself into target cell membranes and causes cell lysis. Small amounts of MAC on the membrane of cells may have a variety of consequences other than cell death.

The lectin complement pathway is initiated by binding of mannose-binding lectin (MBL) and MBL-associated serine protease (MASP) to carbohydrates. The MB1-1 gene (known as LMAN-1 in humans) encodes a type I integral membrane protein localized in the intermediate region between the endoplasmic reticulum and the Golgi. The MBL-2 gene encodes the soluble mannose-binding protein found in serum. In the human lectin pathway, MASP-1 and MASP-2 are involved in the proteolysis of C4 and C2, leading to a C3 convertase described above.

Complement activity is regulated by various mammalian proteins referred to as complement control proteins (CCPs) or regulators of complement activation (RCA) proteins (U.S.

Pat. No. 6,897,290). These proteins differ with respect to ligand specificity and mechanism(s) of complement inhibition. They may accelerate the normal decay of convertases and/or function as cofactors for factor I, to enzymatically cleave C3b and/or C4b into smaller fragments. CCPs are characterized by the presence of multiple (typically 4-56) homologous motifs known as short consensus repeats (SCR), complement control protein (CCP) modules, or SUSHI domains, about 50-70 amino acids in length that contain a conserved motif including four disulfide-bonded cysteines (two disulfide bonds), proline, tryptophan, and many hydrophobic residues. The CCP family includes complement receptor type 1 (CR1; C3b:C4b receptor), complement receptor type 2 (CR2), membrane cofactor protein (MCP; CD46), decay-accelerating factor (DAF), complement factor H (fH), and C4b-binding protein (C4bp). CD59 is a membrane-bound complement regulatory protein unrelated structurally to the CCPs. Complement regulatory proteins normally serve to limit complement activation that might otherwise occur on cells and tissues of the mammalian, e.g., human host.

IV. Complement Inhibitors

General

A variety of different complement inhibitors may be used in various embodiments of the invention. In general, a complement inhibitor can belong to any of a number of compound classes such as peptides, polypeptides, antibodies, small molecules, and nucleic acids (e.g., aptamers, RNAi agents such as short interfering RNAs). In certain embodiments a complement inhibitor inhibits an enzymatic activity of a complement protein. The enzymatic activity may be proteolytic activity, such as ability to cleave another complement protein. In some embodiments, a complement inhibitor inhibits cleavage of C3, C5, or factor B. In some embodiments, a complement inhibitor acts on C3. In some embodiments, a complement inhibitor acts on a complement component that lies upstream of C3 in the complement activation cascade. In some embodiments, a complement inhibitor inhibits activation or activity of at least one soluble complement protein produced in the respiratory system. In certain embodiments a complement inhibitor that inhibits at least the classical pathway of complement activation is used. In certain embodiments a complement inhibitor that inhibits both the classical and the alternative pathway is used. In some embodiments a complement inhibitor that inhibits C3 activation or activity is used. In some embodiments, a complement inhibitor inhibits activation of at least one complement receptor protein expressed in the respiratory system. In certain embodiments the complement receptor protein is a receptor for C3a. In certain embodiments the complement receptor protein is a receptor for C5a.

In some embodiments, a complement inhibitor comprises an antibody that substantially lacks the capacity to activate complement. For example, the antibody may have less than 10%, less than 5%, or less than 1% complement stimulating activity as compared with full length human IgG1. In some embodiments, the antibody comprises a CH2 domain that has reduced ability to bind C1q as compared with human IgG1 CH2 domain. In some embodiments, the antibody contains CH1, CH2, and/or CH3 domains from human IgG4 and/or does not contain CH1, CH2, and/or CH3 domains from human IgG1.

In some embodiments, a complement inhibitor used in, e.g., an inventive dosing regimen, has a molecular weight of 1 kD or less. In some embodiments, a complement inhibitor has a molecular weight between 1 kD and 2 kD, between 2 kD and 5 kD, between 5 kD and 10 kD, between 10 kD and 20 kD, between 20 kD and 30 kD, between 30 kD and 50 kD, between 50 kD and 100 kD, or between 100 kD and 200 kD.

A complement inhibitor may be at least in part identical to a naturally occurring complement inhibiting agent or a variant or fragment thereof. A variety of different complement inhibiting polypeptides are produced by viruses (e.g., Poxviruses, Herpesviruses), bacteria (e.g., *Staphylococcus*), and other microorganisms. Complement inhibiting proteins are produced by various parasites, e.g., ectoparasites, such as ticks. A complement inhibitor can comprise at least a portion of a mammalian complement control or complement regulatory protein or receptor. See Ricklin, D., et al. "Complement-targeted Therapeutics", Nature Biotechnology, 25(11): 1265-75, 2007, for discussion of complement inhibitors that are or have been in preclinical or clinical development for various disorders and may be used in various embodiments of the inventive methods.

In some embodiments a complement inhibitor comprises an adnectin, affibody, anticalin, or other type of polypeptide sometimes used in the art in lieu of an antibody, wherein the polypeptide binds to a complement component.

The following sections discuss non-limiting exemplary complement inhibitors of use in embodiments of the present invention. Complement inhibitors have been classified in various groups for purposes of convenience. It will be understood that certain complement inhibitors fall into multiple categories.

In some embodiments, a complement inhibitor that binds to substantially the same binding site (e.g., a binding site on a complement component such as C3, C5, factor B, factor D, or an active complement split product) as a complement inhibitor described herein is used. In general, the ability of first and second agents to bind to substantially the same site on a target molecule, such as a complement component or receptor, can be assessed using methods known in the art, such as competition assays, molecular modeling, etc. (See, e.g., discussion of compstatin analog mimetics.) Optionally the first and/or second agent can be labeled with a detectable label, e.g., a radiolabel, fluorescent label, etc. Optionally the target molecule, first agent, or second agent is immobilized on a support, e.g., a slide, filter, chip, beads, etc. In some embodiments, a second antibody that binds to substantially the same binding site as a first antibody comprises one or more CDR(s) that are at least 90%, 91%, 92%, 93%, 94%, 95%, 96%, 97%, 98%, 99%, or 100% identical to CDR(s) of the first antibody.

Compounds that Inhibit C3 Activation or Activity

Compstatin Analogs and Mimetics

Compstatin is a cyclic peptide that binds to C3 and inhibits complement activation by, e.g., inhibiting cleavage of C3 to C3a and C3b by convertase. U.S. Pat. No. 6,319,897 describes a peptide having the sequence Ile-[Cys-Val-Val-Gln-Asp-Trp-Gly-His-His-Arg-Cys]-Thr (SEQ ID NO: 1), with the disulfide bond between the two cysteines denoted by brackets. It will be understood that the name "compstatin" was not used in U.S. Pat. No. 6,319,897 but was subsequently adopted in the scientific and patent literature (see, e.g., Morikis, et al., *Protein Sci.*, 7(3):619-27, 1998) to refer to a peptide having the same sequence as SEQ ID NO: 2 disclosed in U.S. Pat. No. 6,319,897, but amidated at the C terminus as shown in Table 2 (SEQ ID NO: 8). The term "compstatin" is used herein consistently with such usage (i.e., to refer to SEQ ID NO: 8). Compstatin analogs that have higher complement inhibiting activity than compstatin have been developed. See, e.g., WO2004/026328 (PCT/US2003/029653), Morikis, D., et al., *Biochem Soc Trans.* 32(Pt 1):28-32, 2004, Mallik, B., et al. *J. Med. Chem.,* 274-286, 2005; Katragadda, M., et al. *J. Med. Chem.,* 49: 4616-4622, 2006; WO2007062249 (PCT/US2006/045539); WO2007044668 (PCT/US2006/039397), WO/2009/046198 (PCT/US2008/078593); WO/2010/127336 (PCT/US2010/033345) and discussion below.

Compstatin analogs may be acetylated or amidated, e.g., at the N-terminus and/or C-terminus. For example, compstatin analogs may be acetylated at the N-terminus and amidated at the C-terminus. Consistent with usage in the art, "compstatin" as used herein, and the activities of compstatin analogs described herein relative to that of compstatin, refer to compstatin amidated at the C-terminus (Mallik, 2005, supra).

Concatamers or multimers of compstatin or a complement inhibiting analog thereof are also of use in the present invention.

As used herein, the term "compstatin analog" includes compstatin and any complement inhibiting analog thereof. The term "compstatin analog" encompasses compstatin and other compounds designed or identified based on compstatin and whose complement inhibiting activity is at least 50% as great as that of compstatin as measured, e.g., using any complement activation assay accepted in the art or substantially similar or equivalent assays. Certain suitable assays are described in U.S. Pat. No. 6,319,897, WO2004/026328, Morikis, supra, Mallik, supra, Katragadda 2006, supra, WO2007062249 (PCT/US2006/045539); WO2007044668 (PCT/US2006/039397), WO/2009/046198 (PCT/US2008/078593); and/or WO/2010/127336 (PCT/US2010/033345). The assay may, for example, measure alternative or classical pathway-mediated erythrocyte lysis or be an ELISA assay. In some embodiments, an assay described in WO/2010/135717 (PCT/US2010/035871) is used.

The activity of a compstatin analog may be expressed in terms of its $IC_{50}$ (the concentration of the compound that inhibits complement activation by 50%), with a lower $IC_{50}$ indicating a higher activity as recognized in the art. The activity of a preferred compstatin analog for use in the present invention is at least as great as that of compstatin. It is noted that certain modifications known to reduce or eliminate complement inhibiting activity and may be explicitly excluded from any embodiment of the invention. The $IC_{50}$ of compstatin has been measured as 12 µM using an alternative pathway-mediated erythrocyte lysis assay (WO2004/026328). It will be appreciated that the precise $IC_{50}$ value measured for a given compstatin analog will vary with experimental conditions (e.g., the serum concentration used in the assay). Comparative values, e.g., obtained from experiments in which $IC_{50}$ is determined for multiple different compounds under substantially identical conditions, are of use. In one embodiment, the $IC_{50}$ of the compstatin analog is no more than the $IC_{50}$ of compstatin. In certain embodiments of the invention the activity of the compstatin analog is between 2 and 99 times that of compstatin (i.e., the analog has an $IC_{50}$ that is less than the $IC_{50}$ of compstatin by a factor of between 2 and 99). For example, the activity may be between 10 and 50 times as great as that of compstatin, or between 50 and 99 times as great as that of compstatin. In certain embodiments of the invention the activity of the compstatin analog is between 99 and 264 times that of compstatin. For example, the activity may be 100, 110, 120, 130, 140, 150, 160, 170, 180, 190, 200, 210, 220, 230, 240, 250, 260, or 264 times as great as that of compstatin. In certain embodiments the activity is between 250 and 300, 300 and 350, 350 and 400, or 400 and 500 times as great as that of compstatin. The invention further contemplates compstatin analogs having activities between 500 and 1000 times that of compstatin, or more, e.g., between 1000 and 2000 times that of compstatin, or more. In certain embodiments the $IC_{50}$ of the compstatin analog is between about 0.2 µM and about 0.5 µM. In certain embodiments the $IC_{50}$ of the compstatin analog is between about 0.1 µM and about 0.2 µM. In certain embodiments the $IC_{50}$ of the compstatin analog is between about 0.05 µM and about 0.1 µM. In certain embodiments the $IC_{50}$ of the compstatin analog is between about 0.001 µM and about 0.05 µM.

The $K_d$ of compstatin binding to C3 can be measured using isothermal titration calorimetry (Katragadda, et al., *J. Biol. Chem.,* 279(53), 54987-54995, 2004). Binding affinity of a variety of compstatin analogs for C3 has been correlated with their activity, with a lower $K_d$ indicating a higher binding affinity, as recognized in the art. A linear correlation between binding affinity and activity was shown for certain analogs tested (Katragadda, 2004, supra; Katragadda 2006, supra). In certain embodiments of the invention the compstatin analog binds to C3 with a $K_d$ of between 0.1 µM and 1.0 µM, between 0.05 µM and 0.1 µM, between 0.025 µM and 0.05 µM, between 0.015 µM and 0.025 µM, between 0.01 µM and 0.015 µM, or between 0.001 µM and 0.01 µM.

Compounds "designed or identified based on compstatin" include, but are not limited to, compounds that comprise an amino acid chain whose sequence is obtained by (i) modifying the sequence of compstatin (e.g., replacing one or more amino acids of the sequence of compstatin with a different amino acid or amino acid analog, inserting one or more amino acids or amino acid analogs into the sequence of compstatin, or deleting one or more amino acids from the sequence of compstatin); (ii) selection from a phage display peptide library in which one or more amino acids of compstatin is randomized, and optionally further modified according to method (i); or (iii) identified by screening for compounds that compete with compstatin or any analog thereof obtained by methods (i) or (ii) for binding to C3 or a fragment thereof. Many useful compstatin analogs comprise a hydrophobic cluster, a β-turn, and a disulfide bridge.

In certain embodiments of the invention the sequence of the compstatin analog comprises or consists essentially of a sequence that is obtained by making 1, 2, 3, or 4 substitutions in the sequence of compstatin, i.e., 1, 2, 3, or 4 amino acids in the sequence of compstatin is replaced by a different standard amino acid or by a non-standard amino acid. In certain embodiments of the invention the amino acid at position 4 is altered. In certain embodiments of the invention the amino acid at position 9 is altered. In certain embodiments of the invention the amino acids at positions 4 and 9 are altered. In certain embodiments of the invention only the amino acids at positions 4 and 9 are altered. In certain embodiments of the invention the amino acid at position 4 or 9 is altered, or in certain embodiments both amino acids 4 and 9 are altered, and in addition up to 2 amino acids located at positions selected from 1, 7, 10, 11, and 13 are altered. In certain embodiments of the invention the amino acids at positions 4, 7, and 9 are altered. In certain embodiments of the invention amino acids at position 2, 12, or both are altered, provided that the alteration preserves the ability of the compound to be cyclized. Such alteration(s) at positions 2 and/or 12 may be in addition to the alteration(s) at position 1, 4, 7, 9, 10, 11, and/or 13. Optionally the sequence of any of the compstatin analogs whose sequence is obtained by replacing one or more amino acids of compstatin sequence further includes up to 1, 2, or 3 additional amino acids at the C-terminus. In one embodiment, the additional amino acid is Gly. Optionally the sequence of any of the compstatin analogs whose sequence is obtained by replacing one or more amino acids of compstatin sequence further includes up to 5, or up to 10 additional amino acids at the C-terminus. It should be understood that compstatin analogs may have any one or more of the characteristics or features of the various embodiments described herein, and characteristics or features of any embodiment may additionally characterize any other embodiment described herein, unless otherwise stated or evident from the context. In certain embodiments of the invention the sequence of the compstatin analog comprises or consists essentially of a sequence identical to that of compstatin except at positions corresponding to positions 4 and 9 in the sequence of compstatin.

Compstatin and certain compstatin analogs having somewhat greater activity than compstatin contain only standard amino acids ("standard amino acids" are glycine, leucine, isoleucine, valine, alanine, phenylalanine, tyrosine, tryptophan, aspartic acid, asparagine, glutamic acid, glutamine, cysteine, methionine, arginine, lysine, proline, serine, threonine and histidine). Certain compstatin analogs having improved activity incorporate one or more non-standard amino acids. Useful non-standard amino acids include singly and multiply halogenated (e.g., fluorinated) amino acids, D-amino acids, homo-amino acids, N-alkyl amino acids, dehydroamino acids, aromatic amino acids (other than phenylalanine, tyrosine and tryptophan), ortho-, meta- or para-aminobenzoic acid, phospho-amino acids, methoxylated amino acids, and α,α-disubstituted amino acids. In certain embodiments of the invention, a compstatin analog is designed by replacing one or more L-amino acids in a compstatin analog described elsewhere herein with the corresponding D-amino acid. Such compounds and methods of use thereof are an aspect of the invention. Exemplary non-standard amino acids of use include 2-naphthylalanine (2-Nal), 1-naphthylalanine (1-Nal), 2-indanylglycine carboxylic acid (2Ig1), dihydrotryptophan (Dht), 4-benzoyl-L-phenylalanine (Bpa), 2-α-aminobutyric acid (2-Abu), 3-α-aminobutyric acid (3-Abu), 4-α-aminobutyric acid (4-Abu), cyclohexylalanine (Cha), homocyclohexylalanine (hCha), 4-fluoro-L-tryptophan (4fW), 5-fluoro-L-tryptophan (5fW), 6-fluoro-L-tryptophan (6fW), 4-hydroxy-L-tryptophan (4OH-W), 5-hydroxy-L-tryptophan (5OH-W), 6-hydroxy-L-tryptophan (6OH-W), 1-methyl-L-tryptophan (1MeW), 4-methyl-L-tryptophan (4MeW), 5-methyl-L-tryptophan (5MeW), 7-aza-L-tryptophan (7aW), α-methyl-L-tryptophan (αMeW), β-methyl-L-tryptophan (βMeW), N-methyl-L-tryptophan (NMeW), ornithine (orn), citrulline, norleucine, γ-glutamic acid, etc.

In certain embodiments of the invention the compstatin analog comprises one or more Trp analogs (e.g., at position 4 and/or 7 relative to the sequence of compstatin). Exemplary Trp analogs are mentioned above. See also Beene, et. al. Biochemistry 41: 10262-10269, 2002 (describing, inter alia, singly- and multiply-halogenated Trp analogs); Babitzke & Yanofsky, J. Biol. Chem. 270: 12452-12456, 1995 (describing, inter alia, methylated and halogenated Trp and other Trp and indole analogs); and U.S. Pat. Nos. 6,214,790, 6,169,057, 5,776,970, 4,870,097, 4,576,750 and 4,299,838. Other Trp analogs include variants that are substituted (e.g., by a methyl group) at the α or β carbon and, optionally, also at one or more positions of the indole ring. Amino acids comprising two or more aromatic rings, including substituted, unsubstituted, or alternatively substituted variants thereof, are of interest as Trp analogs. In certain embodiments of the invention the Trp analog, e.g., at position 4, is 5-methoxy, 5-methyl-, 1-methyl-, or 1-formyl-tryptophan. In certain embodiments of the invention a Trp analog (e.g., at position 4) comprising a 1-alkyl substituent, e.g., a lower alkyl (e.g., $C_1$-$C_5$) substituent is used. In certain embodiments, N(α) methyl tryptophan or 5-methyltryptophan is used. In some embodiments, an analog comprising a 1-alkanoyl substituent, e.g., a lower alkanoyl (e.g., $C_1$-$C_5$) is used. Examples include 1-acetyl-L-tryptophan and L-β-tryptophan.

In certain embodiments the Trp analog has increased hydrophobic character relative to Trp. For example, the indole ring may be substituted by one or more alkyl (e.g., methyl) groups. In certain embodiments the Trp analog participates in a hydrophobic interaction with C3. Such a Trp analog may be located, e.g., at position 4 relative to the sequence of compstatin. In certain embodiments the Trp analog comprises a substituted or unsubstituted bicyclic aromatic ring component or two or more substituted or unsubstituted monocyclic aromatic ring components.

In certain embodiments the Trp analog has increased propensity to form hydrogen bonds with C3 relative to Trp but does not have increased hydrophobic character relative to Trp. The Trp analog may have increased polarity relative to Trp and/or an increased ability to participate in an electrostatic interaction with a hydrogen bond donor on C3. Certain exemplary Trp analogs with an increased hydrogen bond forming character comprise an electronegative substituent on the indole ring. Such a Trp analog may be located, e.g., at position 7 relative to the sequence of compstatin.

In certain embodiments of the invention the compstatin analog comprises one or more Ala analogs (e.g., at position 9 relative to the sequence of compstatin), e.g., Ala analogs that are identical to Ala except that they include one or more $CH_2$ groups in the side chain. In certain embodiments the Ala analog is an unbranched single methyl amino acid such as 2-Abu. In certain embodiments of the invention the compstatin analog comprises one or more Trp analogs (e.g., at position 4 and/or 7 relative to the sequence of compstatin) and an Ala analog (e.g., at position 9 relative to the sequence of compstatin).

In certain embodiments of the invention the compstatin analog is a compound that comprises a peptide that has a sequence of (X'aa)$_n$-Gln-Asp-Xaa-Gly-(X"aa)$_m$, (SEQ ID NO: 2) wherein each X'aa and each X"aa is an independently selected amino acid or amino acid analog, wherein Xaa is Trp or an analog of Trp, and wherein n>1 and m>1 and n+m is between 5 and 21. The peptide has a core sequence of Gln-Asp-Xaa-Gly (SEQ ID NO: 71), where Xaa is Trp or an analog of Trp, e.g., an analog of Trp having increased propensity to form hydrogen bonds with an H-bond donor relative to Trp but, in certain embodiments, not having increased hydrophobic character relative to Trp. For example, the analog may be one in which the indole ring of Trp is substituted with an electronegative moiety, e.g., a halogen such as fluorine. In one embodiment Xaa is 5-fluorotryptophan. Absent evidence to the contrary, one of skill in the art would recognize that any non-naturally occurring peptide whose sequence comprises this core sequence and that inhibits complement activation and/or binds to C3 will have been designed based on the sequence of compstatin. In an alternative embodiment Xaa is an amino acid or amino acid analog other than a Trp analog that allows the Gln-Asp-Xaa-Gly (SEQ ID NO: 71) peptide to form a β-turn.

In certain embodiments of the invention the peptide has a core sequence of X'aa-Gln-Asp-Xaa-Gly (SEQ ID NO: 3), where X'aa and Xaa are selected from Trp and analogs of Trp. In certain embodiments of the invention the peptide has a core sequence of X'aa-Gln-Asp-Xaa-Gly (SEQ ID NO: 3), where X'aa and Xaa are selected from Trp, analogs of Trp, and other amino acids or amino acid analogs comprising at least one aromatic ring. In certain embodiments of the invention the core sequence forms a β-turn in the context of the peptide. The β-turn may be flexible, allowing the peptide to assume two or more conformations as assessed for example, using nuclear magnetic resonance (NMR). In certain embodiments X'aa is an analog of Trp that comprises a substituted or unsubstituted bicyclic aromatic ring component or two or more substituted or unsubstituted monocyclic aromatic ring components. In certain embodiments of the invention X'aa is selected from the group consisting of 2-naphthylalanine, 1-naphthylalanine, 2-indanylglycine carboxylic acid, dihydrotryptophan, and benzoylphenylalanine. In certain embodiments of the invention X'aa is an analog of Trp that has increased hydrophobic character relative to Trp. For example, X'aa may be 1-methyltryptophan. In certain embodiments of the invention Xaa is an analog of Trp that has increased propensity to form hydrogen bonds relative to Trp but, in certain embodiments, not having increased hydrophobic character relative to Trp. In certain embodiments of the invention the analog of Trp that has increased propensity to form hydrogen bonds relative to Trp comprises a modification on the indole ring of Trp, e.g., at position 5, such as a substitution of a halogen atom for an H atom at position 5. For example, Xaa may be 5-fluorotryptophan.

In certain embodiments of the invention the peptide has a core sequence of X'aa-Gln-Asp-Xaa-Gly-X"aa (SEQ ID NO: 4), where X'aa and Xaa are each independently selected from Trp and analogs of Trp and X"aa is selected from His, Ala, analogs of Ala, Phe, and Trp. In certain embodiments of the invention X'aa is an analog of Trp that has increased hydrophobic character relative to Trp, such as 1-methyltryptophan or another Trp analog having an alkyl substituent on the indole ring (e.g., at position 1, 4, 5, or 6). In certain embodiments X'aa is an analog of Trp that comprises a substituted or unsubstituted bicyclic aromatic ring component or two or more substituted or unsubstituted monocyclic aromatic ring components. In certain embodiments of the invention X'aa is selected from the group consisting of 2-naphthylalanine, 1-naphthylalanine, 2-indanylglycine carboxylic acid, dihydrotryptophan, and benzoylphenylalanine. In certain embodiments of the invention Xaa is an analog of Trp that has increased propensity to form hydrogen bonds with C3 relative to Trp but, in certain embodiments, not having increased hydrophobic character relative to Trp. In certain embodiments of the invention the analog of Trp that has increased propensity to form hydrogen bonds relative to Trp comprises a modification on the indole ring of Trp, e.g., at position 5, such as a substitution of a halogen atom for an H atom at position 5. For example, Xaa may be 5-fluorotryptophan. In certain embodiments X"aa is Ala or an analog of Ala such as Abu or another unbranched single methyl amino acid. In certain embodiments of the invention the peptide has a core sequence of X'aa-Gln-Asp-Xaa-Gly-X"aa (SEQ ID NO: 4), where X'aa and Xaa are each independently selected from Trp, analogs of Trp, and amino acids or amino acid analogs comprising at least one aromatic side chain, and X"aa is selected from His, Ala, analogs of Ala, Phe, and Trp. In certain embodiments X"aa is selected from analogs of Trp, aromatic amino acids, and aromatic amino acid analogs.

In certain preferred embodiments of the invention the peptide is cyclic. The peptide may be cyclized via a bond between any two amino acids, one of which is $(X'aa)_n$ and the other of which is located within $(X"aa)_m$. In certain embodiments the cyclic portion of the peptide is between 9 and 15 amino acids in length, e.g., 10-12 amino acids in length. In certain embodiments the cyclic portion of the peptide is 11 amino acids in length, with a bond (e.g., a disulfide bond) between amino acids at positions 2 and 12. For example, the peptide may be 13 amino acids long, with a bond between amino acids at positions 2 and 12 resulting in a cyclic portion 11 amino acids in length.

In certain embodiments the peptide comprises or consists of the sequence X'aa1-X'aa2-X'aa3-X'aa4-Gln-Asp-Xaa-Gly-X"aa1-X"aa2-X"aa3-X"aa4-X"aa5 (SEQ ID NO: 5). In certain embodiments X'aa4 and Xaa are selected from Trp and analogs of Trp, and X'aa1, X'aa2, X'aa3, X"aa1, X"aa2, X"aa3, X"aa4, and X"aa5 are independently selected from among amino acids and amino acid analogs. In certain embodiments X'aa4 and Xaa are selected from aromatic amino acids and aromatic amino acid analogs. Any one or more of X'aa1, X'aa2, X'aa3, X"aa1, X"aa2, X"aa3, X"aa4, and X"aa5 may be identical to the amino acid at the corresponding position in compstatin. In one embodiment, X"aa1 is Ala or a single methyl unbranched amino acid. The peptide may be cyclized via a covalent bond between (i) X'aa1, X'aa2, or X'aa3; and (ii) X"aa2, X"aa3, X"aa4 or X"aa5. In one embodiment the peptide is cyclized via a covalent bond between X'aa2 and X"aa4. In one embodiment the covalently bound amino acid are each Cys and the covalent bond is a disulfide (S—S) bond. In other embodiments the covalent bond is a C—C, C—O, C—S, or C—N bond. In certain embodiments one of the covalently bound residues is an amino acid or amino acid analog having a side chain that comprises a primary or secondary amine, the other covalently bound residue is an amino acid or amino acid analog having a side chain that comprises a carboxylic acid group, and the covalent bond is an amide bond. Amino acids or amino acid analogs having a side chain that comprises a primary or secondary amine include lysine and diaminocarboxylic acids of general structure $NH_2(CH_2)_nCH(NH_2)COOH$ such as 2,3-diaminopropionic acid (dapa), 2,4-diaminobutyric acid (daba), and ornithine (orn), wherein n=1 (dapa), 2 (daba), and 3 (orn), respectively. Examples of amino acids having a side chain that comprises a carboxylic acid group include dicarboxylic amino acids such as glutamic acid and aspartic acid. Analogs such as beta-hydroxy-L-glutamic acid may also be used. In some embodiments a peptide is cyclized with a thioether bond, e.g., as described in PCT/US2011/052442 (WO/2012/040259). For example, in some embodiments a disulfide bond in any of the peptides is replaced with a thioether bond. In some embodiments, a cystathionine is formed. In some embodiments the cystathionine is a delta-cystathionine or a gamma-cystathionine. In some embodiments a modification comprises replacement of a Cys-Cys disulfide bond between cysteines at X'aa2 and X"aa4 in SEQ ID NO: 5 (or corresponding positions in other sequences) with addition of a $CH_2$, to form a homocysteine at X'aa2 or X"aa4, and introduction of a thioether bond, to form a cystathionine. In one embodiment, the cystathionine is a gamma-cystathionine. In another embodiment, the cystathionine is a delta-cystathionine. Another modification of use in certain embodiments comprises replacement of the disulfide bond with a thioether bond without the addition of a $CH_2$, thereby forming a lantithionine. In some embodiments a compstatin analog having a thioether in place of a disulfide bond has increased stability, at least under some conditions, as compared with the compstatin analog having the disulfide bond.

In certain embodiments, the compstatin analog is a compound that comprises a peptide having a sequence:

Xaa1-Cys-Val-Xaa2-Gln-Asp-Xaa2*-Gly-Xaa3-His-Arg-Cys-Xaa4 (SEQ ID NO: 6); wherein:

Xaa1 is Ile, Val, Leu, $B^1$-Ile, $B^1$-Val, $B^1$-Leu or a dipeptide comprising Gly-Ile or $B^1$-Gly-Ile, and $B^1$ represents a first blocking moiety;

Xaa2 and Xaa2* are independently selected from Trp and analogs of Trp;

Xaa3 is His, Ala or an analog of Ala, Phe, Trp, or an analog of Trp;

Xaa4 is L-Thr, D-Thr, Ile, Val, Gly, a dipeptide selected from Thr-Ala and Thr-Asn, or a tripeptide comprising Thr-Ala-Asn, wherein a carboxy terminal —OH of any of the L-Thr, D-Thr, Ile, Val, Gly, Ala, or Asn optionally is replaced by a second blocking moiety $B^2$; and the two Cys residues are joined by a disulfide bond. In some embodiments, Xaa4 is Leu, Nle, His, or Phe or a depeptide selected from Xaa5-Ala and Xaa5-Asn, or a tripeptide Xaa5-Ala-Asn, wherein Xaa5 is selected from Leu, Nle, His or Phe, and wherein a carboxy terminal —OH of any of the L-Thr, D-Thr, Ile, Val, Gly, Leu, Nle, His, Phe, Ala, or Asn optionally is replaced by a second blocking moiety $B^2$; and the two Cys residues are joined by a disulfide bond.

In other embodiments Xaa1 is absent or is any amino acid or amino acid analog, and Xaa2, Xaa2*, Xaa3, and Xaa4 are as defined above. If Xaa1 is absent, the N-terminal Cys residue may have a blocking moiety $B^1$ attached thereto.

In another embodiment, Xaa4 is any amino acid or amino acid analog and Xaa1, Xaa2, Xaa2*, and Xaa3 are as defined above. In another embodiment Xaa4 is a dipeptide selected from the group consisting of: Thr-Ala and Thr-Asn, wherein the carboxy terminal —OH or the Ala or Asn is optionally replaced by a second blocking moiety $B^2$.

In any of the embodiments of the compstatin analog of SEQ ID NO: 6, Xaa2 may be Trp.

In any of the embodiments of the compstatin analog of SEQ ID NO: 6, Xaa2 may be an analog of Trp comprising a substituted or unsubstituted bicyclic aromatic ring component or two or more substituted or unsubstituted monocyclic aromatic ring components. For example, the analog of Trp may be selected from 2-naphthylalanine (2-Nal), 1-naphthylalanine (1-Nal), 2-indanylglycine carboxylic acid (Ig1), dihydrotryptophan (Dht), and 4-benzoyl-L-phenylalanine.

In any of the embodiments of the compstatin analog of SEQ ID NO: 6, Xaa2 may be an analog of Trp having increased hydrophobic character relative to Trp. For example, the analog of Trp may be selected from 1-methyltryptophan, 4-methyltryptophan, 5-methyltryptophan, and 6-methyltryptophan. In one embodiment, the analog of Trp is 1-methyltryptophan. In one embodiment, Xaa2 is 1-methyltryptophan, Xaa2* is Trp, Xaa3 is Ala, and the other amino acids are identical to those of compstatin.

In any of the embodiments of the compstatin analog of SEQ ID NO: 6, Xaa2* may be an analog of Trp such as an analog of Trp having increased hydrogen bond forming propensity with C3 relative to Trp, which, in certain embodiments, does not have increased hydrophobic character relative to Trp. In certain embodiments the analog of Trp comprises an electronegative substituent on the indole ring. For example, the analog of Trp may be selected from 5-fluorotryptophan and 6-fluorotryptophan.

In certain embodiments of the invention Xaa2 is Trp and Xaa2* is an analog of Trp having increased hydrogen bond forming propensity with C3 relative to Trp which, in certain embodiments, does not have increased hydrophobic character relative to Trp. In certain embodiments of the compstatin analog of SEQ ID NO: 6, Xaa2 is analog of Trp having increased hydrophobic character relative to Trp such as an analog of Trp selected from 1-methyltryptophan, 4-methyltryptophan, 5-methyltryptophan, and 6-methyltryptophan, and and Xaa2* is an analog of Trp having increased hydrogen bond forming propensity with C3 relative to Trp which, in certain embodiments, does not have increased hydrophobic character relative to Trp. For example, in one embodiment Xaa2 is methyltryptophan and Xaa2* is 5-fluorotryptophan.

In certain of the afore-mentioned embodiments, Xaa3 is Ala. In certain of the afore-mentioned embodiments Xaa3 is a single methyl unbranched amino acid, e.g., Abu.

The invention further provides compstatin analogs of SEQ ID NO: 6, as described above, wherein Xaa2 and Xaa2* are independently selected from Trp, analogs of Trp, and other amino acids or amino acid analogs that comprise at least one aromatic ring, and Xaa3 is His, Ala or an analog of Ala, Phe, Trp, an analog of Trp, or another aromatic amino acid or aromatic amino acid analog.

In certain embodiments of the invention the blocking moiety present at the N- or C-terminus of any of the compstatin analogs described herein is any moiety that stabilizes a peptide against degradation that would otherwise occur in mammalian (e.g., human or non-human primate) blood or interstitial fluid. For example, blocking moiety $B^1$ could be any moiety that alters the structure of the N-terminus of a peptide so as to inhibit cleavage of a peptide bond between the N-terminal amino acid of the peptide and the adjacent amino acid. Blocking moiety $B^2$ could be any moiety that alters the structure of the C-terminus of a peptide so as to inhibit cleavage of a peptide bond between the C-terminal amino acid of the peptide and the adjacent amino acid. Any suitable blocking moieties known in the art could be used. In certain embodiments of the invention blocking moiety $B^1$ comprises an acyl group (i.e., the portion of a carboxylic acid that remains following removal of the —OH group). The acyl group typically comprises between 1 and 12 carbons, e.g., between 1 and 6 carbons. For example, in certain embodiments of the invention blocking moiety $B^1$ is selected from the group consisting of: formyl, acetyl, proprionyl, butyryl, isobutyryl, valeryl, isovaleryl, etc. In one embodiment, the blocking moiety $B^1$ is an acetyl group, i.e., Xaa1 is Ac-Ile, Ac-Val, Ac-Leu, or Ac-Gly-Ile.

In certain embodiments of the invention blocking moiety $B^2$ is a primary or secondary amine (—$NH_2$ or —$NHR^1$, wherein R is an organic moiety such as an alkyl group).

In certain embodiments of the invention blocking moiety $B^1$ is any moiety that neutralizes or reduces the positive charge that may otherwise be present at the N-terminus at physiological pH. In certain embodiments of the invention blocking moiety $B^2$ is any moiety that neutralizes or reduces the negative charge that may otherwise be present at the C-terminus at physiological pH.

In certain embodiments of the invention, the compstatin analog is acetylated or amidated at the N-terminus and/or C-terminus, respectively. A compstatin analog may be acetylated at the N-terminus, amidated at the C-terminus, and or both acetylated at the N-terminus and amidated at the C-terminus. In certain embodiments of the invention a compstatin analog comprises an alkyl or aryl group at the N-terminus rather than an acetyl group.

In certain embodiments, the compstatin analog is a compound that comprises a peptide having a sequence:

Xaa1-Cys-Val-Xaa2-Gln-Asp-Xaa2*-Gly-Xaa3-His-Arg-Cys-Xaa4 (SEQ ID NO: 7); wherein:

Xaa1 is Ile, Val, Leu, Ac-Ile, Ac-Val, Ac-Leu or a dipeptide comprising Gly-Ile or Ac-Gly-Ile;

Xaa2 and Xaa2* are independently selected from Trp and analogs of Trp;

Xaa3 is His, Ala or an analog of Ala, Phe, Trp, or an analog of Trp;

Xaa4 is L-Thr, D-Thr, Ile, Val, Gly, a dipeptide selected from Thr-Ala and Thr-Asn, or a tripeptide comprising Thr-Ala-Asn, wherein a carboxy terminal —OH of any of L-Thr, D-Thr, Ile, Val, Gly, Ala, or Asn optionally is replaced by —NH$_2$; and the two Cys residues are joined by a disulfide bond. In some embodiments, Xaa4 is Leu, Nle, His, or Phe or a depeptide selected from Xaa5-Ala and Xaa5-Asn, or a tripeptide Xaa5-Ala-Asn, wherein Xaa5 is selected from Leu, Nle, His or Phe, and wherein a carboxy terminal —OH of any of the L-Thr, D-Thr, Ile, Val, Gly, Leu, Nle, His, Phe, Ala, or Asn optionally is replaced by a second blocking moiety B2; and the two Cys residues are joined by a disulfide bond.

In some embodiments, Xaa1, Xaa2, Xaa2*, Xaa3, and Xaa4 are as described above for the various embodiments of SEQ ID NO: 6. For example, in certain embodiments Xaa2* is Trp. In certain embodiments Xaa2 is an analog of Trp having increased hydrophobic character relative to Trp, e.g., 1-methyltryptophan. In certain embodiments Xaa3 is Ala. In certain embodiments Xaa3 is a single methyl unbranched amino acid.

In certain embodiments of the invention Xaa1 is Ile and Xaa4 is L-Thr.

In certain embodiments of the invention Xaa1 is Ile, Xaa2* is Trp, and Xaa4 is L-Thr.

The invention further provides compstatin analogs of SEQ ID NO: 7, as described above, wherein Xaa2 and Xaa2* are independently selected from Trp, analogs of Trp, other amino acids or aromatic amino acid analogs, and Xaa3 is His, Ala or an analog of Ala, Phe, Trp, an analog of Trp, or another aromatic amino acid or aromatic amino acid analog.

In certain embodiments of any of the compstatin analogs described herein, an analog of Phe is used rather than Phe.

Table 2 provides a non-limiting list of compstatin analogs useful in the present invention. The analogs are referred to in abbreviated form in the left column by indicating specific modifications at designated positions (1-13) as compared to the parent peptide, compstatin. Consistent with usage in the art, "compstatin" as used herein, and the activities of compstatin analogs described herein relative to that of compstatin, refer to the compstatin peptide amidated at the C-terminus. Unless otherwise indicated, peptides in Table 2 are amidated at the C-terminus. Bold text is used to indicate certain modifications. Activity relative to compstatin is based on published data and assays described therein (WO2004/026328, WO2007044668, Mallik, 2005; Katragadda, 2006). Where multiple publications reporting an activity were consulted, the more recently published value is used, and it will be recognized that values may be adjusted in the case of differences between assays. It will also be appreciated that in certain embodiments of the invention the peptides listed in Table 2 are cyclized via a disulfide bond between the two Cys residues when used in the therapeutic compositions and methods of the invention. Alternate means for cyclizing the peptides are also within the scope of the invention. As noted above, in various embodiments of the invention one or more amino acid(s) of a compstatin analog (e.g., any of the compstatin analogs disclosed herein) can be an N-alkyl amino acid (e.g., an N-methyl amino acid). For example, and without limitation, at least one amino acid within the cyclic portion of the peptide, at least one amino acid N-terminal to the cyclic portion, and/or at least one amino acid C-terminal to the cyclic portion may be an N-alkyl amino acid, e.g., an N-methyl amino acid. In some embodiments of the invention, for example, a compstatin analog comprises an N-methyl glycine, e.g., at the position corresponding to position 8 of compstatin and/or at the position corresponding to position 13 of compstatin. In some embodiments, one or more of the compstatin analogs in Table 2 contains at least one N-methyl glycine, e.g., at the position corresponding to position 8 of compstatin and/or at the position corresponding to position 13 of compstatin. In some embodiments, one or more of the compstatin analogs in contains at least one N-methyl isoleucine, e.g., at the position corresponding to position 13 of compstatin. For example, a Thr at or near the C-terminal end of a peptide whose sequence is listed in Table 2 may be replaced by N-methyl Ile. As will be appreciated, in some embodiments the N-methylated amino acids comprise N-methyl Gly at position 8 and N-methyl Ile at position 13. In some embodiments the N-methylated amino acids comprise N-methyl Gly in a core sequence such as SEQ ID NO: 3 or SEQ ID NO: 4.

TABLE 2

| Peptide | Sequence | SEQ ID NO: | Activity over compstatin |
|---|---|---|---|
| Compstatin | H-ICVVQDWGHHRCT-CONH2 | 8 | * |
| Ac-compstatin | Ac-ICVVQDWGHHRCT-CONH2 | 9 | 3× more |
| Ac-V4Y/H9A | Ac-ICVYQDWGAHRCT-CONH2 | 10 | 14× more |
| Ac-V4W/H9A -OH | Ac-ICVWQDWGAHRCT-COOH | 11 | 27× more |
| Ac-V4W/H9A | Ac-ICVWQDWGAHRCT-CONH2 | 12 | 45× more |
| Ac-V4W/H9A/T13dT -OH | Ac-ICVWQDWGAHRCdT-COOH | 13 | 55× more |
| Ac-V4(2-Nal)/H9A | Ac-ICV**(2-Nal)QDWGA**HRCT-CONH2 | 14 | 99× more |
| Ac V4(2-Nal)/H9A -OH | Ac-ICV**(2-Nal)QDWGA**HRCT-COOH | 15 | 38× more |
| Ac V4(1-Nal)/H9A -OH | Ac-ICV**(1-Nal)QDWGA**HRCT-COOH | 16 | 30× more |
| Ac-V42Igl/H9A | Ac-ICV**(2-Igl)QDWGA**HRCT-CONH2 | 17 | 39× more |

TABLE 2-continued

| Peptide | Sequence | SEQ ID NO: | Activity over compstatin |
|---|---|---|---|
| Ac-V42Igl/H9A -OH | Ac-ICV(2-Igl)QDWGAHRCT-COOH | 18 | 37x more |
| Ac-V4Dht/H9A -OH | Ac-ICVDhtQDWGAHRCT-COOH | 19 | 5x more |
| Ac-V4(Bpa)/H9A -OH | Ac-ICV**(Bpa)QDWGA**HRCT-COOH | 20 | 49x more |
| Ac-V4(Bpa)/H9A | Ac-ICV**(Bpa)QDWGA**HRCT-CONH2 | 21 | 86x more |
| Ac-V4(Bta)/H9A -OH | Ac-ICV**(Bta)QDWGA**HRCT-COOH | 22 | 65x more |
| Ac-V4(Bta)/H9A | Ac-ICV**(Bta)QDWGA**HRCT-CONH2 | 23 | 64x more |
| Ac-V4W/H9(2-Abu) | Ac-ICVWQDWG(2-Abu)HRCT-CONH2 | 24 | 64x more |
| +G/V4W/H9A +AN -OH | H-GICVWQDWGAHRCTAN-COOH | 25 | 38x more |
| Ac-V4(5fW)/H9A | Ac-ICV**(5fW)QDWGA**HRCT-CONH$_2$ | 26 | 31x more |
| Ac-V4(5-MeW)/H9A | Ac-ICV**(5-methyl-W)QDWGA**HRCT-CONH$_2$ | 27 | 67x more |
| Ac-V4(1-MeW)/H9A | Ac-ICV**(1-methyl-W)QDWGA**HRCT-CONH$_2$ | 28 | 264x more |
| Ac-V4W/W7(5fW)/H9A | Ac-ICVWQD**(5fW)GA**HRCT-CONH$_2$ | 29 | 121x more |
| Ac-V4(5fW)/W7(5fW)/H9A | Ac-ICV**(5fW)QD(5fW)GA**HRCT-CONH$_2$ | 30 | NA |
| Ac-V4(5-MeW)/W7(5fW)H9A | Ac-ICV**(5-methyl-W)QD(5fW)GA**HRCT-CONH$_2$ | 31 | NA |
| Ac-V4(1MeW)/W7(5fW)/H9A | Ac-ICV**(1-methyl-W)QD(5fW)GA**HRCT-CONH$_2$ | 32 | 264x more |
| +G/V4(6fW)/W7(6fW)H9A +N -OH | H-GICV**(6fW)**QD(6fW)GAHRCTN-COOH | 33 | 126x more |
| Ac-V4(1-formyl-W)/H9A | Ac-ICV**(1-formyl-W)QDWGA**HRCT-CONH$_2$ | 34 | 264x more |
| Ac-V4(5-methoxy-W)/H9A | Ac-ICV**(1-methyoxy-W)QDWGA**HRCT-CONH$_2$ | 35 | 76x more |
| G/V4(5f-W)/W7(5fW)/H9A +N -OH | H-GICV**(5fW)QD(5fW)GAHRCTN**-COOH | 36 | 112x more |

NA = not available

In certain embodiments of the compositions and methods of the invention the compstatin analog has a sequence selected from sequences 9-36. In certain embodiments of the compositions and methods of the invention the compstatin analog has a sequence selected from SEQ ID NOs: 14, 21, 28, 29, 32, 33, 34, and 36. In certain embodiments of the compositions and/or methods of the invention the compstatin analog has a sequence selected from SEQ ID NOs: 30 and 31. In one embodiment of the compositions and methods of the invention the compstatin analog has a sequence of SEQ ID NO: 28. In one embodiment of the compositions and methods of the invention the compstatin analog has a sequence of SEQ ID NO: 32. In one embodiment of the compositions and methods of the invention the compstatin analog has a sequence of SEQ ID NO: 34. In one embodiment of the compositions and methods of the invention the compstatin analog has a sequence of SEQ ID NO: 36.

In some embodiments a blocking moiety $B^1$ comprises an amino acid, which may be represented as Xaa0. In some embodiments blocking moiety $B^2$ comprises an amino acid, which may be represented as XaaN. In some embodiments blocking moiety $B^1$ and/or $B^2$ comprises a non-standard amino acid, such as a D-amino acid, N-alkyl amino acid (e.g., N-methyl amino acid). In some embodiments a blocking moiety $B^1$ and/or $B^2$ comprises a non-standard amino acid that is an analog of a standard amino acid. In some embodiments an amino acid analog comprises a lower alkyl, lower alkoxy, or halogen substituent, as compared with a standard amino acid of which it is an analog. In some embodiments a substituent is on a side chain. In some embodiments a substituent is on an alpha carbon atom. In some embodiments, a blocking moiety $B^1$ comprising an amino acid, e.g., a non-standard amino acid, further comprises a moiety $B^{1a}$. For example, blocking moiety $B^1$ may be represented as $B^{1a}$-Xaa0. In some embodiments $B^{1a}$ neutralizes or reduces a positive charge that may otherwise be present at the N-terminus at physiological pH. In some embodiments $B^{1a}$ comprises or consists of, e.g., an acyl group that, e.g., comprises between 1 and 12 carbons, e.g., between 1 and 6 carbons. In certain embodiments blocking moiety $B^{1a}$ is selected from the group consisting of: formyl, acetyl, proprionyl, butyryl, isobutyryl, valeryl, isovaleryl, etc. In some embodiments, a blocking moiety $B^2$ comprising an amino acid, e.g., a non-standard amino acid, may further comprise a moiety $B^{2a}$. For example, blocking moiety $B^2$ may be represented as XaaN-$B^{2a}$, where N represents the appropriate number for the amino acid (which will depend on the numbering used in the rest of the peptide). In some embodiments $B^{2a}$ neutralizes or reduces a negative charge that may otherwise be present at the C-terminus at physiological pH. In some embodiments $B^{2a}$ comprises or consists of a primary or secondary amine (e.g., NH$_2$). It will be understood that a blocking activity of moiety $B^{1a}$-Xaa0 and/or XaaN-$B^{2a}$ may be provided by either or both components of the moiety in various embodiments. In some embodiments a blocking moiety or portion thereof, e.g., an amino acid residue, may contribute to increasing affinity of the compound for C3 or C3b and/or improve the activity of the compound. In some embodiments a contribution to affinity or activity of an amino acid residue may be at least as important as a contribution to blocking activity. For example, in some embodiments Xaa0 and/or XaaN in $B^{1a}$-Xaa0 and/or XaaN-$B^{2a}$ may function mainly to increase affinity or activity of the compound, while $B^{1a}$ and/or $B^{2a}$ may inhibit digestion of and/or neutralize a charge of the peptide. In some embodiments a compstatin analog comprises the amino acid sequence of any of SEQ ID NOs: 5-36, wherein SEQ ID NOs: 5-36 is further extended at the N- and/or C-terminus. In some embodiments, the sequence may be represented as $B^{1a}$-Xaa0-SEQUENCE-XaaN-$B^{2a}$, where SEQUENCE represents any of SEQ ID NOs: 5-36, wherein $B^{1a}$ and $B^{2a}$ may independently be present or absent. For example, in some embodiments a compstatin analog comprises $B^{1a}$-Xaa0-X'aa1-X'aa2-X'aa3-X'aa4-Gln-Asp-Xaa-Gly-X"aa1-X"aa2-X"aa3-X"aa4-X"aa5-XaaN-$B^{2a}$ (SEQ ID NO: 37), where X'aa1-X'aa2-X'aa3-X'aa4, Xaa, X"aa1, X"aa2, X"aa3, X"aa4, and X"aa5 are as set forth above for SEQ ID NO: 5.

In some embodiments a compstatin analog comprises $B^{1a}$-Xaa0-Xaa1-Cys-Val-Xaa2-Gln-Asp-Xaa2*-Gly-Xaa3-His-Arg-Cys-Xaa4-XaaN-$B^{2a}$ (SEQ ID NO: 38), where Xaa1, Xaa2, Xaa2*, Xaa3, and Xaa4 are as set forth above for SEQ ID NO: 6 or wherein Xaa1, Xaa2, Xaa2*, Xaa3, and Xaa4 are as set forth for SEQ ID NO: 6 or SEQ ID NO: 7.

In some embodiments a compstatin analog comprises $B^{1a}$-Xaa0-Xaa1-Xaa2-Xaa3-Xaa4-Xaa5-Xaa6-Xaa7-Xaa8-Xaa9-Xaa10-Xaa11-Xaa12-Xaa13-XaaN-$B^{2a}$ (SEQ ID NO: 39) wherein Xaa1, Xaa2, Xaa3, Xaa4, Xaa5, Xaa6, Xaa7, Xaa8, Xaa9, Xaa10, Xaa11, Xaa12, and Xaa13 are identical to amino acids at positions 1-13 of any of SEQ ID NOs: 9-36.

In some embodiments Xaa0 and/or XaaN in any compstatin analog sequence comprises an amino acid that comprises an aromatic ring having an alkyl substituent at one or more positions. In some embodiments an alkyl substituent is a lower alkyl substituent. For example, in some embodiments an alkyl substituent is a methyl or ethyl group. In some embodiments a substituent is located at any position that does not destroy the aromatic character of the compound. In some embodiments a substituent is located at any position that does not destroy the aromatic character of a ring to which the substituent is attached. In some embodiments a substituent is located at position 1, 2, 3, 4, or 5. In some embodiments Xaa0 comprises an O-methyl analog of tyrosine, 2-hydroxyphenylalanine or 3-hydroxyphenylalanine. For purposes of the present disclosure, a lower case "m" followed by a three letter amino acid abbreviation may be used to specifically indicate that the amino acid is an N-methyl amino acid. For example, where the abbreviation "mGly" appears herein, it denotes N-methyl glycine (also sometimes referred to as sarcosine or Sar). In some embodiments Xaa0 is or comprises mGly, Tyr, Phe, Arg, Trp, Thr, Tyr(Me), Cha, mPhe, mVal, mIle, mAla, DTyr, DPhe, DArg, DTrp, DThr, DTyr(Me), mPhe, mVal, mIle, DAla, or DCha. For example, in some embodiments a compstatin analog comprises a peptide having a sequence $B^1$-Ile-[Cys-Val-Trp(Me)-Gln-Asp-Trp-mGly-Ala-His-Arg-Cys]-mIle-$B^2$ (SEQ ID NO: 40) or $B^1$-Ile-[Cys-Val-Trp(Me)-Gln-Asp-Trp-mGly-Ala-His-Arg-Cys]-mIle-$B^2$ (SEQ ID NO: 41). The two Cys residues are joined by a disulfide bond in the active compounds. In some embodiments the peptide is acetylated at the N-terminus and/or amidated at the C-terminus. In some embodiments $B^1$ comprises $B^{1a}$-Xaa0 and/or $B^2$ comprises XaaN-$B^{2a}$, as described above. For example, in some embodiments $B^1$ comprises or consists of Gly, mGly, Tyr, Phe, Arg, Trp, Thr, Tyr(Me), mPhe, mVal, mIle, mAla, DTyr, DPhe, DTrp, DCha, DAla and $B^2$ comprises NH$_2$, e.g., a carboxy terminal —OH of mIle is replaced by NH$_2$. In some embodiments $B^1$ comprises or consists of mGly, Tyr, DTyr, or Tyr(Me) and $B^2$ comprises NH$_2$, e.g., a carboxy terminal —OH of mIle is replaced by NH$_2$. In some embodiments an Ile at position Xaa1 is replaced by Gly. Complement inhibition potency and/or C3b binding parameters of selected compstatin analogs are described in WO/2010/127336 (PCT/US2010/033345) and/or in Qu, et al., Immunobiology (2012), doi:10.1016/j.imbio.2012.06.003.

In some embodiments a blocking moiety or portion thereof, e.g., an amino acid residue, may contribute to increasing affinity of the compound for C3 or C3b and/or improve the activity of the compound. In some embodiments a contribution to affinity or activity of an amino acid or amino acid analog may be more significant than a blocking activity.

In certain embodiments of the compositions and methods of the invention the compstatin analog has a sequence as set forth in Table 2, but where the Ac— group is replaced by an alternate blocking moiety $B^1$, as described herein. In some embodiments the —NH$_2$ group is replaced by an alternate blocking moiety $B^2$, as described herein.

In one embodiment, the compstatin analog binds to substantially the same region of the β chain of human C3 as does compstatin. In one embodiment the compstatin analog is a compound that binds to a fragment of the C-terminal portion of the β chain of human C3 having a molecular weight of about 40 kDa to which compstatin binds (Soulika, A. M., et al., *Mol. Immunol.*, 35:160, 1998; Soulika, A. M., et al., *Mol. Immunol.* 43(12):2023-9, 2006). In certain embodiments the compstatin analog is a compound that binds to the binding site of compstatin as determined in a compstatin-C3 structure, e.g., a crystal structure or NMR-derived 3D structure. In certain embodiments the compstatin analog is a compound that could substitute for compstatin in a compstatin-C3 structure and would form substantially the same intermolecular contacts with C3 as compstatin. In certain embodiments the compstatin analog is a compound that binds to the binding site of a peptide having a sequence set forth in Table 2, e.g., SEQ ID NO: 14, 21, 28, 29, 32, 33, 34, or 36 or another compstatin analog sequence disclosed herein in a peptide-C3 structure, e.g., a crystal structure. In certain embodiments the compstatin analog is a compound that binds to the binding site of a peptide having SEQ ID NO: 30 or 31 in a peptide-C3 structure, e.g., a crystal structure. In certain embodiments the compstatin analog is a compound that could substitute for the peptide of SEQ ID NO: 9-36, e.g., a compound that could substitute for the peptide of SEQ ID NO: 14, 21, 28, 29, 32, 33, 34, or 36 or another compstatin analog sequence disclosed herein in a peptide-C3 structure and would form substantially the same intermolecular contacts with C3 as the peptide. In certain embodiments the compstatin analog is a compound that could substitute for the peptide of SEQ ID NO: 30 or 31 in a peptide-C3 structure and would form substantially the same intermolecular contacts with C3 as the peptide.

One of ordinary skill in the art will readily be able to determine whether a compstatin analog binds to a fragment of the C-terminal portion of the β chain of C3 using routine experimental methods. For example, one of skill in the art could synthesize a photocrosslinkable version of the compstatin analog by including a photo-crosslinking amino acid such as p-benzoyl-L-phenylalanine (Bpa) in the compound, e.g., at the C-terminus of the sequence (Soulika, A. M., et al, supra). Optionally additional amino acids, e.g., an epitope tag such as a FLAG tag or an HA tag could be included to facilitate detection of the compound, e.g., by Western blotting. The compstatin analog is incubated with the fragment and crosslinking is initiated. Colocalization of the compstatin analog and the C3 fragment indicates binding. Surface plasmon resonance may also be used to determine whether a compstatin analog binds to the compstatin binding site on C3 or a fragment thereof. One of skill in the art would be able to use molecular modeling software programs to predict whether a compound would form substantially the same intermolecular contacts with C3 as would compstatin or a peptide having the sequence of any of the peptides in Table 2, e.g., SEQ ID NO: 14, 21, 28, 29, 32, 33, 34, or 36, or in some embodiments SEQ ID NO: 30 or 31 or another compstatin analog sequence disclosed herein.

Compstatin analogs may be prepared by various synthetic methods of peptide synthesis known in the art via condensation of amino acid residues, e.g., in accordance with conventional peptide synthesis methods, may be prepared by expression in vitro or in living cells from appropriate nucleic acid sequences encoding them using methods known in the art. For example, peptides may be synthesized using standard solid-phase methodologies as described in Malik, supra, Katragadda, supra, WO2004026328, and/or WO2007062249. Potentially reactive moieties such as amino and carboxyl groups, reactive functional groups, etc., may be protected and subsequently deprotected using various protecting groups and methodologies known in the art. See, e.g., "Protective Groups in Organic Synthesis", $3^{rd}$ ed Greene, T. W. and Wuts, P. G., Eds., John Wiley & Sons, New York: 1999. Peptides may be purified using standard approaches such as reversed-phase HPLC. Separation of diasteriomeric peptides, if desired, may be performed using known methods such as reversed-phase HPLC. Preparations may be lyophilized, if desired, and subsequently dissolved in a suitable solvent, e.g., water. The pH of the resulting solution may be adjusted, e.g. to physiological pH, using a base such as NaOH. Peptide preparations may be characterized by mass spectrometry if desired, e.g., to confirm mass and/or disulfide bond formation. See, e.g., Mallik, 2005, and Katragadda, 2006.

A compstatin analog can be modified by addition of a molecule such as polyethylene glycol (PEG) or similar molecules to stabilize the compound, reduce its immunogenicity, increase its lifetime in the body, increase or decrease its solubility, and/or increase its resistance to degradation. Methods for pegylation are well known in the art (Veronese, F. M. & Harris, Adv. Drug Deliv. Rev. 54, 453-456, 2002; Davis, F. F., Adv. Drug Deliv. Rev. 54, 457-458, 2002); Hinds, K. D. & Kim, S. W. Adv. Drug Deliv. Rev. 54, 505-530 (2002; Roberts, M. J., Bentley, M. D. & Harris, J. M. Adv. Drug Deliv. Rev. 54, 459-476; 2002); Wang, Y. S. et al. Adv. Drug Deliv. Rev. 54, 547-570, 2002). A wide variety of polymers such as PEGs and modified PEGs, including derivatized PEGs to which polypeptides can conveniently be attached are described in Nektar Advanced Pegylation 2005-2006 Product Catalog, Nektar Therapeutics, San Carlos, Calif., which also provides details of appropriate conjugation procedures. In another embodiment a compstatin analog is fused to the Fc domain of an immunoglobulin or a portion thereof. In some other embodiments a compstatin analog is conjugated to an albumin moiety or to an albumin binding peptide. Thus in some embodiments a compstatin analog is modified with one or more polypeptide or non-polypeptide components, e.g., the compstatin analog is pegylated or conjugated to another moiety. In some embodiments the component is not the Fc domain of an immunoglobulin or a portion thereof. A compstatin analog can be provided as a multimer or as part of a supramolecular complex, which can include either a single molecular species or multiple different species (e.g., multiple different analogs).

In some embodiments, a compstatin analog of use in methods described herein is a long-acting compstatin analog, that has a terminal half-life of at least 3, 4, 5, 6, or 7 days. In some embodiments a long-acting compstatin analog is a pegylated compstatin analog. Exemplary long-acting compstatin analogs are described below and/or in PCT/US12/37648, entitled "CELL-REACTIVE, LONG-ACTING, OR TARGETED COMPSTATIN ANALOGS AND USES THEREOF", filed May 11, 2012. In some embodiments of any method or composition relating to a compstatin analog, the compstatin analog comprises a compstatin analog whose sequence comprises any of SEQ ID NOs: 3-41, wherein the compstatin analog is a long-acting compstatin analog.

In some embodiments, a compstatin analog is a multivalent compound comprising a plurality of compstatin analog moieties covalently or noncovalently linked to a polymeric backbone or scaffold. The compstatin analog moieties can be identical or different. In certain embodiments of the invention the multivalent compound comprises multiple instances, or copies, of a single compstatin analog moiety. In other embodiments of the invention the multivalent compound comprises one or more instances of each of two of more non-identical compstatin analog moieties, e.g., 3, 4, 5, or more different compstatin analog moieties. In certain embodiments of the invention the number of compstatin analog moieties ("n") is between 2 and 6. In other embodiments of the invention n is between 7 and 20. In other embodiments of the invention n is between 20 and 100. In other embodiments n is between 100 and 1,000. In other embodiments of the invention n is between 1,000 and 10,000. In other embodiments n is between 10,000 and 50,000. In other embodiments n is between 50,000 and 100,000. In other embodiments n is between 100,000 and 1,000,000.

The compstatin analog moieties may be attached directly to the polymeric scaffold or may be attached via a linking moiety that connects the compstatin analog moiety to the polymeric scaffold. The linking moiety may be attached to a single compstatin analog moiety and to the polymeric scaffold. Alternately, a linking moiety may have multiple compstatin analog moieties joined thereto so that the linking moiety attaches multiple compstatin analog moieties to the polymeric scaffold.

In some embodiments, a compstatin analog comprises an amino acid having a side chain comprising a primary or secondary amine, e.g., a Lys residue. For example, any of the compstatin analog sequences disclosed herein may be extended or modified by addition of a linker comprising one or more amino acids, e.g., one or more amino acids comprising a primary or secondary amine, e.g., in a side chain thereof. For example, a Lys residue, or a sequence comprising a Lys residue, is added at the N-terminus and/or C-terminus of the compstatin analog. In some embodiments, the Lys residue is separated from the cyclic portion of the compstatin analog by a rigid or flexible spacer. A linker or spacer may, for example, comprise a substituted or unsubstituted, saturated or unsaturated alkyl chain, oligo(ethylene glycol) chain, and/or other moieties. The length of the chain may be, e.g., between 2 and 20 carbon atoms. In some embodiments the spacer is or comprises a peptide. The peptide spacer may be, e.g., between 1 and 20 amino acids in length, e.g., between 4 and 20 amino acids in length. Suitable spacers can comprise or consist of multiple Gly residues, Ser residues, or both, for example. Optionally, the amino acid having a side chain comprising a primary or secondary amine and/or at least one amino acid in a spacer is a D-amino acid. A PEG moiety or similar molecule or polymeric scaffold may be linked to the primary or secondary amine, optionally via a linker. In some embodiments, a bifunctional linker is used. Abifunctional linker may comprise two reactive functional groups, which may be the same or different in various embodiments. In various embodiments, one or more linkers, spacers, and/or techniques of conjugation described in Hermanson, supra, is used.

Any of a variety of polymeric backbones or scaffolds could be used. For example, the polymeric backbone or scaffold may be a polyamide, polysaccharide, polyanhydride, polyacrylamide, polymethacrylate, polypeptide, polyethylene oxide, or dendrimer. Suitable methods and polymeric backbones are described, e.g., in WO98/46270 (PCT/US98/07171) or WO98/47002 (PCT/US98/06963). In one embodiment, the polymeric backbone or scaffold comprises multiple reactive functional groups, such as carboxylic acids, anhydride, or succinimide groups. The polymeric backbone or scaffold is reacted with the compstatin analogs. In one embodiment, the compstatin analog comprises any of a number of different reactive functional groups, such as carboxylic acids, anhydride, or succinimide groups, which are reacted with appropriate groups on the polymeric backbone. Alternately, monomeric units that could be joined to one another to form a polymeric backbone or scaffold are first reacted with the compstatin analogs and the resulting monomers are polymerized. In another embodiment, short chains are prepolymerized, functionalized, and then a mixture of short chains of different composition are assembled into longer polymers.

In some aspects a moiety such as a polyethylene glycol (PEG) chain or other polymer(s) that, e.g., stabilize the compound, increase its lifetime in the body, increase its solubility, decrease its immunogenicity, and/or increase its resistance to degradation may be referred to herein as a "clearance reducing moiety" (CRM), and a compstatin analog comprising such a moiety may be referred to as a long-acting compstatin analog.

In some aspects, a long-acting compstatin analog comprises a compound of formula M-L-A, wherein A is a moiety that comprises a CRM, L is an optionally present linking portion, and M comprises a compstatin analog moiety. The compstatin analog moiety can comprise any compstatin analog, e.g., any compstatin analog described above, in various embodiments. Formula M-L-A encompasses embodiments in which L-A is present at the N-terminus of the compstatin analog moiety, embodiments in which L-A is present at the C-terminus of the compstatin analog moiety, embodiments in which L-A is attached to a side chain of an amino acid of the compstatin analog moiety, and embodiments where the same or different L-As are present at both ends of M. It will be appreciated that when certain compstatin analog(s) are present as a compstatin analog moiety in a compound of formula M-L-A, a functional group of the compstatin analog will have reacted with a functional group of L to form a covalent bond to A or L. For example, a long-acting compstatin analog in which the compstatin analog moiety comprises a compstatin analog that contains an amino acid with a side chain containing a primary amine ($NH_2$) group (which compstatin analog can be represented by formula $R^1$—($NH_2$)), can have a formula $R^1$—NH-L-A in which a new covalent bond to L (e.g., N—C) has been formed and a hydrogen lost. Thus the term "compstatin analog moiety" includes molecular structures in which at least one atom of a compstatin analog participates in a covalent bond with a second moiety, which may, e.g., modification of a side chain. Similar considerations apply to compstatin analog moieties present in multivalent compounds. In some embodiments, a blocking moiety at the N-terminus or C-terminus of a compstatin analog is replaced by L-A in the structure of a long-acting compstatin analog.

In some embodiments, L comprises an unsaturated moiety such as —CH=CH— or —$CH_2$—CH=CH—; a moiety comprising a non-aromatic cyclic ring system (e.g., a cyclohexyl moiety), an aromatic moiety (e.g., an aromatic cyclic ring system such as a phenyl moiety); an ether moiety (—C—O—C—); an amide moiety (—C(=O)—N—); an ester moiety (—CO—O—); a carbonyl moiety (—C(=O)—); an imine moiety (—C=N—); a thioether moiety (—C—S—C—); an amino acid residue; and/or any moiety that can be formed by the reaction of two compatible reactive functional groups. In certain embodiments, one or more moieties of a linking portion is/are substituted by independent replacement of one or more of the hydrogen (or other) atoms thereon with one or more moieties including, but not limited to aliphatic; aromatic, aryl; alkyl, aralkyl, alkanoyl, aroyl, alkoxy; thio; F; C1; Br; I; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; - or -GRG1 wherein G is —O—, —S—, —NRG2-, —C(=O)—, —S(=O)—, —$SO_2$-, —C(=O)O—, —C(=O)NRG2-, —OC(=O)—, —NRG2C(=O)—, —OC(=O)O—, —OC(=O)NRG2-, —NRG2C(=O)O—, —NRG2C(=O)NRG2-, —C(=S)—, —C(=S)S—, —SC(=S)—, —SC(=S)S—, —C(=NRG2)-, —C(=NRG2)O—, —C(=NRG2)NRG3-, —OC(=NRG2)-, —NRG2C(=NRG3)-, —$NRG2SO_2$-, —$NRG2SO_2NRG3$-, or —$SO_2NRG2$-, wherein each occurrence of RG1, RG2 and RG3 independently includes, but is not limited to, hydrogen, halogen, or an optionally substituted aliphatic, aromatic, or aryl moiety. It will be appreciated that cyclic ring systems when present as substituents may optionally be attached via a linear moiety. Combinations of substituents and variables envisioned by this invention are preferably those that result in the formation of stable compounds useful in any one or more of the methods described herein, e.g., useful for the treatment of one or more disorders and/or for contacting a cell, tissue, or organ, as described herein, and/or useful as intermediates in the manufacture of one or more such compounds.

L can comprise one or more of any of the moieties described in the preceding paragraph, in various embodiments. In some embodiments, L comprises two or more different moieties linked to one another to form a structure typically having a length of between 1 to about 60 atoms, between 1 to about 50 atoms, e.g., between 1 and 40, between 1 and 30, between 1 and 20, between 1 and 10, or between 1 and 6 atoms, where length refers to the number of atoms in the main (longest) chain. In some embodiments, L comprises two or more different moieties linked to one another to form a structure typically having between 1 to about 40, e.g., between 1 and 30, e.g., between 1 and 20, between 1 and 10, or between 1 and 6 carbon atoms in the main (longest) chain.

In some embodiments, a long-acting compstatin analog has an average plasma half-life of at least 1 day, e.g., 1-3 days, 3-7 days, 7-14 days, or 14-28 days, when administered IV at a dose of 10 mg/kg to humans or to non-human primates. In some embodiments, average plasma half-life of a long-acting compstatin analog following administration IV at a dose of 10 mg/kg to humans or to non-human primates is increased by at least a factor of 2, e.g., by a factor of 2-5, 5-10, 10-50, or 50-100-fold as compared with that of a corresponding compstatin analog having the same amino acid sequence (and, if applicable, one or more blocking moiet(ies)) but not comprising the CRM.

In some embodiments, a plasma half-life is a terminal half-life after administration of a single IV dose. In some embodiments, a plasma half-life is a terminal half-life after steady state has been reached following administration of multiple IV doses. In some embodiments, a long-acting compstatin analog achieves a Cmax in plasma at least 5-fold as great as that of a corresponding compstatin analog not comprising the CRM, e.g., between 5- and 50-fold as great, following administration of a single IV dose to a primate, or following administration of multiple IV doses. In some embodiments, a long-acting compstatin analog achieves a Cmax in plasma between 10- and 20-fold as great as that of a corresponding compstatin analog not comprising the CRM following administration of a single IV dose to a primate, or following administration of multiple IV doses. In some embodiments a primate is human. In some embodiments a primate is a non-human primate, e.g., a monkey, such as a Cynomolgus monkey or Rhesus monkey. In some embodiments, renal clearance of a long-acting compstatin analog during the first 24 hours following administration IV at a dose of 10 mg/kg to humans or to non-human primates is reduced by at least a factor of 2, e.g., by a factor of 2-5, 5-10, 10-50, or 50-100-fold as compared with renal clearance of a corresponding compstatin analog. The concentration of compstatin analog can be measured in blood and/or urine samples using, e.g., UV, HPLC, mass spectrometry (MS) or antibody to the CRM, or combinations of such methods, such as LC/MS or LC/MS/MS. Pharmacokinetic parameters such as half-life and clearance can be determined using methods known to those of ordinary skill in the art. Pharmacokinetic analysis can be performed, e.g., with WinNonlin software v 5.2 (Pharsight Corporation, St. Louis, Mo.).

In some embodiments, a long-acting compstatin analog has a molar activity of at least about 10%, 20%, 30%, e.g., between 30% and 40%, between 30% and 50%, between 30% and 60%, between 30% and 70%, between 30% and 80%, between 30% and 90%, or more, of the activity of a corresponding compstatin analog having the same amino acid sequence (and, if applicable, one or more blocking moiet(ies)) but not comprising a CRM. In some embodiments wherein a long-acting compstatin analog comprises multiple compstatin analog moieties, the molar activity of the long-acting compstatin analog is at least about 10%, 20%, or 30%, e.g., between 30% and 40%, between 30% and 50%, between 30% and 60%, between 30% and 70%, between 30% and 80%, between 30% and 90%, or more, of the sum of the activities of said compstatin analog moieties. In some embodiments, a polyethylene glycol (PEG) comprises a $(CH_2CH_2O)_n$ moiety having a molecular weight of at least 500 daltons. In some embodiments, a linker comprises an $(CH_2CH_2O)_n$ moiety having an average molecular weight of between about 500; 1,000; 1,500; 2,000; 5,000; 10,000; 20,000; 30,000; 40,000; 50,000; 60,000; 70,000; 80,000; 90,000; and 100,000 daltons. "Average molecular weight" refers to the number average molecular weight. In some embodiments, the polydispersity D of a $(CH_2CH_2O)n$ moiety is between 1.0005 and 1.50, e.g., between 1.005 and 1.10, 1.15, 1.20, 1.25, 1.30, 1.40, or 1.50, or any value between 1.0005 and 1.50.

In some embodiments, a $(CH_2CH_2O)n$ moiety is monodisperse and the polydispersity of a $(CH_2CH_2O)n$ moiety is 1.0. Such monodisperse $(CH_2CH_2O)n$ moieties are known in the art and are commercially available from Quanta BioDesign (Powell, Ohio), and include, by way of nonlimiting example, monodisperse moieties where n is 2, 4, 6, 8, 12, 16, 20, or 24.

In some embodiments, a compound comprises multiple $(CH_2CH_2O)_n$ moieties wherein the total molecular weight of said $(CH_2CH_2O)_n$ moieties is between about 1,000; 5,000; 10,000; 20,000; 30,000; 40,000; 50,000; 60,000; 70,000; 80,000; 90,000; and 100,000 daltons. In some embodiments, the compound comprises multiple $(CH_2CH_2O)_n$ moieties having defined lengths, e.g., n=4, 6, 8, 10, 12, 14, 16, 18, 20, 22, 24, 26, 28, or 30 or more. In some embodiments, the compound comprises a sufficient number of $(CH_2CH_2O)_n$ moieties having defined lengths to result in a total molecular weight of said $(CH_2CH_2O)_n$ moieties of between about 1,000; 5,000; 10,000; 20,000; 30,000; 40,000; 50,000; 60,000; 70,000; 80,000; 90,000; and 100,000 daltons. In some embodiments n is between about 30 and about 3000. In some embodiments a compstatin analog moiety is attached at each end of a linear PEG. A bifunctional PEG having a reactive functional group at each end of the chain may be used, e.g., as described above. In some embodiments the reactive functional groups are identical while in some embodiments different reactive functional groups are present at each end. In some embodiments, multiple $(CH_2CH_2O)_n$ moieties are provided as a branched structure. The branches may be attached to a linear polymer backbone (e.g., as a comb-shaped structure) or may emanate from one or more central core groups, e.g., as a star structure. In some embodiments, a branched molecule has 3 to 10 $(CH_2CH_2O)_n$ chains. In some embodiments, a branched molecule has 4 to 8 $(CH_2CH_2O)_n$ chains. In some embodiments, a branched molecule has 10, 9, 8, 7, 6, 5, 4, or 3 $(CH_2CH_2O)_n$ chains. In some embodiments, a star-shaped molecule has 10-100, 10-50, 10-30, or 10-20 $(CH_2CH_2O)_n$ chains emanating from a central core group. In some embodiments a long-acting compstatin analog thus may comprise, e.g., 3-10 compstatin analog moieties, e.g., 4-8 compstatin analog moieties, each attached to a $(CH_2CH_2O)_n$ chain via a functional group at the end of the chain. In some embodiments a long-acting compstatin analog may comprise, e.g., 10-100 compstatin analog moieties, each attached to a $(CH_2CH_2O)_n$ chain via a functional group at the end of the chain. In some embodiments, branches (sometimes referred to as "arms") of a branched or star-shaped PEG contain about the same number of $(CH_2CH_2O)$ moieties. In some embodiments, at least some of the branch lengths may differ. It will be understood that in some embodiments one or more $(CH_2CH_2O)_n$ chains does not have a comptain analog moiety attached thereto. In some embodiments at least about 30%, 40%, 50%, 60%, 70%, 80%, 90%, 95%, or 100% of the chains has a compstatin analog moiety attached thereto.

In genera and compounds depicted herein, a polyethylene glycol moiety is drawn with the oxygen atom on the right side of the repeating unit or the left side of the repeating unit. In cases where only one orientation is drawn, the present invention encompasses both orientations (i.e., $(CH_2CH_2O)_n$ and $(OCH_2CH_2)_n$) of polyethylene glycol moieties for a given compound or genus, or in cases where a compound or genus contains multiple polyethylene glycol moieties, all combinations of orientations are encompasses by the present disclosure.

Formulas of some exemplary monofunctional PEGs comprising a reactive functional group are illustrated below. For illustrative purposes, formulas in which the reactive functional group(s) comprise an NHS ester are depicted, but other reactive functional groups could be used, e.g., as described above. In some embodiments, the $(CH_2CH_2O)_n$ are depicted as terminating at the left end with a methoxy group ($OCH_3$) but it will be understood that the chains depicted below and elsewhere herein may terminate with a different OR moiety (e.g., an aliphatic group, an alkyl group, a lower alkyl group, or any other suitable PEG end group) or an OH group. It will also be appreciated that moieties other than those depicted may connect the $(CH_2CH_2O)_n$ moieties with the NHS group in various embodiments.

In some embodiments, a monofunctional PEG is of formula A:

Formula A wherein "Reactive functional group" and n are as defined above and described in classes and subclasses herein;
$R^1$ is hydrogen, aliphatic, or any suitable end group; and
T is a covalent bond or a $C_{1-12}$ straight or branched, hydrocarbon chain wherein one or more carbon units of T are optionally and independently replaced by —O—, —S—, —N($R^x$)—, —C(O)—, —C(O)O—, —OC(O)—, —N($R^x$)C(O)—, —C(O)N($R^x$)—, —S(O)—, —S(O)$_2$—, —N($R^x$)SO$_2$—, or —SO$_2$N($R^x$)—; and
each $R^x$ is independently hydrogen or $C_{1-6}$ aliphatic.

Exemplary monofunctional PEGs of formula A include:

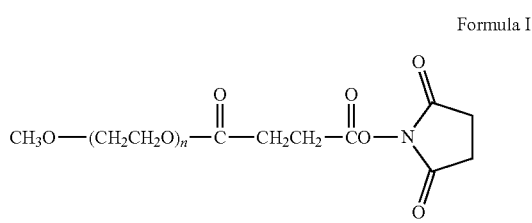

Formula I

In Formula I, the moiety comprising the reactive functional group has the general structure —CO—$(CH_2)_m$—COO—NHS, where m=2. In some embodiments, a monofunctional PEGs has the structure of Formula I, where m is between 1 and 10, e.g., between 1 and 5. For example, in some embodiments m is 3, as shown below:

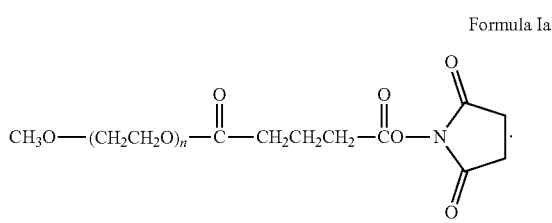

Formula Ia

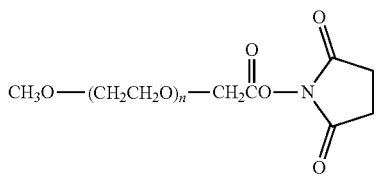

Formula II

In Formula II, the moiety comprising the reactive functional group has the general structure —$(CH_2)_m$—COO—NHS, where m=1. In some embodiments a monofunctional PEG has the structure of Formula II, where m is between 1 and 10 (e.g., wherein m is 5 as shown in Formula III below), or wherein m is 0 (as shown below in Formula IIIa).

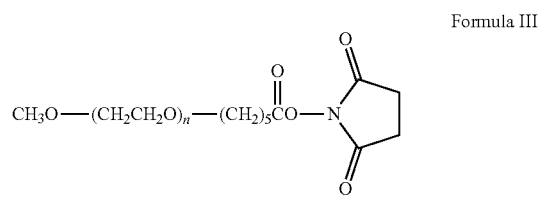

Formula III

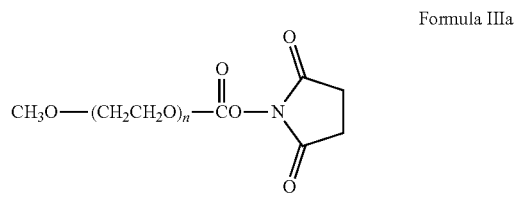

Formula IIIa

In some embodiments a bifunctional linear PEG comprises a moiety comprising a reactive functional group at each of its ends. The reactive functional groups may be the same (homobifunctional) or different (heterobifunctional). In some embodiments the structure of a bifunctional PEG may be symmetric, wherein the same moiety is used to connect the reactive functional group to oxygen atoms at each end of the —$(CH_2CH_2O)_n$ chain. In some embodiments different moieties are used to connect the two reactive functional groups to the PEG portion of the molecule. The structures of exemplary bifunctional PEGs are depicted below. For illustrative purposes, formulas in which the reactive functional group(s) comprise an NHS ester are depicted, but other reactive functional groups could be used.

In some embodiments, a bifunctional linear PEG is of formula B:

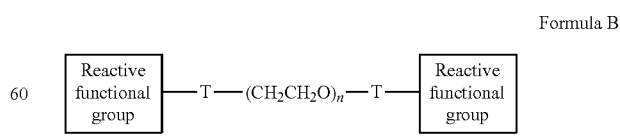

Formula B wherein each T and "Reactive functional group" is independently as defined above and described in classes and subclasses herein, and n is as defined above and described in classes and subclasses herein.

Exemplary bifunctional PEGs of formula B include:

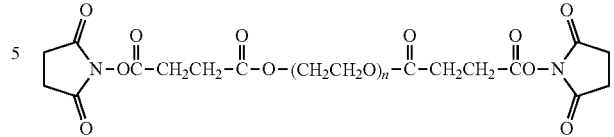
Formula V

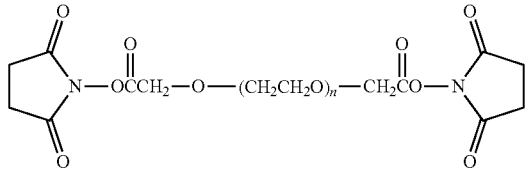
Formula IV

In Formula V, the moiety comprising the reactive functional group has the general structure —CO—$(CH_2)_m$—COO—NHS, where m=2. In some embodiments, a bifunctional PEGs has the structure of Formula V, where m is between 1 and 10, e.g., between 1 and 5.

In Formula IV, the moiety comprising the reactive functional group has the general structure —$(CH_2)_m$—COO—NHS, where m=1. In some embodiments, a bifunctional PEGs has the structure of Formula IV, where m is between 1 and 10, e.g., between 1 and 5.

In some embodiments, a branched, comb, or star-shaped PEG comprises a moiety comprising a reactive functional group at the end of each of multiple —$(CH_2CH_2O)_n$ chains. The reactive functional groups may be the same or there may be at least two different groups. In some embodiments, a branched, comb, or star-shaped PEG is of the following formulae:

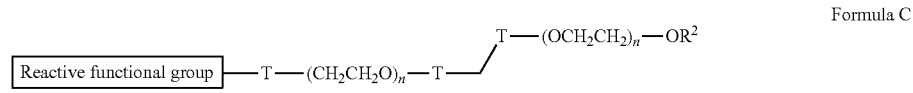
Formula C

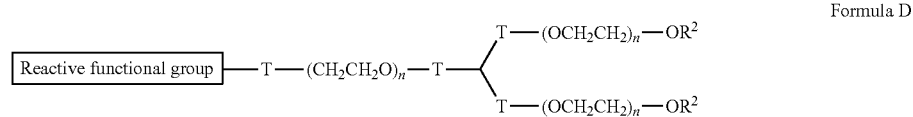
Formula D

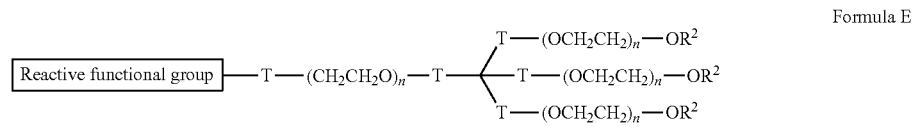
Formula E

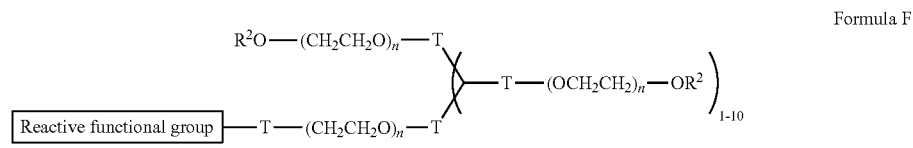
Formula F

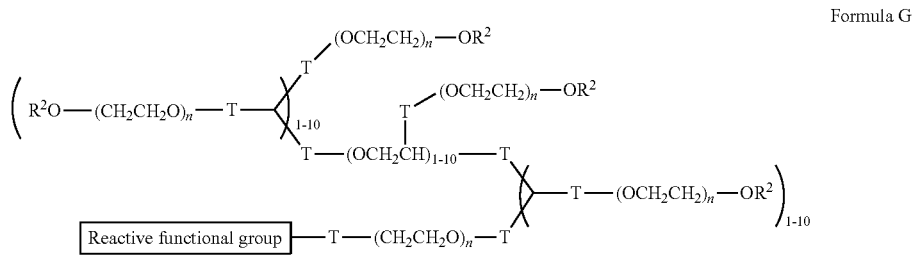
Formula G

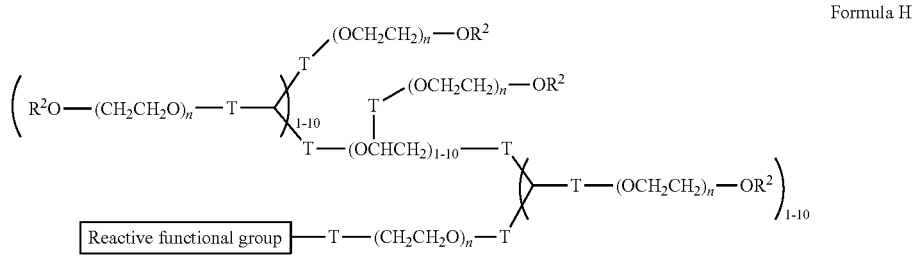
Formula H wherein each $R^2$ is independently a "Reactive functional group" or $R^1$, and each T, n, and "Reactive functional group" is independently as defined above and described in classes and subclasses herein. The structure of exemplary branched PEGs (having 8 arms, or branches) comprising NHS moieties as reactive functional groups is depicted below:

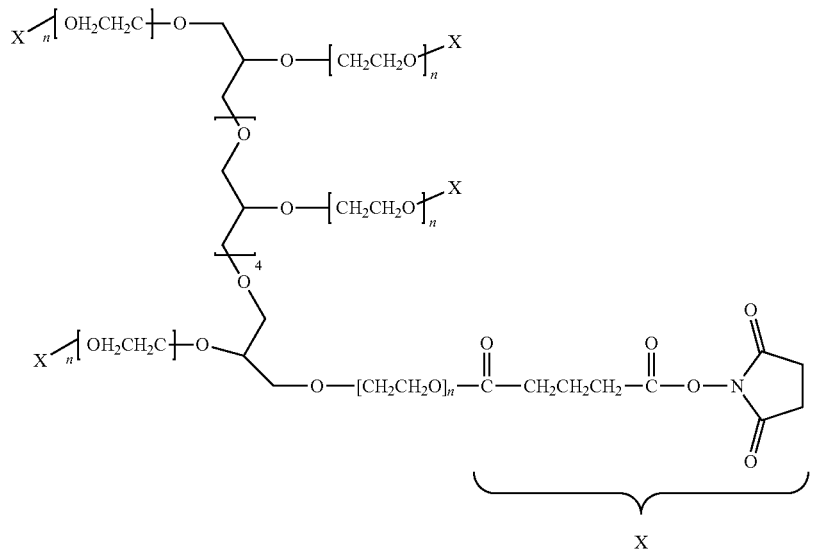

Formula VI

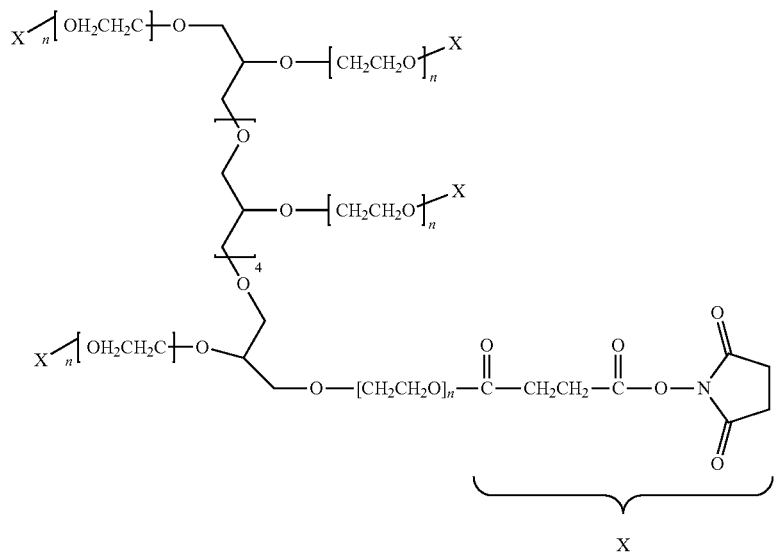

Formula VII

The structure of exemplary branched PEGs (having 4 arms, or branches) comprising NHS moieties as reactive functional groups is depicted below:

Formula VIII

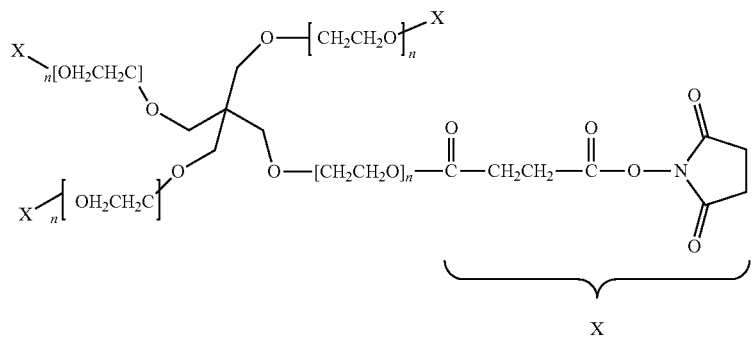

Formula IX

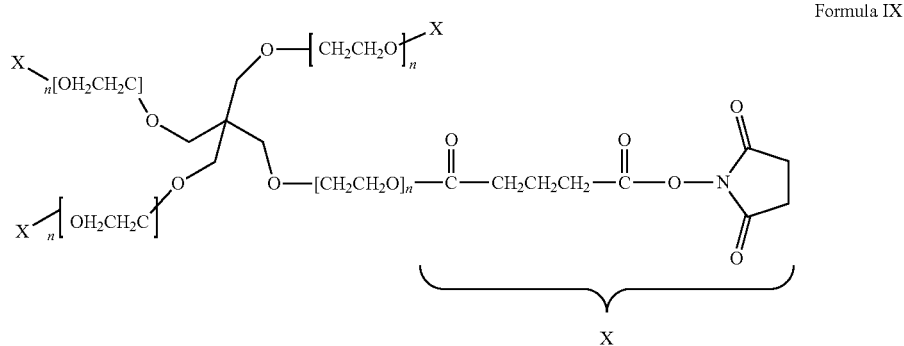

The number of branches emanating from the backbone may be varied. For example, the number 4 in the above formulae VI and VII may be changed to any other integer between 0 and 10 in various embodiments. In certain embodiments, one or more branches does not contain a reactive function group and the branch terminates with a —CH$_2$CH$_2$OH or —CH$_2$CH$_2$OR group, as described above.

In some embodiments a branched PEG has the structure of Formula VII, VIII, or IX (or variants thereof having different numbers of branches) with the proviso that x is

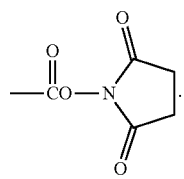

In some embodiments a branched PEG has the structure of Formula VII, VIII, or IX (or variants thereof having different numbers of branches) with the proviso that x is

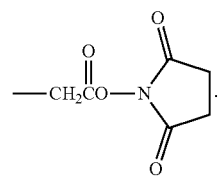

Of course the methylene (CH$_2$) group in the above x moiety may instead comprise a longer alkyl chain (CH$_2$)$_m$, where m is up to 2, 3, 4, 5, 6, 8, 10, 20, or 30, or may comprise one or more other moieties described herein.

In some embodiments, exemplary branched PEGs having NHS or malemide reactive groups are depicted below:

Formula X

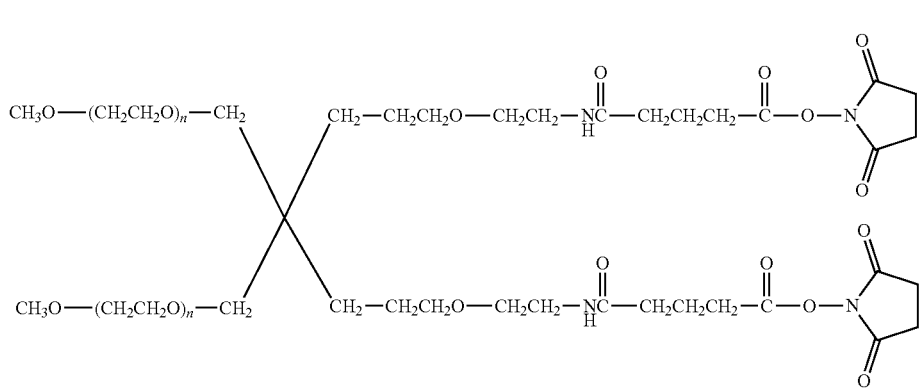

-continued

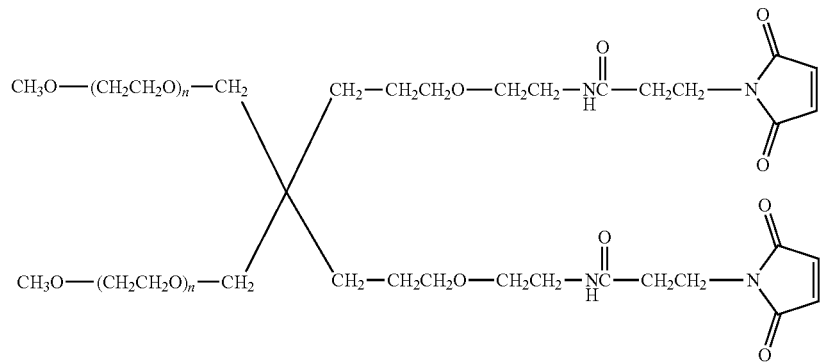

Formula XI

In some embodiments, a variant of Formula X or XI are used, wherein 3 or each of the 4 branches comprise a reactive functional group.

Still other examples of PEGS may be represented as follows:

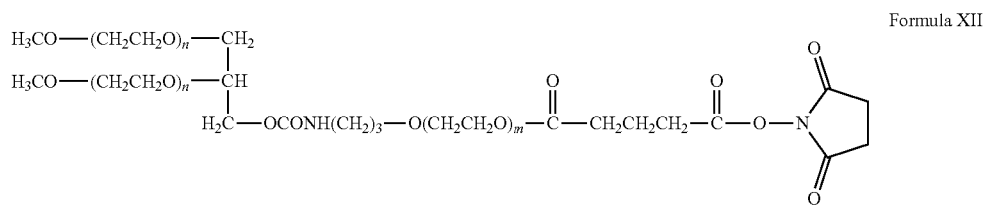

Formula XII

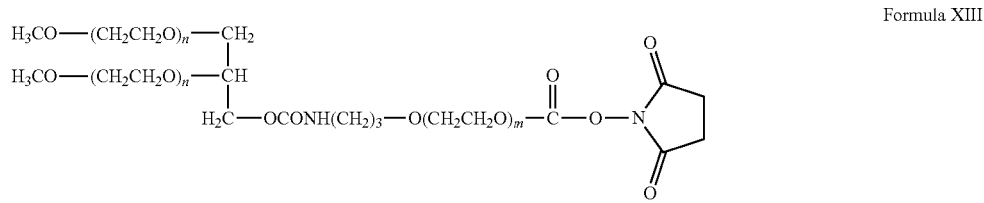

Formula XIII

As noted above, it will be appreciated that, as described herein, in various embodiments any of a variety of moieties may be incorporated between the peptide component and $(CH_2CH_2O)_n$—R moiety of a long-acting compstatin analog, such as an linear alkyl, ester, amide, aromatic ring (e.g., a substituted or unsubstituted phenyl), a substituted or unsubstituted cycloalkyl structure, or combinations thereof. In some embodiments such moiet(ies) may render the compound more susceptible to hydrolysis, which may release the peptide portion of the compound from the CRM. In some embodiments, such release may enhance the in vivo tissue penetration and/or activity of the compound. In some embodiments hydrolysis is general (e.g., acid-base) hydrolysis. In some embodiments hydrolysis is enzyme-catalyzed, e.g., esterase-catalyzed. Of course both types of hydrolysis may occur. Examples of PEGs comprising one or more such moieties and an NHS ester as a reactive functional group are as follows:

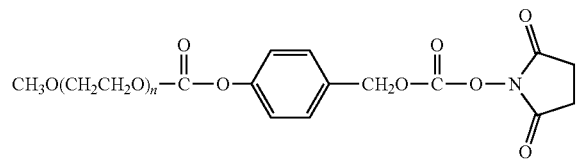

Formula XIV

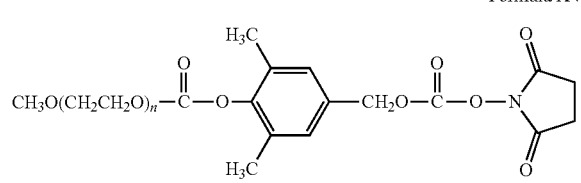

Formula XV

Formula XVI

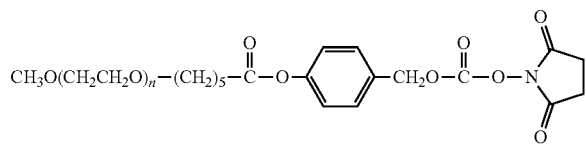

In some embodiments a branched (multi-arm) PEG or star-shaped PEG comprises a pentaerythritol core, hexaglycerin core, or tripentaerythritol core. It will be understood that the branches may not all emanate from a single point in certain embodiments.

Monofunctional, bifunctional, branched, and other PEGs comprising one or more reactive functional groups may be obtained from, e.g., NOF America Corp. White Plains, N.Y. or BOC Sciences 45-16 Ramsey Road Shirley, N.Y. 11967, USA, among others.

In some embodiments a compstatin analog of, e.g., any of SEQ ID NOs: 3-41 is extended by one or more amino acids at the N-terminus, C-terminus, or both, wherein at least one of the amino acids has a side chain that comprises a reactive functional group such as a primary or secondary amine, a sulfhydryl group, a carboxyl group (which may be present as a carboxylate group), a guanidino group, a phenol group, an indole ring, a thioether, or an imidazole ring, wherein the reactive functional group may be used, e.g., to attach a CRM or moiety comprising a CRM. In some embodiments, the amino acid(s) is/are L-amino acids. In some embodiments, any one or more of the amino acid(s) is a D-amino acid. If multiple amino acids are added, the amino acids can be independently selected. In some embodiments, the reactive functional group (e.g., a primary or secondary amine) is used as a target for addition of a moiety comprising a CRM. Amino acids having a side chain that comprises a primary or secondary amine include lysine (Lys) and diaminocarboxylic acids of general structure $NH_2(CH_2)_nCH(NH_2)COOH$ such as 2,3-diaminopropionic acid (dapa), 2,4-diaminobutyric acid (daba), and ornithine (orn), wherein n=1 (dapa), 2 (daba), and 3 (orn), respectively. In some embodiments at least one amino acid is cysteine, aspartic acid, glutamic acid, arginine, tyrosine, tryptophan, methionine, or histidine. Cysteine has a side chain comprising a sulfhydryl group. Aspartic acid and glutamic acid have a side chain comprising a carboxyl group (ionizable to a carboxylate group). Arginine has a side chain comprising a guanidino group. Tyrosine has a side chain comprising a phenol group (ionizable to a phenolate group). Tryptophan has a side chain comprising an indole ring include include, e.g., tryptophan. Methionine has a side chain comprising a thioether group include, e.g., methionine. Histidine has a side chain comprising an imidazole ring. A wide variety of non-standard amino acids having side chains that comprise one or more such reactive functional group(s) are available, including naturally occurring amino acids and amino acids not found in nature. See, e.g., Hughes, B. (ed.), *Amino Acids, Peptides and Proteins in Organic Chemistry*, Volumes 1-4, Wiley-VCH (2009-2011); Blaskovich, M., Handbook on Syntheses of Amino Acids General Routes to Amino Acids, Oxford University Press, 2010. Embodiments in which one or more nonstandard amino acid(s) is/are used to provide a target for addition of a moiety comprising a CRM are encompassed. Any one or more of the amino acid(s) may be protected as appropriate during synthesis of the compound. For example, one or more amino acid(s) may be protected during reaction(s) involving the target amino acid side chain. In some embodiments, wherein a sulfhydryl-containing amino acid is used as a target for addition of a moiety comprising a CRM, the sulfhydryl is protected while the compound is being cyclized by formation of an intramolecular disulfide bond between other amino acids such as cysteines.

In certain discussion herein, an amino acid having a side chain containing an amine group is used as an example. Analogous embodiments are encompassed in which an amino acid having a side chain containing a different reactive functional group is used. In some embodiments, an amino acid having a side chain comprising a primary or secondary amine is attached directly to the N-terminus or C-terminus of any of SEQ ID NOs: 3-41 via a peptide bond. In some embodiments, an amino acid having a side chain comprising a primary or secondary amine is attached to the N- or C-terminus of any of SEQ ID NOs: 3-41 via a linking portion, which may contain any one or more of the linking moieties described above. In some embodiments, at least two amino acids are appended to either or both termini. The two or more appended amino acids may be joined to each other by peptide bonds or at least some of the appended amino acids may be joined to each other by a linking portion, which may contain any one or more of the linking moieties described herein.

It will be understood that a corresponding compstatin analog not comprising the CRM may also lack one or more such amino acids which are present in the long-acting compstatin analog to which it corresponds. Thus, a corresponding compstatin analog comprising any of SEQ ID NOs: 3-41 and lacking a CRM will be understood to "have the same amino acid sequence" as SEQ ID NO: 3-41, respectively. For example, a corresponding compstatin analog comprising the amino acid sequence of SEQ ID NO: 14, 21, 28, 29, 32, 33, 34, or 36 and lacking a CRM will be understood to "have the same amino acid sequence" as SEQ ID NO: 14, 21, 28, 29, 32, 33, 34, or 36, respectively.

For descriptive purposes a peptide having the amino acid sequence Ile-Cys*-Val-(1Me)Trp-Gln-Asp-Trp-Gly-Ala-His-Arg-Cys*-Thr (SEQ ID NO: 42) (corresponding to the compstatin analog of SEQ ID NO: 28, wherein asterisks in SEQ ID NO: 42 represent cysteines joined by a disulfide bond in the active compound, and (1Me)Trp represents 1-methyl-tryptophan)), is used as an exemplary compstatin analog moiety; $(CH_2)_n$ and $(O-CH2-CH2)_n$ are used as examples of linking portions; lysine is used as an example of an amino acid comprising a reactive functional group (in some compounds), and acetylation and amidation of the N- and C-termini, respectively, are used as optionally present exemplary blocking moieties in some compounds and may be represented in italics, i.e., as Ac and $NH_2$ respectively. In some embodiments, SEQ ID NO: 42 is extended to comprise a Lys residue at the N- or C-terminus of the peptide, e.g., as exemplified below for a C-terminal linkage:

(SEQ ID NO: 43)
Ac-Ile-Cys*-Val-(1Me)Trp-Gln-Asp-Trp-Gly-Ala-His-

Arg-Cys*-Thr-Lys-NH₂.

In some embodiments, a Lys residue is attached to the N- or C-terminus of SEQ ID NO: 42 via a peptide linker, e.g., as exemplified below for a C-terminal linkage:

(SEQ ID NO: 44)
Ac-Ile-Cys*-Val-(1Me)Trp-Gln-Asp-Trp-Gly-Ala-His-Arg-Cys*-Thr-(Gly)$_5$-Lys-NH$_2$.

In some embodiments, a linker comprising a primary or secondary amine is added to the N- or C-terminus of a compstatin analog. In some embodiments, the linker comprises an alkyl chain and/or an oligo(ethylene glycol) moiety. For example, NH$_2$(CH$_2$CH$_2$O)nCH$_2$C(=O)OH (e.g., 8-amino-3,6-dioxaoctanoic acid (AEEAc) or 11-amino-3,6,9-trioxaundecanoic acid) or an NHS ester thereof (e.g., an NHS ester of 8-amino-3,6-dioxaoctanoic acid or 11-amino-3,6,9-trioxaundecanoic acid), can be used. In some embodiments, the resulting compound is as follows (wherein the portion contributed by the linker is shown in bold):

(SEQ ID NO: 45)
NH$_2$(CH$_2$)$_5$C(=O)-Ile-Cys-Val-(1Me)Trp-Gln-Asp-Trp-Gly-Ala-His-Arg-Cys-Thr-NH$_2$.

(SEQ ID NO: 46)
NH$_2$(CH$_2$CH$_2$O)$_2$CH$_2$C(=O)-Ile-Cys-Val-(1Me)Trp-Gln-Asp-Trp-Gly-Ala-His-Arg-Cys-Thr-NH$_2$

In some embodiments, a Lys residue is attached to the N- or C-terminus of SEQ ID NO: 42 via a linker comprising a non-peptide portion. For example, the linker can comprise an alkyl chain, oligo(ethylene glycol) chain, and/or cyclic ring system. In some embodiments, 8-AEEAc or an NHS ester thereof is used, resulting (in the case of attachment of Lys at the C-terminus) in the following compound (wherein the portion contributed by 8-AEEAc is shown in bold):

(SEQ ID NO: 47)
Ac-Ile-Cys*-Val-(1Me)Trp-Gln-Asp-Trp-Gly-Ala-His-Arg-Cys*-Thr-NH—CH$_2$CH$_2$OCH$_2$CH$_2$OCH$_2$—C(=O)-Lys-NH$_2$

It will be appreciated that in SEQ ID NOs: 45 and 46, a —C(=O) moiety is attached to the adjacent Ile residue via a C—N bond, wherein the N is part of the amino acid and is not shown. Similarly, in SEQ ID NO: 47, a —C(=O) moiety is attached to the adjacent Lys residue via a C—N bond, wherein the N is part of the amino acid and is not shown. It will also be appreciated that that in SEQ ID NO: 47 the NH moiety is attached to the immediately N-terminal amino acid (Thr), via a C—N bond, wherein the C is the carbonyl carbon of the amino acid and is not shown.

The compounds of SEQ ID NOs: 43-47 can be modified at the primary amine group to produce a long-acting compstatin analog.

Exemplary long-acting compstatin analogs are set forth below, wherein n is sufficient to provide an average molecular weight of between about 500; 1,000; 1,500; 2,000; 5,000; 10,000; 20,000; 30,000; 40,000; 50,000; 60,000; 70,000; 80,000; 90,000; and 100,000 daltons.

(SEQ ID NO: 48)
(CH$_2$CH$_2$O)$_n$C(=O)-Ile-Cys-Val-(1Me)Trp-Gln-Asp-Trp-Gly-Ala-His-Arg-Cys-Thr-NH$_2$)

(SEQ ID NO: 49)
Ac-Ile-Cys*-Val-(1Me)Trp-Gln-Asp-Trp-Gly-Ala-His-Arg-Cys*-Thr-NH—CH$_2$CH$_2$OCH$_2$CH$_2$OCH$_2$—C(=O)-Lys-C(=O)—(CH$_2$CH$_2$O)$n$—NH$_2$ (SEQ ID NO: 50)
Ac-Ile-Cys*-Val-(1Me)Trp-Gln-Asp-Trp-Gly-Ala-His-Arg-Cys*-Thr-Lys-C(=O)—(CH$_2$CH$_2$O)$n$—NH$_2$.

(SEQ ID NO: 51)
Ac-Ile-Cys*-Val-(1Me)Trp-Gln-Asp-Trp-Gly-Ala-His-Arg-Cys*-Thr-(Gly)$_5$-Lys-C(=O)—(CH$_2$CH$_2$O)$n$—NH$_2$ (SEQ ID NO: 52)
Ac-(CH$_2$CH$_2$O)$n$C(=O)Lys-(Gly)5-Ile-Cys*-Val-(1Me)Trp-Gln-Asp-Trp-Gly-Ala-His-Arg-Cys*-Thr-NH$_2$)

(SEQ ID NO: 53)
Ac-(CH$_2$CH$_2$O)$n$C(=O)Lys-Ile-Cys*-Val-(1Me)Trp-Gln-Asp-Trp-Gly-Ala-His-Arg-Cys*-Thr-NH$_2$)

In SEQ ID NO: 48, the (CH$_2$CH$_2$O)n is coupled via an amide bond to the N-terminal amino acid. In SEQ ID NOs: 49-53, the (CH$_2$CH$_2$O)n moiety is coupled via an amide bond to a Lys side chain; thus it will be understood that the NH$_2$ at the C-terminus in SEQ ID NOs: 49, 50, and 51, represents amidation of the C-terminus of the peptide, and it will be understood that in SEQ ID NOs: 52 and 53, the Ac at the N-terminus represents acetylation of the N-terminus of the peptide, as described above. It will also be appreciated by those of ordinary skill in the art that a free end of a (CH$_2$CH$_2$O)$_n$ moiety typically terminates with an (OR) where the underlined O represents the O atom in the terminal (CH$_2$CH$_2$O) group. (OR) is often a moiety such as a hydroxyl (OH) or methoxy (—OCH$_3$) group though other groups (e.g., other alkoxy groups) could be used. Thus SEQ ID NO: 49, for example, may be represented as Ac-Ile-Cys*-Val-(1Me)Trp-Gln-Asp-Trp-Gly-Ala-His-Arg-Cys*-Thr-NH—CH$_2$CH$_2$OCH$_2$CH$_2$OCH$_2$—C(=O)-Lys-(C(=O)—(CH$_2$CH$_2$O)$_n$—R)—NH2 (SEQ ID NO: 54) wherein R is, e.g., either H or CH$_3$ in the case of a linear PEG. In the case of a bifunctional, branched or star-shaped PEG, R represents the remainder of the molecule. Further, it will be understood that the moiety comprising the reactive functional group may vary, as described herein (e.g., according to any of the formulas described herein). For example, long-acting compstatin analogs comprising the same peptide sequence as SEQ ID NO: 54, in which the moiety comprising the reactive functional group comprises an ester and/or alkyl chain may be represented as follows (SEQ ID NO: 55)
Ac-Ile-Cys*-Val-(1Me)Trp-Gln-Asp-Trp-Gly-Ala-His-Arg-Cys*-Thr-NH—CH$_2$CH$_2$OCH$_2$CH$_2$OCH$_2$—C(=O)-Lys-(C(=O)—(CH2)$_m$—(CH$_2$CH$_2$O)$_n$—R)—NH2;

(SEQ ID NO: 56)
Ac-Ile-Cys*-Val-(1Me)Trp-Gln-Asp-Trp-Gly-Ala-His-Arg-Cys*-Thr-NH—CH$_2$CH$_2$OCH$_2$CH$_2$OCH$_2$—C(=O)-Lys-(C(=O)—(CH$_2$)$_m$—C(=O)—(CH$_2$CH$_2$O)$_n$—R)—NH2

(SEQ ID NO: 57)
Ac-Ile-Cys*-Val-(1Me)Trp-Gln-Asp-Trp-Gly-Ala-His-

Arg-Cys*-Thr-NH—CH$_2$CH$_2$OCH$_2$CH$_2$OCH$_2$—C(=O)-Lys- (C(=O)—(CH$_2$)$_m$—C(=O)—(CH$_2$) $j$ (CH$_2$CH$_2$O)$_n$—R)—NH2

In SEQ ID NOs: 55-57 m may range from 1 up to about 2, 3, 4, 5, 6, 7, 8, 10, 15, 20, or 30 in various embodiments, In SEQ ID NOs: 57 j may range from 1 up to about 2, 3, 4, 5, 6, 7, 8, 10, 15, 20, or 30 in various embodiments. It will also be appreciated that, as described herein, in various embodiments other moieties may be incorporated between the Lys-(C(=O)— and (CH$_2$CH$_2$O)$_n$—R, such as an amide, aromatic ring (e.g., a substituted or unsubstituted phenyl), or a substituted or unsubstituted cycloalkyl structure.

In some embodiments a long-acting compstatin analog comprises a variant of SEQ ID NOs: 48-57 in which -Ile-Cys*-Val-(1Me)Trp-Gln-Asp-Trp-Gly-Ala-His-Arg-Cys*-Thr- (SEQ ID NO: 72) is replaced by an amino acid sequence comprising the amino acid sequence of any other compstatin analog, e.g., of any of SEQ ID NOs 3-27 or 29-41, with the proviso that blocking moiet(ies) present at the N- and/or C-termini of a compstatin analog may be absent, replaced by a linker (which may comprise a blocking moiety), or attached to a different N- or C-terminal amino acid present in the corresponding variant(s).

Any compstatin analog, e.g., any compound comprising any of SEQ ID NOs: 3-41 may be attached via its N-terminus or C-terminus directly or indirectly to any moiety comprising a reactive functional group, e.g., any of Formulas I-XVI or Compound I-III, in various embodiments.

In some embodiments a CRM comprises a polypeptide that occurs in human serum, or a fragment thereof or a substantially similar variant of the polypeptide or fragment thereof. In some embodiments the polypeptide, fragment, or variant has a molecular weight of between 5 kD and 150 kD, e.g., at least 5, 10, 20, 30, 40, 50, 60, 70, 80, 90, 100 kd, or more, e.g., between 100 and 120, or 120 and 150 kD. In some embodiments, producing a long-acting compstatin analog comprises reacting a compstatin analog comprising a reactive functional group with one or more amino acid side chains of the polypeptide, wherein the side chain comprises a compatible functional group. In some embodiments, producing a long-acting compstatin analog comprises reacting a compstatin analog comprising a reactive functional group with the N-terminal amine and/or C-terminal carboxyl group of the polypeptide. In some embodiments, producing a long-acting compstatin analog comprises reacting a compstatin analog comprising an amine-reactive functional group with amino acids having a side chain comprising a primary amine (e.g., lysine) and/or with the N-terminal amine of the polypeptide. In some embodiments, producing a long-acting compstatin analog comprises reacting a compstatin analog comprising a carboxyl-reactive functional group with the C-terminal carboxyl group of the polypeptide. In some embodiments a compstatin analog moiety is attached at each terminus of the polypeptide and, optionally, to the side chain of one or more internal amino acids. In some embodiments, producing a long-acting compstatin analog comprises reacting a compstatin analog comprising a sulfhydryl-reactive functional group with one or more sulfhydryl groups of the polypeptide.

In some embodiments, at least one reactive functional group is introduced into the polypeptide. For example, in some embodiments at least one side chain of the polypeptide is modified to convert a first reactive functional group to a different reactive functional group prior to reaction with the compstatin analog. In some embodiments a thiol is introduced. Several methods are available for introducing thiols into biomolecules, including the reduction of intrinsic disulfides, as well as the conversion of amine, aldehyde or carboxylic acid groups to thiol groups. Disulfide crosslinks of cysteines in proteins can be reduced to cysteine residues by dithiothreitol (DTT), tris-(2-carboxyethyl)phosphine (TCEP), or or tris-(2-cyanoethyl)phosphine. Amines can be indirectly thiolated by reaction with succinimidyl 3-(2-pyridyldithio)propionate (SPDP) followed by reduction of the 3-(2-pyridyldithio)propionyl conjugate with DTT or TCEP. Amines can be indirectly thiolated by reaction with succinimidyl acetylthioacetate followed by removal of the acetyl group with 50 mM hydroxylamine or hydrazine at near-neutral pH. Amines can be directly thiolated by reaction with 2-iminothiolane, which preserve the overall charge of the molecule and introduces a free thiol. Tryptophan residues in thiol-free proteins can be oxidized to mercaptotryptophan residues, which can then be modified by iodoacetamides or maleimides. A polypeptide comprising one or more thiols may be reacted with a compstatin analog comprising a maleimide group, such as Ac-Ile-Cys*-Val-Trp(1-Me)-Gln-Asp-Trp-Gly-Ala-His-Arg-Cys*-Thr-AEEAc-Lys-(C(=O)—(CH$_2$)$_5$-Mal)-NH$_2$ (SEQ ID NO: 58) to generate a long-acting compstatin analog.

In some embodiments the polypeptide is recombinantly produced. In some embodiments the polypeptide is at least in part recombinantly produced (e.g., in bacteria or in eukaryotic host cells such as fungal, insect, plant, or vertebrate) and/or at least in part produced using chemical synthesis. In some embodiments the polypeptide is purified. In some embodiments the polypeptide is glycosylated. In some embodiments the polypeptide is non-glycosylated. In some embodiments the polypeptide is human serum albumin (HSA). In some embodiments a substantially similar variant of the polypeptide is sufficiently similar to the polypeptide of which it is a variant so as to not be recognized as foreign by a normal immune system of a subject, e.g., a human subject. In some embodiments alterations in the sequence of substantially similar variant as compared with the polypeptide of which it is a variant are selected so as to avoid generating MHC Class I epitopes. Various methods known in the art can be used to predict whether a sequence comprises an MHC Class I epitope.

The structure of compstatin is known in the art, and NMR structures for a number of compstatin analogs having higher activity than compstatin are also known (Malik, supra). Structural information may be used to design compstatin mimetics. In some embodiments, a compstatin mimetic is any compound that competes with compstatin or any compstatin analog (e.g., a compstatin analog whose sequence is set forth in Table 2) for binding to C3 or a fragment thereof (such as a 40 kD fragment of the β chain to which compstatin binds). In some embodiments, the compstatin mimetic has an activity equal to or greater than that of compstatin. In some embodiments, the compstatin mimetic is more stable, orally available, or has a better bioavailability than compstatin. The compstatin mimetic may be a peptide, nucleic acid, or small molecule. In certain embodiments the compstatin mimetic is a compound that binds to the binding site of compstatin as determined in a compstatin-C3 structure, e.g., a crystal structure or a 3-D structure derived from NMR experiments. In certain embodiments the compstatin mimetic is a compound that could substitute for compstatin in a compstatin-C3 structure and would form substantially the same intermolecular contacts with C3 as compstatin. In certain embodiments the compstatin mimetic is a compound that binds to the binding site of a peptide having a sequence set forth in Table 2, e.g., SEQ ID NO: 14, 21, 28, 29, 32, 33, 34, or 36 or other compstatin analog sequence or in certain embodiments SEQ ID NO: 30 or 31, in a peptide-C3 structure. In certain embodiments the compstatin mimetic is a compound that could substitute for a peptide having a sequence set forth in Table 2, e.g., SEQ ID NO: 14, 21, 28, 29, 32, 33, 34, or 36 or other compstatin analog sequence or in certain embodiments SEQ ID NO: 30 or 31, in a peptide-C3 structure and would form substantially the same intermolecular contacts with C3 as the peptide. In certain embodiments the compstatin mimetic has a non-peptide backbone but has side chains arranged in a sequence designed based on the sequence of compstatin.

One of skill in the art will appreciate that once a particular desired conformation of a short peptide has been ascertained, methods for designing a peptide or peptidomimetic to fit that conformation are well known. See, e.g., G. R. Marshall (1993), Tetrahedron, 49: 3547-3558; Hruby and Nikiforovich (1991), in Molecular Conformation and Biological Interactions, P. Balaram & S. Ramasehan, eds., Indian Acad. of Sci., Bangalore, PP. 429-455), Eguchi M, Kahn M., Mini Rev Med Chem., 2(5):447-62, 2002. Of particular relevance to the present invention, the design of peptide analogs may be further refined by considering the contribution of various side chains of amino acid residues, e.g., for the effect of functional groups or for steric considerations as described in the art for compstatin and analogs thereof, among others.

It will be appreciated by those of skill in the art that a peptide mimic may serve equally well as a peptide for the purpose of providing the specific backbone conformation and side chain functionalities required for binding to C3 and inhibiting complement activation. Accordingly, it is contemplated as being within the scope of the present invention to produce and utilize C3-binding, complement-inhibiting compounds through the use of either naturally-occurring amino acids, amino acid derivatives, analogs or non-amino acid molecules capable of being joined to form the appropriate backbone conformation. A non-peptide analog, or an analog comprising peptide and non-peptide components, is sometimes referred to herein as a "peptidomimetic" or "isosteric mimetic," to designate substitutions or derivations of a peptide that possesses much the same backbone conformational features and/or other functionalities, so as to be sufficiently similar to the exemplified peptides to inhibit complement activation. More generally, a compstatin mimetic is any compound that would position pharmacophores similarly to their positioning in compstatin, even if the backbone differs.

The use of peptidomimetics for the development of high-affinity peptide analogs is well known in the art. Assuming rotational constraints similar to those of amino acid residues within a peptide, analogs comprising non-amino acid moieties may be analyzed, and their conformational motifs verified, by means of the Ramachandran plot (Hruby & Nikiforovich 1991), among other known techniques.

One of skill in the art will readily be able to establish suitable screening assays to identify additional compstatin mimetics and to select those having desired inhibitory activities. For example, compstatin or an analog thereof could be labeled (e.g., with a radioactive or fluorescent label) and contacted with C3 in the presence of different concentrations of a test compound. The ability of the test compound to diminish binding of the compstatin analog to C3 is evaluated. A test compound that significantly diminishes binding of the compstatin analog to C3 is a candidate compstatin mimetic. For example, a test compound that diminishes steady-state concentration of a compstatin analog-C3 complex, or that diminishes the rate of formation of a compstatin analog-C3 complex by at least 25%, or by at least 50%, is a candidate compstatin mimetic. One of skill in the art will recognize that a number of variations of this screening assay may be employed. Compounds to be screened include natural products, libraries of aptamers, phage display libraries, compound libraries synthesized using combinatorial chemistry, etc. The invention encompasses synthesizing a combinatorial library of compounds based upon the core sequence described above and screening the library to identify compstatin mimetics. Any of these methods could also be used to identify new compstatin analogs having higher inhibitory activity than compstatin analogs tested thus far.

Other Compounds that Inhibit C3 Activation or Activity

Other compounds, e.g., polypeptides, small molecules, monoclonal antibodies, aptamers, etc., that bind to C3 or C3a receptors (C3aR) are of use in certain embodiments of the invention. In certain embodiments the complement inhibitor comprises an Efb protein from *Staphylococcus aureus* or a variant or derivative or mimetic thereof that can bind to C3 and inhibit its activation and/or bind to and inhibit C3b. Exemplary agents are described in PCT Application Pub. WO/2004/094600. In certain embodiments the complement inhibitor comprises a *Staphylococcus* complement inhibitor (SCIN) protein from *Staphylococcus aureus* or a variant or derivative or mimetic of such protein that can bind to C3 convertase and inhibit its activation and/or bind to and inhibit C3b. Aptamers that bind to and inhibit C3 may be identified using methods such as SELEX. U.S. Pat. Pub. No. 20030191084 discloses aptamers that bind to C1q, C3 and C5.

In some embodiments, a protease that degrades C3 may be used as a complement inhibitor. For example, U.S. Pat. No. 6,676,943 discloses human complement C3-degrading protein from *Streptococcus pneumoniae*. Such proteins, or variants thereof, may be used in certain embodiments of the invention.

U.S. Pat. No. 5,942,405, PCT/IB2006/002557 (WO/2007/034277—ARYL SUBSTITUTED IMIDAZO [4,5-C] PYRIDINE COMPOUNDS AS C3A RECEPTOR ANTAGONISTS); PCT/IB2006/002568 (WO/2007/034282—DIARYL-IMIDAZOLE COMPOUNDS CONDENSED WITH A HETEROCYCLE AS C3A RECEPTOR ANTAGONISTS) PCT/IB2006/002561 (WO2007034278—FUSED IMIDAZOLE DERIVATIVES AS C3A RECEPTOR ANTAGONISTS) PCT/US2007/026237 (WO2008079371) MODULATORS OF C3A RECEPTOR AND METHODS OF USE THEREOF disclose exemplary C3aR antagonists. In some embodiments, an RNAi agent that inhibits expression of C3 or C3aR may be used.

Compounds that Inhibit Factor B Activation or Activity

In certain embodiments a complement inhibitor inhibits activation or activity of factor B. For example, the complement inhibitor may bind to factor B and, e.g., inhibit activation of factor B. Exemplary agents that inhibit activation or activity of factor B include, e.g., antibodies, antibody fragments, peptides, small molecules, and aptamers. Exemplary antibodies that inhibit factor B are described in U.S. Pat. Pub. No. 20050260198. In certain embodiments an antibody or antigen-binding fragment selectively binds to factor B within the third short consensus repeat (SCR)

domain. In certain embodiments the antibody prevents formation of a C3bBb complex. In certain embodiments the antibody or antigen-binding fragment prevents or inhibits cleavage of factor B by factor D. In some embodiments, an antibody binds to the Bb portion of factor B. PCT/US2008/074489 (WO/2009/029669) discloses exemplary antibodies, e.g., the antibody produced by the hybridoma clone deposited under ATCC Accession Number PTA-8543. In some embodiments, a humanized version of said antibody is used, which may be an antibody fragment. In certain embodiments a complement inhibitor, e.g., antibody, small molecule, aptamer, polypeptide, or peptide, binds to substantially the same binding site on factor B as an antibody described in U.S. Pat. Pub. No. 20050260198 or WO/2009/029669. In some embodiments, the complement inhibitor comprises the monoclonal antibody fragment known as TA106 (formerly under development by Taligen Therapeutics), or antibody, small molecule, aptamer, polypeptide, or peptide, binds to substantially the same binding site on factor B as TA106 is used. In some embodiments, a peptide that binds to and inhibits factor B is identified using, for example, a method such as phage display. In some embodiments, a complement inhibitor comprises an aptamer that binds to and inhibits factor B. In some embodiments, an RNAi agent that inhibits expression of factor B may be used.

Compounds that Inhibit Factor D Activity

In certain embodiments the complement inhibitor inhibits factor D. For example, the complement inhibitor may bind to factor D. Exemplary agents include antibodies, antibody fragments, peptides, small molecules, and aptamers. Exemplary antibodies that inhibit factor D are described in U.S. Pat. No. 7,112,327. In certain embodiments the complement inhibitor is an antibody, small molecule, aptamer, or polypeptide that binds to substantially the same binding site on factor D as an antibody described in U.S. Pat. No. 7,112,327. FCFD4514S (formerly under development by Tanox as TNX-234), is a humanized monoclonal antibody fragment that binds Factor D. In certain embodiments the complement inhibitor comprises FCFD4514S or an antibody, small molecule, aptamer, or polypeptide that binds to substantially the same binding site on factor D as FCFD4514S. Exemplary polypeptides that inhibit alternative pathway activation and are believed to inhibit factor D are disclosed in U.S. Pub. No. 20040038869. Use of peptides that bind to and inhibit factor D, which may be identified using methods such as phage display, is within the scope of the invention. Use of aptamers that bind to and inhibit factor D, which may be identified using methods such as SELEX, is within the scope of the invention. In some embodiments, an RNAi agent that inhibits expression of factor D may be used.

Mammalian Complement Regulatory Proteins and Complement Receptors

In some embodiments the complement inhibitor comprises at least a portion of a mammalian, e.g., human, complement regulatory protein or complement receptor. Examples of complement regulatory proteins include, e.g., CFH, CFH related proteins (such as CFHR1), CFI, CR1, DAF, MCP, CD59, C4bp, and complement receptor 2 inhibitor trispanning (CRIT; Inal, J., et al, J Immunol., 174(1): 356-66, 2005). In some embodiments the complement regulatory polypeptide is one that is normally membrane-bound in its naturally occurring state. In some embodiments of the invention a fragment of such polypeptide that lacks some or all of a transmembrane and/or intracellular domain is used. Soluble forms of complement receptor 1 (sCR1), or soluble portions of other complement receptors, for example, are of use in certain embodiments. For example the compounds known as TP10 or TP20 (Avant Therapeutics) can be used. In some embodiments a soluble complement control protein, e.g., CFH or a CFH related protein, is used. In some embodiments the complement inhibitor is a C3b/C4b Complement Receptor-like molecule such as those described in U.S. Pat. Pub. No. 20020192758. Variants and fragments of mammalian complement regulatory proteins or receptors that retain complement inhibiting activity can be used in certain embodiments.

Chimeric Complement Inhibitors

In certain embodiments of the invention the complement inhibitor comprises a chimeric polypeptide comprising a first polypeptide that inhibits complement activation, linked, e.g., covalently linked, to a second polypeptide that inhibits complement activation and/or that binds to a complement component or complement activation product. In some embodiments, at least one of the polypeptides comprises at least a portion of a mammalian complement regulatory protein. The chimeric polypeptide may contain one or more additional domains located, e.g., between the first and second polypeptides or at a terminus. For example, the first and second polypeptides can be separated by a spacer polypeptide.

In some embodiments, the first and second polypeptides each comprise at least a portion of a mammalian complement regulatory protein. In some embodiments complement inhibitor comprises at least a portion of DAF and at least a portion of MCP. Exemplary chimeric polypeptides are disclosed, e.g., in U.S. Pat. No. 5,679,546, e.g., CAB-2 (also known as MLN-2222). In some embodiments the polypeptide comprises at least 4 SCR domains of at least one mammalian complement regulatory protein or complement receptor. In some embodiments the polypeptide comprises at least 4 SCR domains of each of first and second distinct mammalian complement regulatory proteins.

In some embodiments, a chimeric polypeptide comprises at least a portion of complement receptor 1 (CR1), complement receptor 2 (CR2), complement receptor 3 (CR3), complement receptor 4 (CR4) or a variant or fragment of CR1, CR2, CR3, or CR4 that binds to one or more complement components or complement activation products such as C3b, iC3b, C3d, and/or C3dg. In some embodiments, the polypeptide comprises at least 4 SCRs, e.g., at least 4 SCRs of CR1 or CR2. For example, the polypeptide can comprise the 4 N-terminal SCRs of CR2 (e.g., residues 1-250 of the mature protein). In some embodiments the chimeric polypeptide comprises at least 4 SCR domains of a mammalian complement regulatory protein and at least 4 SCR domains of a mammalian complement receptor.

Compounds that Inhibit Properdin

In some embodiments of the invention antiproperdin antibodies, antibody fragment, or other anti-properdin agents are used. See, e.g., U.S. Pat. Pub. No. 20030198636 or PCT/US2008/068530 (WO/2009/110918—ANTI-PROPERDIN ANTIBODIES) for examples.

Compounds that Inhibit Components of Lectin Pathway

In some embodiments the compounds inhibit one or more components of the lectin pathway. See, e.g., WO/2007/117996) METHODS FOR TREATING CONDITIONS ASSOCIATED WITH MASP-2 DEPENDENT COMPLEMENT ACTIVATION.

Compounds that Inhibit C5 Activation or Activity

In certain embodiments the complement inhibitor inhibits activation of C5. For example, the complement inhibitor may bind to C5 and inhibit its cleavage. In some embodiments, the complement inhibitor inhibits physical interaction of C5 with C5 convertase by, e.g., binding to C5 or C5 convertase or to C5 at a site that would ordinarily participate in such physical interaction. Exemplary agents that inhibit C5 activation include antibodies, antibody fragments, polypeptides, small molecules, and aptamers. Exemplary compounds, e.g., antibodies, that bind to C5 are described, for example, in U.S. Pat. No. 6,534,058; PCT/US95/05688 (WO 1995/029697), PCT/EP2010/007197 (WO2011063980); U.S. Pat. Pub. No. 20050090448; and U.S. Pat. Pub. No. 20060115476. U.S. Pat. Pub. No. 20060105980 discloses aptamers that bind to and inhibit C5. In some embodiments, a humanized anti-C5 monoclonal antibody, e.g., eculizumab (also known as h5G1.1-mAb; Soliris®) (Alexion), or a fragment or derivative thereof that binds to C5. In some embodiments, an antibody comprising at least some of the same complementarity determining regions (CDR1, CDR2 and/or CDR3), e.g., all of CDR1, CDR2, and CDR3, as those of eculizumab's heavy chain and/or light chain is used. In some embodiments, the antibody comprises at least some of the same framework regions as eculizumab. In some embodiments, an antibody that binds to substantially the same binding site on C5 as eculizumab is used. In some embodiments, pexelizumab (also known as h5G1.1-scFv), a humanized, recombinant, single-chain antibody derived from h5G1.1-mAb, is used. In certain embodiments the complement inhibitor comprises a *Staphylococcus* SSL7 protein from *Staphylococcus aureus* or a variant or derivative or mimetic of such protein that can bind to C5 and inhibit its cleavage.

As noted above, bispecific or multispecific antibodies can be used. For example, PCT/US2010/039448 (WO/2010/151526) discloses bispecific antibodies described as binding to two or more different proteins, wherein at least two of the proteins are selected from C5a, C5b, a cellular receptor for C5a (e.g., C5aR1 or C5L2), the C5b-9 complex, and a component or intermediate of terminal complement such as C5b-6, C5b-7, or C5b-8. In some embodiments an RNAi agent that inhibits expression of C5 or C5aR may be used.

In some embodiments, a complement inhibitor known as OmCI, or a variant, derivative, or mimetic thereof, is used. OmCI binds to C5 and inhibits its activation most likely by inhibiting interaction with convertase. OmCI is naturally produced by the tick *Ornithodoros moubata*. See, e.g., PCT/GB2004/002341 (WO/2004/106369) and PCT/GB2010/000213 (WO/2010/100396), for description of OmCI and certain variants thereof. It has been shown that OmCI binds to eicosanoids, in particular leukotriene (LKs), e.g., LTB4. In some embodiments, an OmCI polypeptide (or a variant, derivative, or fragment thereof) that retains the capacity to binds to a LK, e.g., LTB4, is used. In some embodiments, an OmCI polypeptide (or a variant, derivative, or fragment thereof) that has reduced capacity or substantially lacks capacity to bind to a LK, e.g., LTB4, is used.

In some embodiments the agent is an antagonist of a C5a receptor (C5aR). In some embodiments, the C5aR antagonist comprises a peptide. Exemplary C5a receptor antagonists include a variety of small cyclic or acyclic peptides such as those described in March, D R, et al., Mol. Pharmacol., 65(4), 2004, and in Woodruff, T M, et al., J Pharmacol Exp Ther., 314(2):811-7, 2005, U.S. Pat. No. 6,821,950; U.S. Ser. No. 11/375,587; and/or PCT/US06/08960 (WO2006/099330), or a mimetic thereof. In certain embodiments the complement inhibitor binds to C5aR and inhibits binding of C5a thereto. In certain embodiments a cyclic peptide comprising the sequence [OPdChaWR] (SEQ ID NO: 59) is used. In certain embodiments a cyclic peptide comprising the sequence [KPdChaWR] (SEQ ID NO: 60) is used. In certain embodiments a peptide comprising the sequence $(Xaa)_n$[OPdChaWR] (SEQ ID NO: 61) is used, wherein Xaa is an amino acid residue and n is between 1 and 5. In certain embodiments a peptide comprising the sequence $(Xaa)_n$[KPdChaWR] (SEQ ID NO: 62) is used, wherein Xaa is an amino acid residue and n is between 1 and 5. In certain embodiments n is 1. In certain embodiments n is 1 and Xaa is a standard or nonstandard aromatic amino acid. For example, the peptides F-[OPdChaWR] (SEQ ID NO: 63), F-[KPdChaWR] (SEQ ID NO: 64); Cin-[OPdChaWR] (SEQ ID NO: 65), and HCin-[OPdChaWR] (SEQ ID NO: 66) are of use in certain embodiments. Optionally the free terminus comprises a blocking moiety, e.g., the terminal amino acid is acetylated. For example, in some embodiments the C5aR antagonist is AcF-[OPdChaWR] (SEQ ID NO: 67) (also known as PMX-53). (Abbreviations: O: ornithine; Cha: cyclohexylalanine; Cin: cinnamoyl; Hcin: hydrocinnamoyl; square brackets denote internal peptide bond). In some embodiments, a C5aR antagonist comprises a compound, e.g., a peptide, disclosed in U.S. Pat. Pub. No. 20060183883 (U.S. Ser. No. 10/564,788), e.g., a compound as represented therein by formula I, formula II, formula IV, formula V, or formula VI. An exemplary C5aR antagonist is the peptide known as JPE-1375 (Jerini AG, Germany).

In some embodiments, a C5aR antagonist is a small molecule. Various small molecule C5aR antagonists are disclosed in the following references: PCT/US2005/015897 (WO/2005/110416; 4,5-DISUBSTITUTED-2-ARYL PYRIMIDINES); PCT/EP2006/005141 (WO2006128670); PCT/US2008/072902 (WO/2009/023669; SUBSTITUTED 5,6,7,8-TETRAHYDROQUINOLINE DERIVATIVES); PCT/US2009/068941 (WO/2010/075257; C5AR ANTAGONISTS). An exemplary small molecule C5aR antagonist is CCX168 (ChemoCentryx, Mountain View, Calif.).

In certain embodiments the complement inhibitor is an agent, e.g., an antibody, small molecule, aptamer, or polypeptide, that binds to substantially the same binding site on C5 or C5aR as a compound described in any of the aforementioned references disclosing agents that bind to C5 or C5aR. In some embodiments the complement inhibitor is not an antagonist of a C5a receptor.

Multimodal Complement Inhibitors

In certain embodiments of the invention the complement inhibitor binds to more than one complement protein and/or inhibits more than one step in a complement activation pathway. Such complement inhibitors are referred to herein as "multimodal". In certain embodiments of the invention the complement inhibitor comprises a virus complement control protein (VCCP). The invention contemplates use of any of the agents described in U.S. Ser. No. 11/247,886 and PCT/US2005/36547. Poxviruses and herpesviruses are families of large, complex viruses with a linear double-stranded DNA genome. Certain of these viruses encode immunomodulatory proteins that are believed to play a role in pathogenesis by subverting one or more aspects of the normal immune response and/or fostering development of a more favorable environment in the host organism (Kotwal, G J, *Immunology Today,* 21(5), 242-248, 2000). Among these are VCCPs. Poxvirus complement control proteins are members of the complement control protein (CCP) superfamily and typically contain 4 SCR modules. In certain embodiments the VCCP is a poxvirus complement control protein (PVCCP). The PVCCP can comprise a sequence encoded by, e.g., vaccinia virus, variola major virus, variola minor virus, cowpox virus, monkeypox virus, ectromelia virus, rabbitpox virus, myxoma virus, Yaba-like disease virus, or swinepox virus. In other embodiments the VCCP is a herpesvirus complement control protein (HVCCP). The HVCCP can comprise a sequence encoded by a *Macaca fuscata* rhadinovirus, cercopithecine herpesvirus 17, or human herpes virus 8. In other embodiments the HVCCP comprises a sequence encoded by herpes simplex virus saimiri ORF 4 or ORF 15 (Albrecht, J C. & Fleckenstein, B., J. Virol., 66, 3937-3940, 1992; Albrecht, J., et al., Virology, 190, 527-530, 1992).

The VCCP may inhibit the classical complement pathway, the alternate complement pathway, the lectin pathway, or any two or more of these. In certain embodiments of the invention the VCCP, e.g., a PVCCP, binds to C3b, C4b, or both. In certain embodiments of the invention the PVCCP comprises one or more putative heparin binding sites (K/R-X-K/R) and/or possesses an overall positive charge. In some embodiments the PVCCP comprises at least 3 SCR modules (e.g., modules 1-3), e.g., 4 SCR modules. The PVCCP protein can be a precursor of a mature PVCCP (i.e., can include a signal sequence that is normally cleaved off when the protein is expressed in virus-infected cells) or can be a mature form (i.e., lacking the signal sequence).

Vaccinia complement control protein (VCP) is a virus-encoded protein secreted from vaccinia infected cells. VCP is 244 amino acids in length, contains 4 SCRs, and is naturally produced by intracellular cleavage of a 263 amino acid precursor. VCP runs as an ~35 kD protein in a 12% SDS/polyacrylamide gel under reducing conditions and has a predicted molecular mass of about 28.6 kD. VCP is described in U.S. Pat. Nos. 5,157,110 and 6,140,472, and in Kotwal, G K, et al., Nature, 355, 176-178, 1988. FIGS. 3A and 3B of U.S. Ser. No. 11/247,886 and PCT/US2005/36547 (WO2006042252) show the sequence of the precursor and mature VCP proteins, respectively. VCP has been shown to inhibit the classical pathway of complement activation via its ability to bind to C3 and C4 and act as a cofactor for factor I mediated cleavage of these components as well as promoting decay of existing convertase (Kotwal, G K, et al., Science, 250, 827-830, 1990; McKenzie et al., J. Infect. Dis., 1566, 1245-1250, 1992). It has also been shown to inhibit the alternative pathway by causing cleavage of C3b into iC3b and thereby preventing the formation of the alternative pathway C3 convertase (Sahu, A, et al., J. Immunol., 160, 5596-5604, 1998). VCP thus blocks complement activation at multiple steps and reduces levels of the proinflammatory chemotactic factors C3a, C4a, and C5a.

VCP also possesses the ability to strongly bind heparin in addition to heparan sulfate proteoglycans. VCP contains two putative heparin binding sites located in modules 1 and 4 (Jha, P and Kotwal, G J, and references therein). VCP is able to bind to the surface of endothelial cells, possibly via interaction with heparin and/or heparan sulfate at the cell surface, resulting in decreased antibody binding (Smith, S A, et al., J. Virol., 74(12), 5659-5666, 2000). VCP can be taken up by mast cells and possibly persist in tissue for lengthy periods of time, thereby potentially prolonging its activity (Kotwal, G J, et al., In G P. Talwat, et al. (eds), $10^{th}$ International Congress of Immunology, Monduzzi Editore, Bologna, Italy, 1998). In addition, VCP can reduce chemotactic migration of leukocytes by blocking chemokine binding (Reynolds, D, et al., in S. Jameel and L. Villareal (ed., *Advances in animal virology*. Oxford and IBN Publishing, New Delhi, India, 1999). VCP and other PVCCPs have a relatively small size relative to mammalian CCPs, which is advantageous for delivery in the present invention.

Figure 6:
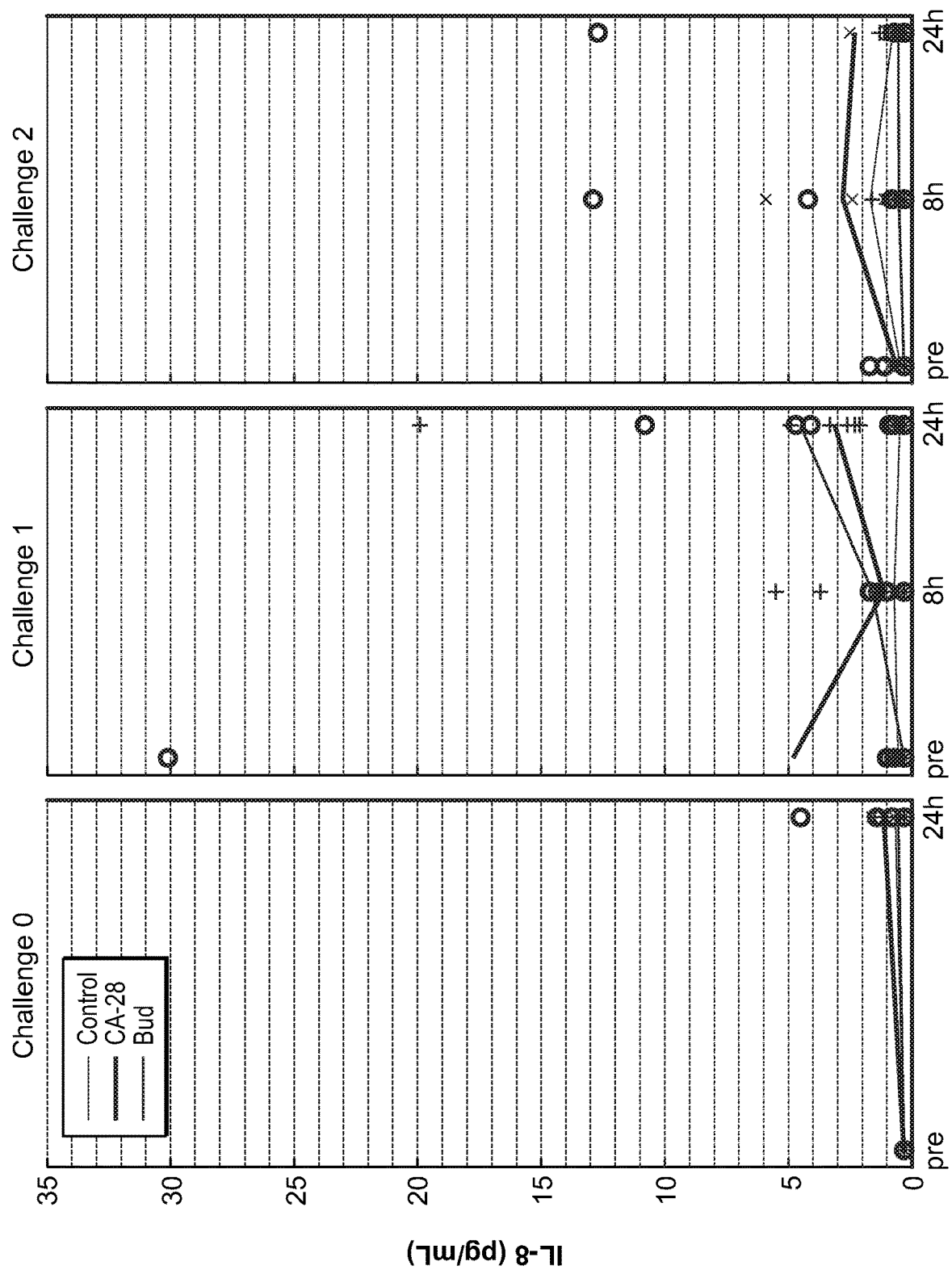
Figure 7:
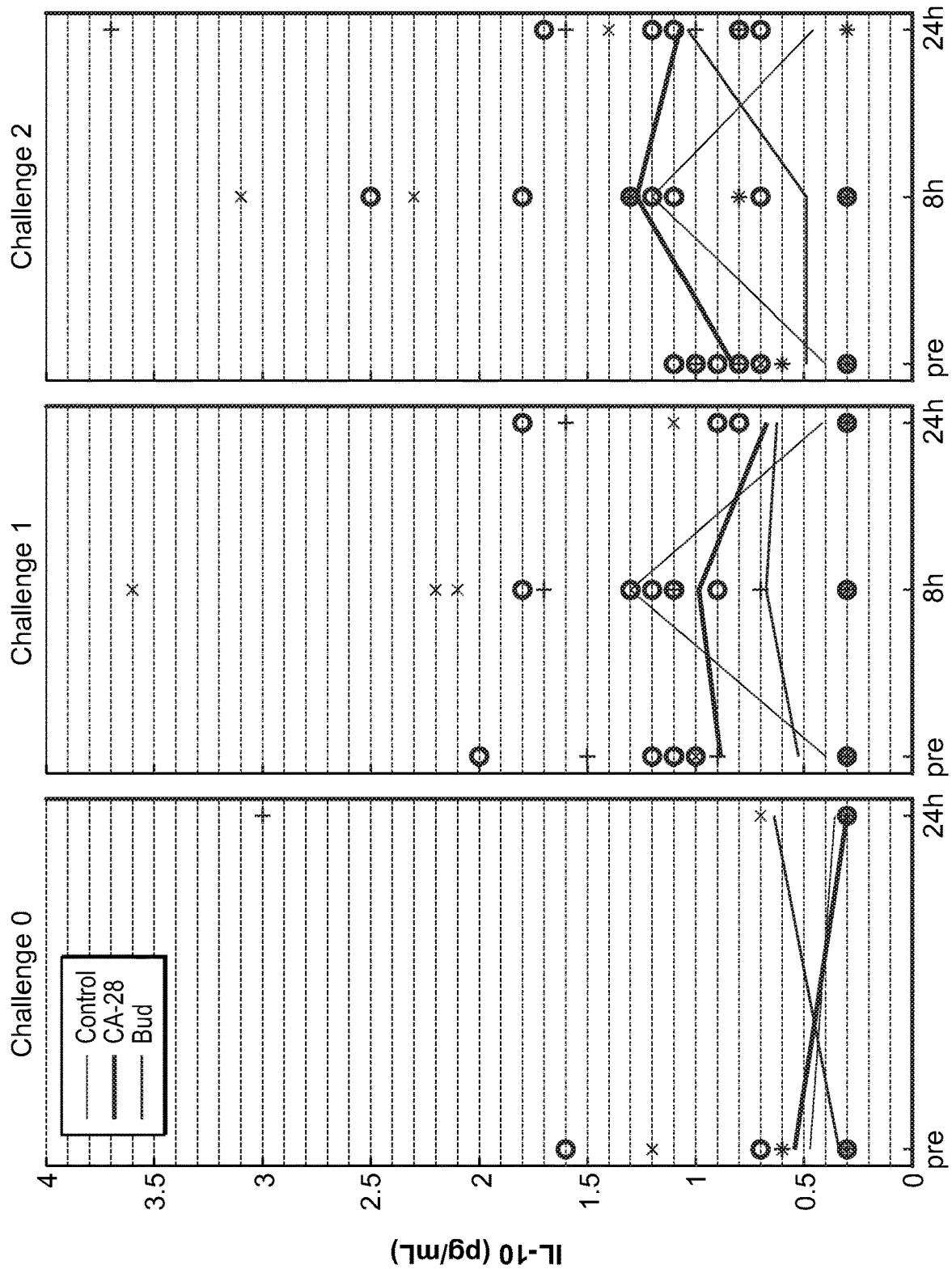
Figure 8:
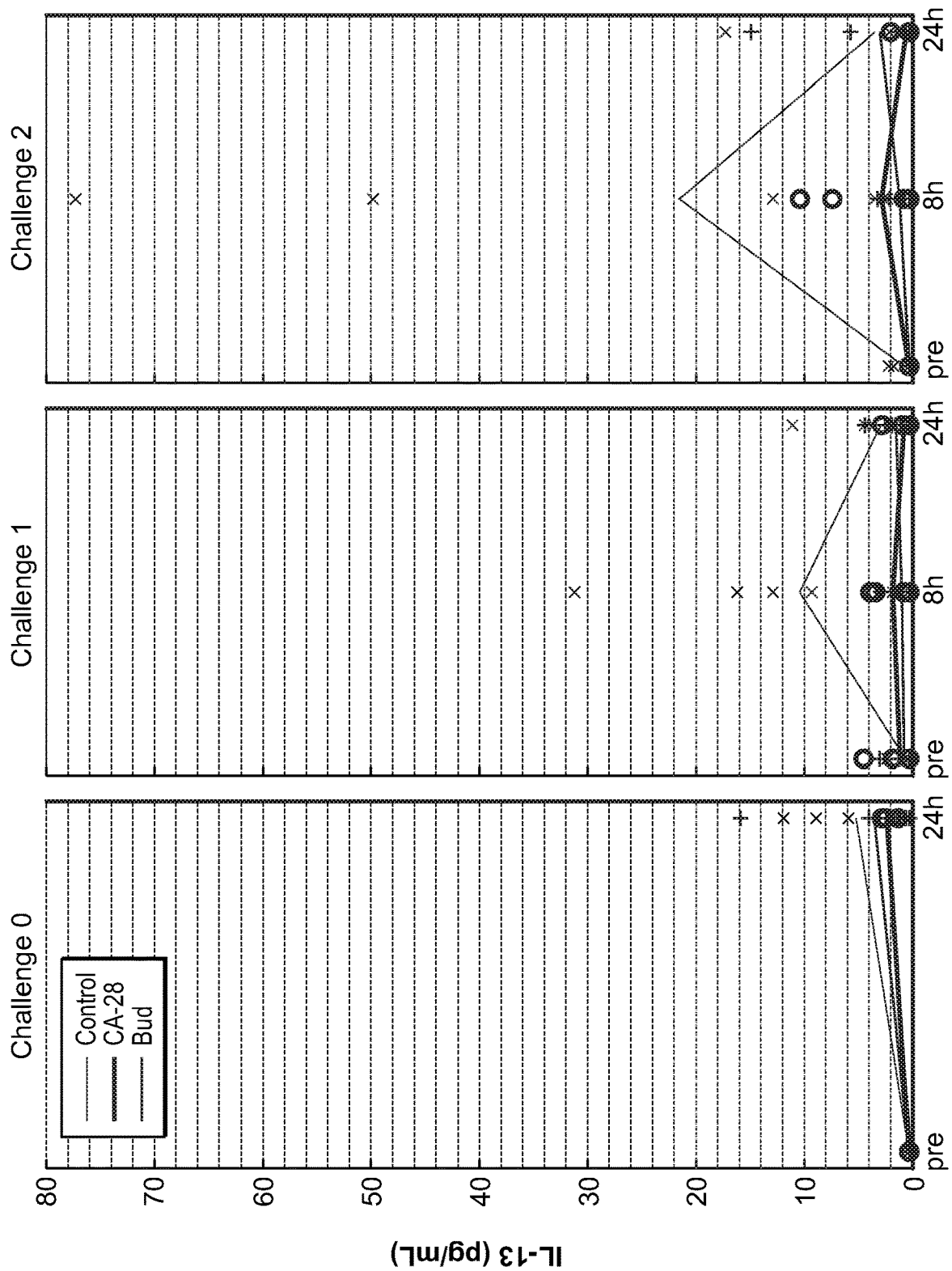
Figure 9:
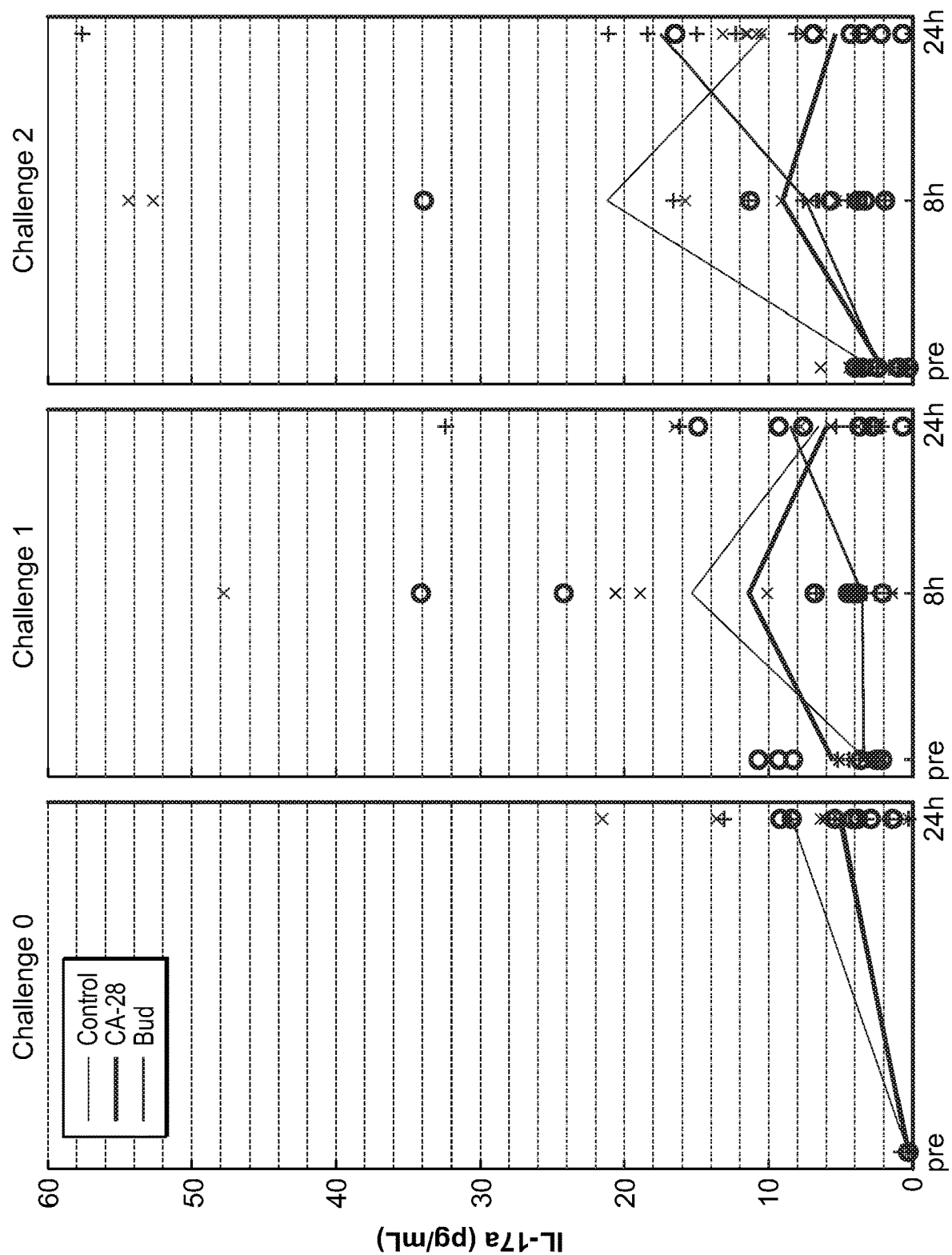
Figure 10:
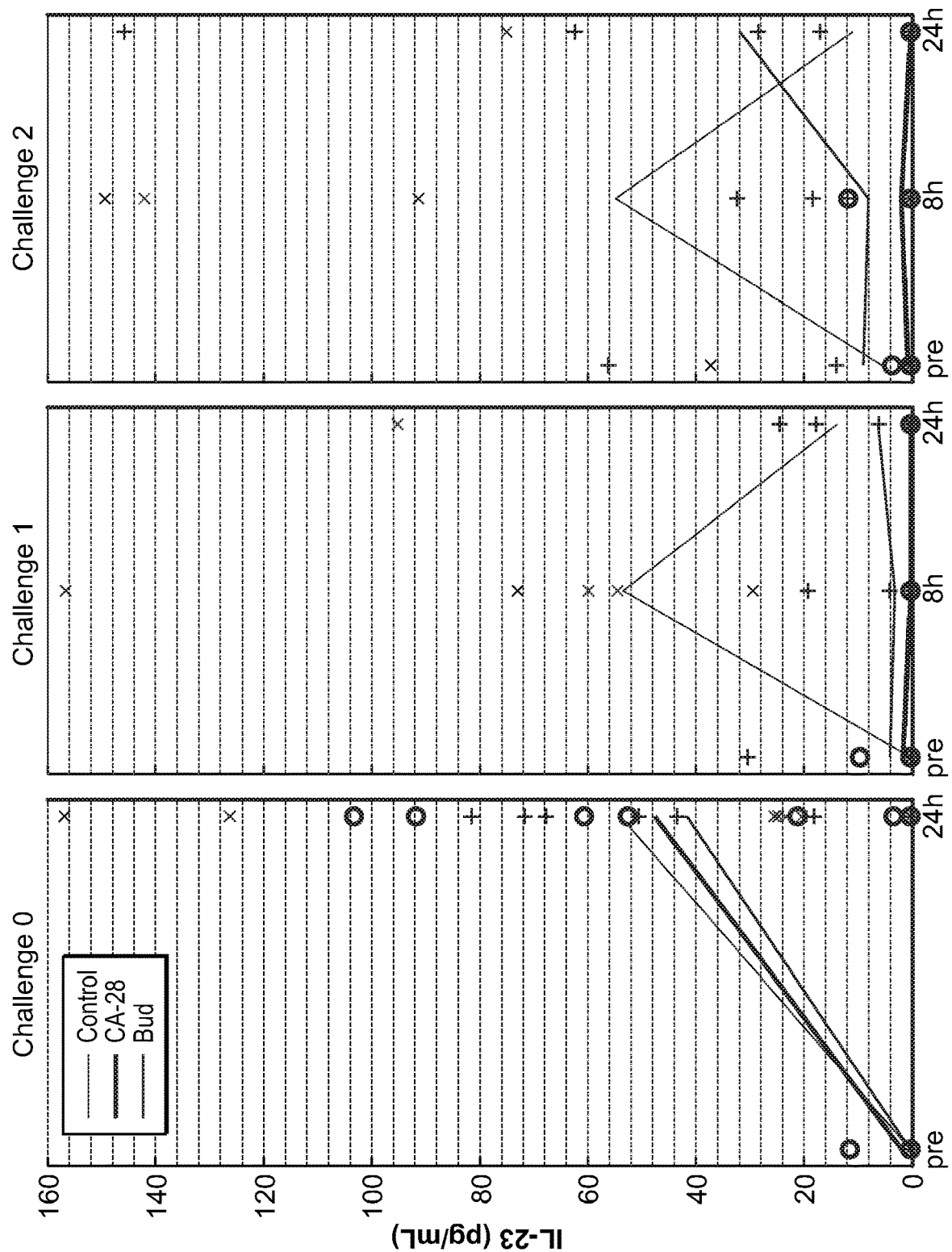

Variola virus major and minor encode proteins that are highly homologous to VCP and are referred to as smallpox inhibitor of complement enzymes (SPICE) (Rosengard, A M, et al., Proc. Natl. Acad. Sci., 99(13), 8803-8813. U.S. Pat. No. 6,551,595). SPICE from various variola strains sequenced to date differs from VCP by about 5% (e.g., about 11 amino acid differences). Similarly to VCP, SPICE binds to C3b and C4b and causes their degradation, acting as a cofactor for factor I. However, SPICE degrades C3b approximately 100 times as fast as VCP and degrades C4b approximately 6 times as fast as VCP. The amino acid sequence of SPICE is presented in FIG. 6 (SEQ ID NO: 12) of U.S. Ser. No. 11/247,886 and PCT/US2005/36547 (WO2006042252) and can be described as follows. Referring to FIG. 6 of U.S. Ser. No. 11/247,886 and PCT/US2005/36547 (WO2006042252), a signal sequence extends from amino acid 1 to about amino acid 19. Four SCRs extend from about amino acid 20 to amino acid 263. Each SCR is characterized by four cysteine residues. The four cysteine residues form two disulfide bonds in the expressed protein. The boundaries of each SCR are best defined by the first and fourth cysteine residues in the sequence that forms the disulfide bonds of the SCR. An invariant tryptophan residue is present between cysteine 3 and cysteine 4 of each SCR. SCR1 extends from amino acid 20 or 21 to amino acid 81. Both residues are cysteines that may be involved in disulfide bonding. SCR2 extends from amino acid 86 to amino acid 143. SCR3 extends from amino acid 148 to amino acid 201. SCR4 extends from amino acid 206 to amino acid 261. The SCRs include the complement binding locations of SPICE. SPICE or any of the portions thereof that inhibit complement activation, e.g., SPICE and SPICE-related polypeptides containing four SCRs, such as those described in U.S. Pat. No. 6,551,595, are of use in the present invention.

Complement control proteins from cowpox virus (referred to as inflammation modulatory protein, IMP) and monkeypox virus (referred to herein as monkeypox virus complement control protein, MCP) have also been identified and sequenced (Miller, C G, et al., Virology, 229, 126-133, 1997 and Uvarova, E A and Shchelkunov, S N, Virus Res., 81(1-2), 39-45, 2001). MCP differs from the other PVCCPs described herein in that it contains a truncation of the C-terminal portion of the fourth SCR.

It will be appreciated that the exact sequence of complement control proteins identified in different virus isolates may differ slightly. Such proteins fall within the scope of the present invention. Complement control proteins from any such isolate may be used, provided that the protein has not undergone a mutation that substantially abolishes its activity. Thus the sequence of a VCCP such as SPICE or VCP may differ from the exact sequences presented herein or under the accession numbers listed in Table 3. It will also be appreciated that a number of amino acid alterations, e.g., additions, deletions, or substitutions such as conservative amino acid substitutions, may be made in a typical polypeptide such as a VCCP without significantly affecting its activity, such that the resulting protein is considered equivalent to the original polypeptide. The viral polypeptides identified by accession number in Table 3 below are of use in various embodiments of the invention.

TABLE 3

Representative Viral Complement Control Proteins

| Virus | Protein | Accession | Virus Type |
|---|---|---|---|
| Variola | D12L | NP_042056 | Orthopoxvirus |
|  | D15L (SPICE) | AAA69423 | Orthopoxvirus |

TABLE 3-continued

Representative Viral Complement Control Proteins

| Virus | Protein | Accession | Virus Type |
|---|---|---|---|
| Vaccinia | VCP | AAO89304 | Orthopoxvirus |
| Cowpox | CPXV034 | AAM13481 | Orthopoxvirus |
|  | C17L | CAA64102 | Orthopoxvirus |
| Monkeypox | D14L | AAV84857 | Orthopoxvirus |
| Ectromelia virus | Complement control protein | CAE00484 | Orthopoxvirus |
| Rabbitpox | RPXV017 | AAS49730 | Orthopoxvirus |
| Macaca fuscata rhadinovirus | JM4 | AAS99981 | Rhadinavirus (Herpesvirus) |
| Cercopithecine herpesvirus 17 | Complement binding protein (ORF4) | NP_570746 | Herpesvirus |
| Human herpes virus 8 | Complement binding protein (ORF4) | AAB62602 | Herpesvirus |

In addition to the VCCPs described above, a number of other viral proteins exist that interfere with one or more steps in a complement pathway. These proteins are also of use in certain embodiments of the present invention. Certain of these proteins do not necessarily display clear homology to cellular complement regulators known to date. For example, HSV-1, HSV-2, VZV, PRV, BHV-1, EHV-1, and EHV-4 all encode versions of a conserved glycoprotein known as gC (Schreurs, et al., *J Virol.,* 62, 2251-2257, 1988; Mettenleiter, et al, *J. Virol.,* 64, 278-286; 1990; Herold, et al., *J Virol.,* 65, 1090-1098; 1991). With the exception of VZV, the gC protein encoded by these viruses binds to C3b (Friedman, et al., *Nature,* 309, 633-634,1984; Huemer, et al., *Virus Res.,* 23, 271-280, 1993) gC1 (from HSV-1) accelerates decay of the classical pathway C3 convertase and inhibits binding of properdin and C5 to C3. Purified EBV virions possess an activity that accelerates decay of the alternative pathway C3 convertase and serves as a cofactor for the complement regulatory protein factor 1 (Mold et al., *J Exp Med,* 168, 949-969, 1988). The foregoing proteins are referred to collectively as virus complement interfering proteins (VCIPs). By any of a variety of means, such as interfering with one or more steps of complement activation, accelerating decay of a complement component, and/or enhancing activity of a complement regulatory protein, these VCIPs are said to inhibit complement. Any of these proteins, or derivatives thereof, e.g., fragments or variants thereof, can be used as a therapeutic agent in the invention. As in the case of VCCPs, will be appreciated that the exact sequence of VCIPs identified in different virus isolates may differ slightly. Such proteins fall within the scope of the present invention.

In certain embodiments of the invention a fragment or variant of a VCCP or VCIP is locally administered to a subject. Preferred fragments and variants of a PVCCP possess at least one of the following activities: (i) ability to bind to C3, C3b, or both; (ii) ability to act as a cofactor for factor I cleavage of C3; (iii) ability to bind to C4, C4b, or both; (iv) ability to act as a cofactor for factor I cleavage of C4; (v) ability to accelerate decay of existing C3 convertase of the classical pathway, alternate pathway, or both; (vi) ability to bind heparin; (vii) ability to bind to heparan sulfate proteoglycans; (viii) ability to reduce chemotactic migration of leukocytes; (ix) ability to block chemokine (e.g, MIP-1$\alpha$) binding, e.g., to the surface of a cell (e.g., a leukocyte or endothelial cell surface); (x) ability to inhibit antibody binding to class I MHC molecules; (xi) ability to inhibit the classical complement pathway; (xii) ability to inhibit the alternative complement pathway; and (xiii) ability to inhibit complement-mediated cell lysis. Preferred PVCCP fragments and variants display complement binding activity, by which is meant ability to detectably bind to one or more complement components, preferably (in the case of VCCPs) selected from the group consisting of: C3, C3b, C4, and C4b. Preferred fragments or variants of HVCCPs may also display ability to detectably bind to one or more complement components. Preferably the binding of the VCCP to the complement component is specific. It will be understood that a VCCP may be able to bind to only a single complement component or may be able to bind to more than one different complement component.

In certain embodiments of the invention the PVCCP fragment or variant comprises at least 3 SCR modules (e.g., modules 1-3), preferably 4 SCR modules. Preferably each of the SCR modules displays significant sequence identity to an SCR module found in a naturally occurring PVCCP, e.g., VCP or SPICE. Preferably the multiple SCR modules are arranged in an N to C manner so as to maximize overall identity to a naturally occurring PVCCP. If the sequence of a PVCCP fragment or variant contains an SCR domain that differs from the SCR consensus sequence at one or more positions, in certain embodiments of the invention the amino acid(s) at the one or more differing positions is identical to that found at a corresponding position in the most closely related SCR found in a naturally occurring PVCCP. In certain embodiments the PVCCP variant comprises at least one SCR module from a first PVCPP and at least one SCR module from a second PVCPP. In certain embodiments the PVCCP variant comprises at least one SCR module from a PVCCP and at least one SCR from a mammalian complement control protein (RCA protein). Any number of SCR modules, e.g., 1, 2, 3, 4, or more can come from any particular PVCCP or RCA protein in various embodiments of the invention. All such combinations and permutations are contemplated, even if not explicitly set forth herein.

Generally a fragment or variant of a naturally occurring VCCP or VCIP possesses sufficient structural similarity to its naturally occurring counterpart that it is recognized by a polyclonal antibody that recognizes the naturally occurring counterpart. In certain embodiments of the invention a fragment or variant of a VCCP possesses sufficient structural similarity to VCP or SPICE so that when its 3-dimensional structure (either actual or predicted structure) is superimposed on the structure of VCP or SPICE, the volume of overlap is at least 70%, preferably at least 80%, more preferably at least 90% of the total volume of the VCP structure. A partial or complete 3-dimensional structure of the fragment or variant may be determined by crystallizing the protein as described for VCP (Murthy, 2001). Alternately, an NMR solution structure can be generated, as performed for various VCP fragments (Wiles, A P, et al., *J. Mol. Biol.* 272, 253-265, 1997). A modeling program such as MODELER (Sali, A. and Blundell, T L, *J. Mol. Biol.,* 234, 779-815, 1993), or any other modeling program, can be used to generate a predicted structure. The model can be based on the VCP structure and/or any known SCR structure. The PROSPECT-PSPP suite of programs can be used (Guo, J T, et al., *Nucleic Acids Res.* 32(Web Server issue):W522-5, Jul. 1, 2004). Similar methods may be used to generate a structure for SPICE.

Fragments or variants of a VCCP or VCIP may be generated by any available means, a large number of which are known in the art. For example, VCCPs, VCIPs, and fragments or variants thereof can be produced using recombinant DNA technology as described below. A VCCP or VCIP fragment may be chemically synthesized, produced using PCR amplification from a cloned VCCP or VCIP sequence, generated by a restriction digest, etc. Sequences for a VCCP variant may be generated by random mutagenesis of a VCCP sequence (e.g., using X-rays, chemical agents, or PCR-based mutagenesis), site-directed mutagenesis (e.g., using PCR or oligonucleotide-directed mutagenesis, etc. Selected amino acids can be changed or added.

While not wishing to be bound by any theory, it is likely that amino acid differences between naturally occurring PVCCPs occur at positions that are relevant in conferring differences in particular properties such as ability to bind heparin, activity level, etc. For example, VCP and SPICE differ at only 11 amino acids, but SPICE has a much higher activity as a cofactor for cleavage of C3b (e.g., cleavage occurs at a much faster rate with SPICE than with VCP). The amino acid differences are likely to be responsible for the differential activities of the two proteins. The amino acids at these positions are attractive candidates for alteration to identify variants that have yet greater activity.

Additional Complement Inhibitors

In some embodiments a complement inhibitor is a naturally occurring mammalian complement regulatory protein or a fragment or derivative thereof. For example, the complement regulatory protein may be CR1, DAF, MCP, CFH, or CFI. In some embodiments of the invention the complement regulatory polypeptide is one that is normally membrane-bound in its naturally occurring state. In some embodiments of the invention a fragment of such polypeptide that lacks some or all of a transmembrane and/or intracellular domain is used. Soluble forms of complement receptor 1 (sCR1), for example, are of use in the invention. For example the compounds known as TP10 or TP20 (Avant Therapeutics) can be used. C1 inhibitor (C1-INH) is also of use. In some embodiments a soluble complement control protein, e.g., CFH, is used. In some embodiments of the invention the polypeptide is modified to increase its solubility.

In some embodiments, a complement inhibitor is a C1s inhibitor. For example, U.S. Pat. No. 6,515,002 describes compounds (furanyl and thienyl amidines, heterocyclic amidines, and guanidines) that inhibit C1s. U.S. Pat. Nos. 6,515,002 and 7,138,530 describe heterocyclic amidines that inhibit C1s. U.S. Pat. No. 7,049,282 describes peptides that inhibit classical pathway activation. Certain of the peptides comprise or consist of WESNGQPENN (SEQ ID NO: 68) or KTISKAKGQPREPQVYT (SEQ ID NO: 69) or a peptide having significant sequence identity and/or three-dimensional structural similarity thereto. In some embodiments these peptides are identical or substantially identical to a portion of an IgG or IgM molecule. U.S. Pat. No. 7,041,796 discloses C3b/C4b Complement Receptor-like molecules and uses thereof to inhibit complement activation. U.S. Pat. No. 6,998,468 discloses anti-C2/C2a inhibitors of complement activation. U.S. Pat. No. 6,676,943 discloses human complement C3-degrading protein from *Streptococcus pneumoniae*.

V. Anti-Th17 Agents

An anti-Th17 agent is any agent that inhibits formation, survival, and/or activity of Th17 cells or that inhibits production or a biological activity of a Th17 cell effector molecule such as IL-17. In some embodiments an anti-Th17 agent inhibits development, proliferation, survival, and/or maturation of Th17 cells. In some embodiments, an anti-Th17 agent inhibits production and/or a biological activity of IL-6, IL-21, IL-23, and/or IL-1β. In some embodiments, an anti-Th17 agent inhibits production and/or activity of a Th17 effector cytokine, e.g., IL-17A, IL-17F, IL-21, and/or IL-22. Exemplary anti-Th17 agents include, e.g., agents that bind to a Th17-associated cytokine or agents that bind to a receptor for a Th17-associated cytokine and, e.g., block interaction of the receptor with the endogenous cytokine but do not themselves significantly activate the receptor. Exemplary anti-Th17 agents include, e.g., antibodies, aptamers, soluble receptor fragments (e.g., soluble extracellular domain of the relevant cytokine receptor) or other polypeptides, peptides, small molecules, etc. In some embodiments, an anti-Th17 agent comprises an antibody that substantially lacks the capacity to activate complement. For example, the antibody may have less than 10%, less than 5%, or less than 1% complement stimulating activity as compared with full length human IgG1. In some embodiments, the antibody comprises a CH2 domain that has reduced ability to bind C1q as compared with human IgG1 CH2 domain. In some embodiments, the antibody contains CH1, CH2, and/or CH3 domains from human IgG4 and/or does not contain CH1, CH2, and/or CH3 domains from human IgG1.

In some embodiments, an anti-Th17 agent has a molecular weight of 1 kD or less. In some embodiments, an anti-Th17 agent has a molecular weight between 1 kD and 2 kD, between 2 kD and 5 kD, between 5 kD and 10 kD, between 10 kD and 20 kD, between 20 kD and 30 kD, between 30 kD and 50 kD, between 50 kD and 100 kD, or between 100 kD and 200 kD.

In some embodiments an anti-Th17 agent comprises an adnectin, affibody, anticalin, or other type of polypeptide sometimes used in the art in lieu of an antibody, wherein the polypeptide binds to a Th17-associated cytokine or cytokine receptor.

A variety of anti-Th17 agents, e.g., agents that inhibit one or more Th17-associated cytokines, are known in the art and may be used in various embodiments.

Sequences of polypeptides of interest herein, e.g., Th17-associated cytokines and their receptors, are well known in the art and available in public databases such as those available through Entrez at the National Center for Biotechnology Information website or Universal Protein Resource website. Exemplary databases include, e.g., GenBank, RefSeq, Gene, Protein, Nucleotide, UniProtKB/SwissProt, UniProtKB/Trembl, and the like. In general, sequences, e.g., mRNA and polypeptide sequences, in the NCBI Reference Sequence database may be used as gene product sequences for a gene of interest. Such sequences may be used, e.g., to produce a polypeptide useful as an antigen or reagent for production, isolation, or characterization of an agent that binds to the gene product. It will be appreciated that multiple alleles of a gene may exist among individuals of the same species. For example, differences in one or more nucleotides (e.g., up to about 1%, 2%, 3-5% of the nucleotides) of the nucleic acids encoding a particular protein may exist among individuals of a given species. Due to the degeneracy of the genetic code, such variations often do not alter the encoded amino acid sequence, although DNA polymorphisms that lead to changes in the sequence of the encoded proteins can exist. Examples of polymorphic variants can be found in, e.g., the Single Nucleotide Polymorphism Database (dbSNP), available at the NCBI website (Sherry S T, et al. (2001). "dbSNP: the NCBI database of genetic variation". Nucleic Acids Res. 29 (1): 308-311; Kitts A, and Sherry S, (2009). The single nucleotide polymorphism database (dbSNP) of nucleotide sequence variation in The NCBI Handbook [Internet]. McEntyre J, Ostell J, editors. Bethesda (Md.): National Center for Biotechnology Information (US); 2002). Multiple isoforms of certain proteins may exist, e.g., as a result of alternative RNA splicing or editing. In general, where aspects of this disclosure pertain to a gene or gene product, embodiments pertaining to allelic variants or isoforms are encompassed unless indicated otherwise. Certain embodiments may be directed to particular sequence(s), e.g., particular allele(s) or isoform(s).

Table 4 lists Gene ID and NCBI RefSeq accession numbers for certain human Th17-associated cytokines and their receptors. It will be appreciated that certain of the protein sequences are precursor sequences. The mature form of the protein would lack a secretion signal sequence present in the precursor. It will be appreciated that the sequences described under the respective accession numbers for the cytokines and cytokine receptors listed in Table 4 are exemplary and that naturally occurring variants, e.g., allelic variants, are encompassed in various embodiments. Furthermore, it will be appreciated that for purposes of generating a useful binding agent (e.g., an antibody) for use as a detection reagent or therapeutic agent, variant sequences, short peptide segments, etc., may be used in certain embodiments.

TABLE 4

Gene ID and Accession Numbers for Certain Th17-Associated Cytokines and their Receptors Protein and mRNA

| Gene Official Symbol/Name | Alternate name and comments | Gene ID | mRNA accession number | Protein accession number |
|---|---|---|---|---|
| IL23A/interleukin 23, alpha subunit | p19 | 51561 | NM_016584 | NP_057668 |
| IL12B/interleukin 12B | p40; IL23 beta subunit. | 3593 | NM_002187 | NP_002178 |
| IL23R/interleukin 23 receptor | alpha subunit of the IL23 receptor | 149233 | NM_144701 | NP_653302 |
| IL12RB/interleukin 12 receptor, beta 1 | beta subunit of the IL23 receptor | 3594 | NM_005535 (isoform 1) NM_153701 (isoform 2) | NP_005526 (isoform 1) NP_714912 (isoform 2) |
| IL17A | | 3605 | NM_002190 | NP_002181 |
| IL17F | | 112744 | NM_052872 | NP_443104 |
| IL-17RA/ interleukin 17 receptor A | | 23765 | NM_014339 | NP_055154 |

In some embodiments an anti-Th17 agent is an anti-IL-23 agent. An IL-23 agent is an agent (e.g., a molecule or complex) that partially or fully bocks, inhibits, neutralizes, prevents or interferes with a biological activity of IL-23. In some embodiments a biological activity of IL-23 is the ability to induce IL-17 production by activated T cells. IL-23 is a heterodimeric cytokine composed of two subunits. The IL-23 beta subunit, also called p40, is shared with another cytokine, interleukin-12 (IL-12). The IL-23 alpha subunit is also called p19. The IL-23 subunits are joined by a disulfide bond. IL-23 signals via binding to a heterodimeric receptor, composed of IL-12Rbeta1 (IL12RB1), which is shared by the IL-12 receptor, and IL-23R (Parham C, et al. (2002) J. Immunol. 168 (11): 5699-708). IL-23R associates constitutively with Janus kinase 2 (JAK2), and also binds to transcription activator STAT3 in a ligand-dependent manner. The IL-23 signal transduction cascade parallels those of various other cytokines, in that ligand binding leads to activation of JAKs. The JAKs then phosphorylate the IL-23R at key sites, forming docking sites for the STATs. Subsequently, the JAKs phosphorylate the STATs, which dimerize and translocate to the nucleus where they activate target genes. In some embodiments an anti-IL-23 agent comprises an antibody that binds to the p19 or p40 subunit of IL-23. In some embodiments an anti-IL-23 agent, e.g., an anti-IL-23 antibody, binds to the p40 subunit and inhibits both IL-23 and IL-12.

Certain anti-IL-23 agents and methods of identifying and/or making such agents are disclosed in U.S. Ser. No. 10/697,599. For example, screening methods and assays that may be readily employed by the ordinary skilled artisan to identify and/or produce a variety of anti-IL-23 agents (referred to sometimes as "IL-23 antagonists" in U.S. Ser. No. 10/697,599) are disclosed.

In certain embodiments an anti-IL-23 antibody that binds to the p40 subunit of IL-23 is ustekinumab or a fragment thereof. Ustekinumab (experimental name CNTO 1275, proprietary commercial name Stelara®, Centocor; CAS Number: 815610-63-0) is a human monoclonal antibody of the IgG1 subclass. Exemplary anti-IL-23 antibodies that bind to the p19 subunit of human IL-23, and isolated nucleic acids that encode at least one anti-IL-23p19 antibody, vectors, host cells, and methods of making, are described in U.S. Ser. No. 11/617,503. Additional anti-IL-23 antibodies that bind to the p19 subunit are described in U.S. Ser. No. 11/762,738.

In some embodiments an anti-IL-23 agent comprises an IL-23p40 specific immunoglobulin derived proteins (see, e.g., U.S. Ser. No. 11/768,582).

In some embodiments an IL-23 inhibitor comprises a polypeptide comprising a soluble IL-23R or a variant or fragment thereof capable of binding to IL-23 in solution. In some embodiments a soluble IL-23R lacks the portion of IL-23R encoded by exon 9 of the IL-23R alpha gene. See, e.g., Yu, R Y, J Immunol. (2010) 15; 185(12):7302-8. In some embodiments a soluble IL-23R lacks the portion of IL-23 encoded by exon 9 and at least a portion of exon 8 of the IL-23R alpha gene.

In some embodiments, IL-23 activity is inhibited by interfering with IL-23 signal transduction, e.g., by inhibiting one or more processes or proteins involved in the IL-23 signal transduction pathway. For example, in some embodiments IL-23 signaling is inhibited using a JAK inhibitor or a STAT inhibitor. In some embodiments a JAK inhibitor inhibits JAK expression. Methods of use to inhibit JAK expression in some embodiments include the use of RNAi agents (e.g., siRNA) or antisense oligonucleotides. In some embodiments a JAK inhibitor inhibits JAK binding to IL-23 receptor. In some embodiments a JAK inhibitor inhibits JAK dimerization. In some embodiments a JAK inhibitor inhibits JAK kinase activity. For example, in some embodiments a JAK inhibitor binds to the JAK kinase domain, e.g., to the ATP binding site. Numerous JAK inhibitors are known in the art. For example, INCB028050 is an orally bioavailable JAK1/JAK2 inhibitor with reported nanomolar potency against JAK1 (5.9 nM) and JAK2 (5.7 nM) (Fridman, J S, et al., J Immunol. 2010; 184(9):5298-307). INCB028050 is reported to inhibit intracellular signaling of multiple proinflammatory cytokines including IL-6 and IL-23 at concentrations <50 nM. Small molecule JAK2 inhibitors include, e.g., AZD1480 and AZ960.

In some embodiments a STAT inhibitor inhibits STAT expression. Methods of use to inhibit STAT expression in some embodiments include the use of RNAi agents (e.g., siRNA) or antisense oligonucleotides. In some embodiments a STAT inhibitor inhibits STAT binding to JAK. In some embodiments a STAT inhibitor inhibits STAT dimerization or nuclear translocation. In some embodiments a STAT inhibitor comprises a phosphopeptide which, e.g., competes with STAT for binding to phosphorylated JAK. WO/2008/151037 discloses certain peptide-based STAT inhibitors of use in certain embodiments. In some embodiments a STAT inhibitor inhibits STAT binding to DNA. For example, a decoy oligonucleotide comprising a sequence substantially identical to an endogenous DNA sequence to which STAT naturally binds in human cells may bind to STAT and prevent it from binding to its endogenous binding site(s). Small molecule STAT3 inhibitors include, e.g., STA-21, IS3 295, and S3I-M2001. See Huang, S., Clin Cancer Res 2007; 13:1362-1366 and references therein, which are incorporated herein by reference, for further information regarding certain STAT inhibitors.

In some embodiments an anti-Th17 agent is an anti-IL-17 agent. An IL-17 agent is an agent (e.g., a molecule or complex) that partially or fully bocks, inhibits, neutralizes, prevents or interferes with a biological activity of IL-17. Exemplary anti-IL-17 polypeptides, e.g., anti-IL-17 antibodies, are described in, e.g., U.S. Ser. No. 11/658,344. Additional anti-IL-17 antibodies are described in U.S. Ser. No. 11/762,738. In some embodiments an anti-IL-17 agent comprises at least a portion of an IL-17 receptor, wherein the portion binds to IL-17. Exemplary IL-17 receptor polypeptides are disclosed in, e.g., U.S. Ser. No. 09/022,260.

It will be understood that a polypeptide comprising a binding domain of any of the various anti-Th17 antibodies or other polypeptides described herein can be transferred into other polypeptide backbones or used as isolated agents in certain embodiments. It will further be understood that variants may be used. For example, a variant may be at least 90%, 91%, 92%, 93%, 94%, 95%, 96%, 97%, 98%, 99%, or more identical to a binding domain of a receptor. In some embodiments an antibody that competes with a particular antibody known in the art for binding to a cytokine of interest may be used. In some embodiments an antibody of the IgG class is modified so that it lacks an Fc domain that may activate complement. For example, a variable domain of an IgG1 antibody may be grafted to a constant region of an IgG4 antibody.

VI. Pharmaceutical Compositions and Administration Approaches

Suitable preparations, e.g., substantially pure preparations of a complement inhibitor may be combined with pharmaceutically acceptable carriers or vehicles, etc., to produce an appropriate pharmaceutical composition. The term "pharmaceutically acceptable carrier or vehicle" refers to a non-toxic carrier or vehicle that does not destroy the pharmacological activity of the compound with which it is formulated. One of skill in the art will understand that a carrier or vehicle is "non-toxic" if it is compatible with administration to a subject in an amount appropriate to deliver the compound without causing undue toxicity. Pharmaceutically acceptable carriers or vehicles that may be used include, but are not limited to, water, physiological saline, Ringer's solution, sodium acetate or potassium acetate solution, 5% dextrose, and the like. The composition may include other components as appropriate for the formulation desired, e.g., as discussed herein. Supplementary active compounds, e.g., compounds independently useful for treating a subject suffering from a respiratory disorder, can also be incorporated into the compositions. The invention provides such pharmaceutical compositions comprising a complement inhibitor and, optionally, a second active agent useful for treating a subject suffering from a respiratory disorder.

In some embodiments, the invention provides a pharmaceutically acceptable complement inhibitor or pharmaceutically acceptable composition comprising a complement inhibitor, packaged together with a package insert (label) approved by a government agency responsible for regulating pharmaceutical agents, e.g., the U.S. Food & Drug Administration. In some embodiments, the invention provides a pharmaceutical pack comprising: (a) a pharmaceutically acceptable complement inhibitor in concentrated or solid form (e.g., as a lyophilized powder); (b) a pharmaceutically acceptable carrier, diluent, or vehicle. In some embodiments, a carrier, diluent, or vehicle is suitable for use to deliver the composition using a nebulizer. In some embodiments, a suitable carrier, diluent, or vehicle may be provided separately or acquired by a health care provider from an appropriate source. Optionally a pack contains instructions for dissolving or diluting the complement inhibitor in the carrier, diluent, or vehicle to produce a composition for administration. In some embodiments a package insert states one or more indications that include one or more chronic complement-mediated disorders, e.g., one or more chronic respiratory disorders, e.g., asthma or COPD. In some embodiments, the package insert states particular patient and/or disease characteristics or criteria that define a patient population or disease category for treatment of which the composition has been approved for use. In some embodiments, the package insert specifies that the composition may be or should be administered according to a method of the present invention, e.g., according to a dosing schedule and/or using a dosing interval described herein.

In general, a pharmaceutical composition can be administered to a subject by any suitable route of administration including, but not limited to, intravenous, intramuscular, subcutaneously, by the respiratory route, etc. In some embodiments, local administration to a tissue or organ affected by a complement-mediated disorder is used. It will be understood that "administration" encompasses directly administering a compound or composition to a subject, instructing a third party to administer a compound or composition to a subject, prescribing or suggesting a compound or composition to a subject (e.g., for self-administration), self-administration, and, as appropriate, other means of making a compound or composition available to a subject. If administration is accomplished using an implanted reservoir, administration can refer to causing release of a composition or compound from the reservoir.

Pharmaceutical compositions suitable for injectable use (e.g., intravenous administration, subcutaneous or intramuscular administration) typically include sterile aqueous solutions (where water soluble) or dispersions and sterile powders for the extemporaneous preparation of sterile injectable solutions or dispersion. Sterile solutions can be prepared by incorporating the compound in the required amount in an appropriate solvent, optionally with one or a combination of ingredients such as buffers such as acetates, citrates, lactates or phosphates; agents for the adjustment of tonicity such as sodium chloride or dextrose; antibacterial agents such as benzyl alcohol or methyl parabens; antioxidants such as ascorbic acid, glutathione, or sodium bisulfite; chelating agents such as ethylenediaminetetraacetic acid; and other suitable ingredients etc., as desired, followed by filter-based sterilization. One of skill in the art will be aware of numerous physiologically acceptable compounds that may be included in a pharmaceutical composition. Other useful compounds include, for example, carbohydrates, such as glucose, sucrose, lactose; dextrans; amino acids such as glycine; polyols such as mannitol. These compounds may, for example, serve as bulking agents and/or stabilizers, e.g., in a powder and/or when part of the manufacture or storage process involves lyophilization. Surfactant(s) such as Tween-80, Pluronic-F108/F68, deoxycholic acid, phosphatidylcholine, etc., may be included in a composition, e.g., to increase solubility or to provide microemulsion to deliver hydrophobic drugs. pH can be adjusted with acids or bases, such as hydrochloric acid or sodium hydroxide, if desired. The parenteral preparation can be enclosed in ampoules, disposable syringes or infusion bags or multiple dose vials made of glass or plastic. Preferably solutions for injection are sterile and acceptably free of endotoxin.

Generally, dispersions are prepared by incorporating the active compound into a sterile vehicle which contains a basic dispersion medium and appropriate other ingredients from those enumerated above. In the case of sterile powders for the preparation of sterile injectable solutions, methods of preparation can include vacuum drying and freeze-drying which yields a powder of the active ingredient plus any additional desired ingredient, e.g., from a previously sterile-filtered solution thereof.

For administration by the respiratory route (inhalation), a complement inhibitor may be delivered in the form of an aerosol spray from a pressured container or dispenser which contains a suitable propellant. A metered dose inhaler (MDI), dry powder inhaler, or nebulizer may be used. The aerosol may comprise liquid and/or dry particles (e.g., dry powders, large porous particles, etc.). Suitable aqueous vehicles useful in various embodiments include water or saline, optionally including an alcohol. In some embodiments the composition comprises a surfactant suitable for introduction into the lung. Other excipients suitable for pulmonary administration can be used.

A variety of different devices are available for respiratory administration. Nebulizers are devices that transform solutions or suspensions of medications into aerosols that are suitable for deposition in the lower airway. Nebulizer types include jet nebulizers, ultrasonic wave nebulizers, and vibrating mesh nebulizers. A partial list of available vibrating mesh nebulizers includes eFlow (Pari), i-Neb (Respironics), MicroAir (Omron), IH50 Nebulizer (Beurer), and Aeroneb® (Aerogen). A Respimat® Soft Mist™ Inhaler (Boeringer Ingelheim) may be used. A metered dose inhaler (MDI) is a handheld aerosol device that uses a propellant to deliver the therapeutic agent. MDIs include a pressurized metal canister that contains pharmacological agent in suspension or solution, propellant, surfactant (typically), and metering valve. Chloroflourocarbons (CFCs) had been widely used as propellants but have been largely replaced by hydrofluorocarbons (HFCs, also known as hydrofluoroalkanes (HFA)) such as HFC-134a and HFC-227ea. Carbon dioxide and nitrogen are other alternatives. A dry powder inhaler (DPI) is a breath-actuated device that delivers the drug in the form of particles contained in a capsule or blister that is punctured prior to use and typically does not employ a propellant. Examples of DPIs currently used to deliver medications for treating asthma and/or COPD include, e.g., Diskus, Aerolizer, HandiHaler, Twisthaler, Flexhaler. Such devices may be used to deliver a complement inhibitor in various embodiments of the invention. Other exemplary DPI devices that may be used in various embodiments include 3M™ Taper and 3M Conix™, TAIFUN® (AKELA Pharma), Acu-Breathe™ (Respirics).

Inhalation accessory devices (IADs) generally fall into 2 categories: spacers and holding chambers. Spacers and holding chambers extend the mouthpiece of the inhaler and direct the mist of medication toward the mouth, reducing medication lost into the air. Using a spacer with an MDI can help reduce the amount of drug that sticks to the back of the throat, improving direction and deposition of medication delivered by MDIs. Valved holding chambers (VHCs) allow for a fine cloud of medication to stay in the spacer until the patient breathes it in through a one-way valve, drawing the dose of medicine into the lungs. Examples include Aerochamber and Optichamber.

Particulate compositions may be characterized on the basis of various parameters such as the fine particle fraction (FPF), the emitted dose, the average particle density, and the mass median aerodynamic diameter (MMAD). Suitable methods are known in the art, some of which are described in U.S. Pat. Nos. 6,942,868 and 7,048,908 and U.S. Publication Nos. 20020146373, 20030012742, and 20040092470. In certain embodiments aerosol particles are between approximately 0.5 μm-10 μm (MMAD), e.g., about 5 μm for respiratory delivery, though smaller or larger particles could also be used. In certain embodiments particles having a mass mean aerodynamic diameter of between 1 μm and 25 μm, e.g., between 1 μm and 10 μm, are used.

A dry particle composition containing particles smaller than about 1 mm in diameter is also referred to herein as a dry powder. A "dry" composition has a relatively low liquid content, so that the particles are readily dispersible, e.g., in a dry powder inhalation device to form an aerosol or spray. A "powder" consists largely or essentially entirely of finely dispersed solid particles that are relatively free flowing and capable of being readily dispersed in an inhalation device and subsequently inhaled by a subject, preferably so that a significant fraction of the particles can reach a desired portion of the respiratory tract. In certain embodiments large porous particles having mean geometric diameters ranging between 3 and 15 μm and tap density between 0.04 and 0.6 $g/cm^3$ are used. See, e.g., U.S. Pat. No. 7,048,908; Edwards, D. et al, Science 276:1868-1871, 1997; and Vanbever, R., et al., Pharmaceutical Res. 16:1735-1742, 1999).

Various considerations for respiratory delivery that may be useful in embodiments of the present invention are discussed in Bisgaard, H., et al., (eds.), Drug Delivery to the Lung, Vol. 26 in "Lung Biology in Health and Disease", Marcel Dekker, New York, 2002. Aerosol devices are discussed, e.g., in Dolovich M B, Dhand R. Lancet. (2011) 377(9770):1032-45.

Oral administration may be used in certain embodiments. Oral compositions generally include an inert diluent or an edible carrier. For the purpose of oral therapeutic administration, the active compound can be incorporated with excipients and used in the form of tablets, troches, or capsules, e.g., gelatin capsules. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. A liquid composition can also be administered orally. Formulations for oral delivery may incorporate agents to improve stability within the gastrointestinal tract and/or to enhance absorption.

For topical application, a complement inhibitor may be formulated in a suitable ointment containing the active component suspended or dissolved in one or more carriers. Carriers for topical administration include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated as a suitable lotion or cream containing a compstatin analog suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol, and water.

Systemic administration can also be by transmucosal or transdermal means. For transmucosal or transdermal administration, penetrants appropriate to the barrier to be permeated may be used in the formulation. Such penetrants are generally known in the art, and include, for example, for transmucosal administration, detergents, bile salts, and fusidic acid derivatives. Transmucosal administration can be accomplished, e.g., through the use of nasal sprays or suppositories. In some embodiments, intranasal administration is used, e.g., to administer a complement inhibitor to a subject in need of treatment for nasal polyposis, chronic rhinosinusitis, or allergic rhinitis. For transdermal administration, the active compounds are typically formulated into ointments, salves, gels, or creams as generally known in the art.

The compounds can also be prepared in the form of suppositories (e.g., with conventional suppository bases such as cocoa butter and other glycerides) or retention enemas for rectal delivery.

Methods of local administration to the eye include, e.g., intraocular administration, e.g., intraocular injection, e.g., intravitreal injection. In some embodiments, administration is by choroidal injection, transscleral injection, eyedrops or eye ointments, transretinal, subconjunctival bulbar, intravitreal injection, suprachoroidal injection, subtenon injection, scleral pocket or scleral cutdown injection.

In certain embodiments of the invention, a complement inhibitor is prepared with carrier(s) that will protect the compound against rapid elimination from the body, such as a controlled release formulation, including implants and microencapsulated delivery systems. For example, a compound may be incorporated into or encapsulated in a microparticle or nanoparticle formulation. Biodegradable, biocompatible polymers can be used, such as ethylene vinyl acetate, polyanhydrides, polyglycolic acid, collagen, polyorthoesters, polyethers, polylactic acid, PLGA, etc. Liposomes or other lipid-based particles can be used as pharmaceutically acceptable carriers. These can be prepared according to methods known to those skilled in the art, for example, as described in U.S. Pat. No. 4,522,811 and/or other references listed herein. Depot formulations containing a complement inhibitor may be used. The complement inhibitor is released from the depot over time. One of ordinary skill in the art will appreciate that the materials and methods selected for preparation of a controlled release formulation, implant, etc., should be such as to retain activity of the compound. In some embodiments, a composition is free or essentially free of one or more carrier(s) whose primary or only intended purpose or effect would be to result in sustained or controlled release of an active agent, e.g., a complement inhibitor.

In some embodiments, a complement inhibitor is used in combination with one or more additional active agent(s) useful to treat a disorder of interest herein (see, e.g., Brunton, L L, et al. (eds.), Goodman and Gilman's The Pharmacological Basis of Therapeutics, (e.g., 11th or 12th edition), McGraw-Hill, for examples of such agents.) In some embodiments one or more additional active agents is administered in the same composition as a complement inhibitor. In some embodiments one or more additional active agents is administered in a separate composition, which separate composition may be administered prior to, at approximately the same time as, or after administration of a complement inhibitor. In some embodiments, use of a complement inhibitor allows reduction in dose and/or frequency of administration of an additional active agent while maintaining at least equivalent disease control and/or benefit to the subject. It will be understood that pharmaceutical compositions comprising an additional active agent may be prepared using pharmaceutically acceptable carriers and/or preparation methods described herein or known in the art, and administered using routes of administration described herein or known in the art.

In some embodiments a second active agent is an agent that interferes with the DC-Th17-B-Ab-C-DC cycle by a mechanism distinct from direct inhibition of a complement component or complement activation. In some embodiments a second active agent may be an anti-IL-23 agent or anti-IL-17 agent. In some embodiments a pharmaceutical composition or pharmaceutical pack comprises a second active agent that interferes with the DC-Th17-B-Ab-C-DC cycle. In some embodiments a package insert specifies that two agents are to be administered in combination. In some embodiments a complement inhibitor, e.g., a compstatin analog, may be added to any treatment regimen that comprises an anti-Th17 agent. In some embodiments such addition permits a lower dose or increased dosing interval of the anti-Th17 agent to be used, without reduction in efficacy. In some embodiments such addition results in increased efficacy.

When two or more therapies (e.g., compounds or compositions) are used or administered "in combination" with each other, they may be given at the same time, within overlapping time periods, or sequentially (e.g., separated by up to 2-4 weeks in time), in various embodiments of the invention. They may be administered via the same route or different routes in various embodiments. They may be administered in either order in various embodiments. In some embodiments, the compounds or compositions are administered within 4, 8, 12, 24, 48, 72, or 96 hours of each other. In some embodiments, a first agent is administered prior to or after administration of the second agent, e.g., sufficiently close in time that the two agents are present at useful levels within the body at least once. In some embodiments, the agents are administered sufficiently close together in time such that no more than 90% of the earlier administered composition has been metabolized to inactive metabolites or eliminated, e.g., excreted, from the body, at the time the second compound or composition is administered. In some embodiments, the agents are administered sufficiently close together in time such that no more than 2 weeks has elapsed since the earlier administered agent has been metabolized to inactive metabolites or eliminated, e.g., excreted, from the body, at the time the second agent is administered. In some embodiments administration of two agents (e.g., a complement inhibitor and a second agent that interferes with the DC-Th17-B-Ab-C-DC cycle act additively, resulting in an effect that would not be achieved by either agent alone. In some embodiments administration of two agents (e.g., a complement inhibitor and a second agent that interferes with the DC-Th17-B-Ab-C-DC cycle act synergistically, resulting in an effect that is greater than an additive effect and/or is qualitatively different to an additive effect in a clinically and/or statistically significant way.

It will be appreciated that a complement inhibitor and/or additional active agent(s) can be provided as a pharmaceutically acceptable salt. Pharmaceutically acceptable salts include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Also, pharmaceutically-acceptable salts can be prepared as alkaline metal or alkaline earth salts, such as sodium, potassium or calcium salts, if appropriate depending on the identity of the active agent.

It will be understood that the pharmaceutically acceptable carriers, compounds, and preparation methods mentioned herein are exemplary and non-limiting. See, e.g., Remington: The Science and Practice of Pharmacy. 21st Edition. Philadelphia, Pa. Lippincott Williams & Wilkins, 2005, for additional discussion of pharmaceutically acceptable compounds and methods of preparing pharmaceutical compositions of various types.

A compound or composition, e.g., a pharmaceutical composition, can be used or administered to a subject in an effective amount. In some embodiments, an "effective amount" of an active agent, e.g., a complement inhibitor, (or composition containing an active agent) refers to an amount of the active agent (or composition) sufficient to elicit one or more biological response(s) of interest in, for example, a subject to whom the active agent (or composition) is administered. As will be appreciated by those of ordinary skill in the art, the absolute amount of a particular agent that is effective may vary depending on such factors as the biological endpoint, the particular active agent, the target tissue, etc. Those of ordinary skill in the art will further understand that an "effective amount" may be administered in a single dose, or may be achieved by administration of multiple doses. For example, in some embodiments, an effective amount may be an amount sufficient to achieve one or more of the following: (i) reduce the severity of one or more manifestations (e.g., one or more symptoms or signs) of a chronic respiratory disorder; (ii) cause a reduction in frequency and/or severity of exacerbations (which reduction may result in, e.g., decreased days of school or work lost, decreased physician and/or emergency room visits, decreased hospitalization events, and/or decreased mortality); (iii) permit a reduction in use of standard medication for the disorder while maintaining at least equivalent disease control; and/or (iv) inhibit or prevent a long-term pathological change associated with the disorder; and/or (v) improve daily function. In many embodiments, a therapeutically relevant effective amount at least in part reduces one or more manifestations (e.g., symptoms) of a chronic disorder and/or returns one or more physiological or biochemical parameters or indicators associated with or causative of a chronic disorder at least partially to normal. For example, in some embodiments, an effective amount may be an amount sufficient to achieve one or more of the following: (i) reduce the severity of one or more manifestations (e.g., one or more symptoms or signs) of a chronic respiratory disorder; (ii) reduce the magnitude of EAR, LAR, and/or DAR (as assessed, for example, by maximum reduction in $FEV_1$ and/or maximum reduction in PEF measured within a relevant time period following an allergen challenge); (iii) reduce likelihood of developing an EAR, LAR, and/or DAR; (iv) cause a reduction in frequency and/or severity of exacerbations (which reduction may result in, e.g., decreased days of school or work lost, decreased physician and/or emergency room visits, decreased hospitalization events, and/or decreased mortality); (v) permit a reduction in use of ICS, OCS, leukotriene modifiers, and/or Xolair while maintaining at least equivalent disease control; (vi) inhibit or prevent airway remodeling; (vii) improve daily function and/or exercise tolerance; and/or (viii) reduce one or more indicators of airway inflammation. In many embodiments in which an agent is administered to a subject in need of treatment for a chronic respiratory disorder, a therapeutically relevant effective amount at least in part reduces one or more manifestations (e.g., symptoms) of a chronic respiratory disorder and/or returns one or more physiological or biochemical parameters or indicators associated with or causative of a chronic respiratory disorder at least partially to normal.

Indicators of airway inflammation include, e.g., the presence of increased numbers of inflammation-associated cells such as white blood cells (e.g., eosinophils, lymphocytes, macrophages, and/or neutrophils) and/or inflammatory mediators (e.g., chemokines (e.g., eotaxin, thymus and activation-regulated chemokine (TARC), macrophage-derived chemokine (MDC)), cytokines (e.g., TNFalpha, IL-1beta, IL-4, IL-5, IL-13, IL-25), histamine, cysteinyl leukotrienes, nitric oxide) in the airways, as compared with a suitable reference level, e.g., a normal level. For example, the number and/or concentration of cells and/or mediators may be above the upper limit of the normal range in subjects not suffering from a disorder (where "normal range" typically refers to a range of within ±2 standard deviations from a mean value in a population of subjects) or may be greater than a value (or average value) measured in that subject when the subject's disorder is well controlled. A reduction in symptom severity and/or frequency can be statistically significant and/or clinically meaningful within the sound judgment of a physician or other medical practitioner. Determining whether a disorder is well controlled is within the sound judgment of a physician or other medical practitioner. Art-accepted guidelines may be used.

In some embodiments an effective amount results in reduction of at least one parameter associated with Th17 cells and/or Th17 activity. In some embodiments an effective amount reduces the level of at least one cytokine associated with Th17 cells and/or Th17 activity, e.g., a cytokine that promotes Th17 cell formation and/or activity or a cytokine produced by Th17 cells. In some embodiments a cytokine is IL-17, IL21, IL-22, or IL-23. In some embodiments an effective amount results in a shift from Th17 to Treg cells. In some embodiments a shift from Th17 cells to Treg cells is reflected in an immune micro-environment that is relatively rich in IL-10 and relatively poor in IL-17 and IL-23.

For treatment of AMD, an effective amount may be an amount sufficient to achieve one or more of the following: (i) inhibit or prevent drusen formation; (ii) cause a reduction in drusen number and/or size (drusen regression); (iii) cause a reduction in or prevent lipofuscin deposits; (iv) inhibit or prevent visual loss or slow the rate of visual loss; (v) inhibit choroidal neovascularization or slow the rate of choroidal neovascularization; (vi) cause a reduction in size and/or number of lesions characterized by choroidal neovascularization; (vii) inhibit choroidal neovascularization or slow the rate of retinal neovascularization; (viii) cause a reduction in size and/or number of lesions characterized by retinal neovascularization; (ix) improve visual acuity and/or contrast sensitivity; (x) inhibit or prevent photoreceptor or RPE cell atrophy or apoptosis, or reduce the rate of photoreceptor or RPE cell atrophy or apoptosis; (xi) inhibit or prevent progression of non-exudative macular degeneration to exudative macular degeneration; (xii) reduce one or more indicia of inflammation, e.g., the presence of inflammation-associated cells such as white blood cells (e.g., neutrophils, macrophages) in the eye, the presence of endogenous inflammatory mediators, one or more symptoms such as eye pain, redness, light sensitivity, blurred vision and floaters, etc.

One of skill in the art will be aware of appropriate methods to assess the afore-mentioned biological effects and other biological effects of interest. Symptoms can be assessed using standardized instruments (e.g., questionnaires) known in the art. Any of a variety of different health-related quality of life (HRQOL) instruments can be used, which can be generic or specifically associated with the respiratory system (e.g., asthma and/or COPD-specific). Pulmonary function tests, particularly spirometry, can be used to measure parameters of lung function that are frequently altered in subjects with chronic respiratory disorders, such as $FEV_1$, FVC, $FEV_1$/FVC, PEF, etc. Allergen challenge can be performed, e.g., as described in Kelly M M. J Allergy Clin Immunol. 125(2):349-356, 2010 or studies described in Cockcroft, D W, et al. Can Respir J. 14(7): 414-418, 2007. Myofibroblasts synthesize collagen and are believed to play an important role in airway remodeling in disorders characterized by chronic airway inflammation such as asthma and COPD. These cells are increased in the airways of asthmatic individuals 24 h after allergen challenge. Inhibition of the increase in airway wall myofibroblasts that would otherwise occur following allergen challenge may indicate decreased airway remodeling potential. Alternately or additionally, features associated with airway remodeling such as smooth muscle hyperplasia, goblet cell hyperplasia, and/or subepithelial collagen deposition can be assessed.

Bronchial hyperreactivity can be assessed using, for example, "direct" and "indirect" challenge tests, which refer to the mode of action of the agents in relation to smooth muscle contraction. Methacholine chloride and histamine diphosphate are most commonly used as direct smooth muscle stimuli. The most frequently used indirect stimuli are hypertonic saline, adenosine monophosphate (AMP), and mannitol. Challenge testing can be performed, e.g., according to guidelines published by the ERS (Sterk P J, et al. Airway responsiveness. Standardized challenge testing with pharmacological, physical and sensitizing stimuli in adults. Report Working Party Standardization of Lung Function Tests, European Community for Steel and Coal. Official Statement of the European Respiratory Society. Eur Respir J Suppl 1993; 16:53-83) and ATS (Crapo, R O, et al., Guidelines for methacholine and exercise challenge testing-1999. Am J Respir Crit Care Med 2000; 161:309-329). Two suitable methods for inhaling aqueous solutions of pharmacologic stimuli that may be used are the 2-minute tidal breathing method and the dosimeter method. Bronchoconstriction causes increased airway resistance. PC(X) (where X is a number, typically between 10 and 100) refers to the amount of stimulus required to cause a decrease of X % in airway resistance. In general, persons with bronchial hyperreactivity, exhibit a decreased PC(X) than normal individuals. For example individuals with bronchial hyperreactivity may have a methacholine PC(20)<4 mg/ml, while individuals with bronchial hyperactivity may have a PC(20)>4 mg/ml. In some embodiments, an effective amount of a therapeutic agent increases PC(X) in subjects suffering from a chronic respiratory disorder characterized by bronchial hyperreactivity relative to control subjects.

Inflammation-associated cells and/or mediators may be assessed, for example, in a suitable sample such as induced sputum, BAL fluid, and/or airway tissue sample (e.g., obtained from a biopsy such as an endobronchial biopsy). Cells, e.g., inflammation-associated cells can be detected and optionally quantified using, e.g., electron microscopy, optical microscopy (optionally using suitable chemical stains or antibodies to particular markers (immunohistochemistry), flow cytometry, or other suitable methods. Mediator (e.g., cytokine) levels may be measured using, e.g., antibody-based assays such as ELISA assays, bead array assays (such as the Luminex xMAP technology or Cytometric Bead Array (CBA) system from BD Biosciences), antibody array assays, or appropriate bioassays. Expression of mediators can alternately or additionally be assessed by measuring the level of mRNA encoding such mediators (e.g., using any suitable method for measuring RNA level such as reverse transcription PCR, hybridization to oligonucleotide or cDNA arrays, RNA-Seq (e.g., methods making use of high-throughput sequencing technologies to sequence cDNA to obtain information about RNA in a sample), etc.).

Exercise tolerance may be assessed, e.g., by testing performance on a 6 minute walk test (e.g., wherein improved exercise tolerance is evidenced by an increase in the distance a subject is able to walk in 6 minutes), shuttle walk test, and/or cardiopulmonary exercise testing. See, e.g., ATS Statement: Guidelines for the Six-Minute Walk Test (2002) for discussion of 6 minute walk test.

In general, a control subject can be, e.g., an untreated subject or a subject treated with a placebo. An "untreated subject" may be a subject who has not received treatment with a complement inhibitor within the preceding 6 months. In some embodiments, an untreated subject has not received treatment with an ICS, OCS, LTRA, and/or LABA within at least the preceding 4 weeks. In some embodiments, an untreated subject has not received treatment with an anti IgE agent within at least the preceding 12 weeks. Historical control information can be used. In some embodiments, a subject can serve as his or her own control. For example, one or more parameters can be measured once or more prior to treatment and once or more during and/or following treatment. In some embodiments, an "active control" (or "active comparator") is used, wherein a biological effect of the complement inhibitor is compared with that of a compound known to affect the parameter being assessed. For example, a compound that is approved for use as a controller medication in asthma may be used. It will be appreciated that if an active comparator is used as a control, an effective amount of a complement inhibitor may have less, more, or about the same effect as the active comparator at one or more time points in various embodiments.

In some embodiments, one or more biological effect(s) of a complement inhibitor is evident when tested at multiple time points during a dosing interval of the instant invention, wherein said time points encompass at least 75% of the dosing interval, e.g., at least 80%, 85%, 90%, 95%, or more of the dosing interval. In some embodiments, one or more biological effect(s) of a complement inhibitor is evident when tested at or near the end of the dosing interval, where "near the end of the dosing interval" means up to 2 days before the end of the dosing interval, e.g., on the day before the end of the dosing interval.

In some embodiments, an animal model is used, for example, to help guide selection of a dose, dose range, or formulation for testing in human, to assess one or more biological effect(s), etc. Commonly used animal models for airway inflammation and/or asthma involve inhalation of *Ascaris suum* antigen. For example, inhalation of *Ascaris suum* antigen by allergic monkeys (e.g., cynomolgus monkey; *Macaca fascicularis*) causes an early bronchoconstriction and delayed allergic reaction, including a pulmonary inflammatory infiltrate. See, e.g., Mellado, M., et al., J Pharmacol Exp Ther. (2008) 324(2):769-75; Zou, J., et al. Genome Biol. 2002; 3(5):research0020. Epub 2002 Apr. 11. Similar models exist in mice, sheep, guinea pigs, etc. In some embodiments, a significant reduction in allergen-induced EAR, LAR, and/or AHR (e.g., as assessed using methacholine challenge) and/or a significant increase in PC(X), in treated animals as compared with untreated animals, indicates effectiveness. In some embodiments, a reduction in EAR, LAR, and/or AHR remains evident at the end of a dosing interval selected according to the instant invention (e.g., immediately prior to the next dose).

In general, appropriate doses of complement inhibitor or other active agent depend at least in part upon the potency of the complement inhibitor or other active agent, route of administration, etc. In general, dose ranges that are effective and well tolerated can be selected by one of ordinary skill in the art. Such doses can be determined using clinical trials as known in the art. Optionally, a dose may be be tailored to the particular recipient, for example, through administration of increasing doses until a preselected desired response is achieved, such as a preselected desired degree of complement inhibition and/or preselected desired reduction in response to allergen challenge, reduction in bronchial hyper-reactivity, and/or reduction in one or more symptoms of the disorder. If desired, the specific dose level for any particular subject may be selected based at least in part upon a variety of factors including the activity of the specific compound employed, the particular condition being treated and/or its severity, the age, body weight, general health, route of administration, any concurrent medication, and/or the degree of complement protein expression or activity measured in one or more samples obtained from the subject. In some embodiments an effective amount or dose ranges from about 0.001 to 500 mg/kg body weight, e.g., about 0.01 to 100 mg/kg body weight, e.g., about 0.1 to 50 mg/kg body about 0.1 to 20 mg/kg body weight, e.g., about 1 to 10 mg/kg.

Example 1: Effect of a Potent Compstatin Analog in *Ascaris suum* Animal Model of Asthma A potent compstatin analog having the amino acid sequence of the compstatin analog of SEQ ID NO: 28, was synthesized using standard methods. Briefly, amino acids were obtained as Fmoc-protected amino acids, in which the α-amino group of each amino acid was protected with Fmoc. Side chain functional groups were also blocked with various appropriate protective groups. Synthesis was accomplished following the solid phase methodology described by Merrifield (J. Amer. Chem. Soc. 85, 2149 (1963)). Chain assembly was performed on solid phase, at the conclusion of which the N-terminus was acetylated; the peptide was then cleaved from the solid phase and simultaneously deprotected via acidolysis using TFA and amidated. The linear peptide was then oxidized and purified. A study designed to evaluate the efficacy of CA-28 after 14 days of administration in a non-human primate model of asthma was performed. In this study, a dose of 15 mg/kg of CA-28 in a 2.0% glycerol solution was administered to anesthetized animals (cynomolgus monkeys) via intratracheal nebulization once a day for 14 consecutive days using a pneumatic nebulizer (Pari LC Plus, Pari USA, Midlothian, Va.). Budesonide (10 mg/kg, administered once daily for 9 days as a powder using an insufflator), a glucocorticoid used for treatment of asthma, was used as a positive control. Primary endpoints included the effects on broncheoalveolar lavage (BAL) cell counts, cytokine levels, and acute pulmonary function changes as assessed by airway resistance (RL) and dynamic compliance (CDYN) after challenges with *Ascaris suum* (*A. suum*).

Animals were subjected to challenge with *A. suum* at 3 time points (prior to initial dose—Challenge), on day 14 (Challenge 1, i.e., the last day of dosing), and on day 30 (Challenge 2). While each animal was anesthetized, a single dose of *A. suum* antigen was administered via intermittent positive pressure breathing with a ventilator and in-line nebulizer over 15 breaths. Each animal was administered an optimum response dose (ORD) which is the dose of antigen (dilution) that has historically elicited a >40% increase in lung resistance ($R_L$) and a >35% decrease in dynamic compliance ($C_{DYN}$). Blood was collected by venipuncture and analyzed for routine clinical chemistry and hematology parameters.

Broncheoalveolar lavage (BAL) was performed by guiding a pediatric fiberoptic bronchoscope past the carina to wedge in a major bronchus. An attempt was made to lavage different lung fields at each time point. Three washes of sterile saline (20 mL each) were instilled and immediately aspirated for collection into tubes. The first wash collection was placed into one 50 mL conical tube while the second and third wash collections were combined into a second 50 mL conical tube. The samples were placed on wet ice or in a refrigerator set to maintain 4° C. until transport. The cell pellets from the different wash combinations (1st/2nd/3rd wash) were combined and analyzed for total and differential cell counts. From stained slides, BAL cell morphology and differential were determined by counting a minimum of 200 nucleated cells from all washes (cell pellets were combined from all washes), if available, if less than 200 nucleated cells were available this is documented in the study records and results. Relative and absolute counts were determined for macrophages, eosinophils, neutrophils, lymphocytes, and mast cells. Erythrocytes, ciliated respiratory cells, and squamous epithelial cells were not counted. BAL samples were analyzed for eotaxin, RANTES, IL-4, IL-5, IL-6, IL-8, IL-10, IL-13, IL-17a, IL-23, and INF-γ using qualified methods.

Results

Following aerosol *A. suum* antigen challenge during Challenge 0 (control challenge prior to dosing), all animals exhibited a severe bronchoconstrictor response, which was associated with increases in lung resistance (RL) and decreases in dynamic compliance (CDYN) followed by pulmonary eosinophilia.

CA-28 did not affect the acute phase bronchoconstriction resulting from *A. suum* challenge at either Challenge 2 (on the last day of CA-28 dosing) or Challenge 2 (28 days after the cessation of dosing).

CA-28 resulted in slight, improvement (reduction) in eosinophilia following Challenges 1 and 2. However, eosinophil counts were higher in the baseline samples collected right after dosing and prior to the first *A. suum* challenge.

Treatment with inhaled CA-28 at 15 mg/kg in a vehicle comprised of 2.0% glycerol in water resulted in lower levels of most upregulated cytokines and chemokines as compared to animals treated with vehicle control in the treatment session, in a way that was comparable to Budesonide in many case, most notably eotaxin, IFN-γ, IL-4, IL-13, and IL-23, although the suppression did not reach statistical significance in most cases, due to the intrinsic high variability of the data and the low number of animals. The most remarkable data was the total suppression of IL-23 in CA-28 treated animals observed at all time points following Challenges 1 and 2. Inhibition of most of the other cytokines appeared to be present even following Challenge 2 in CA-28 treated groups. CA-28 upregulated baseline levels of IL-10, a key regulatory cytokines, following both Challenges 1 and 2. Data are presented in graphical format in FIGS. 1-11.

The data are consistent with the conclusion that CA-28 creates a protective immune micro-environment (high IL-10, low IFNγ/IL-4/IL-13/IL-17/IL-23) both when the drug is present in the lung (Challenge 1) and 27 days following washout of the drug (Challenge 2) (assuming a 1 day washout for both CA-28 and Budesonide). In particular, IL-17 and 11-23 levels in CA-28 treated animals 24 hours following Challenge 2 were lower than those in control animals, suggesting a sustained beneficial effect. In the case of Budesonide the IL-17/IL-23 axis appears to be upregulated 24 hours following Challenge 2.

Those skilled in the art will recognize, or be able to ascertain using no more than routine experimentation, many equivalents to the specific embodiments of the invention described herein. The scope of the present invention is not intended to be limited to the above Description, but rather is as set forth in the appended claims. It will be appreciated that the invention is in no way dependent upon particular results achieved in any specific example or with any specific embodiment. Articles such as "a", "an" and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. For example, and without limitation, it is understood that where claims or description indicate that a residue at a particular position may be selected from a particular group of amino acids or amino acid analogs, the invention includes individual embodiments in which the residue at that position is any of the listed amino acids or amino acid analogs. The invention also includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims or from the description above is introduced into another claim. For example, any claim that is dependent on another claim can be modified to include one or more elements, limitations, clauses, or descriptive terms, found in any other claim that is dependent on the same base claim. Furthermore, where the claims recite a composition, it is to be understood that methods of administering the composition according to any of the methods disclosed herein, and methods of using the composition for any of the purposes disclosed herein are included within the scope of the invention, and methods of making the composition according to any of the methods of making disclosed herein are included within the scope of the invention, unless otherwise indicated or unless it would be evident to one of ordinary skill in the art that a contradiction or inconsistency would arise. Methods of treating a subject can include a step of providing a subject in need of such treatment (e.g., a subject who has had, or is at increased risk of having, a disease), a step of diagnosing a subject as having a disease and/or a step of selecting a subject for treatment with a complement inhibitor and/or anti-Th17 agent. In some embodiments a method of treatment comprises monitoring a subject for a Th17 biomarker. In some embodiments a method of treatment comprises monitoring a subject for a Th17 biomarker and retreating the subject based at least in part on the result of such monitoring, e.g., administering a complement inhibitor to the subject if the biomarker indicates a resurgence of Th17 cells and/or Th17-associated activity.

Where elements are presented as lists, it is to be understood that each subgroup of the elements is also disclosed, and any element(s) can be removed from the group. For purposes of conciseness only some of these embodiments have been specifically recited herein, but the invention includes all such embodiments. It should also be understood that, in general, where the invention, or aspects or embodiments of the invention, is/are referred to as comprising particular elements, features, etc., certain embodiments of the invention or aspects of the invention consist, or consist essentially of, such elements, features, etc.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. Any embodiment, aspect, element, feature, etc., of the present invention may be explicitly excluded from the claims. For example, any complement inhibitor, anti-Th117 agent, carrier, formulation, formulation component, disorder, subject population or characteristic(s), dosing interval, administration route, or combination thereof can be explicitly excluded.

We claim:

1. A method of treating a subject in need of treatment for a chronic respiratory disorder or other chronic complement-mediated disorder, the method comprising administering multiple doses of a complement inhibitor to the subject according to a dosing schedule, wherein successive doses of the complement inhibitor are administered by a respiratory route on average:
   (i) between 2 weeks and 6 weeks after the plasma concentration of the complement inhibitor decreases to no more than 20% of the maximum plasma concentration that was reached after the previous dose; or
   (ii) between 2 weeks and 6 weeks after plasma complement activation capacity has returned to at least 50% of baseline after the previous dose.

2. A method of treating a subject in need of treatment for a chronic respiratory disorder or other chronic complement-mediated disorder, the method comprising administering multiple doses of a complement inhibitor to the subject according to a dosing schedule,
   wherein successive doses of the complement inhibitor are administered by a respiratory route on average at least 2 weeks after the plasma concentration of the complement inhibitor decreases to no more than 20% of the maximum plasma concentration that was reached after the previous dose.

3. The method of claim 1, wherein at least 5 doses are administered.

4. The method of claim 1, wherein the subject is in need of treatment for asthma, chronic obstructive pulmonary disease (COPD), or both.

5. The method of claim 1, wherein the complement inhibitor acts on C3 or upstream of C3 in the complement cascade.

6. The method of claim 1, wherein the complement inhibitor inhibits cleavage of C3, C5, or factor B.

7. The method of claim 1, wherein the complement inhibitor comprises an antibody, aptamer, peptide, polypeptide, or small molecule.

8. The method of claim 7, wherein the complement inhibitor comprises an antibody, aptamer, peptide, polypeptide, or small molecule that binds to C3, C5, factor B, or factor D.

9. The method of claim 1, wherein the complement inhibitor comprises a compstatin analog.

10. The method of claim 2, wherein at least 5 doses are administered.

11. The method of claim 2, wherein the subject is in need of treatment for asthma, chronic obstructive pulmonary disease (COPD), or both.

12. The method of claim 2, wherein the complement inhibitor acts on C3 or upstream of C3 in the complement cascade.

13. The method of claim 2, wherein the complement inhibitor inhibits cleavage of C3, C5, or factor B.

14. The method of claim 2, wherein the complement inhibitor comprises an antibody, aptamer, peptide, polypeptide, or small molecule.

15. The method of claim 14, wherein the complement inhibitor comprises an antibody, aptamer, peptide, polypeptide, or small molecule that binds to C3, C5, factor B, or factor D.

16. The method of claim 2, wherein the complement inhibitor comprises a compstatin analog.

17. A method of treating a subject in need of treatment for a chronic respiratory disorder or other chronic complement-mediated disorder, the method comprising administering multiple doses of a complement inhibitor to the subject according to a dosing schedule in which successive doses are administered by a respiratory route on average:

(i) at least 2 weeks after the plasma concentration of the complement inhibitor decreases to no more than 20% of the maximum plasma concentration that was reached after the previous dose;

(ii) at least 2 weeks after plasma complement activation capacity has returned to at least 50% of baseline after the previous dose; or (iii) at least 2 weeks after the plasma concentration of the complement inhibitor decreases to no more than 1% of the maximum plasma concentration that was reached after the previous dose.

18. The method of claim 17, wherein at least 5 doses are administered.

19. The method of claim 17, wherein the subject is in need of treatment for asthma, chronic obstructive pulmonary disease (COPD), or both.

20. The method of claim 17, wherein the complement inhibitor acts on C3 or upstream of C3 in the complement cascade.

21. The method of claim 17, wherein the complement inhibitor inhibits cleavage of C3, C5, or factor B.

22. The method of claim 17, wherein the complement inhibitor comprises an antibody, aptamer, peptide, polypeptide, or small molecule.

23. The method of claim 22, wherein the complement inhibitor comprises an antibody, aptamer, peptide, polypeptide, or small molecule that binds to C3, C5, factor B, or factor D.

24. The method of claim 17, wherein the complement inhibitor comprises a compstatin analog.

* * * * *

SEQUENCE LISTING

<160> NUMBER OF SEQ ID NOS: 72

<210> SEQ ID NO 1
<211> LENGTH: 13
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (2)..(12)
<223> OTHER INFORMATION: Disulfide bond

<400> SEQUENCE: 1

Ile Cys Val Val Gln Asp Trp Gly His His Arg Cys Thr
1               5                   10

<210> SEQ ID NO 2
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(19)
<223> OTHER INFORMATION: Any independently selected amino acid or amino
      acid analog
<220> FEATURE:
<221> NAME/KEY: misc_feature
<222> LOCATION: (1)..(19)
<223> OTHER INFORMATION: This region may encompass 2 to 19 residues,
      wherein some residues may be absent
<220> FEATURE:
<221> NAME/KEY: MOD_RES
<222> LOCATION: (22)..(22)
<223> OTHER INFORMATION: Trp or an analog of Trp
<220> FEATURE:
<221> NAME/KEY: MOD_RES
<222> LOCATION: (24)..(42)
<223> OTHER INFORMATION: Any independently selected amino acid or amino
      acid analog
<220> FEATURE:
<221> NAME/KEY: misc_feature
<222> LOCATION: (24)..(42)
<223> OTHER INFORMATION: This region may encompass 2 to 19 residues,
      wherein some residues may be absent

<400> SEQUENCE: 2

Xaa Xaa Xaa Xaa Xaa Xaa Xaa Xaa Xaa Xaa Xaa Xaa Xaa Xaa Xaa Xaa
1               5                   10                  15

Xaa Xaa Xaa Gln Asp Xaa Gly Xaa Xaa Xaa Xaa Xaa Xaa Xaa Xaa Xaa
            20                  25                  30

Xaa Xaa Xaa Xaa Xaa Xaa Xaa Xaa Xaa Xaa
        35                  40

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Trp or an analog of Trp
<220> FEATURE:
<221> NAME/KEY: MOD_RES
<222> LOCATION: (4)..(4)
<223> OTHER INFORMATION: Trp or an analog of Trp
<220> FEATURE:
<223> OTHER INFORMATION: see specification as filed for detailed
      description of substitutions and preferred embodiments

<400> SEQUENCE: 3
```

```
Xaa Gln Asp Xaa Gly
1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Trp or an analog of Trp
<220> FEATURE:
<221> NAME/KEY: MOD_RES
<222> LOCATION: (4)..(4)
<223> OTHER INFORMATION: Trp or an analog of Trp
<220> FEATURE:
<221> NAME/KEY: MOD_RES
<222> LOCATION: (6)..(6)
<223> OTHER INFORMATION: His, Ala, analogs of Ala, Phe or Trp
<220> FEATURE:
<223> OTHER INFORMATION: see specification as filed for detailed
      description of substitutions and preferred embodiments

<400> SEQUENCE: 4

Xaa Gln Asp Xaa Gly Xaa
1               5

<210> SEQ ID NO 5
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(3)
<223> OTHER INFORMATION: Any independently selected amino acid or amino
      acid analog
<220> FEATURE:
<221> NAME/KEY: MOD_RES
<222> LOCATION: (4)..(4)
<223> OTHER INFORMATION: Trp or analog of Trp
<220> FEATURE:
<221> NAME/KEY: MOD_RES
<222> LOCATION: (7)..(7)
<223> OTHER INFORMATION: Trp or analog of Trp
<220> FEATURE:
<221> NAME/KEY: MOD_RES
<222> LOCATION: (9)..(13)
<223> OTHER INFORMATION: Any independently selected amino acid or amino
      acid analog
<220> FEATURE:
<223> OTHER INFORMATION: see specification as filed for detailed
      description of substitutions and preferred embodiments

<400> SEQUENCE: 5

Xaa Xaa Xaa Xaa Gln Asp Xaa Gly Xaa Xaa Xaa Xaa Xaa
1               5                   10

<210> SEQ ID NO 6
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
```

```
<223> OTHER INFORMATION: Ile, Val, Leu, B1-Ile, B1-Val, B1-Leu or a
      dipeptide comprising Gly-Ile or B1-Gly-Ile, wherein B1 represents
      a first blocking moiety
<220> FEATURE:
<221> NAME/KEY: misc_feature
<222> LOCATION: (1)..(2)
<223> OTHER INFORMATION: This region may encompass 1 to 2 residues,
      wherein some positions may be absent
<220> FEATURE:
<221> NAME/KEY: misc_feature
<222> LOCATION: (3)..(13)
<223> OTHER INFORMATION: Disulfide bond
<220> FEATURE:
<221> NAME/KEY: MOD_RES
<222> LOCATION: (5)..(5)
<223> OTHER INFORMATION: Independently selected from Trp or analogs of
      Trp
<220> FEATURE:
<221> NAME/KEY: MOD_RES
<222> LOCATION: (8)..(8)
<223> OTHER INFORMATION: Independently selected from Trp or analogs of
      Trp
<220> FEATURE:
<221> NAME/KEY: MOD_RES
<222> LOCATION: (10)..(10)
<223> OTHER INFORMATION: His, Ala or an analog of Ala, Phe, Trp or an
      analog of Trp
<220> FEATURE:
<221> NAME/KEY: MOD_RES
<222> LOCATION: (14)..(16)
<223> OTHER INFORMATION: L-Thr, D-Thr, Ile, Val, Gly, a dipeptide
      selected from Thr-Ala or Thr-Asn, or a tripeptide comprising Thr-
      Ala-Asn, wherein a c-term -OH of any of the L-Thr, D-Thr, Ile,
      Val, Gly, Ala or Asn is optionally replaced by a second blocking
      moiety
<220> FEATURE:
<221> NAME/KEY: misc_feature
<222> LOCATION: (14)..(16)
<223> OTHER INFORMATION: This region may encompass 1 to 3 residues,
      wherein some positions may be absent
<220> FEATURE:
<223> OTHER INFORMATION: see specification as filed for detailed
      description of substitutions and preferred embodiments

<400> SEQUENCE: 6

Xaa Xaa Cys Val Xaa Gln Asp Xaa Gly Xaa His Arg Cys Xaa Xaa Xaa
1               5                   10                  15

<210> SEQ ID NO 7
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Ile, Val, Leu, Ac-Ile, Ac-Val, Ac-Leu or a
      dipeptide comprising Gly-Ile or Ac-Gly-Ile
<220> FEATURE:
<221> NAME/KEY: misc_feature
<222> LOCATION: (1)..(2)
<223> OTHER INFORMATION: This region may encompass 1 to 2 residues,
      wherein some positions may be absent
<220> FEATURE:
<221> NAME/KEY: misc_feature
<222> LOCATION: (3)..(13)
<223> OTHER INFORMATION: Disulfide bond
<220> FEATURE:
<221> NAME/KEY: MOD_RES
<222> LOCATION: (5)..(5)
<223> OTHER INFORMATION: Independently selected from Trp or analogs of
      Trp
<220> FEATURE:
<221> NAME/KEY: MOD_RES
<222> LOCATION: (8)..(8)
```

```
<223> OTHER INFORMATION: Independently selected from Trp or analogs of
      Trp
<220> FEATURE:
<221> NAME/KEY: MOD_RES
<222> LOCATION: (10)..(10)
<223> OTHER INFORMATION: His, Ala or an analog of Ala, Phe, Trp or an
      analog of Trp
<220> FEATURE:
<221> NAME/KEY: MOD_RES
<222> LOCATION: (14)..(16)
<223> OTHER INFORMATION: L-Thr, D-Thr, Ile, Val, Gly, a dipeptide
      selected from Thr-Ala or Thr-Asn, or a tripeptide comprising Thr-
      Ala-Asn, wherein a c-term -OH of any of L-Thr, D-Thr, Ile, Val,
      Gly, Ala, or Asn is optionally replaced by -NH2
<220> FEATURE:
<221> NAME/KEY: misc_feature
<222> LOCATION: (14)..(16)
<223> OTHER INFORMATION: This region may encompass 1 to 3 residues,
      wherein some positions may be absent
<220> FEATURE:
<223> OTHER INFORMATION: see specification as filed for detailed
      description of substitutions and preferred embodiments

<400> SEQUENCE: 7

Xaa Xaa Cys Val Xaa Gln Asp Xaa Gly Xaa His Arg Cys Xaa Xaa Xaa
1               5                   10                  15

<210> SEQ ID NO 8
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<223> OTHER INFORMATION: C-term CONH2

<400> SEQUENCE: 8

Ile Cys Val Val Gln Asp Trp Gly His His Arg Cys Thr
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term CONH2

<400> SEQUENCE: 9

Ile Cys Val Val Gln Asp Trp Gly His His Arg Cys Thr
1               5                   10

<210> SEQ ID NO 10
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term CONH2

<400> SEQUENCE: 10
```

Ile Cys Val Tyr Gln Asp Trp Gly Ala His Arg Cys Thr
1               5                   10

<210> SEQ ID NO 11
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term COOH

<400> SEQUENCE: 11

Ile Cys Val Trp Gln Asp Trp Gly Ala His Arg Cys Thr
1               5                   10

<210> SEQ ID NO 12
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term CONH2

<400> SEQUENCE: 12

Ile Cys Val Trp Gln Asp Trp Gly Ala His Arg Cys Thr
1               5                   10

<210> SEQ ID NO 13
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (13)..(13)
<223> OTHER INFORMATION: d-Thr
<220> FEATURE:
<223> OTHER INFORMATION: C-term COOH

<400> SEQUENCE: 13

Ile Cys Val Trp Gln Asp Trp Gly Ala His Arg Cys Thr
1               5                   10

<210> SEQ ID NO 14
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: 2-Nal
<220> FEATURE:
<223> OTHER INFORMATION: C-term CONH2

<400> SEQUENCE: 14

```
Ile Cys Val Ala Gln Asp Trp Gly Ala His Arg Cys Thr
1               5                   10

<210> SEQ ID NO 15
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: 2-Nal
<220> FEATURE:
<223> OTHER INFORMATION: C-term COOH

<400> SEQUENCE: 15

Ile Cys Val Ala Gln Asp Trp Gly Ala His Arg Cys Thr
1               5                   10

<210> SEQ ID NO 16
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: 1-Nal
<220> FEATURE:
<223> OTHER INFORMATION: C-term COOH

<400> SEQUENCE: 16

Ile Cys Val Ala Gln Asp Trp Gly Ala His Arg Cys Thr
1               5                   10

<210> SEQ ID NO 17
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: 2-Igl
<220> FEATURE:
<223> OTHER INFORMATION: C-term CONH2

<400> SEQUENCE: 17

Ile Cys Val Gly Gln Asp Trp Gly Ala His Arg Cys Thr
1               5                   10

<210> SEQ ID NO 18
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

<223> OTHER INFORMATION: N-term Ac
<220> FEATURE:
<221> NAME/KEY: MOD_RES
<222> LOCATION: (4)..(4)
<223> OTHER INFORMATION: 2-Igl
<220> FEATURE:
<223> OTHER INFORMATION: C-term COOH

<400> SEQUENCE: 18

Ile Cys Val Gly Gln Asp Trp Gly Ala His Arg Cys Thr
1               5                   10

<210> SEQ ID NO 19
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: Dht
<220> FEATURE:
<223> OTHER INFORMATION: C-term COOH

<400> SEQUENCE: 19

Ile Cys Val Trp Gln Asp Trp Gly Ala His Arg Cys Thr
1               5                   10

<210> SEQ ID NO 20
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: Bpa
<220> FEATURE:
<223> OTHER INFORMATION: C-term COOH

<400> SEQUENCE: 20

Ile Cys Val Phe Gln Asp Trp Gly Ala His Arg Cys Thr
1               5                   10

<210> SEQ ID NO 21
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: Bpa
<220> FEATURE:
<223> OTHER INFORMATION: C-term CONH2

<400> SEQUENCE: 21

Ile Cys Val Phe Gln Asp Trp Gly Ala His Arg Cys Thr
1               5                   10

```
<210> SEQ ID NO 22
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: Bta
<220> FEATURE:
<223> OTHER INFORMATION: C-term COOH

<400> SEQUENCE: 22

Ile Cys Val Xaa Gln Asp Trp Gly Ala His Arg Cys Thr
1               5                   10

<210> SEQ ID NO 23
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: Bta
<220> FEATURE:
<223> OTHER INFORMATION: C-term CONH2

<400> SEQUENCE: 23

Ile Cys Val Xaa Gln Asp Trp Gly Ala His Arg Cys Thr
1               5                   10

<210> SEQ ID NO 24
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (9)..(9)
<223> OTHER INFORMATION: 2-Abu
<220> FEATURE:
<223> OTHER INFORMATION: C-term CONH2

<400> SEQUENCE: 24

Ile Cys Val Trp Gln Asp Trp Gly Xaa His Arg Cys Thr
1               5                   10

<210> SEQ ID NO 25
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<223> OTHER INFORMATION: C-term COOH
```

```
<400> SEQUENCE: 25

Gly Ile Cys Val Trp Gln Asp Trp Gly Ala His Arg Cys Thr Ala Asn
1               5                   10                  15

<210> SEQ ID NO 26
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: 5f-Trp
<220> FEATURE:
<223> OTHER INFORMATION: C-term CONH2

<400> SEQUENCE: 26

Ile Cys Val Trp Gln Asp Trp Gly Ala His Arg Cys Thr
1               5                   10

<210> SEQ ID NO 27
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: 5-methyl-Trp
<220> FEATURE:
<223> OTHER INFORMATION: C-term CONH2

<400> SEQUENCE: 27

Ile Cys Val Trp Gln Asp Trp Gly Ala His Arg Cys Thr
1               5                   10

<210> SEQ ID NO 28
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: 1-methyl-Trp
<220> FEATURE:
<223> OTHER INFORMATION: C-term CONH2

<400> SEQUENCE: 28

Ile Cys Val Trp Gln Asp Trp Gly Ala His Arg Cys Thr
1               5                   10

<210> SEQ ID NO 29
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<223> OTHER INFORMATION: N-term Ac
<220> FEATURE:
<221> NAME/KEY: MOD_RES
<222> LOCATION: (7)..(7)
<223> OTHER INFORMATION: 5f-Trp
<220> FEATURE:
<223> OTHER INFORMATION: C-term CONH2

<400> SEQUENCE: 29

Ile Cys Val Trp Gln Asp Trp Gly Ala His Arg Cys Thr
1               5                   10

<210> SEQ ID NO 30
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: 5f-Trp
<220> FEATURE:
<221> NAME/KEY: MOD_RES
<222> LOCATION: (7)..(7)
<223> OTHER INFORMATION: 5f-Trp
<220> FEATURE:
<223> OTHER INFORMATION: C-term CONH2

<400> SEQUENCE: 30

Ile Cys Val Trp Gln Asp Trp Gly Ala His Arg Cys Thr
1               5                   10

<210> SEQ ID NO 31
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: 5-methyl-Trp
<220> FEATURE:
<221> NAME/KEY: MOD_RES
<222> LOCATION: (7)..(7)
<223> OTHER INFORMATION: 5f-Trp
<220> FEATURE:
<223> OTHER INFORMATION: C-term CONH2

<400> SEQUENCE: 31

Ile Cys Val Trp Gln Asp Trp Gly Ala His Arg Cys Thr
1               5                   10

<210> SEQ ID NO 32
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
```

```
<223> OTHER INFORMATION: 1-methyl-Trp
<220> FEATURE:
<221> NAME/KEY: MOD_RES
<222> LOCATION: (7)..(7)
<223> OTHER INFORMATION: 5f-Trp
<220> FEATURE:
<223> OTHER INFORMATION: C-term CONH2

<400> SEQUENCE: 32

Ile Cys Val Trp Gln Asp Trp Gly Ala His Arg Cys Thr
1               5                   10

<210> SEQ ID NO 33
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (5)..(5)
<223> OTHER INFORMATION: 6f-Trp
<220> FEATURE:
<221> NAME/KEY: MOD_RES
<222> LOCATION: (8)..(8)
<223> OTHER INFORMATION: 6f-Trp
<220> FEATURE:
<223> OTHER INFORMATION: C-term COOH

<400> SEQUENCE: 33

Gly Ile Cys Val Trp Gln Asp Trp Gly Ala His Arg Cys Thr Asn
1               5                   10                  15

<210> SEQ ID NO 34
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: 1-formyl-Trp
<220> FEATURE:
<223> OTHER INFORMATION: C-term CONH2

<400> SEQUENCE: 34

Ile Cys Val Trp Gln Asp Trp Gly Ala His Arg Cys Thr
1               5                   10

<210> SEQ ID NO 35
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: 1-methoxy-Trp
<220> FEATURE:
<223> OTHER INFORMATION: C-term CONH2

<400> SEQUENCE: 35
```

```
Ile Cys Val Trp Gln Asp Trp Gly Ala His Arg Cys Thr
1               5                   10

<210> SEQ ID NO 36
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (5)..(5)
<223> OTHER INFORMATION: 5f-Trp
<220> FEATURE:
<221> NAME/KEY: MOD_RES
<222> LOCATION: (8)..(8)
<223> OTHER INFORMATION: 5f-Trp
<220> FEATURE:
<223> OTHER INFORMATION: C-term COOH

<400> SEQUENCE: 36

Gly Ile Cys Val Trp Gln Asp Trp Gly Ala His Arg Cys Thr Asn
1               5                   10                  15

<210> SEQ ID NO 37
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (2)..(4)
<223> OTHER INFORMATION: Any independently selected amino acid or amino
      acid analog
<220> FEATURE:
<221> NAME/KEY: MOD_RES
<222> LOCATION: (5)..(5)
<223> OTHER INFORMATION: Trp or analog of Trp
<220> FEATURE:
<221> NAME/KEY: MOD_RES
<222> LOCATION: (8)..(8)
<223> OTHER INFORMATION: Trp or analog of Trp
<220> FEATURE:
<221> NAME/KEY: MOD_RES
<222> LOCATION: (10)..(14)
<223> OTHER INFORMATION: Any independently selected amino acid or amino
      acid analog
<220> FEATURE:
<221> NAME/KEY: MOD_RES
<222> LOCATION: (15)..(15)
<223> OTHER INFORMATION: Any amino acid
<220> FEATURE:
<223> OTHER INFORMATION: see specification as filed for detailed
      description of substitutions and preferred embodiments

<400> SEQUENCE: 37

Xaa Xaa Xaa Xaa Xaa Gln Asp Xaa Gly Xaa Xaa Xaa Xaa Xaa Xaa
1               5                   10                  15

<210> SEQ ID NO 38
<211> LENGTH: 18
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (2)..(3)
<223> OTHER INFORMATION: Ile, Val, Leu, B1-Ile, B1-Val, B1-Leu or a
      dipeptide comprising Gly-Ile or B1-Gly-Ile, wherein B1 represents
      a first blocking moiety
<220> FEATURE:
<221> NAME/KEY: misc_feature
<222> LOCATION: (2)..(3)
<223> OTHER INFORMATION: This region may encompass 1 to 2 residues,
      wherein some positions may be absent
<220> FEATURE:
<221> NAME/KEY: misc_feature
<222> LOCATION: (4)..(14)
<223> OTHER INFORMATION: Disulfide bond
<220> FEATURE:
<221> NAME/KEY: MOD_RES
<222> LOCATION: (6)..(6)
<223> OTHER INFORMATION: Independently selected from Trp or analogs of
      Trp
<220> FEATURE:
<221> NAME/KEY: MOD_RES
<222> LOCATION: (9)..(9)
<223> OTHER INFORMATION: Independently selected from Trp or analogs of
      Trp
<220> FEATURE:
<221> NAME/KEY: MOD_RES
<222> LOCATION: (11)..(11)
<223> OTHER INFORMATION: His, Ala or an analog of Ala, Phe, Trp or an
      analog of Trp
<220> FEATURE:
<221> NAME/KEY: MOD_RES
<222> LOCATION: (15)..(17)
<223> OTHER INFORMATION: L-Thr, D-Thr, Ile, Val, Gly, a dipeptide
      selected from Thr-Ala or Thr-Asn, or a tripeptide comprising Thr-
      Ala-Asn, wherein a c-term -OH of any of the L-Thr, D-Thr, Ile,
      Val, Gly, Ala or Asn is optionally replaced by a second blocking
      moiety
<220> FEATURE:
<221> NAME/KEY: misc_feature
<222> LOCATION: (15)..(17)
<223> OTHER INFORMATION: This region may encompass 1 to 3 residues,
      wherein some positions may be absent
<220> FEATURE:
<221> NAME/KEY: MOD_RES
<222> LOCATION: (18)..(18)
<223> OTHER INFORMATION: Any amino acid
<220> FEATURE:
<223> OTHER INFORMATION: see specification as filed for detailed
      description of substitutions and preferred embodiments

<400> SEQUENCE: 38

Xaa Xaa Xaa Cys Val Xaa Gln Asp Xaa Gly Xaa His Arg Cys Xaa Xaa
1               5                   10                  15

Xaa Xaa

<210> SEQ ID NO 39
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (2)..(2)
```

```
<223> OTHER INFORMATION: Ile or Gly
<220> FEATURE:
<221> NAME/KEY: MOD_RES
<222> LOCATION: (3)..(3)
<223> OTHER INFORMATION: Ile or Cys
<220> FEATURE:
<221> NAME/KEY: MOD_RES
<222> LOCATION: (4)..(4)
<223> OTHER INFORMATION: Val or Cys
<220> FEATURE:
<221> NAME/KEY: MOD_RES
<222> LOCATION: (5)..(5)
<223> OTHER INFORMATION: Val, Tyr, Trp, 2-Nal, 1-Nal, 2-Igl, Dht, Bpa,
      Bta, 5f-Trp, 5-methyl-Trp, 1-methyl-Trp, 1-formyl-Trp or
      1-methyoxy-Trp
<220> FEATURE:
<221> NAME/KEY: MOD_RES
<222> LOCATION: (6)..(6)
<223> OTHER INFORMATION: Gln, Trp, 6f-Trp or 5f-Trp
<220> FEATURE:
<221> NAME/KEY: MOD_RES
<222> LOCATION: (7)..(7)
<223> OTHER INFORMATION: Asp or Gln
<220> FEATURE:
<221> NAME/KEY: MOD_RES
<222> LOCATION: (8)..(8)
<223> OTHER INFORMATION: Trp, Asp or 5f-Trp
<220> FEATURE:
<221> NAME/KEY: MOD_RES
<222> LOCATION: (9)..(9)
<223> OTHER INFORMATION: Gly, Trp, 6f-Trp or 5f-Trp
<220> FEATURE:
<221> NAME/KEY: MOD_RES
<222> LOCATION: (10)..(10)
<223> OTHER INFORMATION: His, Ala, 2-Abu or Gly
<220> FEATURE:
<221> NAME/KEY: MOD_RES
<222> LOCATION: (11)..(11)
<223> OTHER INFORMATION: His or Ala
<220> FEATURE:
<221> NAME/KEY: MOD_RES
<222> LOCATION: (12)..(12)
<223> OTHER INFORMATION: Arg or His
<220> FEATURE:
<221> NAME/KEY: MOD_RES
<222> LOCATION: (13)..(13)
<223> OTHER INFORMATION: Cys or Arg
<220> FEATURE:
<221> NAME/KEY: MOD_RES
<222> LOCATION: (14)..(14)
<223> OTHER INFORMATION: Thr, d-Thr or Cys
<220> FEATURE:
<221> NAME/KEY: MOD_RES
<222> LOCATION: (15)..(15)
<223> OTHER INFORMATION: Any amino acid
<220> FEATURE:
<223> OTHER INFORMATION: see specification as filed for detailed
      description of substitutions and preferred embodiments

<400> SEQUENCE: 39

Xaa Xaa Xaa Xaa Xaa Xaa Xaa Xaa Xaa Xaa Xaa Xaa Xaa Xaa Xaa
1               5                   10                  15

<210> SEQ ID NO 40
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: misc_feature
<222> LOCATION: (3)..(13)
```

```
<223> OTHER INFORMATION: Disulfide bond
<220> FEATURE:
<221> NAME/KEY: MOD_RES
<222> LOCATION: (5)..(5)
<223> OTHER INFORMATION: Trp(Me)
<220> FEATURE:
<221> NAME/KEY: MOD_RES
<222> LOCATION: (9)..(9)
<223> OTHER INFORMATION: mGly
<220> FEATURE:
<221> NAME/KEY: MOD_RES
<222> LOCATION: (14)..(14)
<223> OTHER INFORMATION: mIle
<220> FEATURE:
<221> NAME/KEY: MOD_RES
<222> LOCATION: (15)..(15)
<223> OTHER INFORMATION: Any amino acid
<220> FEATURE:
<223> OTHER INFORMATION: see specification as filed for detailed
      description of substitutions and preferred embodiments

<400> SEQUENCE: 40

Xaa Ile Cys Val Trp Gln Asp Trp Gly Ala His Arg Cys Ile Xaa
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: misc_feature
<222> LOCATION: (3)..(13)
<223> OTHER INFORMATION: Disulfide bond
<220> FEATURE:
<221> NAME/KEY: MOD_RES
<222> LOCATION: (5)..(5)
<223> OTHER INFORMATION: Trp(Me)
<220> FEATURE:
<221> NAME/KEY: MOD_RES
<222> LOCATION: (9)..(9)
<223> OTHER INFORMATION: mGly
<220> FEATURE:
<221> NAME/KEY: MOD_RES
<222> LOCATION: (14)..(14)
<223> OTHER INFORMATION: mIle
<220> FEATURE:
<221> NAME/KEY: MOD_RES
<222> LOCATION: (15)..(15)
<223> OTHER INFORMATION: Any amino acid
<220> FEATURE:
<223> OTHER INFORMATION: see specification as filed for detailed
      description of substitutions and preferred embodiments

<400> SEQUENCE: 41

Xaa Ile Cys Val Trp Gln Asp Trp Gly Ala His Arg Cys Ile Xaa
1               5                   10                  15

<210> SEQ ID NO 42
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (2)..(12)
<223> OTHER INFORMATION: Disulfide bond
```

```
<220> FEATURE:
<221> NAME/KEY: MOD_RES
<222> LOCATION: (4)..(4)
<223> OTHER INFORMATION: (1Me)Trp

<400> SEQUENCE: 42

Ile Cys Val Trp Gln Asp Trp Gly Ala His Arg Cys Thr
1               5                   10

<210> SEQ ID NO 43
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<223> OTHER INFORMATION: C-term NH2

<400> SEQUENCE: 43

Ile Cys Val Trp Gln Asp Trp Gly Ala His Arg Cys Thr Lys
1               5                   10

<210> SEQ ID NO 44
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<223> OTHER INFORMATION: C-term NH2

<400> SEQUENCE: 44

Ile Cys Val Trp Gln Asp Trp Gly Ala His Arg Cys Thr Gly Gly
1               5                   10                  15

Gly Gly Lys

<210> SEQ ID NO 45
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2(CH2)5C(=O)
<220> FEATURE:
<221> NAME/KEY: MOD_RES
<222> LOCATION: (4)..(4)
<223> OTHER INFORMATION: (1Me)Trp
<220> FEATURE:
```

```
<223> OTHER INFORMATION: C-term NH2

<400> SEQUENCE: 45

Ile Cys Val Trp Gln Asp Trp Gly Ala His Arg Cys Thr
1               5                   10

<210> SEQ ID NO 46
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2(CH2CH2O)2CH2C(=O)
<220> FEATURE:
<221> NAME/KEY: MOD_RES
<222> LOCATION: (4)..(4)
<223> OTHER INFORMATION: (1Me)Trp
<220> FEATURE:
<223> OTHER INFORMATION: C-term NH2

<400> SEQUENCE: 46

Ile Cys Val Trp Gln Asp Trp Gly Ala His Arg Cys Thr
1               5                   10

<210> SEQ ID NO 47
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<221> NAME/KEY: MOD_RES
<222> LOCATION: (14)..(14)
<223> OTHER INFORMATION: NH-CH2CH2OCH2CH2OCH2-C(=O)-Lys
<220> FEATURE:
<223> OTHER INFORMATION: C-term NH2

<400> SEQUENCE: 47

Ile Cys Val Trp Gln Asp Trp Gly Ala His Arg Cys Thr Lys
1               5                   10

<210> SEQ ID NO 48
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term (CH2CH2O)nC(=O)
<220> FEATURE:
<221> NAME/KEY: MOD_RES
<222> LOCATION: (4)..(4)
<223> OTHER INFORMATION: (1Me)Trp
<220> FEATURE:
<223> OTHER INFORMATION: C-term NH2
<220> FEATURE:
<223> OTHER INFORMATION: see specification as filed for detailed
      description of substitutions and preferred embodiments
```

```
<400> SEQUENCE: 48

Ile Cys Val Trp Gln Asp Trp Gly Ala His Arg Cys Thr
1               5                   10

<210> SEQ ID NO 49
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<221> NAME/KEY: MOD_RES
<222> LOCATION: (14)..(14)
<223> OTHER INFORMATION: NH-CH2CH2OCH2CH2OCH2-C(=O)-Lys-C(=O)-(CH2CH2O)n
<220> FEATURE:
<223> OTHER INFORMATION: C-term NH2
<220> FEATURE:
<223> OTHER INFORMATION: see specification as filed for detailed
      description of substitutions and preferred embodiments

<400> SEQUENCE: 49

Ile Cys Val Trp Gln Asp Trp Gly Ala His Arg Cys Thr Lys
1               5                   10

<210> SEQ ID NO 50
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<221> NAME/KEY: MOD_RES
<222> LOCATION: (14)..(14)
<223> OTHER INFORMATION: Lys-C(=O)-(CH2CH2O)n
<220> FEATURE:
<223> OTHER INFORMATION: C-term NH2
<220> FEATURE:
<223> OTHER INFORMATION: see specification as filed for detailed
      description of substitutions and preferred embodiments

<400> SEQUENCE: 50

Ile Cys Val Trp Gln Asp Trp Gly Ala His Arg Cys Thr Lys
1               5                   10

<210> SEQ ID NO 51
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<223> OTHER INFORMATION: N-term Ac
<220> FEATURE:
<221> NAME/KEY: misc_feature
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<221> NAME/KEY: MOD_RES
<222> LOCATION: (19)..(19)
<223> OTHER INFORMATION: Lys-C(=O)-(CH2CH2O)n
<220> FEATURE:
<223> OTHER INFORMATION: C-term NH2
<220> FEATURE:
<223> OTHER INFORMATION: see specification as filed for detailed
      description of substitutions and preferred embodiments

<400> SEQUENCE: 51

Ile Cys Val Trp Gln Asp Trp Gly Ala His Arg Cys Thr Gly Gly Gly
1               5                   10                  15

Gly Gly Lys

<210> SEQ ID NO 52
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: (CH2CH2O)nC(=O)Lys
<220> FEATURE:
<221> NAME/KEY: misc_feature
<222> LOCATION: (8)..(18)
<223> OTHER INFORMATION: Disulfide bond
<220> FEATURE:
<221> NAME/KEY: MOD_RES
<222> LOCATION: (10)..(10)
<223> OTHER INFORMATION: (1Me)Trp
<220> FEATURE:
<223> OTHER INFORMATION: C-term NH2
<220> FEATURE:
<223> OTHER INFORMATION: see specification as filed for detailed
      description of substitutions and preferred embodiments

<400> SEQUENCE: 52

Lys Gly Gly Gly Gly Gly Ile Cys Val Trp Gln Asp Trp Gly Ala His
1               5                   10                  15

Arg Cys Thr

<210> SEQ ID NO 53
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: (CH2CH2O)nC(=O)Lys
<220> FEATURE:
<221> NAME/KEY: misc_feature
<222> LOCATION: (3)..(13)
```

```
<223> OTHER INFORMATION: Disulfide bond
<220> FEATURE:
<221> NAME/KEY: MOD_RES
<222> LOCATION: (5)..(5)
<223> OTHER INFORMATION: (1Me)Trp
<220> FEATURE:
<223> OTHER INFORMATION: C-term NH2
<220> FEATURE:
<223> OTHER INFORMATION: see specification as filed for detailed
      description of substitutions and preferred embodiments

<400> SEQUENCE: 53

Lys Ile Cys Val Trp Gln Asp Trp Gly Ala His Arg Cys Thr
1               5                   10

<210> SEQ ID NO 54
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<221> NAME/KEY: MOD_RES
<222> LOCATION: (14)..(14)
<223> OTHER INFORMATION: NH-CH2CH2OCH2CH2OCH2-C(=O)-Lys-(C(=O)-
      (CH2CH2O)n-R)
<220> FEATURE:
<223> OTHER INFORMATION: C-term NH2
<220> FEATURE:
<223> OTHER INFORMATION: see specification as filed for detailed
      description of substitutions and preferred embodiments

<400> SEQUENCE: 54

Ile Cys Val Trp Gln Asp Trp Gly Ala His Arg Cys Thr Lys
1               5                   10

<210> SEQ ID NO 55
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<221> NAME/KEY: MOD_RES
<222> LOCATION: (14)..(14)
<223> OTHER INFORMATION: NH-CH2CH2OCH2CH2OCH2-C(=O)-Lys-(C(=O)-(CH2)m-
      (CH2CH2O)n-R)
<220> FEATURE:
<223> OTHER INFORMATION: C-term NH2
<220> FEATURE:
<223> OTHER INFORMATION: see specification as filed for detailed
      description of substitutions and preferred embodiments
```

```
<400> SEQUENCE: 55

Ile Cys Val Trp Gln Asp Trp Gly Ala His Arg Cys Thr Lys
1               5                   10

<210> SEQ ID NO 56
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<221> NAME/KEY: MOD_RES
<222> LOCATION: (14)..(14)
<223> OTHER INFORMATION: NH-CH2CH2OCH2CH2OCH2-C(=O)-Lys-(C(=O)-(CH2)m-
      C(=O)-(CH2CH2O)n-R)
<220> FEATURE:
<223> OTHER INFORMATION: C-term NH2
<220> FEATURE:
<223> OTHER INFORMATION: see specification as filed for detailed
      description of substitutions and preferred embodiments

<400> SEQUENCE: 56

Ile Cys Val Trp Gln Asp Trp Gly Ala His Arg Cys Thr Lys
1               5                   10

<210> SEQ ID NO 57
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<221> NAME/KEY: MOD_RES
<222> LOCATION: (14)..(14)
<223> OTHER INFORMATION: NH-CH2CH2OCH2CH2OCH2-C(=O)-Lys-(C(=O)-
      (CH2)m-C(=O)-(CH2)j(CH2CH2O)n-R)
<220> FEATURE:
<223> OTHER INFORMATION: C-term NH2
<220> FEATURE:
<223> OTHER INFORMATION: see specification as filed for detailed
      description of substitutions and preferred embodiments

<400> SEQUENCE: 57

Ile Cys Val Trp Gln Asp Trp Gly Ala His Arg Cys Thr Lys
1               5                   10

<210> SEQ ID NO 58
<211> LENGTH: 14
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: misc_feature
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp
<220> FEATURE:
<221> NAME/KEY: MOD_RES
<222> LOCATION: (14)..(14)
<223> OTHER INFORMATION: AEEAc-Lys-(C(=O)-(CH2)5-Mal)
<220> FEATURE:
<223> OTHER INFORMATION: C-term NH2
<220> FEATURE:
<223> OTHER INFORMATION: see specification as filed for detailed
      description of substitutions and preferred embodiments

<400> SEQUENCE: 58

Ile Cys Val Trp Gln Asp Trp Gly Ala His Arg Cys Thr Lys
1               5                   10

<210> SEQ ID NO 59
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(5)
<223> OTHER INFORMATION: Cyclic
<220> FEATURE:
<221> NAME/KEY: MOD_RES
<222> LOCATION: (1)..(1)
<223> OTHER INFORMATION: Ornithine
<220> FEATURE:
<221> NAME/KEY: MOD_RES
<222> LOCATION: (3)..(3)
<223> OTHER INFORMATION: dCha

<400> SEQUENCE: 59

Xaa Pro Ala Trp Arg
1               5

<210> SEQ ID NO 60
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(5)
<223> OTHER INFORMATION: Cyclic
<220> FEATURE:
<221> NAME/KEY: MOD_RES
<222> LOCATION: (3)..(3)
<223> OTHER INFORMATION: dCha

<400> SEQUENCE: 60

Lys Pro Ala Trp Arg
1               5

<210> SEQ ID NO 61
<211> LENGTH: 10
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid and this region may encompass
      1 to 5 residues, wherein some positions may be
      absent
<220> FEATURE:
<221> NAME/KEY: MOD_RES
<222> LOCATION: (6)..(6)
<223> OTHER INFORMATION: Ornithine
<220> FEATURE:
<221> NAME/KEY: misc_feature
<222> LOCATION: (6)..(10)
<223> OTHER INFORMATION: Cyclic
<220> FEATURE:
<221> NAME/KEY: MOD_RES
<222> LOCATION: (8)..(8)
<223> OTHER INFORMATION: dCha

<400> SEQUENCE: 61

Xaa Xaa Xaa Xaa Xaa Xaa Pro Ala Trp Arg
1               5                   10

<210> SEQ ID NO 62
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid and this region may encompass
      1 to 5 residues, wherein some positions may be
      absent
<220> FEATURE:
<221> NAME/KEY: misc_feature
<222> LOCATION: (6)..(10)
<223> OTHER INFORMATION: Cyclic
<220> FEATURE:
<221> NAME/KEY: MOD_RES
<222> LOCATION: (8)..(8)
<223> OTHER INFORMATION: dCha

<400> SEQUENCE: 62

Xaa Xaa Xaa Xaa Xaa Lys Pro Ala Trp Arg
1               5                   10

<210> SEQ ID NO 63
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ornithine
<220> FEATURE:
<221> NAME/KEY: misc_feature
<222> LOCATION: (2)..(6)
<223> OTHER INFORMATION: Cyclic
<220> FEATURE:
<221> NAME/KEY: MOD_RES
<222> LOCATION: (4)..(4)
<223> OTHER INFORMATION: dCha

<400> SEQUENCE: 63
```

Phe Xaa Pro Ala Trp Arg
1               5

<210> SEQ ID NO 64
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (2)..(6)
<223> OTHER INFORMATION: Cyclic
<220> FEATURE:
<221> NAME/KEY: MOD_RES
<222> LOCATION: (4)..(4)
<223> OTHER INFORMATION: dCha

<400> SEQUENCE: 64

Phe Lys Pro Ala Trp Arg
1               5

<210> SEQ ID NO 65
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term cinnamoyl
<220> FEATURE:
<221> NAME/KEY: MOD_RES
<222> LOCATION: (1)..(1)
<223> OTHER INFORMATION: Ornithine
<220> FEATURE:
<221> NAME/KEY: misc_feature
<222> LOCATION: (1)..(5)
<223> OTHER INFORMATION: Cyclic
<220> FEATURE:
<221> NAME/KEY: MOD_RES
<222> LOCATION: (3)..(3)
<223> OTHER INFORMATION: dCha

<400> SEQUENCE: 65

Xaa Pro Ala Trp Arg
1               5

<210> SEQ ID NO 66
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H-cinnamoyl
<220> FEATURE:
<221> NAME/KEY: MOD_RES
<222> LOCATION: (1)..(1)
<223> OTHER INFORMATION: Ornithine
<220> FEATURE:
<221> NAME/KEY: misc_feature
<222> LOCATION: (1)..(5)
<223> OTHER INFORMATION: Cyclic
<220> FEATURE:
<221> NAME/KEY: MOD_RES
<222> LOCATION: (3)..(3)
<223> OTHER INFORMATION: dCha

<400> SEQUENCE: 66

Xaa Pro Ala Trp Arg

<210> SEQ ID NO 67
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (2)..(2)
<223> OTHER INFORMATION: Ornithine
<220> FEATURE:
<221> NAME/KEY: misc_feature
<222> LOCATION: (2)..(6)
<223> OTHER INFORMATION: Cyclic
<220> FEATURE:
<221> NAME/KEY: MOD_RES
<222> LOCATION: (4)..(4)
<223> OTHER INFORMATION: dCha

<400> SEQUENCE: 67

Phe Xaa Pro Ala Trp Arg
1               5

<210> SEQ ID NO 68
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Trp Glu Ser Asn Gly Gln Pro Glu Asn Asn
1               5                   10

<210> SEQ ID NO 69
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Lys Thr Ile Ser Lys Ala Lys Gly Gln Pro Arg Glu Pro Gln Val Tyr
1               5                   10                  15

Thr

<210> SEQ ID NO 70
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 70

His His His His His His
1               5

<210> SEQ ID NO 71
<211> LENGTH: 4
<212> TYPE: PRT
<213> ORGANISM: Artificial Sequence

```
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Trp or an analog of Trp
<220> FEATURE:
<223> OTHER INFORMATION: see specification as filed for detailed
      description of substitutions and preferred embodiments

<400> SEQUENCE: 71

Gln Asp Xaa Gly
1

<210> SEQ ID NO 72
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (2)..(12)
<223> OTHER INFORMATION: Disulfide bond
<220> FEATURE:
<221> NAME/KEY: MOD_RES
<222> LOCATION: (4)..(4)
<223> OTHER INFORMATION: (1Me)Trp

<400> SEQUENCE: 72

Ile Cys Val Trp Gln Asp Trp Gly Ala His Arg Cys Thr
1               5                   10
```